(12) United States Patent
Ewer et al.

(10) Patent No.: US 10,993,815 B2
(45) Date of Patent: May 4, 2021

(54) METHODS AND INSTRUMENTATION FOR INTERVERTEBRAL CAGE EXPANSION

(71) Applicant: IMDS LLC, Providence, UT (US)

(72) Inventors: Darin Ewer, Providence, UT (US); David Koch, North Logan, UT (US); Nathan W. Erickson, Beaver Dam, UT (US); Daniel J. Triplett, Providence, UT (US)

(73) Assignee: IMDS LLC, Providence, UT (US)

( * ) Notice: Subject to any disclaimer, the term of this patent is extended or adjusted under 35 U.S.C. 154(b) by 294 days.

(21) Appl. No.: 15/793,950

(22) Filed: Oct. 25, 2017

(65) Prior Publication Data

US 2018/0110629 A1   Apr. 26, 2018

Related U.S. Application Data

(60) Provisional application No. 62/412,781, filed on Oct. 25, 2016.

(51) Int. Cl.
*A61F 2/44* (2006.01)
*A61F 2/46* (2006.01)
*A61F 2/30* (2006.01)
*A61B 17/17* (2006.01)
*A61F 2/28* (2006.01)

(52) U.S. Cl.
CPC ............ *A61F 2/4611* (2013.01); *A61F 2/442* (2013.01); *A61F 2/4455* (2013.01); *A61B 17/1757* (2013.01); *A61F 2/4603* (2013.01); *A61F 2002/2835* (2013.01); *A61F 2002/3055* (2013.01); *A61F 2002/30329* (2013.01); *A61F 2002/30331* (2013.01); *A61F 2002/30471* (2013.01); *A61F 2002/30545* (2013.01); *A61F 2002/30556* (2013.01); *A61F 2002/30579* (2013.01); *A61F 2002/4625* (2013.01); *A61F 2002/4627* (2013.01); *A61F 2002/4629* (2013.01); *A61F 2002/4638* (2013.01)

(58) Field of Classification Search
USPC .............. 606/99, 86 A, 914–916, 104, 86 B
See application file for complete search history.

(56) References Cited

U.S. PATENT DOCUMENTS

| | | | |
|---|---|---|---|
| 619,413 | A | 2/1899 | Higgins |
| 4,164,225 | A | 8/1979 | Johnson |
| 4,657,550 | A | 4/1987 | Daher |
| 4,834,757 | A | 5/1989 | Brantigan |
| 4,863,476 | A | 9/1989 | Shepperd |

(Continued)

FOREIGN PATENT DOCUMENTS

| AU | 2013206287 A1 | 7/2013 |
|---|---|---|
| AU | 2013262504 B2 | 4/2017 |

(Continued)

*Primary Examiner* — Sameh R Boles
(74) *Attorney, Agent, or Firm* — Maywood IP Law; David Meibos

(57) ABSTRACT

An instrument may be coupled to a multi-axis expandable intervertebral cage so that the cage may be inserted into an intervertebral space, expanded along multiple different directions, filled with bone graft, and locked with a fastener. The instrument may be part of an instrument set that includes auxiliary instruments to determine implant size, insert bone graft into the cage, and deliver the fastener.

9 Claims, 72 Drawing Sheets

(56) References Cited

U.S. PATENT DOCUMENTS

| | | |
|---|---|---|
| 5,059,193 A | 10/1991 | Kuslich |
| 5,171,278 A | 12/1992 | Pisharodi |
| 5,290,312 A | 3/1994 | Kojimoto |
| 5,306,310 A | 4/1994 | Siebels |
| 5,336,223 A | 8/1994 | Rogers |
| 5,390,683 A | 2/1995 | Pisharodi |
| 5,405,391 A | 4/1995 | Hednerson |
| 5,425,772 A | 6/1995 | Brantigan |
| 5,443,514 A | 8/1995 | Steffee |
| 5,458,641 A | 10/1995 | Ramirez Jimenez |
| 5,554,191 A | 9/1996 | Lahille |
| 5,571,192 A | 11/1996 | Schonhoffer |
| 5,653,762 A | 8/1997 | Pisharodi |
| 5,653,763 A | 8/1997 | Errico |
| 5,658,335 A | 8/1997 | Allen |
| 5,665,122 A | 9/1997 | Kambin |
| 5,693,100 A | 12/1997 | Pisharodi |
| 5,702,455 A | 12/1997 | Saggar |
| 5,716,415 A | 2/1998 | Steffee |
| 5,776,198 A | 7/1998 | Rabbe |
| 5,782,832 A | 7/1998 | Larsen |
| 5,865,848 A | 2/1999 | Baker |
| 5,980,522 A | 11/1999 | Koros |
| 5,989,290 A | 11/1999 | Biedermann |
| 6,015,436 A | 1/2000 | Schonhoffer |
| 6,039,761 A | 3/2000 | Li |
| 6,045,579 A | 4/2000 | Hochshuler |
| 6,080,193 A | 6/2000 | Hochshuler |
| 6,093,207 A | 7/2000 | Pisharodi |
| 6,102,950 A | 8/2000 | Vaccaro |
| 6,117,174 A | 9/2000 | Nolan |
| 6,126,689 A | 10/2000 | Brett |
| 6,126,869 A | 10/2000 | Haaland |
| 6,129,763 A | 10/2000 | Chauvin |
| 6,159,244 A | 12/2000 | Suddaby |
| 6,174,334 B1 | 1/2001 | Suddaby |
| 6,176,881 B1 | 1/2001 | Schär |
| 6,183,517 B1 | 2/2001 | Suddaby |
| 6,190,413 B1 | 2/2001 | Sutcliffe |
| 6,190,414 B1 | 2/2001 | Young |
| 6,193,755 B1 | 2/2001 | Metz-Stavenhagen |
| 6,193,756 B1 | 2/2001 | Studer |
| 6,193,757 B1 | 2/2001 | Foley |
| 6,200,348 B1 | 3/2001 | Biedermann |
| 6,214,050 B1 | 4/2001 | Huene |
| 6,296,647 B1 | 10/2001 | Robioneck |
| 6,299,644 B1 | 10/2001 | Vanderschot |
| 6,332,895 B1 | 12/2001 | Suddaby |
| 6,395,034 B1 | 5/2002 | Suddaby |
| 6,413,278 B1 | 7/2002 | Marchosky |
| 6,419,705 B1 | 7/2002 | Erickson |
| 6,436,140 B1 | 8/2002 | Liu |
| 6,454,806 B1 | 9/2002 | Cohen |
| 6,491,724 B1 | 12/2002 | Ferree |
| 6,562,074 B2 | 5/2003 | Gerbec |
| 6,582,431 B1 | 6/2003 | Ray |
| 6,648,917 B2 | 11/2003 | Gerbec |
| 6,660,038 B2 | 12/2003 | Boyer, II |
| 6,666,891 B2 | 12/2003 | Boehm, Jr. |
| 6,685,742 B1 | 2/2004 | Jackson |
| 6,706,070 B1 | 3/2004 | Wagner |
| 6,709,458 B2 | 3/2004 | Michelson |
| 6,723,126 B1 | 4/2004 | Berry |
| 6,730,126 B2 | 5/2004 | Boehm, Jr. |
| 6,746,484 B1 | 6/2004 | Liu |
| 6,833,006 B2 | 12/2004 | Foley |
| 6,852,129 B2 | 2/2005 | Gerbec |
| 6,863,673 B2 | 3/2005 | Gerbec |
| 6,893,464 B2 | 5/2005 | Kiester |
| 7,070,598 B2 | 7/2006 | Lim |
| 7,513,900 B2 | 4/2009 | Carrison |
| 7,625,377 B2 | 12/2009 | Veldhuizen |
| 7,799,081 B2 | 9/2010 | McKinley |
| 7,824,427 B2 | 11/2010 | Perez-Cruet |
| 7,846,206 B2 | 12/2010 | Oglaza |
| 7,879,098 B1 | 2/2011 | Simmons, Jr. |
| 7,922,729 B2 | 4/2011 | Michelson |
| 8,012,207 B2 | 9/2011 | Kim |
| 8,097,018 B2 | 1/2012 | Malandain |
| 8,097,035 B2 | 1/2012 | Glenn |
| 8,109,972 B2 | 2/2012 | Zucherman |
| 8,110,004 B2 | 2/2012 | Valdevit |
| 8,152,837 B2 | 4/2012 | Altarac |
| 8,317,798 B2 | 11/2012 | Lim |
| 8,323,344 B2 | 12/2012 | Galley |
| 8,409,291 B2 | 4/2013 | Blackwell |
| 8,491,657 B2 | 7/2013 | Attia |
| 8,496,709 B2 | 7/2013 | Schell |
| 8,506,635 B2 | 8/2013 | Palmatier |
| 8,541,355 B2 | 9/2013 | Fleckenstein |
| 8,568,481 B2 | 10/2013 | Olmos |
| 8,579,907 B2 | 11/2013 | Lim |
| 8,628,576 B2 | 1/2014 | Triplett |
| 8,652,174 B2 | 2/2014 | Gabelberger |
| 8,663,329 B2 | 3/2014 | Ernst |
| 8,678,576 B2 | 3/2014 | Edombingo |
| 8,685,095 B2 | 4/2014 | Miller |
| 8,777,993 B2 | 7/2014 | Siegal |
| 8,778,027 B2 | 7/2014 | Medina |
| 8,808,385 B1 | 8/2014 | Smith |
| 8,900,305 B2 | 12/2014 | Stad |
| 8,926,704 B2 | 1/2015 | Glerum |
| 8,940,048 B2 | 1/2015 | Butler |
| 9,060,876 B1 | 6/2015 | To |
| 9,308,099 B2 | 4/2016 | Triplett |
| 9,445,918 B1 | 9/2016 | Lin |
| 9,913,727 B2 | 3/2018 | Thommen |
| 2001/0032017 A1 | 10/2001 | Alfaro |
| 2002/0010511 A1 | 1/2002 | Michelson |
| 2003/0229355 A1 | 12/2003 | Keller |
| 2004/0002758 A1 | 1/2004 | Landry |
| 2004/0034430 A1 | 2/2004 | Falahee |
| 2005/0177235 A1 | 8/2005 | Baynham |
| 2005/0182416 A1 | 8/2005 | Lim |
| 2005/0222681 A1 | 10/2005 | Richley |
| 2005/0234555 A1 | 10/2005 | Sutton |
| 2005/0278036 A1 | 12/2005 | Leonard |
| 2006/0142858 A1 | 6/2006 | Colleran |
| 2006/0167547 A1 | 7/2006 | Suddaby |
| 2007/0043440 A1 | 2/2007 | William |
| 2007/0049935 A1 | 3/2007 | Edidin |
| 2007/0067034 A1 | 3/2007 | Chirico |
| 2007/0118222 A1 | 5/2007 | Lang |
| 2007/0198089 A1 | 8/2007 | Moskowitz |
| 2007/0219634 A1 | 9/2007 | Greenhalgh |
| 2007/0260315 A1 | 11/2007 | Foley |
| 2007/0282449 A1 | 12/2007 | de Villiers |
| 2008/0033440 A1 | 2/2008 | Moskowitz |
| 2008/0045968 A1 | 2/2008 | Yu |
| 2008/0082167 A1 | 4/2008 | Edidin |
| 2008/0108990 A1 | 5/2008 | Mitchell |
| 2008/0114367 A1 | 5/2008 | Meyer |
| 2008/0167657 A1 | 7/2008 | Greenhalgh |
| 2008/0183204 A1 | 7/2008 | Greenhalgh |
| 2008/0195152 A1 | 8/2008 | Altarac |
| 2008/0219604 A1 | 9/2008 | Chen |
| 2008/0221686 A1 | 9/2008 | Ferree |
| 2008/0243255 A1 | 10/2008 | Butler |
| 2008/0249604 A1 | 10/2008 | Donovan |
| 2008/0281346 A1 | 11/2008 | Greenhalgh |
| 2008/0288072 A1 | 11/2008 | Kohm |
| 2008/0288078 A1 | 11/2008 | Kohm |
| 2008/0319549 A1 | 12/2008 | Greenhalgh |
| 2009/0076607 A1 | 3/2009 | Aalsma |
| 2009/0157084 A1 | 6/2009 | Aalsma |
| 2009/0198338 A1 | 8/2009 | Phan |
| 2009/0222093 A1 | 9/2009 | Liu |
| 2009/0222100 A1 | 9/2009 | Cipoletti |
| 2009/0281628 A1 | 11/2009 | Oglaza |
| 2010/0082109 A1 | 4/2010 | Greenhalgh |
| 2010/0185291 A1 | 7/2010 | Jimenez |
| 2010/0249720 A1 | 9/2010 | Biyani |
| 2010/0286783 A1 | 11/2010 | Lechmann |
| 2010/0305705 A1 | 12/2010 | Butler |

(56) References Cited

U.S. PATENT DOCUMENTS

| | | |
|---|---|---|
| 2010/0318127 A1 | 12/2010 | Phan |
| 2011/0004307 A1 | 1/2011 | Ahn |
| 2011/0125270 A1 | 5/2011 | Paul |
| 2011/0172774 A1 | 7/2011 | Varela |
| 2011/0270396 A1 | 11/2011 | Leibowitz |
| 2011/0276141 A1 | 11/2011 | Caratsch |
| 2011/0282453 A1 | 11/2011 | Greenhalgh |
| 2011/0319997 A1 | 12/2011 | Glerum |
| 2012/0004732 A1 | 1/2012 | Goel |
| 2012/0053642 A1 | 3/2012 | Lozier |
| 2012/0071977 A1 | 3/2012 | Oglaza |
| 2012/0083887 A1 | 4/2012 | Purcell |
| 2012/0083889 A1 | 4/2012 | Purcell |
| 2012/0123546 A1 | 5/2012 | Medina |
| 2012/0136442 A1 | 5/2012 | Kleiner |
| 2012/0150241 A1 | 6/2012 | Ragab |
| 2012/0185045 A1* | 7/2012 | Morris ............ A61F 2/442 623/17.11 |
| 2012/0185047 A1 | 7/2012 | Wooley |
| 2012/0185049 A1 | 7/2012 | Varela |
| 2012/0215313 A1 | 8/2012 | Saidha |
| 2012/0215316 A1 | 8/2012 | Mohr |
| 2012/0226357 A1 | 9/2012 | Varela |
| 2012/0245691 A1 | 9/2012 | Reimels |
| 2013/0079882 A1 | 3/2013 | Wolfe |
| 2013/0079883 A1 | 3/2013 | Butler |
| 2013/0144391 A1 | 6/2013 | Siegal |
| 2013/0158669 A1 | 6/2013 | Sungarian |
| 2013/0190876 A1 | 7/2013 | Drochner |
| 2013/0297029 A1 | 11/2013 | Kana |
| 2013/0310939 A1 | 11/2013 | Fabian |
| 2013/0325128 A1 | 12/2013 | Perloff |
| 2014/0031940 A1 | 1/2014 | Banouskou |
| 2014/0039622 A1 | 2/2014 | Glerum |
| 2014/0052253 A1 | 2/2014 | Perloff |
| 2014/0088714 A1 | 3/2014 | Miller |
| 2014/0121774 A1 | 5/2014 | Glerum |
| 2014/0128977 A1 | 5/2014 | Glerum |
| 2014/0172106 A1 | 6/2014 | To |
| 2014/0188224 A1 | 7/2014 | Dmuschewsky |
| 2014/0194991 A1 | 7/2014 | Jimenez |
| 2014/0194992 A1 | 7/2014 | Medina |
| 2014/0257484 A1 | 9/2014 | Flower |
| 2014/0277490 A1 | 9/2014 | Perloff |
| 2014/0379086 A1 | 12/2014 | Elahinia |
| 2015/0012098 A1 | 1/2015 | Eastlack |
| 2015/0018951 A1 | 1/2015 | Loebl |
| 2015/0073552 A1 | 3/2015 | To |
| 2015/0257894 A1 | 9/2015 | Levy |
| 2015/0351923 A1 | 12/2015 | Emstad |
| 2015/0351928 A1 | 12/2015 | Butler |
| 2016/0199194 A1 | 7/2016 | Slater |
| 2017/0056200 A1 | 3/2017 | Koch |
| 2019/0231548 A1 | 8/2019 | Ewer |
| 2020/0205992 A1 | 7/2020 | Bernard |

FOREIGN PATENT DOCUMENTS

| | | |
|---|---|---|
| CA | 2567274 C | 11/2014 |
| CN | 202458786 U | 10/2012 |
| EP | 0260044 A1 | 3/1988 |
| EP | 1006956 A1 | 6/2000 |
| EP | 2793960 A1 | 10/2014 |
| EP | 3038566 A1 | 7/2016 |
| EP | 2729092 B1 | 9/2016 |
| EP | 2693989 B1 | 9/2017 |
| WO | WO1998034568 A1 | 8/1998 |
| WO | WO2000025706 A1 | 5/2000 |
| WO | WO2002076335 A2 | 10/2002 |
| WO | WO2003032812 A2 | 4/2003 |
| WO | WO2005112834 A2 | 12/2005 |
| WO | WO2008070863 A2 | 6/2008 |
| WO | WO2009037509 A1 | 3/2009 |
| WO | WO2009092102 A1 | 7/2009 |
| WO | WO2010078468 A2 | 7/2010 |
| WO | WO2010105181 A1 | 9/2010 |
| WO | WO2012047712 A1 | 4/2012 |
| WO | WO2012112596 A1 | 8/2012 |
| WO | WO2012141715 A1 | 10/2012 |
| WO | WO2013052807 A2 | 4/2013 |
| WO | WO2013109346 A1 | 7/2013 |
| WO | WO2013173767 A1 | 11/2013 |
| WO | WO2014144696 | 9/2014 |
| WO | WO2014151162 A1 | 9/2014 |
| WO | WO2014164625 A1 | 10/2014 |
| WO | WO2015009998 A1 | 1/2015 |
| WO | WO2015031291 A1 | 3/2015 |
| WO | WO2015063719 A1 | 3/2015 |
| WO | WO2017035155 A1 | 3/2017 |

* cited by examiner

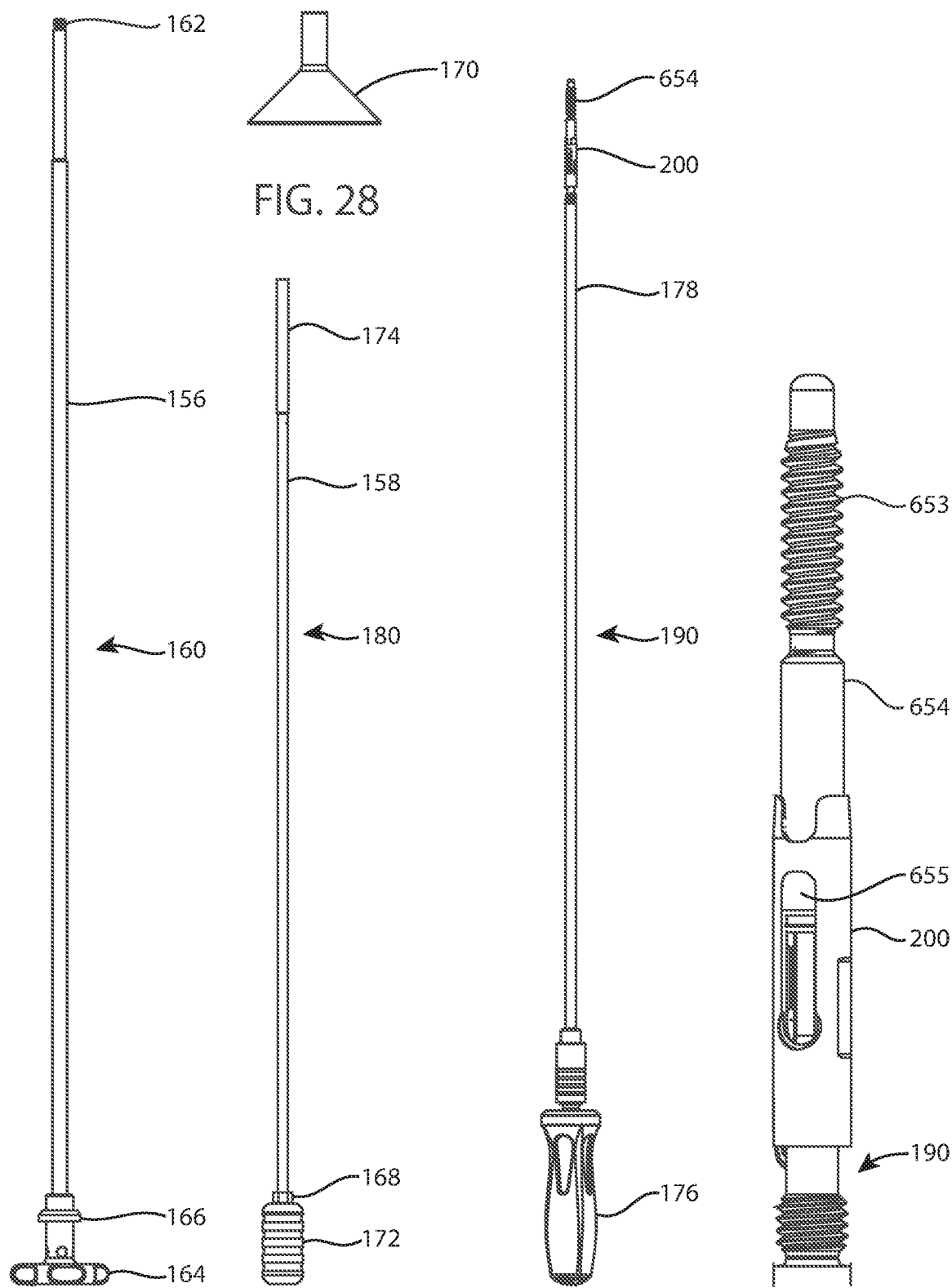

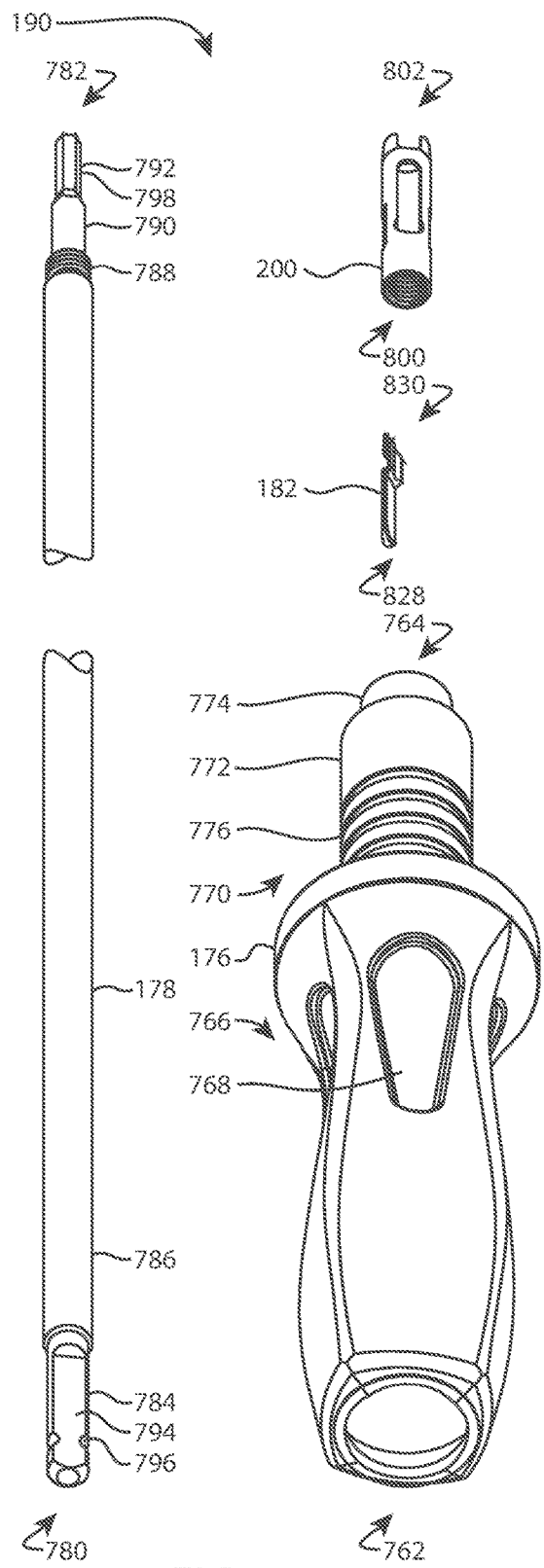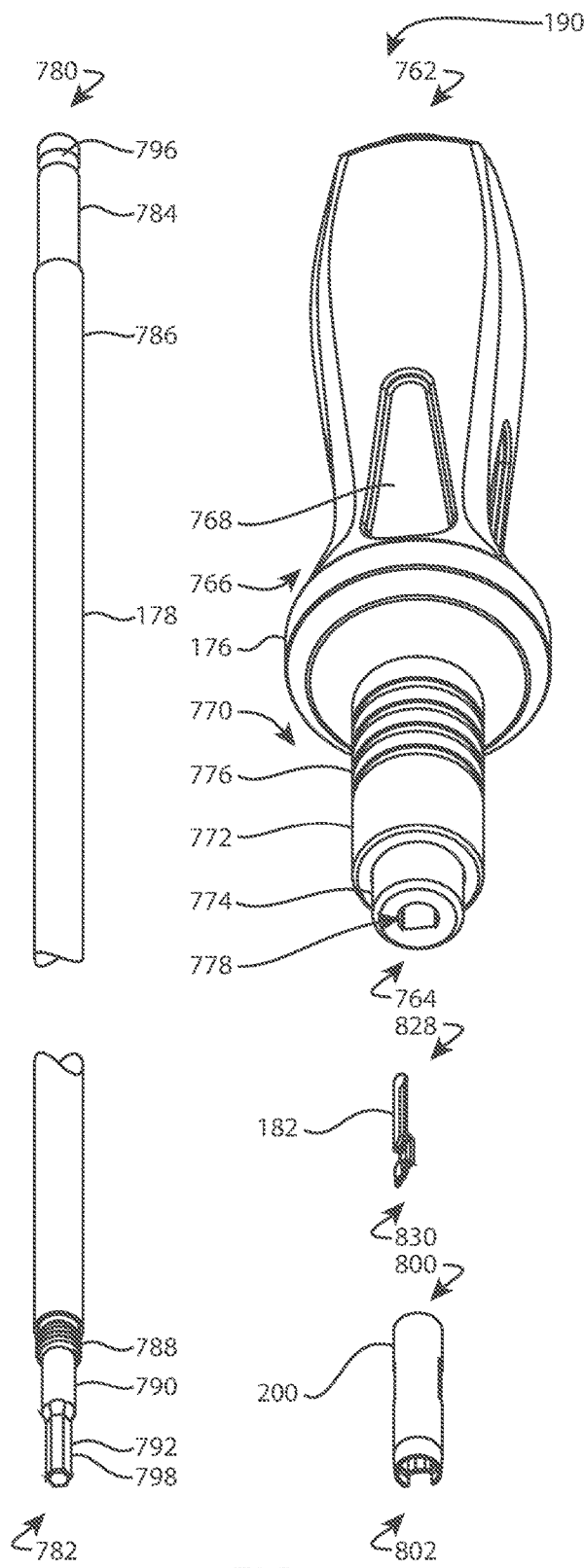
FIG. 37
FIG. 38

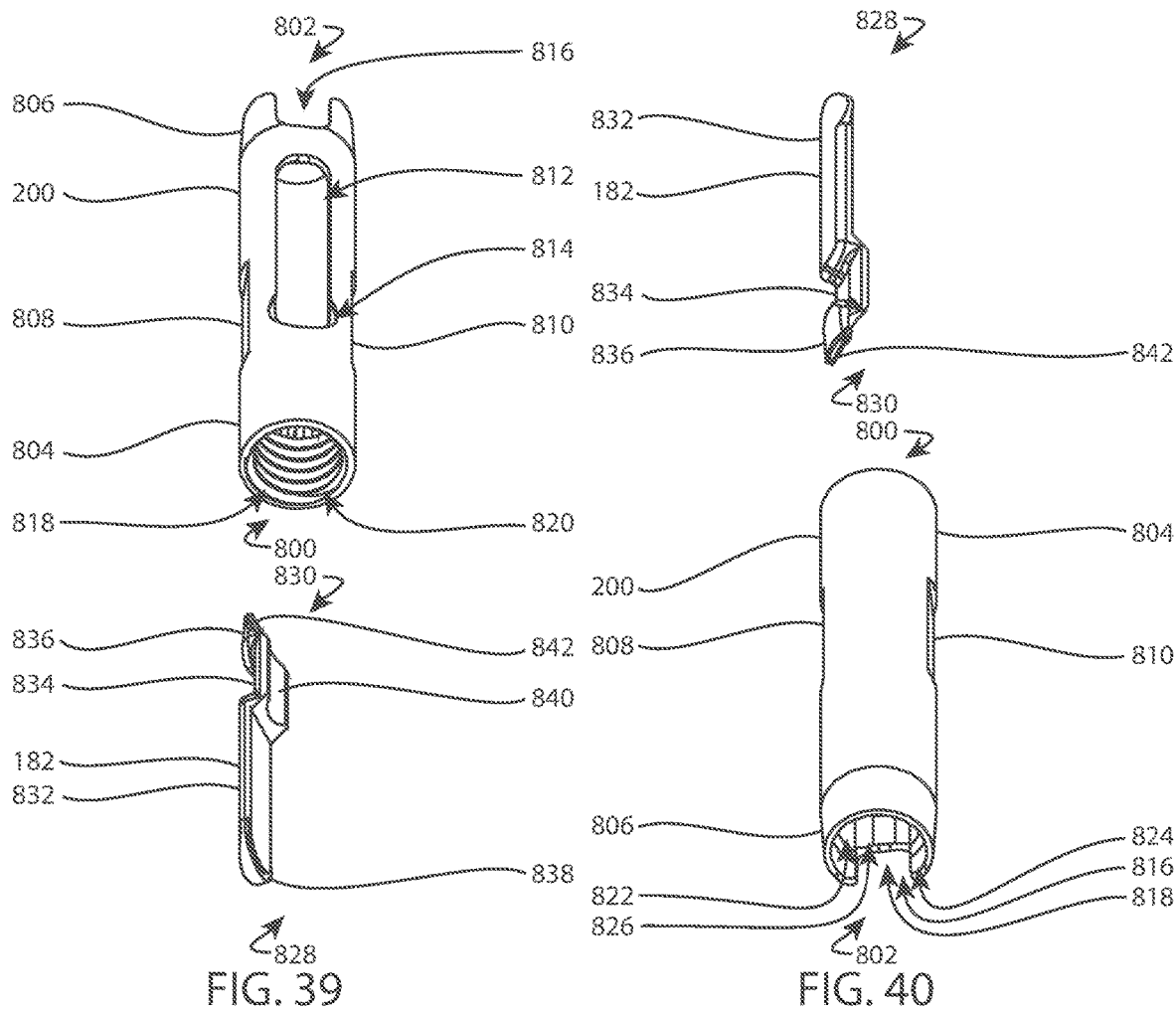
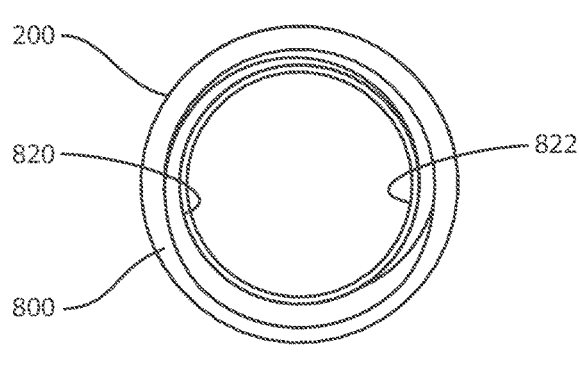
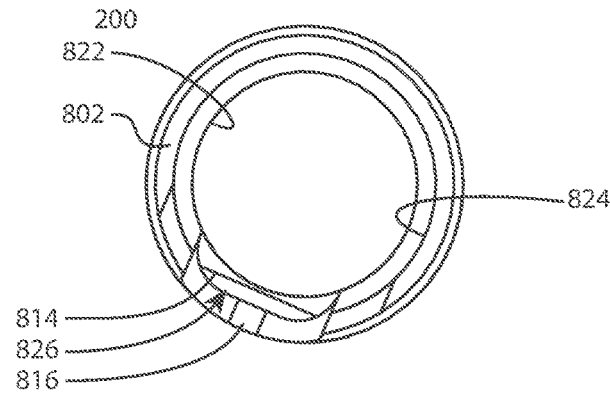
FIG. 39  FIG. 40  FIG. 41  FIG. 42

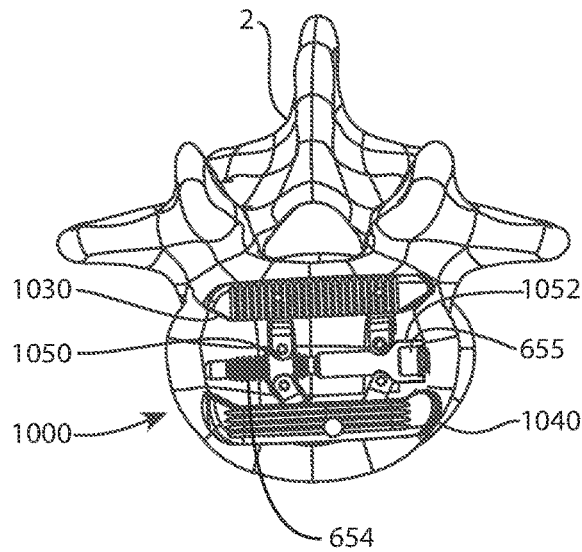
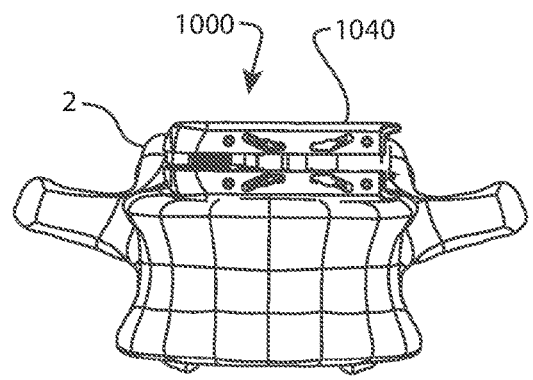
FIG. 60  FIG. 61
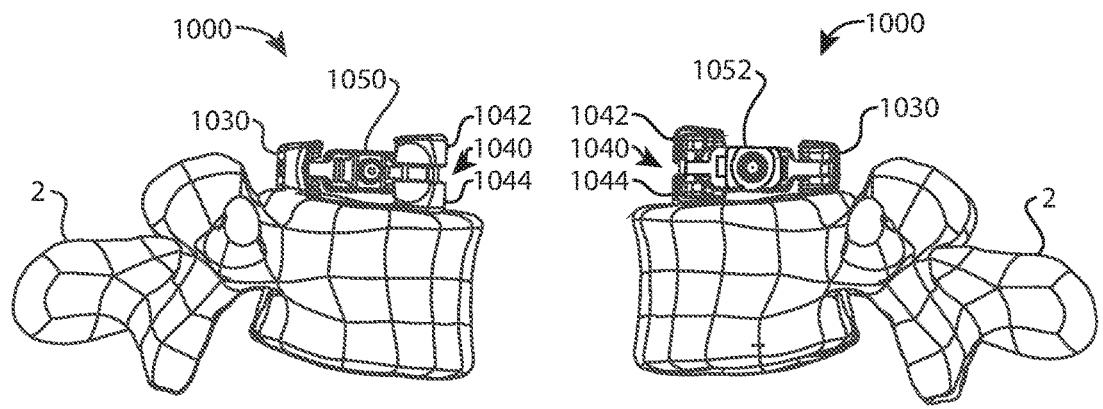
FIG. 62  FIG. 63

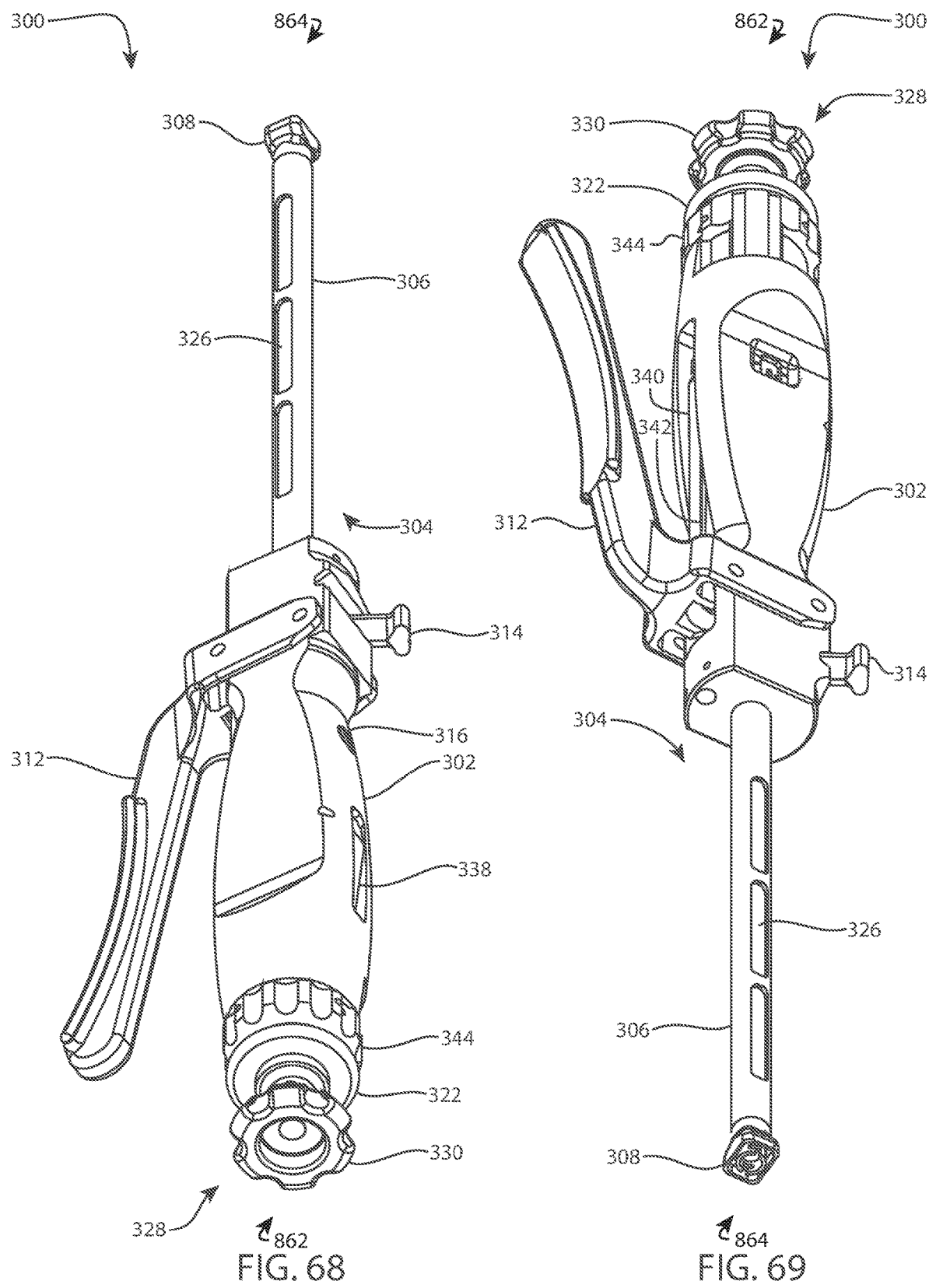

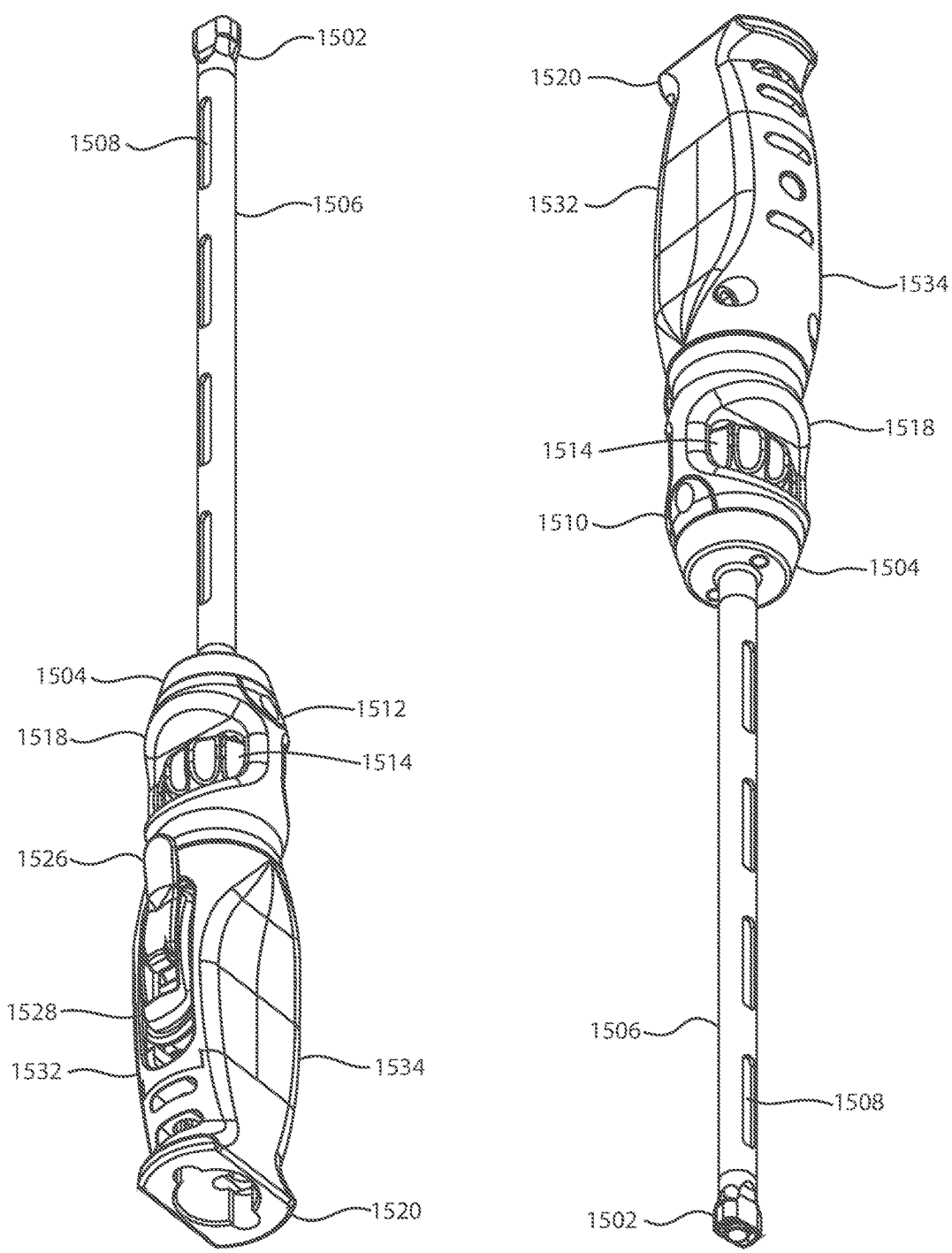

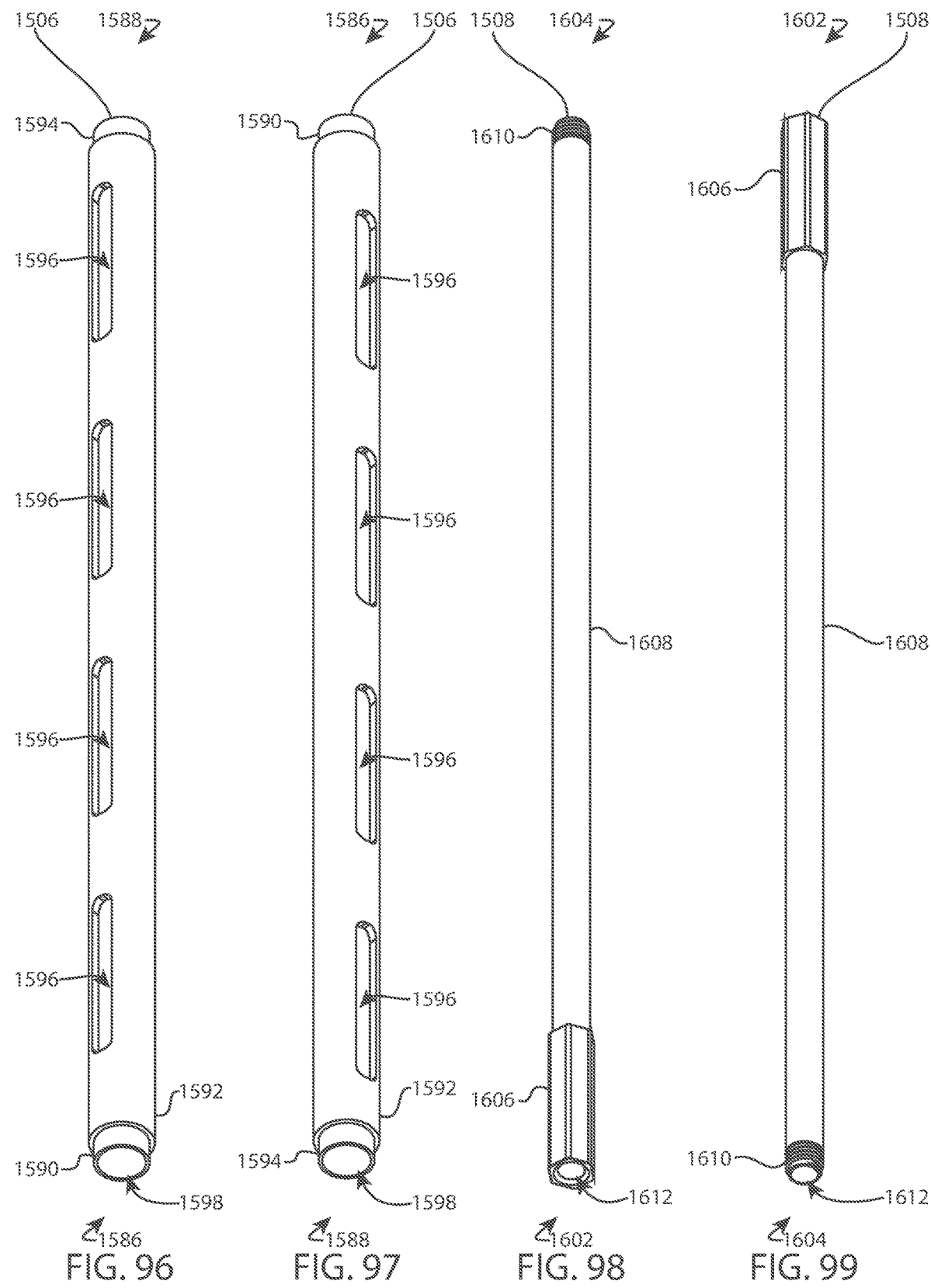

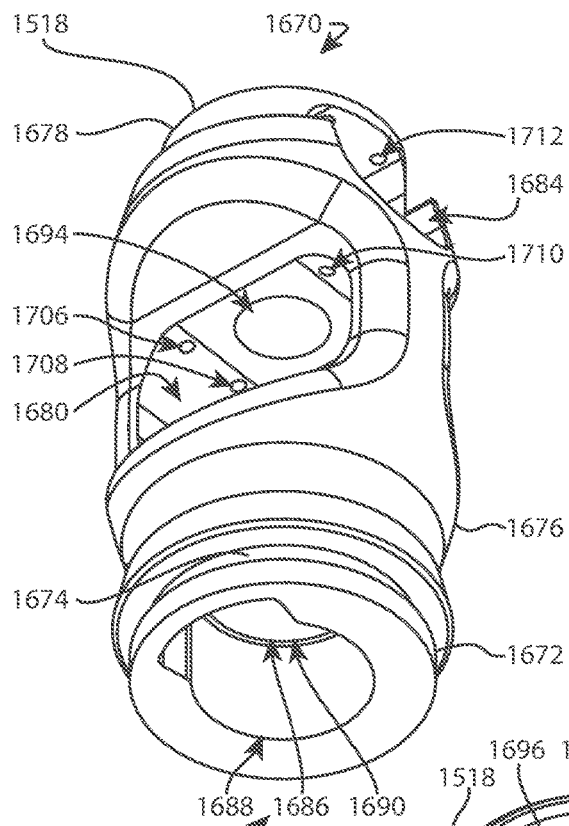
FIG. 106
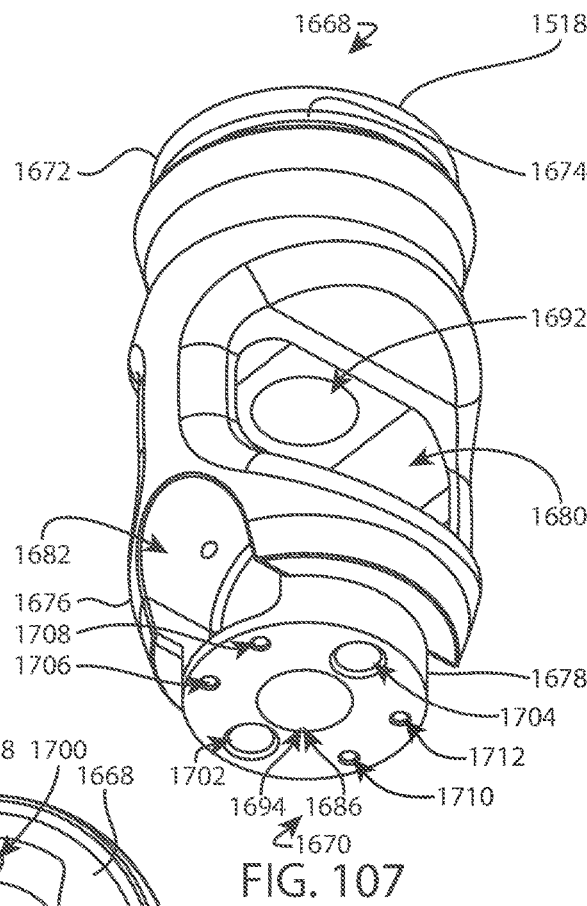
FIG. 107
FIG. 108
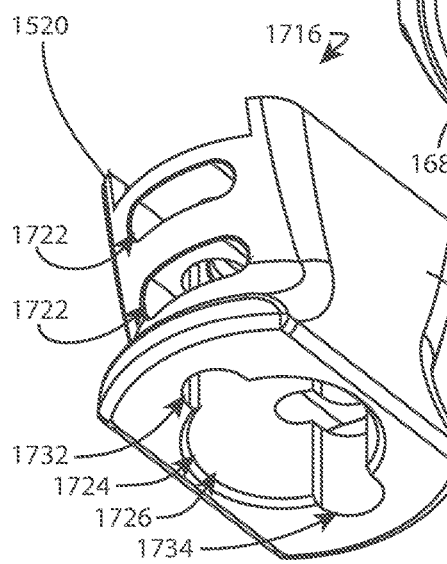
FIG. 109
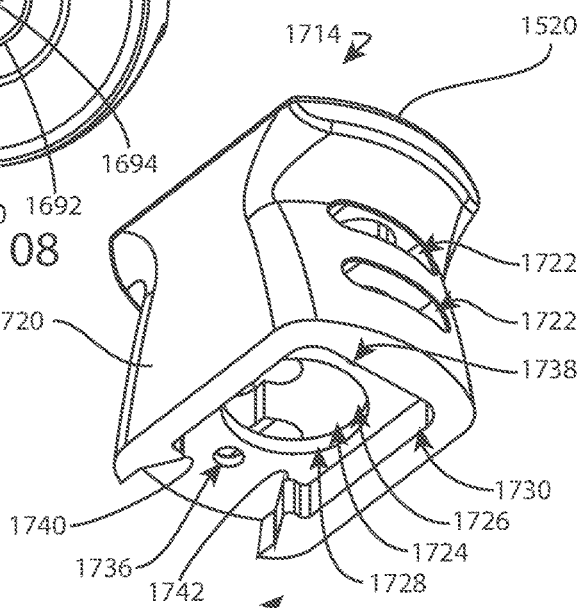
FIG. 110

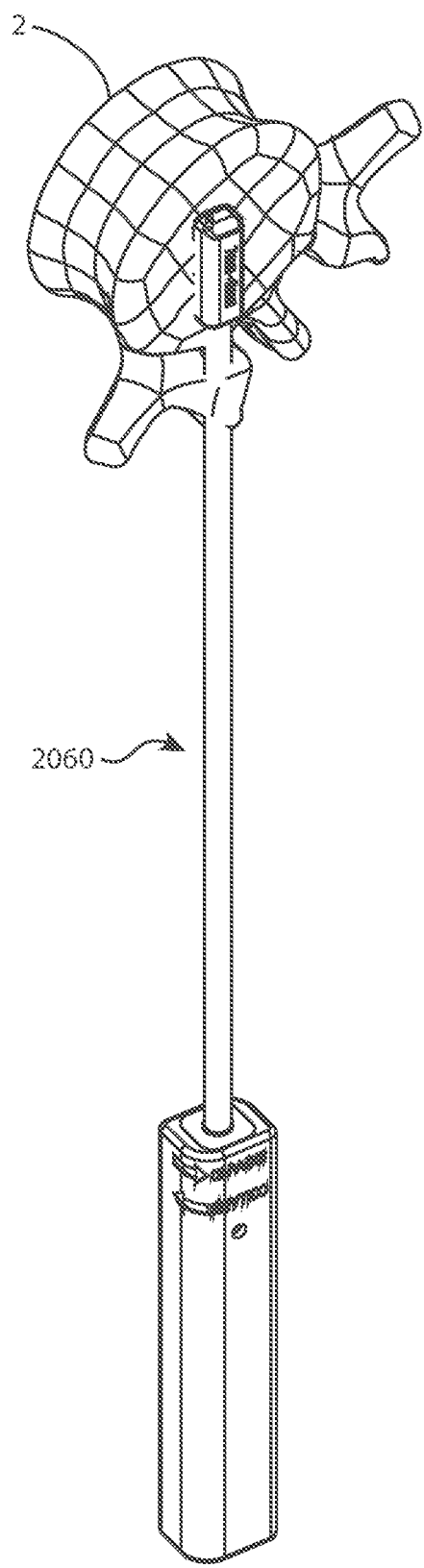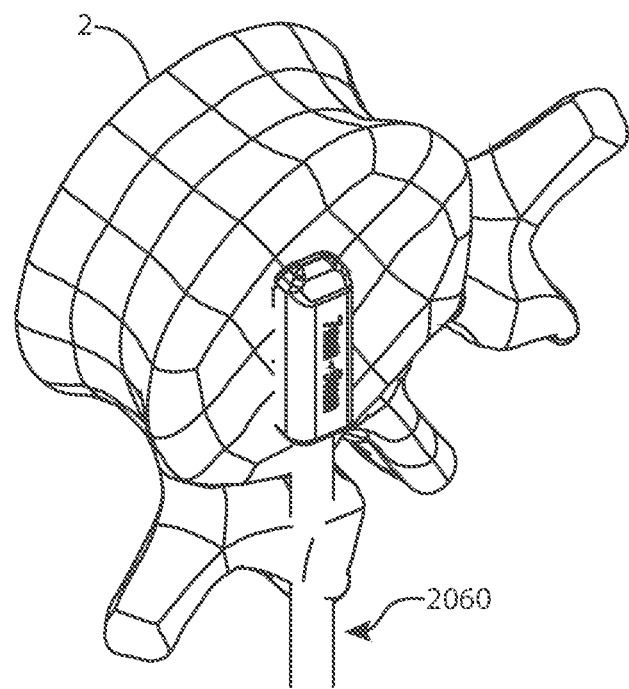
FIG. 143
FIG. 144

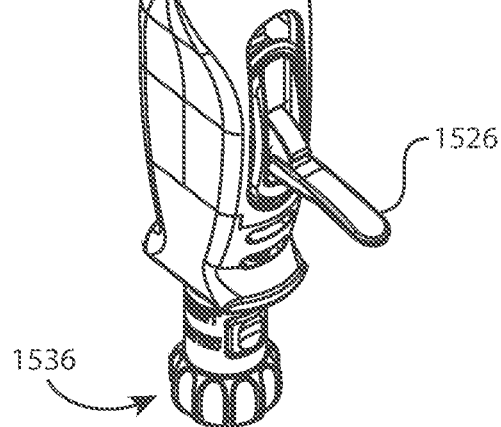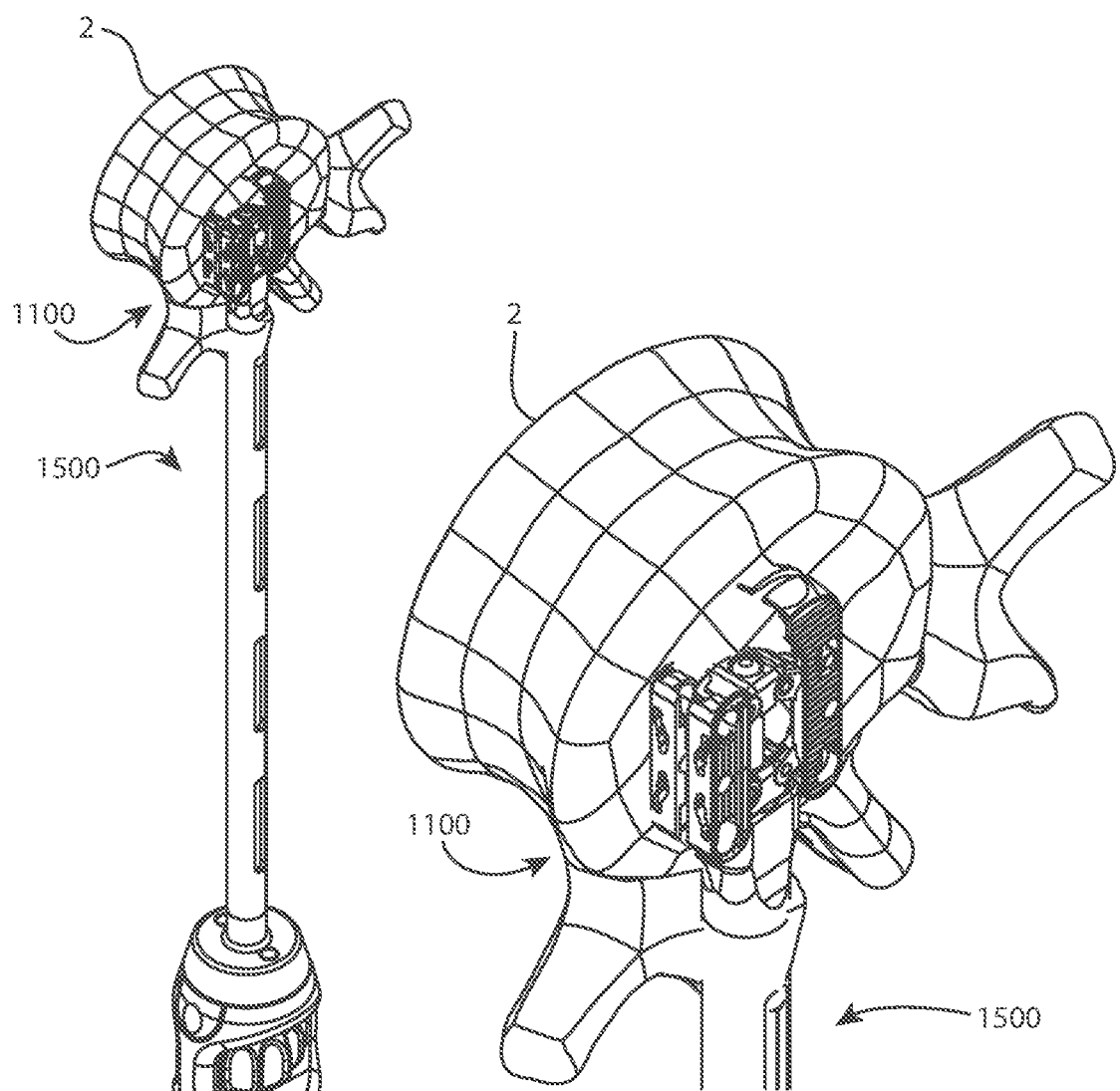
FIG. 156
FIG. 155

METHODS AND INSTRUMENTATION FOR INTERVERTEBRAL CAGE EXPANSION

CROSS-REFERENCE TO RELATED APPLICATIONS

The present application claims the benefit of U.S. Provisional Patent Application No. 62/412,781, entitled METHODS AND INSTRUMENTATION FOR INTERVERTEBRAL CAGE EXPANSION, which was filed on Oct. 25, 2016.

The foregoing is incorporated by reference as though set forth herein in its entirety.

TECHNICAL FIELD

The present disclosure relates to instruments and methods for implantation and expansion of an intervertebral implant. The instruments and methods described herein may be used to expand an intervertebral implant or spacer which is capable of being expanded in one or more directions: horizontally (laterally) and/or vertically (cephalocaudally). More specifically, an embodiment of the instruments and methods described herein may be used to implant and expand the intervertebral cages described in pending U.S. patent application Ser. No. 15/244,446, entitled EXPANDABLE INTERVERTEBRAL IMPLANTS, filed on Aug. 23, 2016, which is incorporated by reference as though set forth in its entirety.

BACKGROUND

There is a need for an instrument that may be coupled to a multi-axis expandable intervertebral cage so that the cage may be inserted into an intervertebral space, expanded along multiple different directions, filled with bone graft, and/or locked with a fastener. There is also a need for an instrument set that includes the implant insertion instrument and auxiliary instruments to determine implant size, insert bone graft into the cage, and deliver the fastener.

The implant insertion instruments disclosed herein address certain characteristics of the expandable intervertebral cages. The cages expand horizontally and/or vertically as first and second implant end bodies are drawn together along a longitudinal instrument axis. Each of the implant insertion instruments includes a connector that couples to the first implant end body and a draw bar that couples to the second implant end body. The draw bar may be rotatable about the instrument axis to connect with and disconnect from the second implant end body, however the draw bar does not rotate about the axis during implant expansion. In some examples, in order to expand the implant, the implant insertion instrument may first be actuated to lock the draw bar to prevent axial rotation, then actuated to accomplish implant expansion. These actuations may be coupled together so as to occur together.

In some examples, the implant insertion instruments disclosed herein also address certain characteristics of specific approaches to the intervertebral space in the spine. For example, in transforaminal lumbar interbody fusion (TLIF), a patient may be in the prone position (face down) and the approach trajectory may lie in the transverse plane of the operative intervertebral space and inclined about 30 degrees from the sagittal plane (vertical) or 60 degrees from the coronal plane (horizontal). The weight of the implant insertion instrument thus causes a nontrivial force moment on the implant which tends to rotate the implant laterally out of position. Disclosed implant insertion instruments have removable handle assemblies to reduce instrument weight and thus the force moment on the implant.

In some examples, the implant insertion instruments disclosed herein also provide a useful and convenient collateral function for a graft funnel, wherein the funnel may be used to unthread an implant retainer shaft after bone graft has been delivered to the operative site.

SUMMARY

The various systems and methods of the present technology have been developed in response to the present state of the art, and in particular, in response to the problems and needs in the art that have not yet been fully solved by currently available expandable implants and related instruments. The systems and methods of the present technology may provide improved instruments and methods for implanting expandable implants, such as spinal interbody fusion spacers.

To achieve the foregoing, and in accordance with the technology as embodied and broadly described herein, in an aspect of the technology, an instrument includes: a first instrument part that is removably connectable to a first implant part of an implant; and a second instrument part that is removably connectable to a second implant part of the implant; wherein, when the first instrument part is connected to the first implant part, the second instrument part is connected to the second implant part, and the instrument is actuated, the first instrument part and the first implant part translate relative to the second instrument part and the second implant part along a central longitudinal first axis of the instrument without rotating about the first axis during instrument actuation for implant expansion.

Embodiments of this aspect may include any or all of the following attributes. The first instrument part includes a draw bar that is removably connectable to the first implant part by rotation of the draw bar about the first axis; wherein the instrument further includes an actuator and a rotation lock; wherein instrument actuation includes movement of the actuator in engagement with the draw bar to translate the draw bar relative to the second instrument part and the second implant part along the first axis; wherein when the rotation lock is engaged, the draw bar cannot rotate about the first axis, wherein when the rotation lock is disengaged, the draw bar is free to rotate about the first axis; wherein the instrument includes a first state in which the actuator is disengaged from the draw bar, the rotation lock is disengaged, and the draw bar is free to translate along and rotate about the first axis, wherein the instrument includes a second state in which the actuator is engaged with the draw bar, the rotation lock is engaged, and the draw bar is prevented from rotating about the first axis. The rotation lock includes a rotation lock ring and a spline insert, wherein the rotation lock ring and the draw bar are fixed together for rotation about the first axis, wherein the spline insert is fixed in translation along and rotation about the first axis, wherein the spline insert is removably connectable to the rotation lock ring; wherein when the rotation lock is engaged, the spline insert is connected to the rotation lock ring so that the rotation lock ring cannot rotate about the first axis, wherein when the rotation lock is disengaged, the spline insert is disconnected from the rotation lock ring so that the rotation lock ring is free to rotate about the first axis; wherein the actuator and the rotation lock are coupled together so that the actuator engages the draw bar when the rotation lock is engaged and the actuator disengages from the draw bar when the rotation lock is disengaged. The draw bar includes threads; wherein the actuator includes a threaded slider, wherein the threaded slider includes threads that engage the threads of the draw bar, wherein instrument actuation includes rotation of the threaded slider threads in engagement with the draw bar threads to translate the draw bar relative to the second instrument part and the second implant part along the first axis. The first instrument part includes a draw bar that is removably connectable to the first implant part by rotation of the draw bar about the first axis; wherein the instrument further includes a shuttle and an actuator; wherein the shuttle is fixed in rotation about the first axis, wherein the shuttle and the draw bar are fixed together for translation along the first axis, wherein instrument actuation includes movement of the actuator in engagement with the shuttle to translate the shuttle and the draw bar relative to the second instrument part and the second implant part along the first axis; The instrument of claim 5, wherein the shuttle includes threads, wherein the actuator includes a threaded driver, wherein the threaded driver includes threads that engage the threads of the shuttle, wherein instrument actuation includes rotation of the threaded driver threads in engagement with the shuttle threads to translate the shuttle and the draw bar relative to the second instrument part and the second implant part along the first axis. The the shuttle includes a series of transverse grooves, wherein the actuator includes a ratchet mechanism, wherein the ratchet mechanism includes a drive link that engages the series of transverse grooves, wherein instrument actuation includes translation of the drive link in engagement with the series of transverse grooves to translate the shuttle and the draw bar relative to the second instrument part and the second implant part along the first axis.

In another aspect of the technology, an instrument includes a first instrument part that is removably connectable to a first implant part of an implant by rotation of the first instrument part relative to the first implant part about a central longitudinal axis of the instrument; and a second instrument part that is removably connectable to a second implant part of the implant; wherein, when the first instrument part is connected to the first implant part, the second instrument part is connected to the second implant part, and the instrument is actuated, the first instrument part and the first implant part translate relative to the second instrument part and the second implant part along the central longitudinal axis of the instrument so that the first implant part approaches the second implant part, wherein the first instrument part is prevented from rotating about the central longitudinal axis while the first instrument part and the first implant part are translating.

Embodiments of this aspect may include any or all of the following attributes. The instrument further includes an actuator and a rotation lock; wherein instrument actuation includes movement of the actuator in engagement with the first instrument part to translate the first instrument part relative to the second instrument part and the second implant part along the first axis; wherein when the rotation lock is engaged, the first instrument part is prevented from rotating about the central longitudinal axis, wherein when the rotation lock is disengaged, the first instrument part is free to rotate about the first axis; wherein the instrument includes a first state in which the actuator is disengaged from the first instrument part, the rotation lock is disengaged, and the first instrument part is free to translate along and rotate about the first axis, wherein the instrument includes a second state in which the actuator is engaged with the first instrument part, the rotation lock is engaged, and the first instrument part is prevented from rotating about the first axis. The rotation lock includes a rotation lock ring and a spline insert, wherein the rotation lock ring and the first instrument part are fixed together for rotation about the first axis, wherein the spline insert is fixed in translation along and rotation about the first axis, wherein the spline insert is removably connectable to the rotation lock ring; wherein when the rotation lock is engaged, the spline insert is connected to the rotation lock ring so that the rotation lock ring cannot rotate about the first axis, wherein when the rotation lock is disengaged, the spline insert is disconnected from the rotation lock ring so that the rotation lock ring is free to rotate about the first axis; wherein the actuator and the rotation lock are coupled together so that the actuator engages the first instrument part when the rotation lock is engaged and the actuator disengages from the first instrument part when the rotation lock is disengaged. The first instrument part includes threads; wherein the actuator includes a threaded slider, wherein the threaded slider includes threads that engage the threads of the first instrument part, wherein instrument actuation includes rotation of the threaded slider threads in engagement with the first instrument part threads to translate the first instrument part relative to the second instrument part and the second implant part along the first axis. The instrument further includes a shuttle and an actuator; wherein the shuttle is fixed in rotation about the first axis, wherein the shuttle and the first instrument part are fixed together for translation along the first axis, wherein instrument actuation includes movement of the actuator in engagement with the shuttle to translate the shuttle and the first instrument part relative to the second instrument part and the second implant part along the first axis; The shuttle includes threads, wherein the actuator includes a threaded driver, wherein the threaded driver includes threads that engage the threads of the shuttle, wherein instrument actuation includes rotation of the threaded driver threads in engagement with the shuttle threads to translate the shuttle and the first instrument part relative to the second instrument part and the second implant part along the first axis. The shuttle includes a series of transverse grooves, wherein the actuator includes a ratchet mechanism, wherein the ratchet mechanism includes a drive link that engages the series of transverse grooves, wherein instrument actuation includes translation of the drive link in engagement with the series of transverse grooves to translate the shuttle and the first instrument part relative to the second instrument part and the second implant part along the first axis.

In yet another aspect of the technology, an instrument includes a draw bar that is removably connectable to a first implant part of an implant by rotation of the draw bar relative to the first implant part about a central longitudinal axis of the instrument, wherein the draw bar is carried at a first end of a first shaft; and a second instrument part that is removably connectable to a second implant part of the implant, wherein the second instrument part is carried at a first end of a second shaft; wherein the instrument is actuatable to translate the draw bar toward the second instrument part along the central longitudinal axis so that the draw bar does not rotate about the central longitudinal axis during instrument actuation.

Embodiments of this aspect may include any or all of the following attributes. The instrument further includes an actuator and a rotation lock; wherein instrument actuation includes movement of the actuator in engagement with the draw bar to translate the draw bar relative to the second instrument part and the second implant part along the first axis; wherein when the rotation lock is engaged, the draw bar cannot rotate about the first axis, wherein when the rotation lock is disengaged, the draw bar is free to rotate about the first axis; wherein the instrument includes a first state in which the actuator is disengaged from the draw bar, the rotation lock is disengaged, and the draw bar is free to translate along and rotate about the first axis, wherein the instrument includes a second state in which the actuator is engaged with the draw bar, the rotation lock is engaged, and the draw bar is prevented from rotating about the first axis. The rotation lock includes a rotation lock ring and a spline insert, wherein the rotation lock ring and the draw bar are fixed together for rotation about the first axis, wherein the spline insert is fixed in translation along and rotation about the first axis, wherein the spline insert is removably connectable to the rotation lock ring; wherein when the rotation lock is engaged, the spline insert is connected to the rotation lock ring so that the rotation lock ring cannot rotate about the first axis, wherein when the rotation lock is disengaged, the spline insert is disconnected from the rotation lock ring so that the rotation lock ring is free to rotate about the first axis; wherein the actuator and the rotation lock are coupled together so that the actuator engages the draw bar when the rotation lock is engaged and the actuator disengages from the draw bar when the rotation lock is disengaged. The draw bar includes threads; wherein the actuator includes a threaded slider, wherein the threaded slider includes threads that engage the threads of the draw bar, wherein instrument actuation includes rotation of the threaded slider threads in engagement with the draw bar threads to translate the draw bar relative to the second instrument part and the second implant part along the first axis. The instrument further includes a shuttle and an actuator; wherein the shuttle is fixed in rotation about the first axis, wherein the shuttle and the draw bar are fixed together for translation along the first axis, wherein instrument actuation includes movement of the actuator in engagement with the shuttle to translate the shuttle and the draw bar relative to the second instrument part and the second implant part along the first axis. The shuttle includes threads, wherein the actuator includes a threaded driver, wherein the threaded driver includes threads that engage the threads of the shuttle, wherein instrument actuation includes rotation of the threaded driver threads in engagement with the shuttle threads to translate the shuttle and the draw bar relative to the second instrument part and the second implant part along the first axis. The shuttle includes a series of transverse grooves, wherein the actuator includes a ratchet mechanism, wherein the ratchet mechanism includes a drive link that engages the series of transverse grooves, wherein instrument actuation includes translation of the drive link in engagement with the series of transverse grooves to translate the shuttle and the draw bar relative to the second instrument part and the second implant part along the first axis.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 26 is a top view of the draw bar assembly of FIG. 2;

FIG. 27 is a top view of a tamp assembly;

FIG. 28 is a top view of a funnel;

FIG. 29 is a top view of a screwdriver assembly coupled to a lockout screw;

FIG. 30 is a distal detail view of the screwdriver assembly and lockout screw of FIG. 29;

FIG. 37 is an exploded perspective view of the screwdriver assembly of FIG. 29;

FIG. 38 is another exploded perspective view of the screwdriver assembly of FIG. 29, from a different direction;

FIG. 39 is a perspective view of a screw holder and a screw holder catch of the screwdriver assembly of FIG. 29;

FIG. 40 is another perspective view of a screw holder and a screw holder catch of the screwdriver assembly of FIG. 29, from a different direction;

FIG. 41 is a proximal end view of the screw holder of FIG. 40;

FIG. 42 is a distal end view of the screw holder of FIG. 40;

FIG. 60 is a top view of the implant and vertebra of FIG. 58;

FIG. 61 is an anterior view of the implant and vertebra of FIG. 58;

FIG. 62 is a right lateral view of the implant and vertebra of FIG. 58;

FIG. 63 is a left lateral view of the implant and vertebra of FIG. 58;

FIG. 68 is a perspective view of the instrument of FIG. 64;

FIG. 69 is another perspective view of the instrument of FIG. 64, from a different direction;

FIG. 90 is a perspective view of the instrument of FIG. 86;

FIG. 91 is another perspective view of the instrument of FIG. 86, from a different direction;

FIG. 96 is a perspective view of an inserter shaft of the instrument of FIG. 86;

FIG. 97 is another perspective view of the inserter shaft of FIG. 96, from a different direction;

FIG. 98 is a perspective view of an implant retainer shaft of the instrument of FIG. 86;

FIG. 99 is another perspective view of the implant retainer shaft of FIG. 98, from a different direction;

FIG. 106 is a perspective view of an inserter handle of the instrument of FIG. 86;

FIG. 107 is another perspective view of the inserter handle of FIG. 106, from a different direction;

FIG. 108 is a proximal end view of the inserter handle of FIG. 106;

FIG. 109 is a perspective view of a strike plate of the instrument of FIG. 86;

FIG. 110 is another perspective view of the strike plate of FIG. 109, from a different direction;

FIG. 119 is a side view of the slider button of FIG. 117;

FIG. 120 is a perspective view of a threaded slider of the instrument of FIG. 86;

FIG. 121 is another perspective view of the threaded slider of FIG. 120, from a different direction;

FIG. 122 is a perspective view of a knob top part of the instrument of FIG. 86;

FIG. 123 is another perspective view of the knob top part of FIG. 122, from a different direction;

FIG. 124 is a perspective view of a knob bottom part of the instrument of FIG. 86;

FIG. 125 is another perspective view of the knob bottom part of FIG. 124, from a different direction;

FIG. 126 is a perspective view of a draw bar assembly for use with the instrument of FIG. 86;

FIG. 127 is another perspective view of the draw bar assembly of FIG. 126, from a different direction;

FIG. 128 is an exploded perspective view of the draw bar assembly of FIG. 126;

FIG. 129 is another exploded perspective view of the draw bar assembly of FIG. 126, from a different direction;

FIG. 130 is a perspective view of a trial assembly for use with the instrument of FIG. 86;

Figure 43:
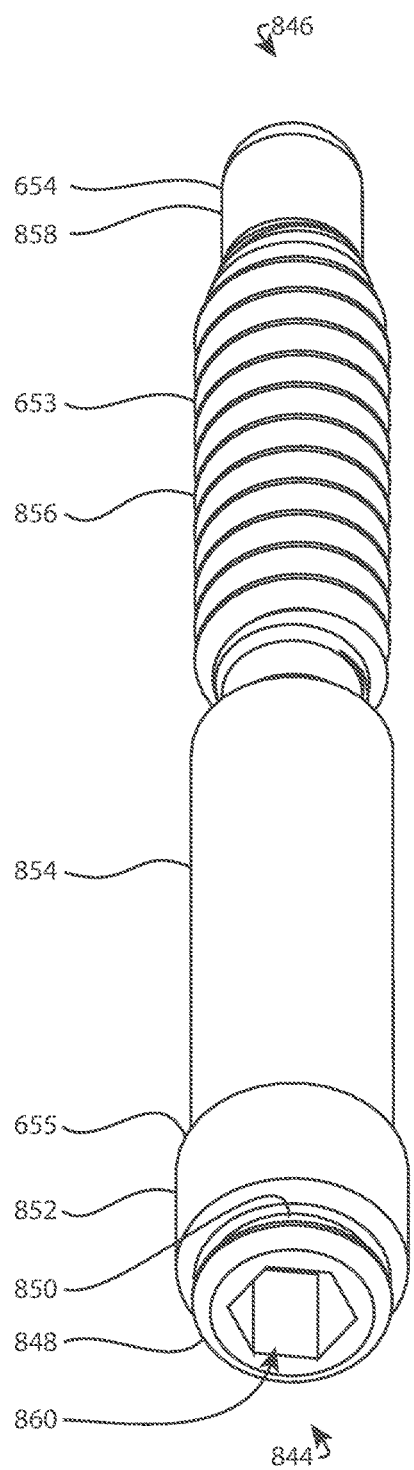
FIG. 43 is a perspective view of the lockout screw of FIG. 29.
Figure 86:
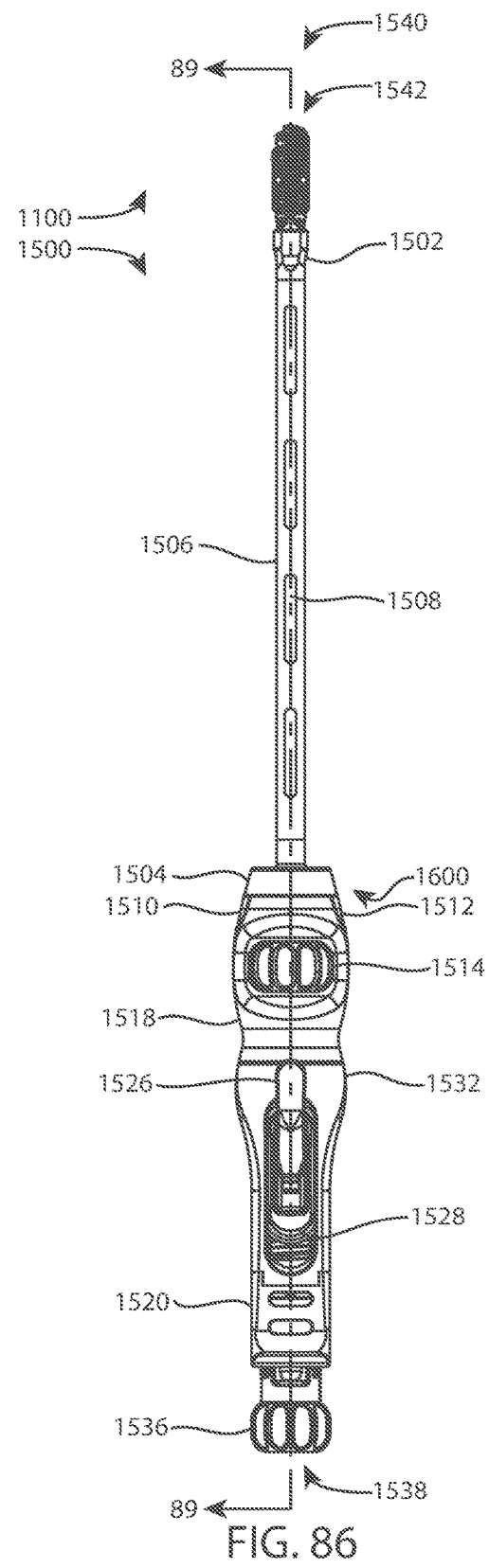
FIG. 86 is a top view of another insertion and expansion instrument coupled to another expandable intervertebral implant.
Figure 87:
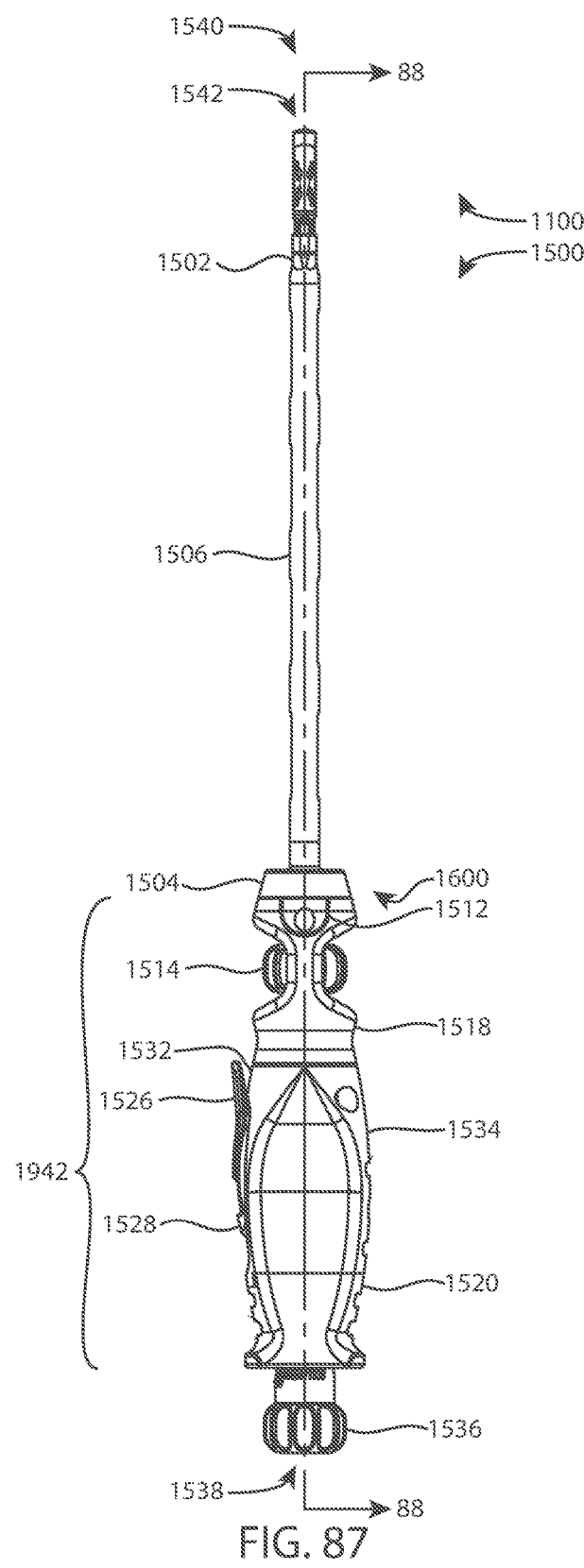
FIG. 87 is a side view of the instrument and implant of FIG. 86.
Figure 88:
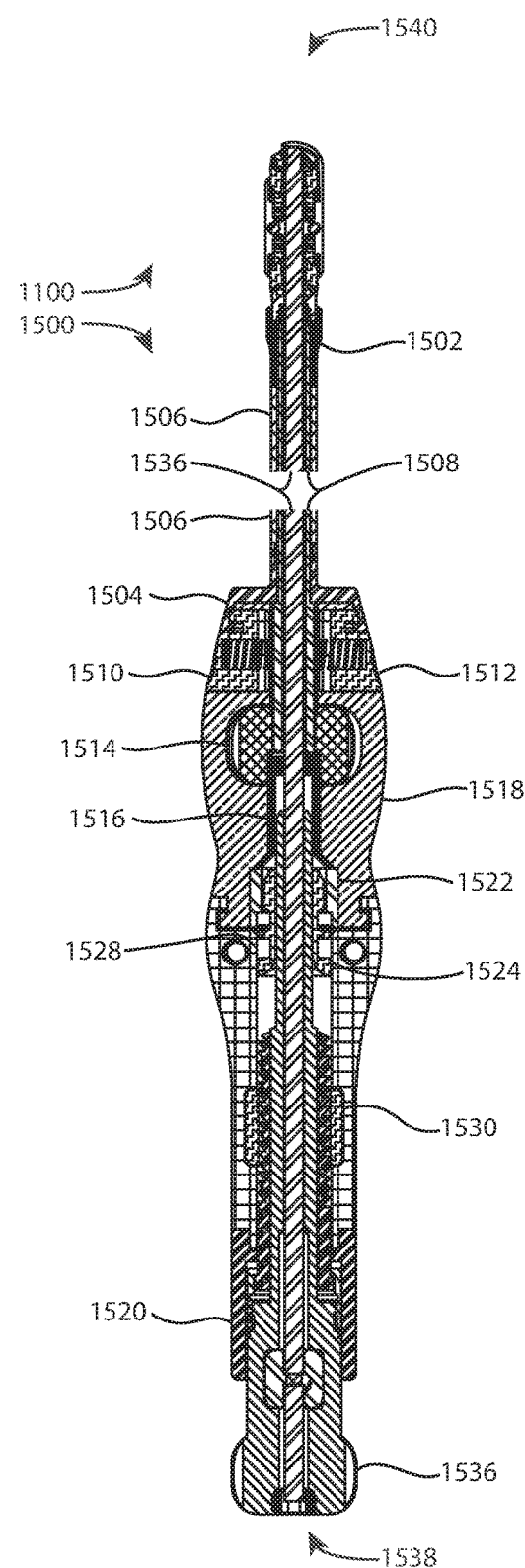
FIG. 88 is a cross-sectional view of the instrument and implant of FIG. 87, taken along line 88-88 of FIG. 87.
Figure 89:
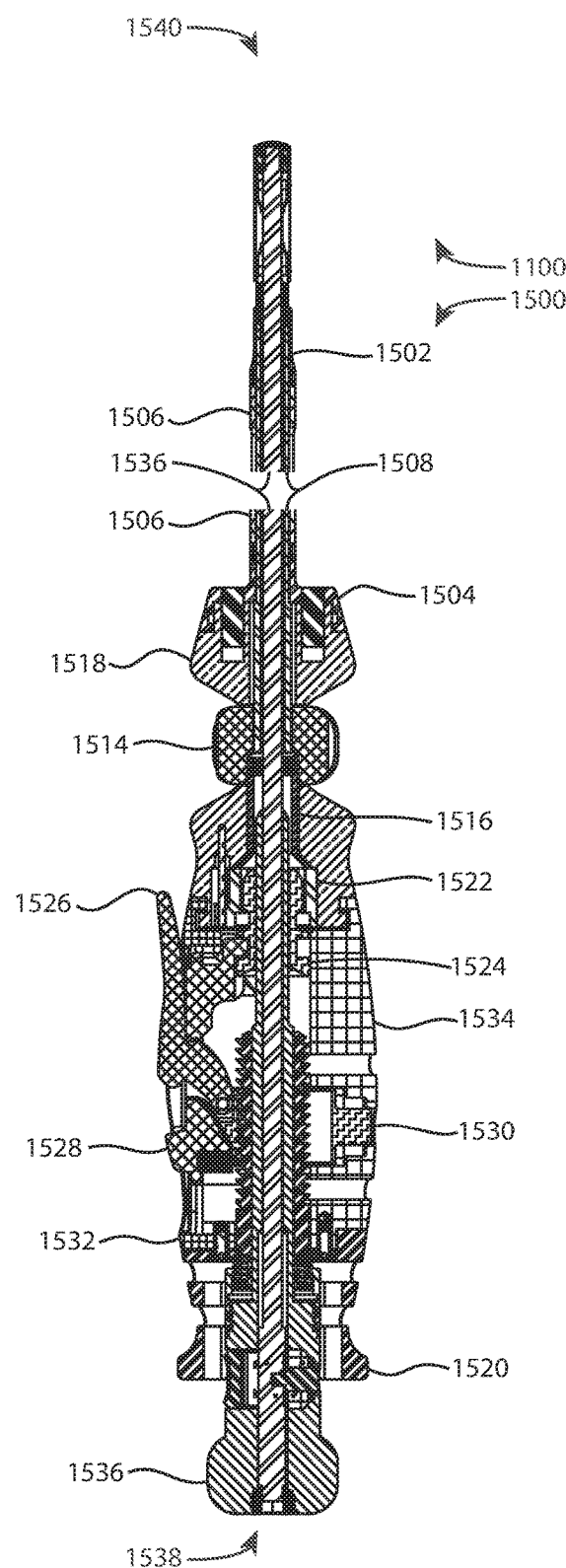
FIG. 89 is a cross-sectional view of the instrument and implant of FIG. 86, taken along line 89-89 of FIG. 86.
Figures 126, 127:
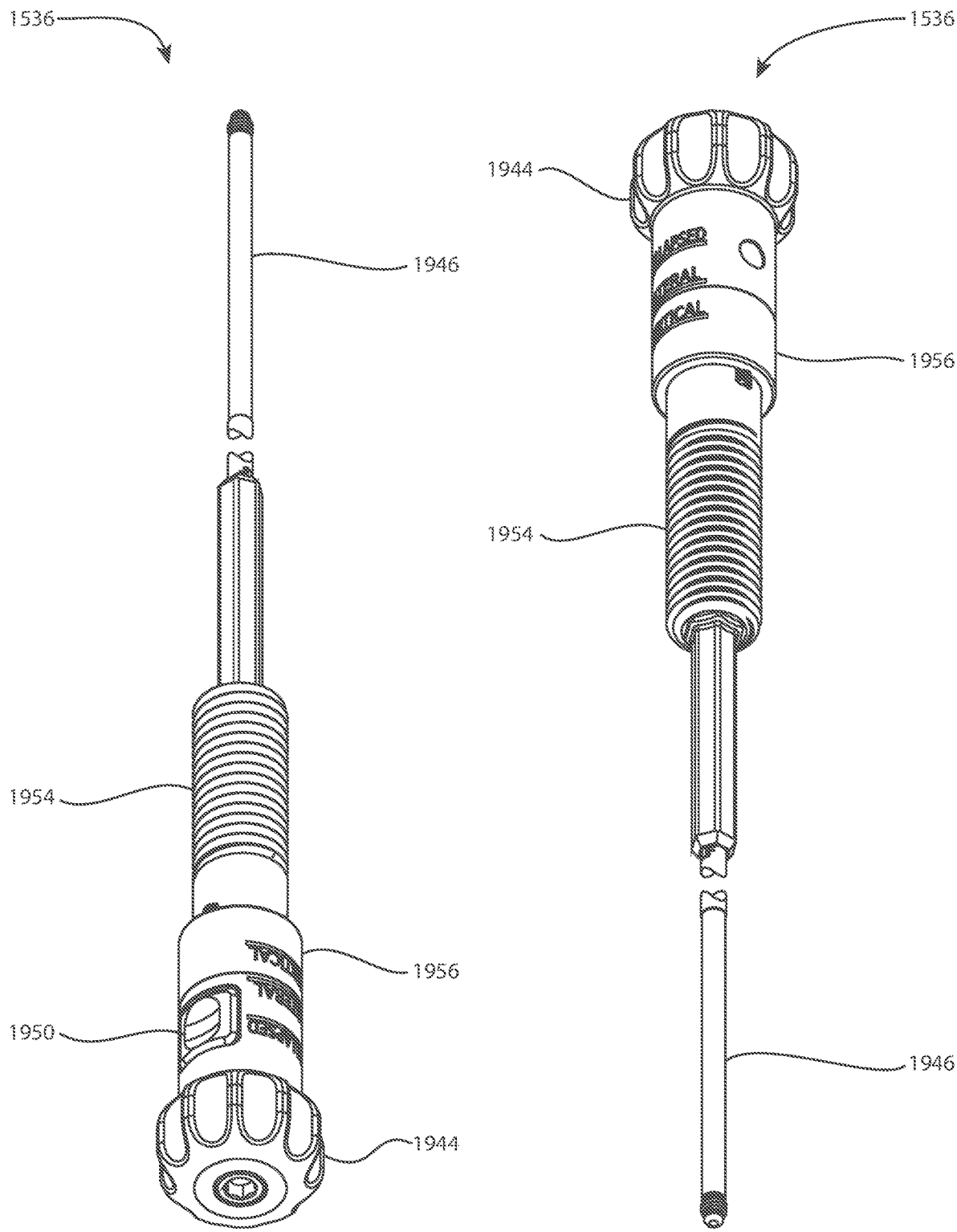
Figure 128:
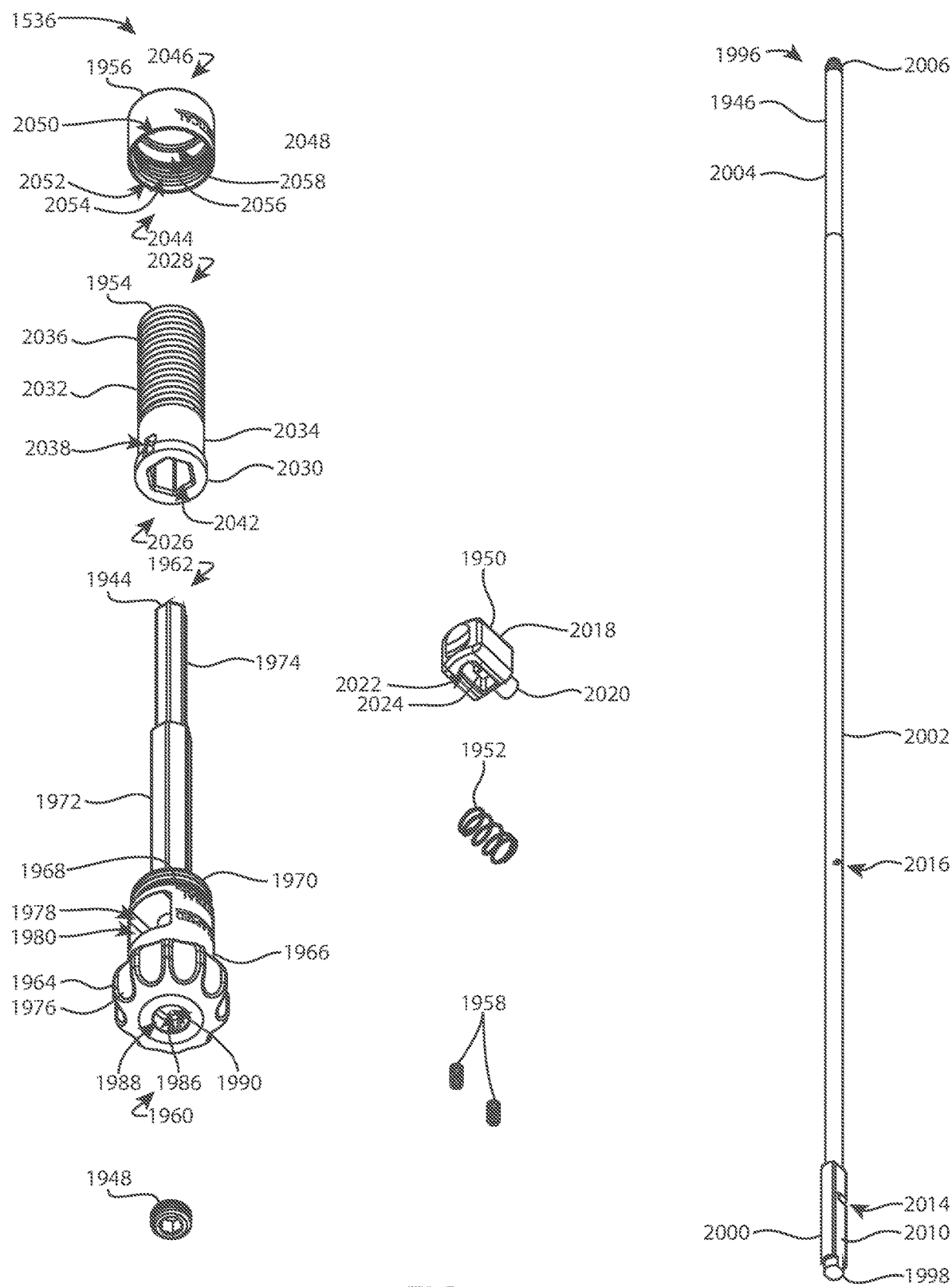
Figure 129:
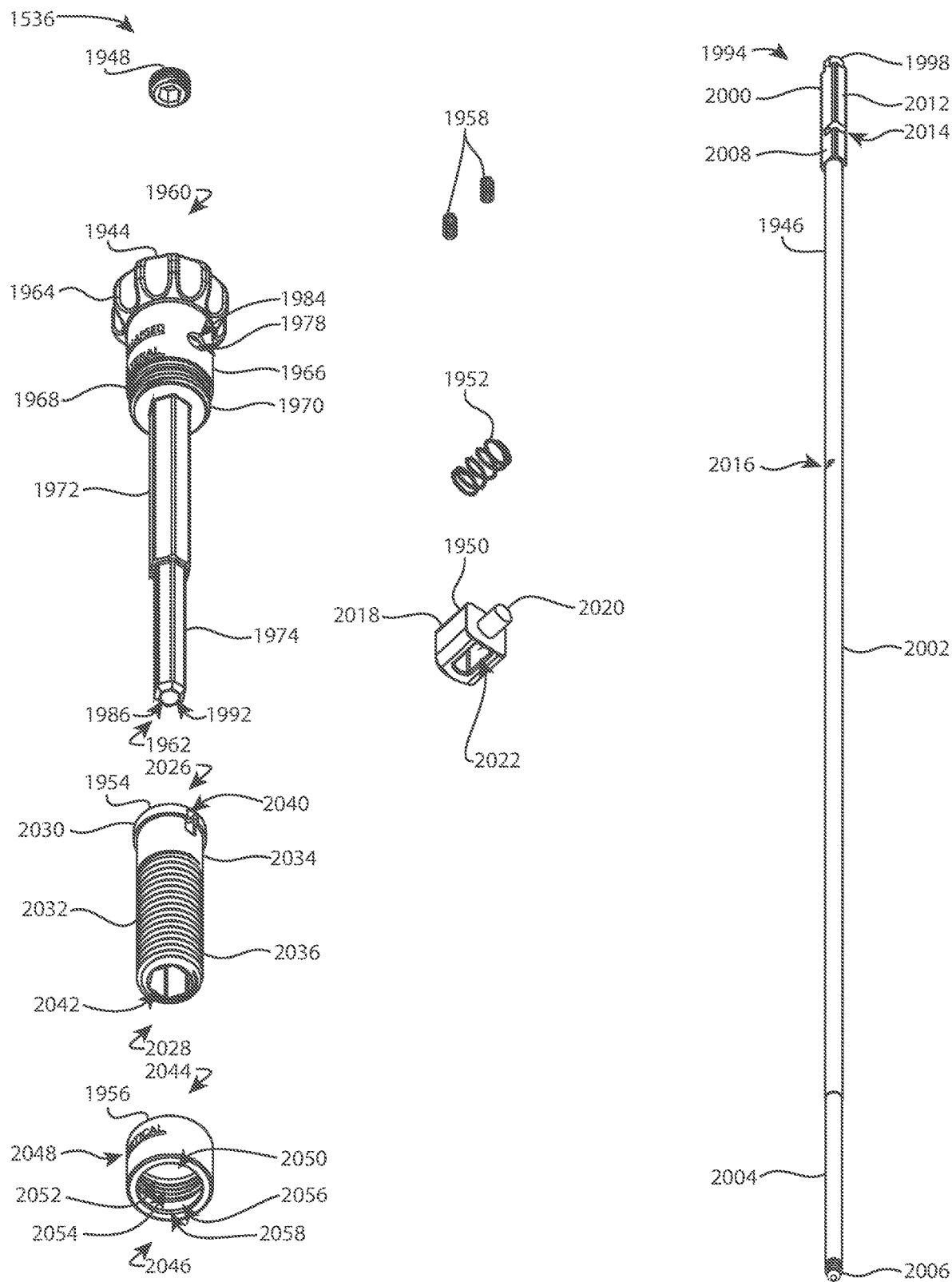
Figure 130:
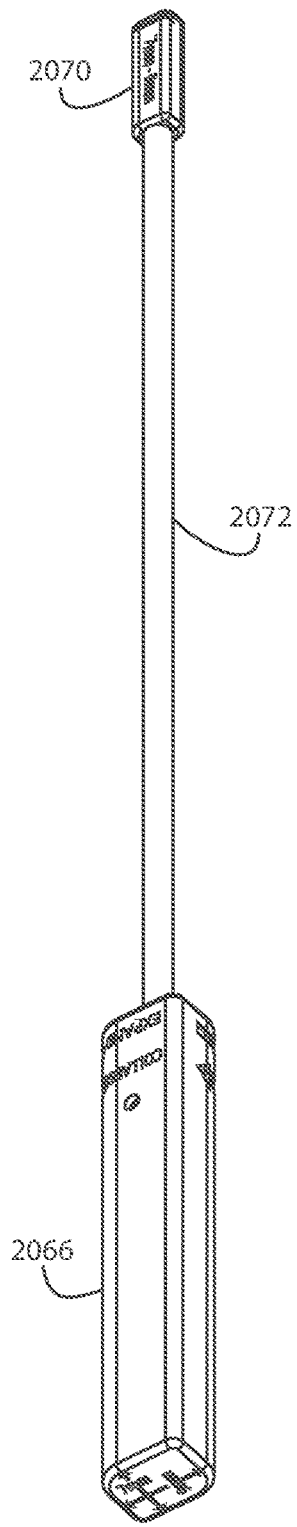
Figure 131:
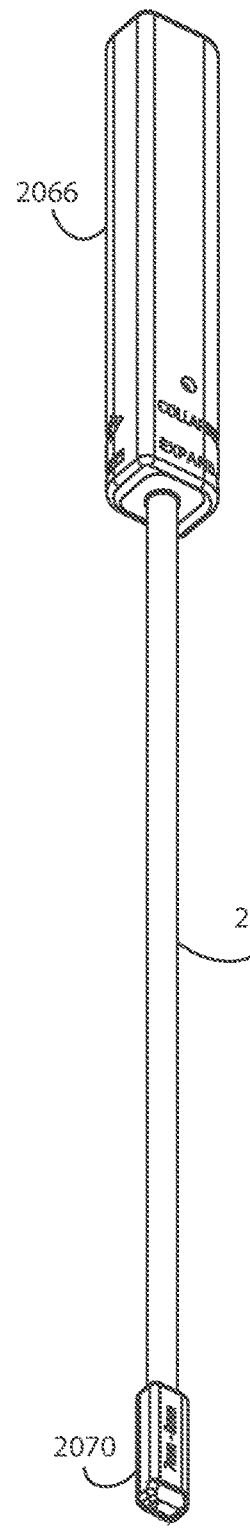
Figure 132:
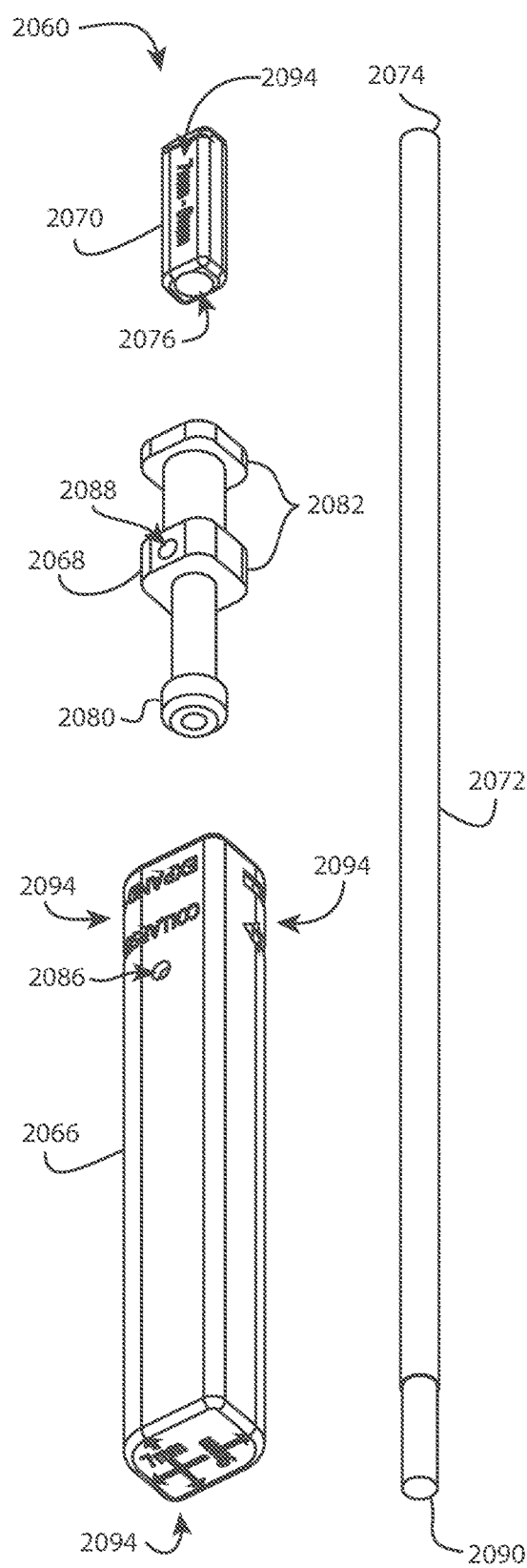
Figure 133:
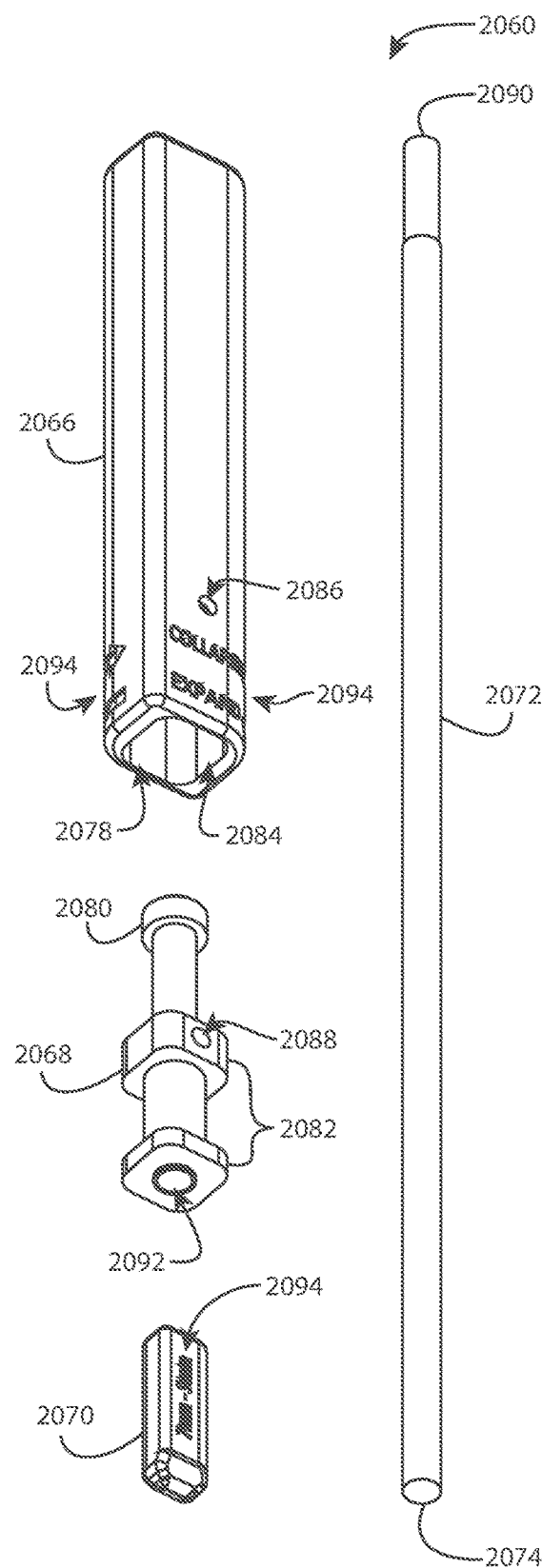
Figure 134:
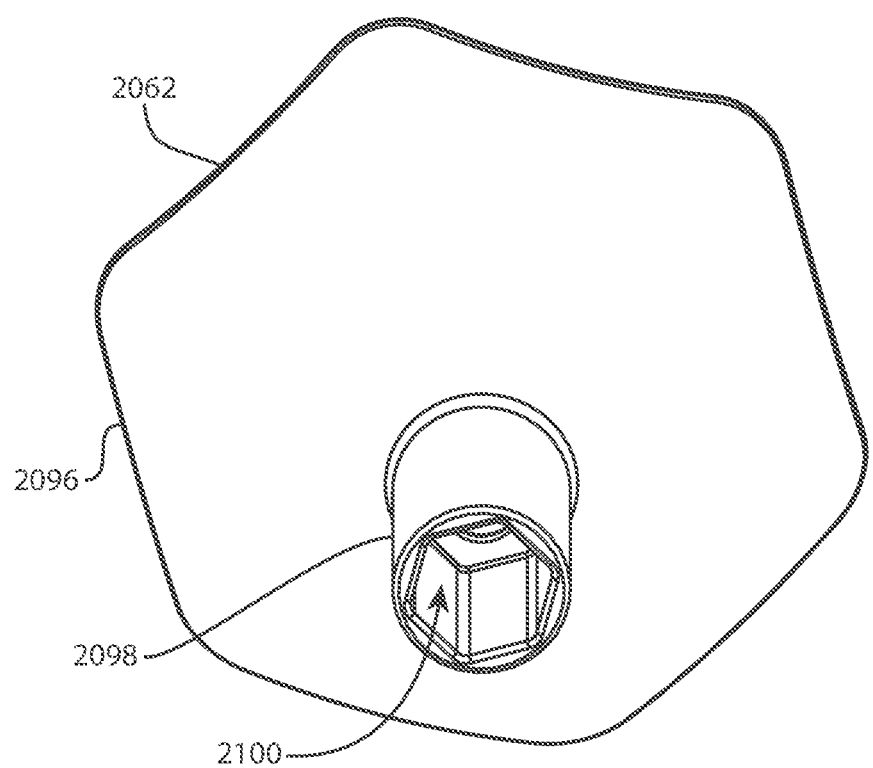
Figure 135:
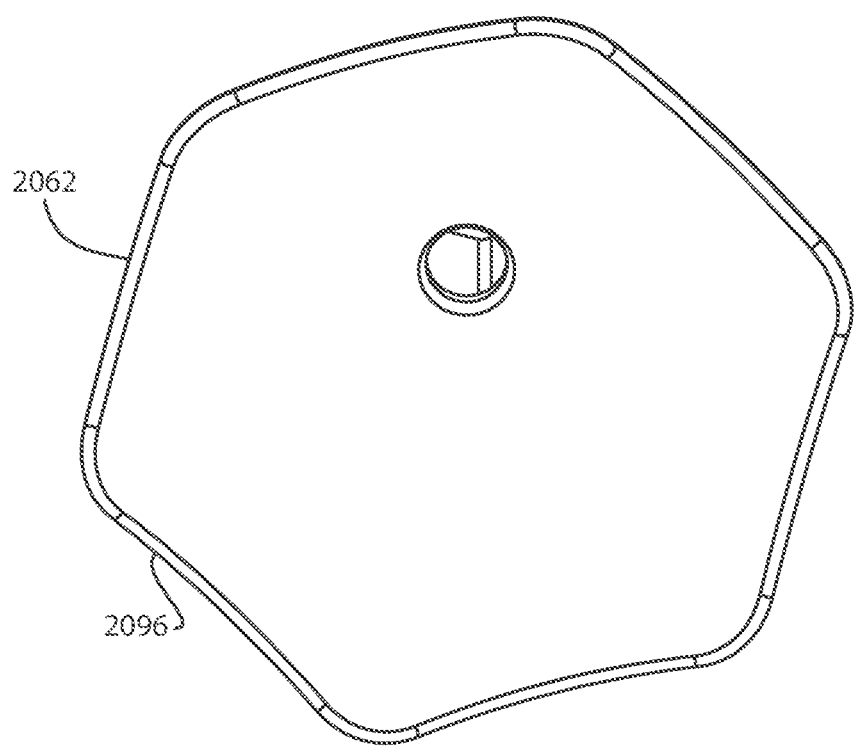
Figure 136:
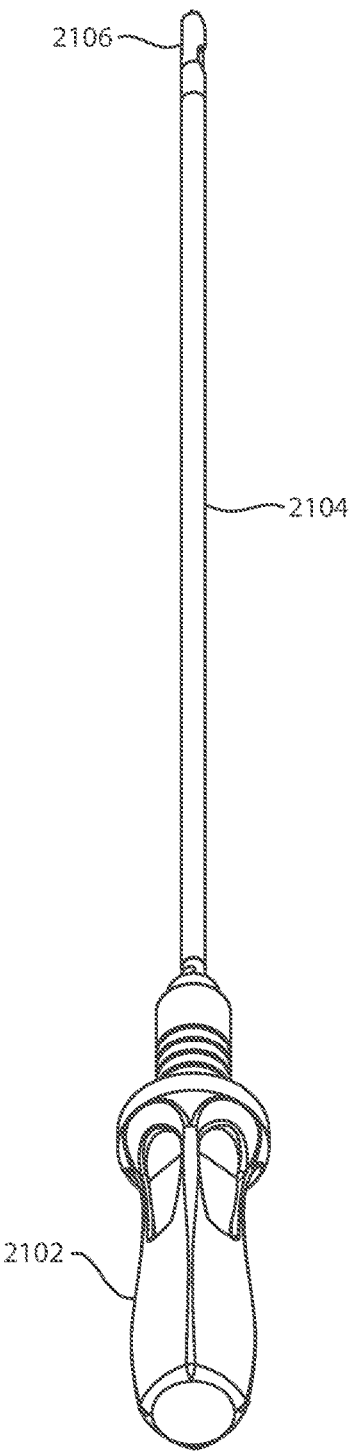
Figure 137:
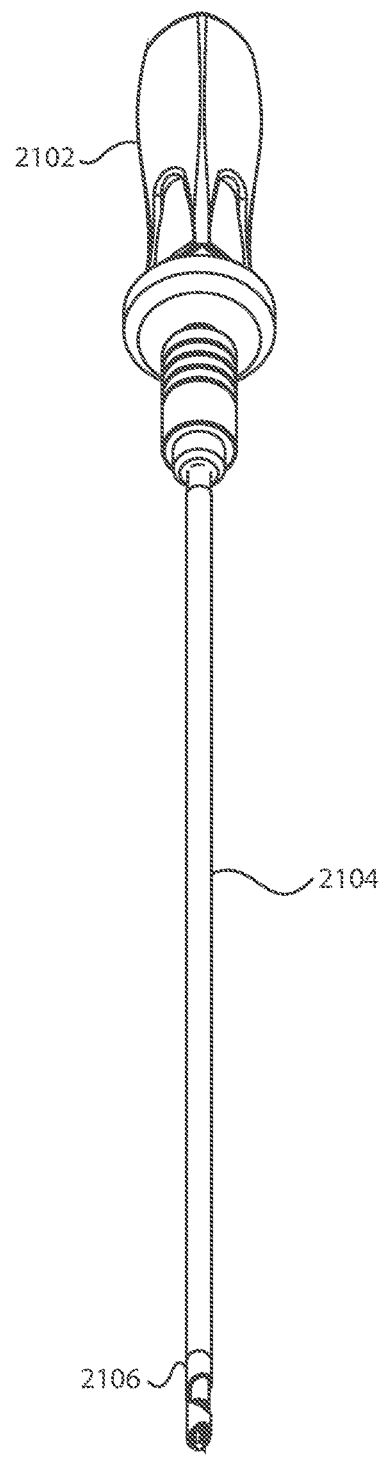
Figures 138, 139:
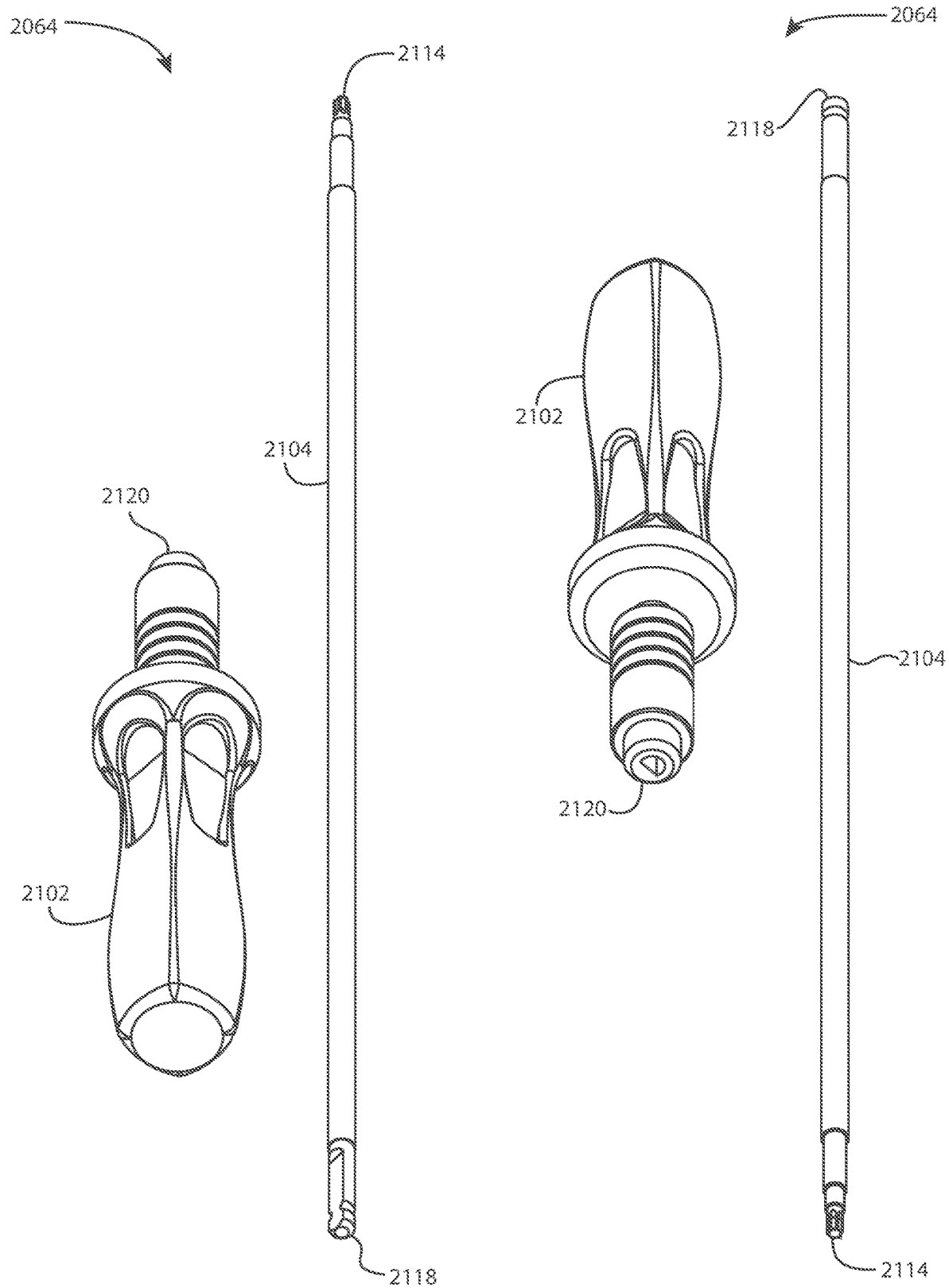
Figure 140:
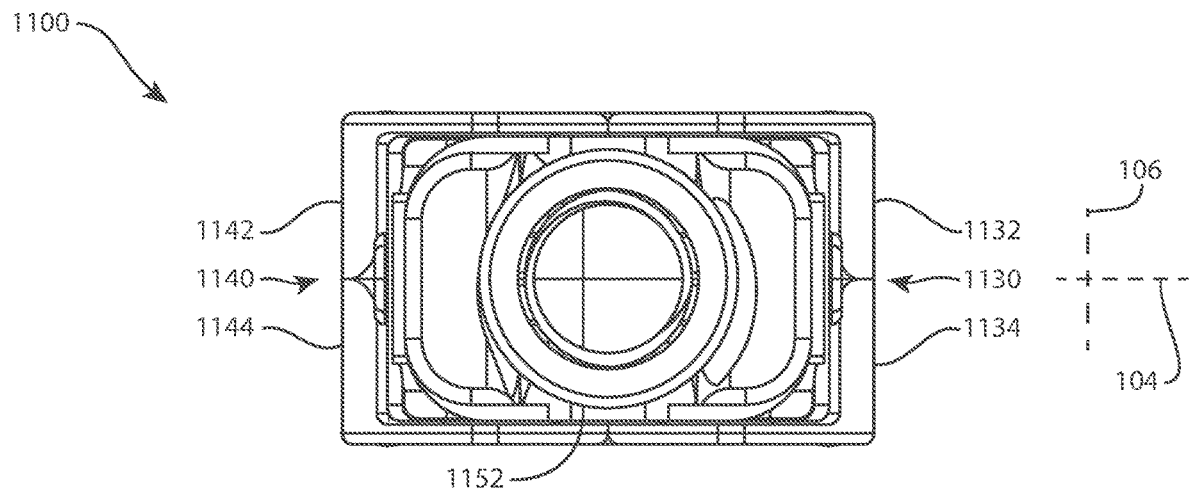
Figure 141:
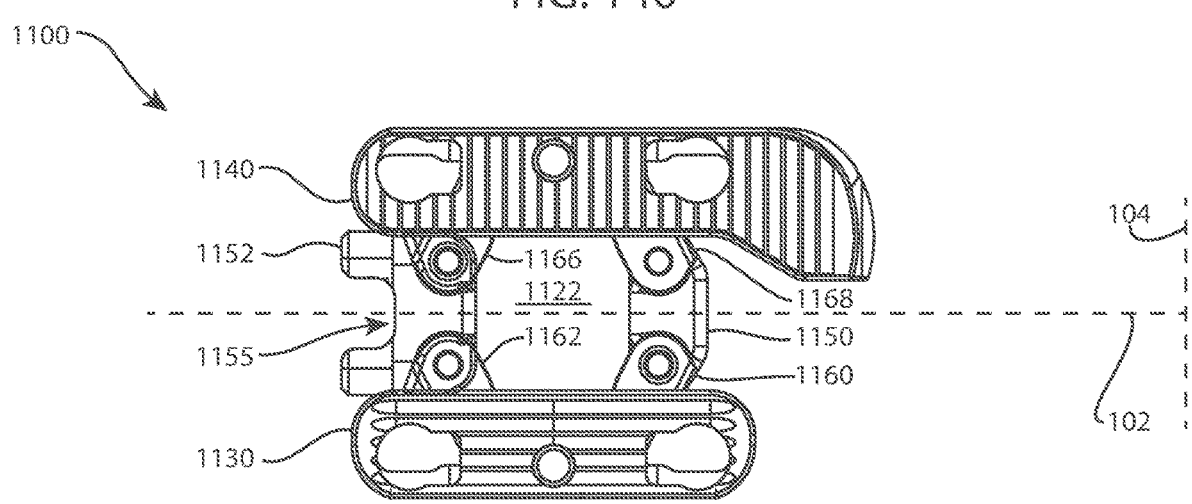
Figure 142:
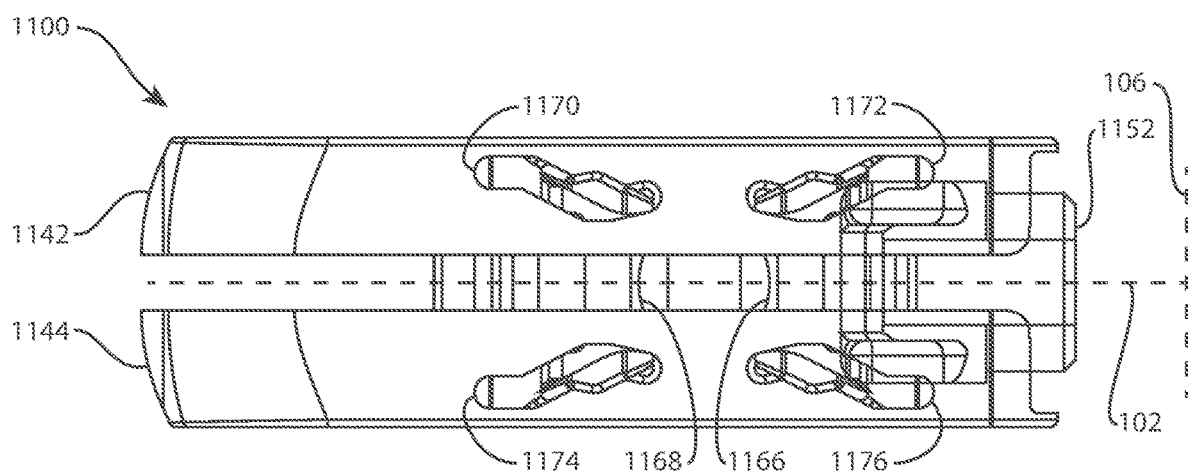
Figure 145:
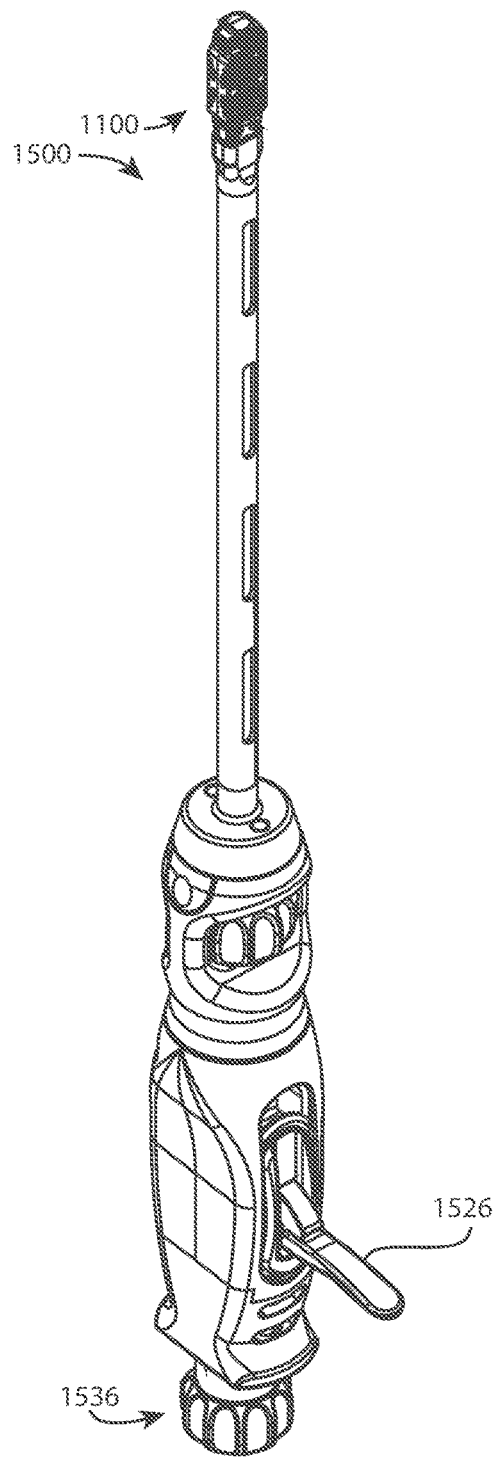
Figure 146:
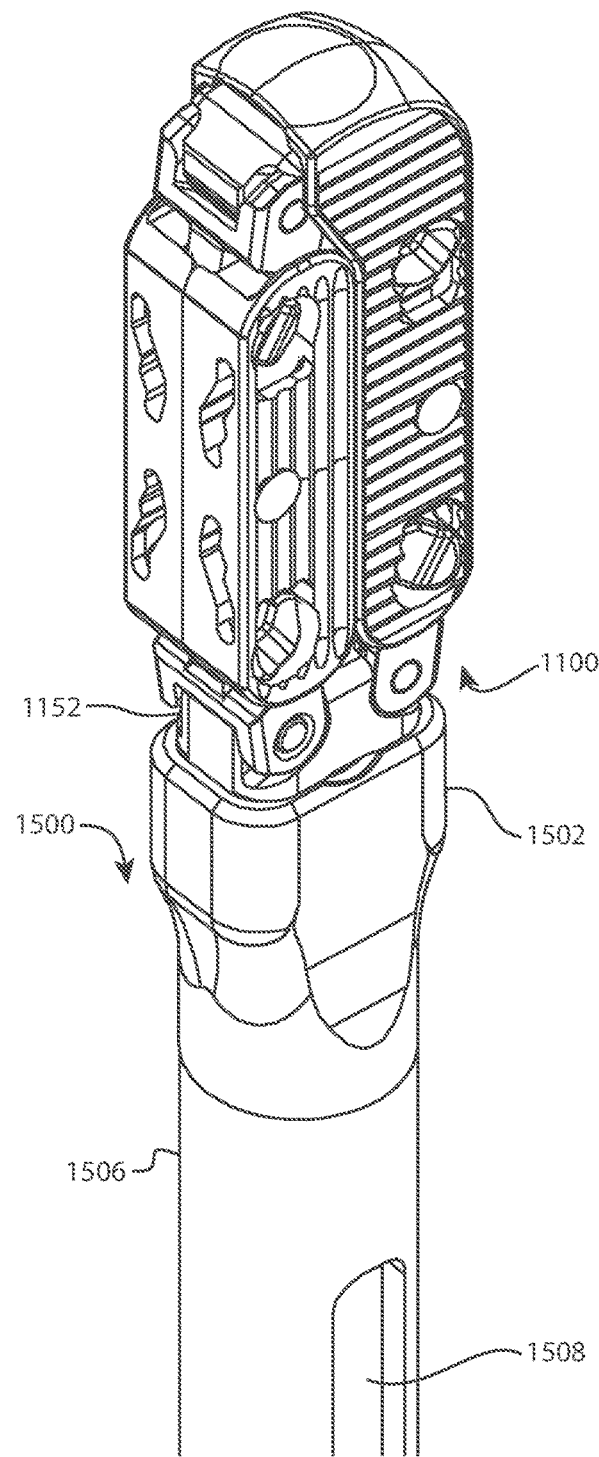
Figure 147:
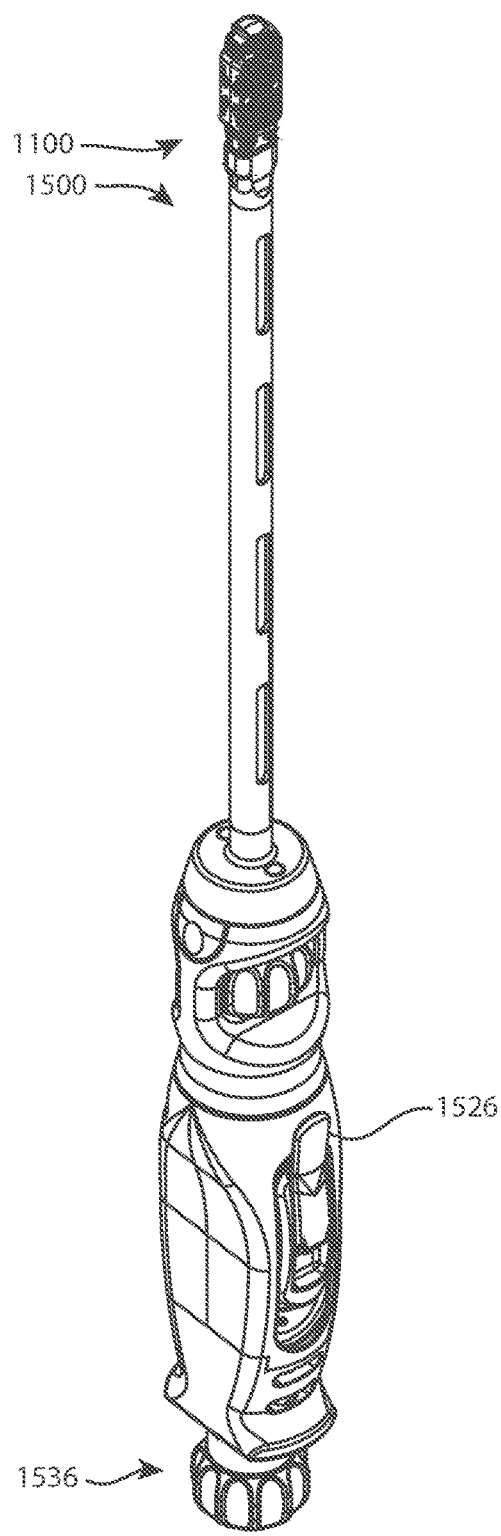
Figure 148:
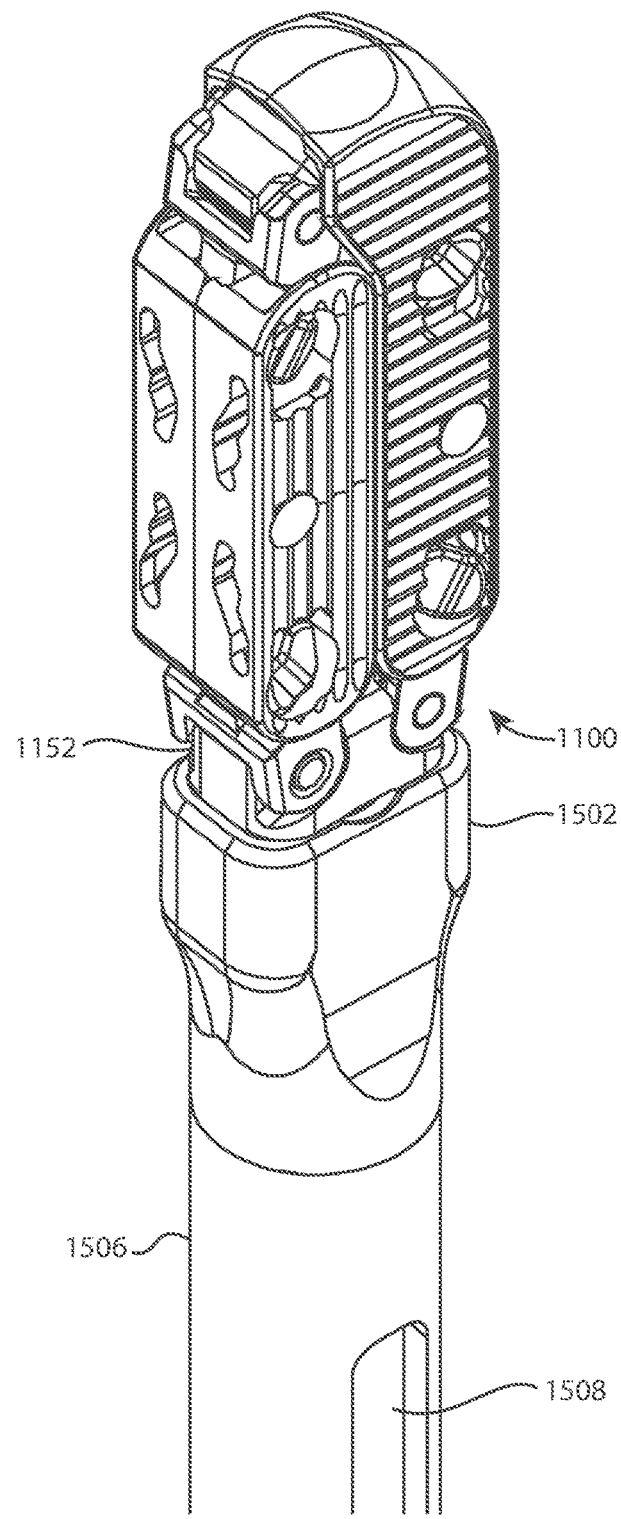
Figures 149, 150:
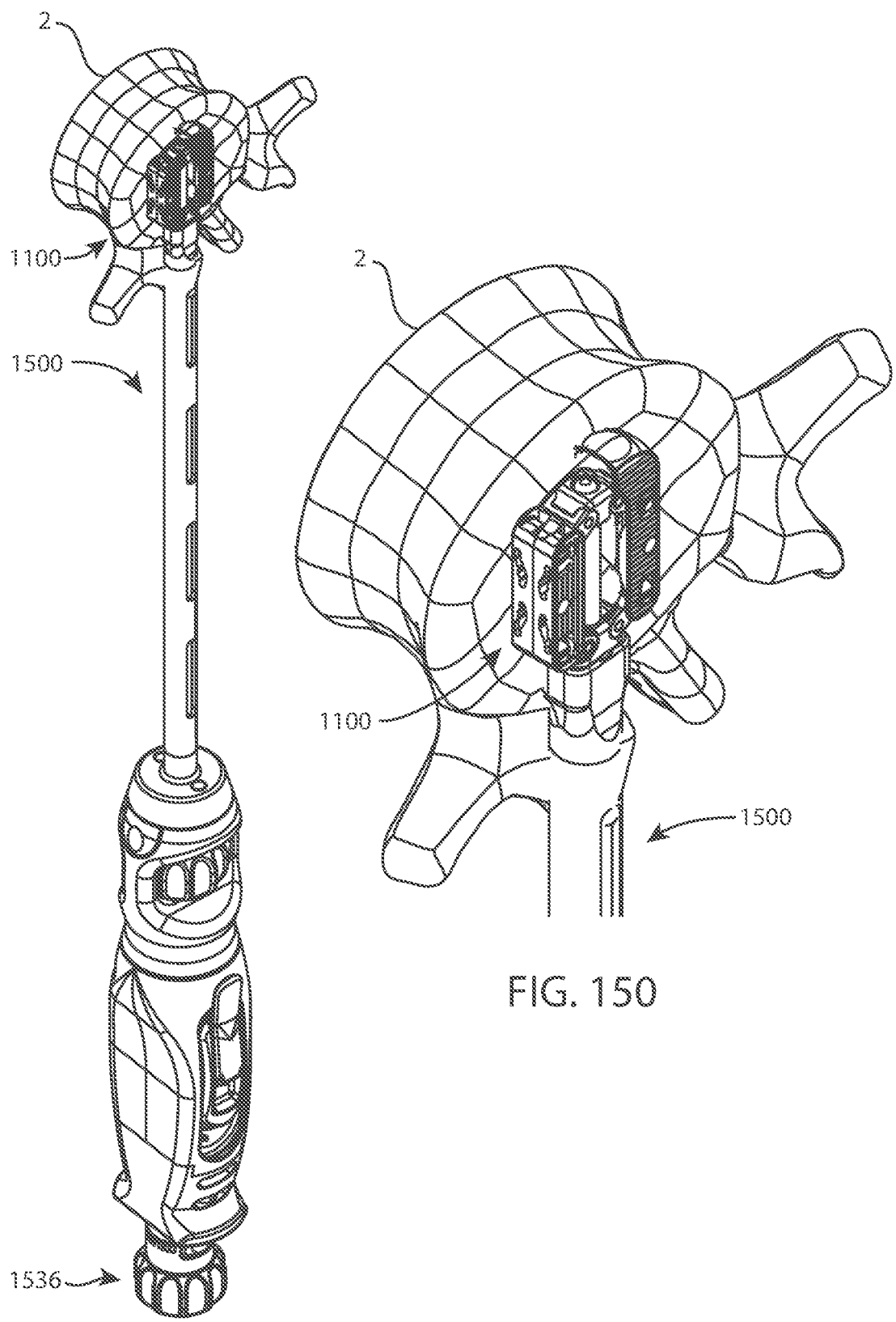
Figures 151, 152:
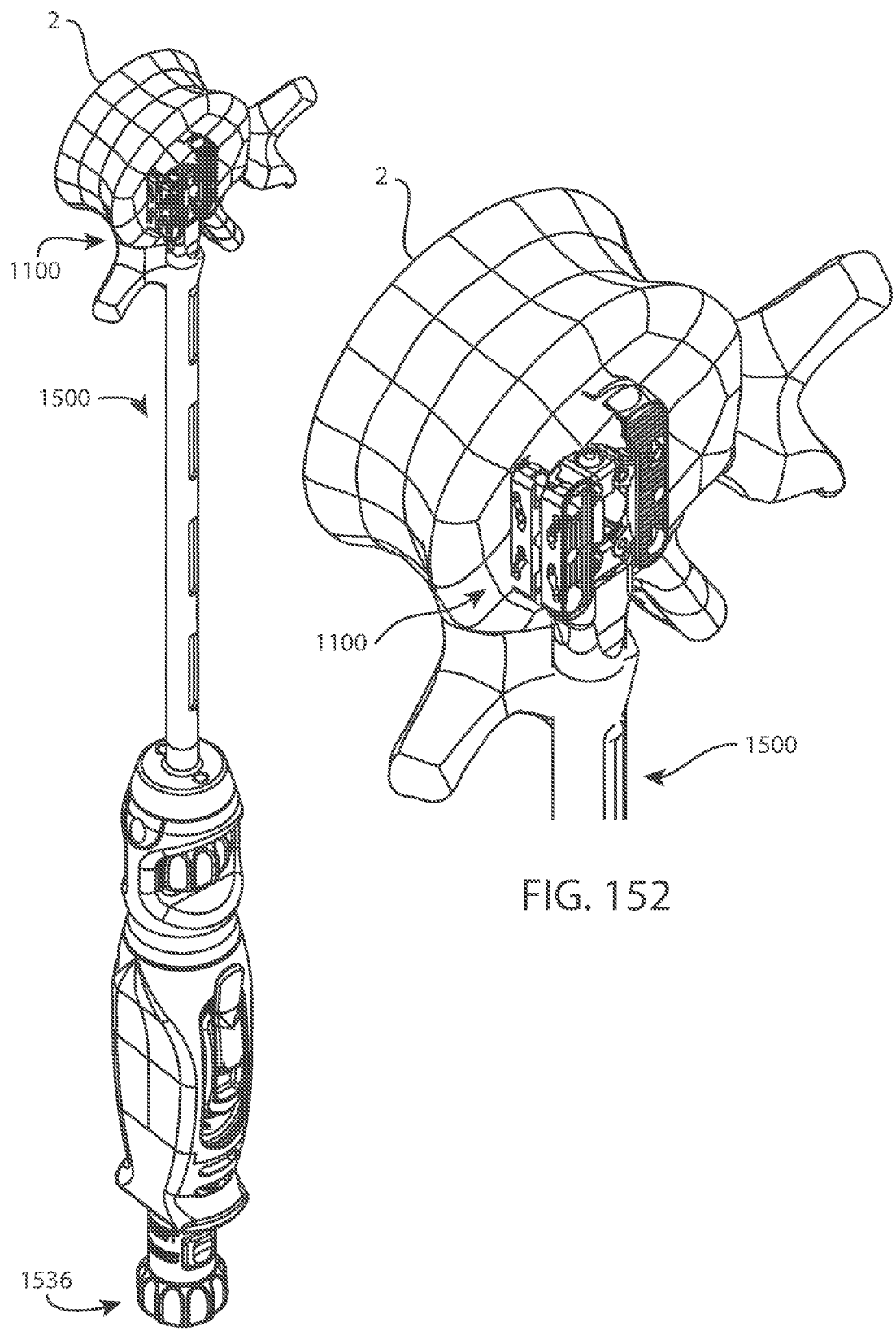
Figures 153, 154:
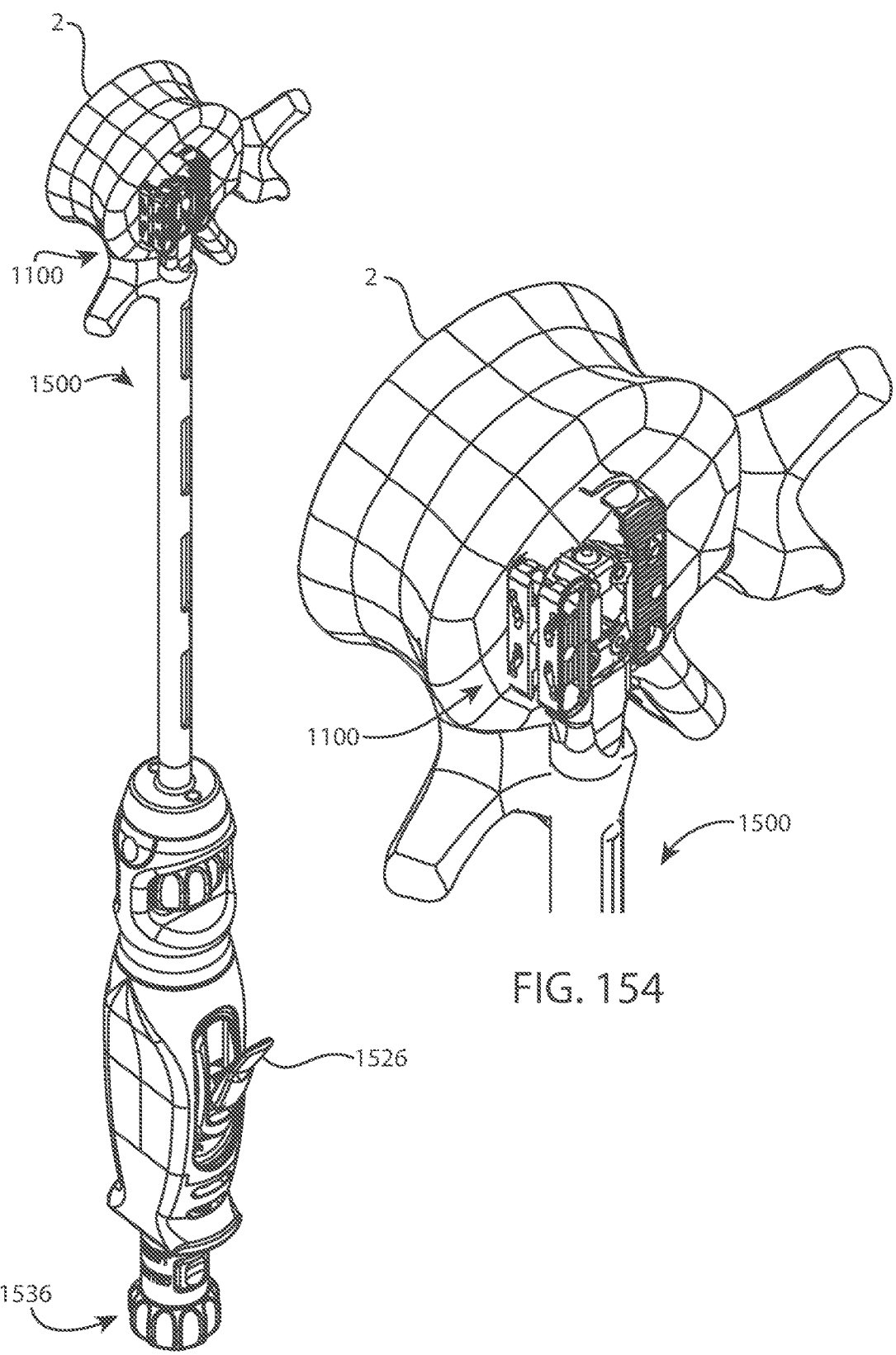
Figure 157:
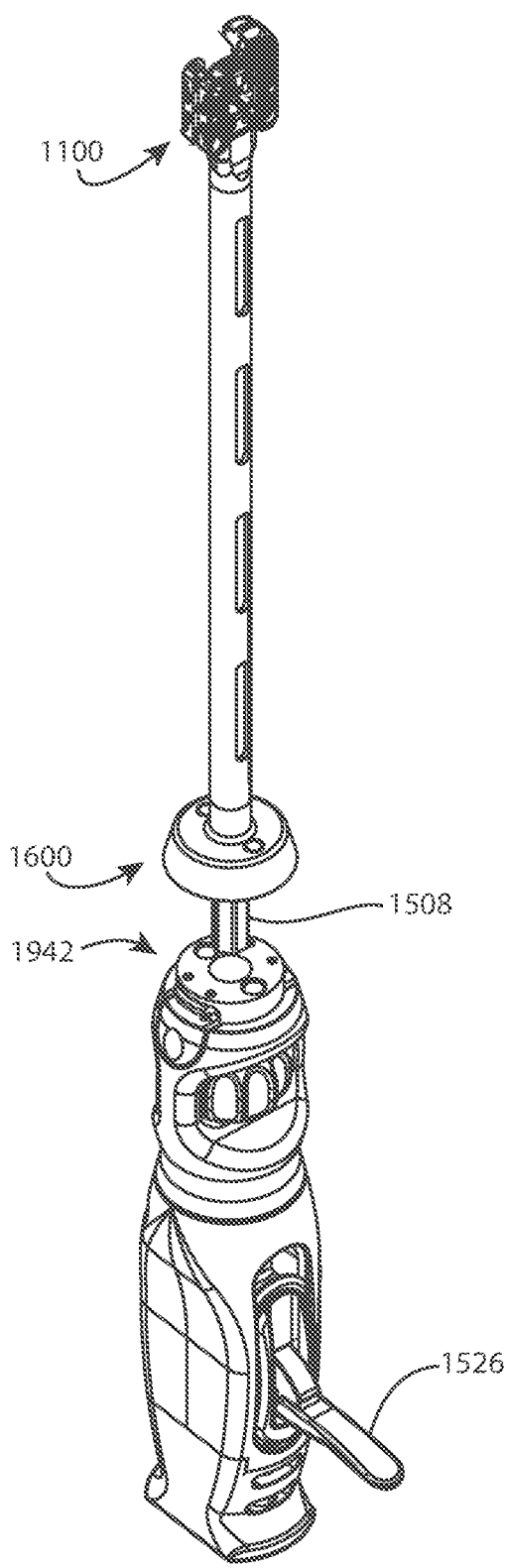
Figure 158:
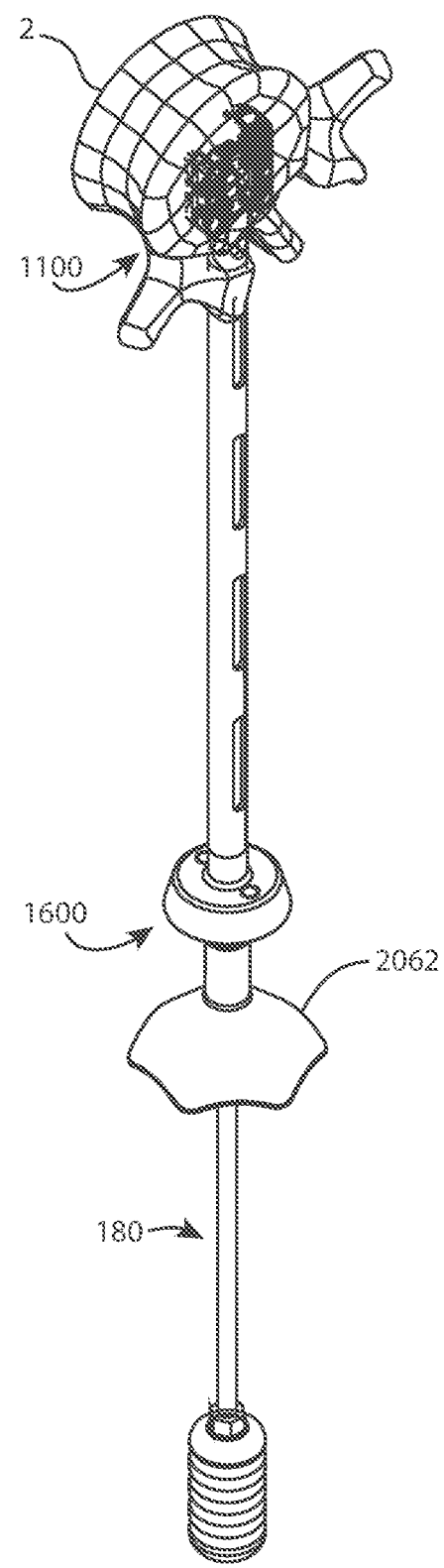
Figure 159:
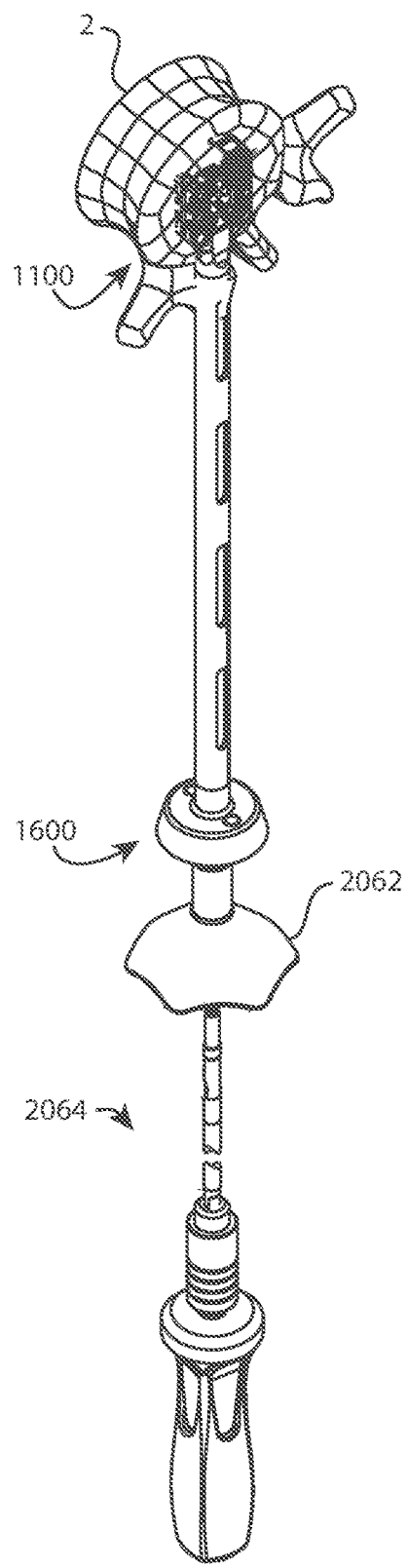
Figure 160:
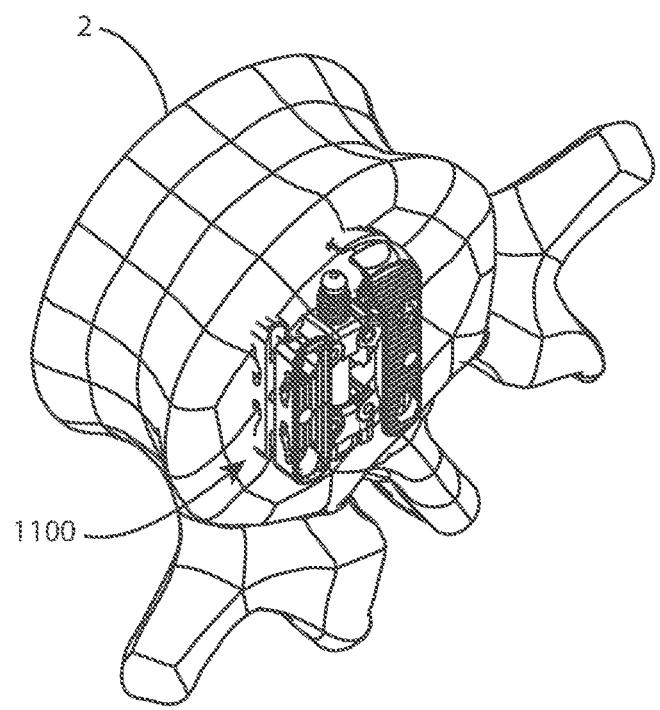

FIG. 131 is another perspective view of the trial assembly of FIG. 130, from a different direction;

FIG. 132 is an exploded perspective view of the trial assembly of FIG. 130;

FIG. 133 is another exploded perspective view of the trial assembly of FIG. 130, from a different direction;

FIG. 134 is a perspective view of a funnel for use with the instrument of FIG. 86;

FIG. 135 is another perspective view of the funnel of FIG. 134, from a different direction;

FIG. 136 is a perspective view of a screwdriver assembly for use with the instrument of FIG. 86;

FIG. 137 is another perspective view of the screwdriver assembly of FIG. 136, from a different direction;

FIG. 138 is an exploded perspective view of the screwdriver assembly of FIG. 136;

FIG. 139 is another exploded perspective view of the screwdriver assembly of FIG. 136, from a different direction;

FIG. 140 is a rear or second end view of the implant of FIG. 86 in a collapsed configuration;

FIG. 141 is a top view of the implant of FIG. 86;

FIG. 142 is a side view of the implant of FIG. 86;

FIG. 143 is a perspective view of the trial assembly of FIG. 130 adjacent a vertebral body;

FIG. 144 is a distal detail perspective view of the trial assembly and vertebral body of FIG. 143;

FIG. 145 is a perspective view of the instrument and implant of FIG. 86 coupled to the draw bar assembly of FIG. 126, the slider button of the instrument in a proximal position;

FIG. 146 is a distal detail perspective view of the instrument and implant of FIG. 145;

FIG. 147 is a perspective view of the instrument, draw bar assembly, and implant of FIG. 145, the slider button of the instrument in a distal position;

FIG. 148 is a distal detail perspective view of the instrument and implant of FIG. 147;

FIG. 149 is a perspective view of the instrument, draw bar assembly, and implant of FIG. 144, the implant adjacent a vertebral body and in a laterally expanded configuration;

FIG. 150 is a distal detail perspective view of the instrument, implant, and vertebra of FIG. 149;

FIG. 151 is a perspective view of the instrument, draw bar assembly, and implant of FIG. 149, the implant adjacent a vertebral body and in a laterally and vertically expanded configuration;

FIG. 152 is a distal detail perspective view of the instrument, implant, and vertebra of FIG. 151;

FIG. 153 is a perspective view of the instrument, draw bar assembly, and implant of FIG. 151, the implant adjacent a vertebral body and in a laterally and vertically expanded configuration, the slider button of the instrument released;

FIG. 154 is a distal detail perspective view of the instrument, implant, and vertebra of FIG. 153;

FIG. 155 is a perspective view of the instrument, draw bar assembly, and implant of FIG. 153, the implant adjacent a vertebral body and in a laterally and vertically expanded configuration, the slider button in the proximal position;

FIG. 156 is a distal detail perspective view of the instrument, implant, and vertebra of FIG. 155;

FIG. 157 is a perspective view of the instrument and implant of FIG. 155, the implant in a laterally and vertically expanded configuration, a handle assembly of the instrument partially removed from a shaft assembly of the instrument;

FIG. 158 is a perspective view of the shaft assembly and implant of FIG. 157, the implant adjacent a vertebral body and in a laterally and vertically expanded configuration, with the funnel of FIG. 134 and the tamp assembly of FIG. 27 coupled to the shaft assembly;

FIG. 159 is a perspective view of the shaft assembly, implant, and funnel of FIG. 158, the implant adjacent a vertebral body and in a laterally and vertically expanded configuration, with the screwdriver assembly of FIG. 136 coupled to the lockout screw of FIG. 43 and oriented for insertion into the shaft assembly;

FIG. 160 is a perspective view of the implant and lockout screw of FIG. 159 adjacent a vertebral body and in a laterally and vertically expanded configuration;

DETAILED DESCRIPTION

Exemplary embodiments of the technology will be best understood by reference to the drawings, wherein like parts are designated by like numerals throughout. It will be readily understood that the components of the technology, as generally described and illustrated in the FIGS. herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. Proximal means located toward a center of a body, or toward a user. Distal means located away from the center of the body, or away from a user. These descriptive terms may be applied to an animate or inanimate body.

Standard spinal descriptive terminology is used herein with the ordinary and customary meanings.

Figure 1:
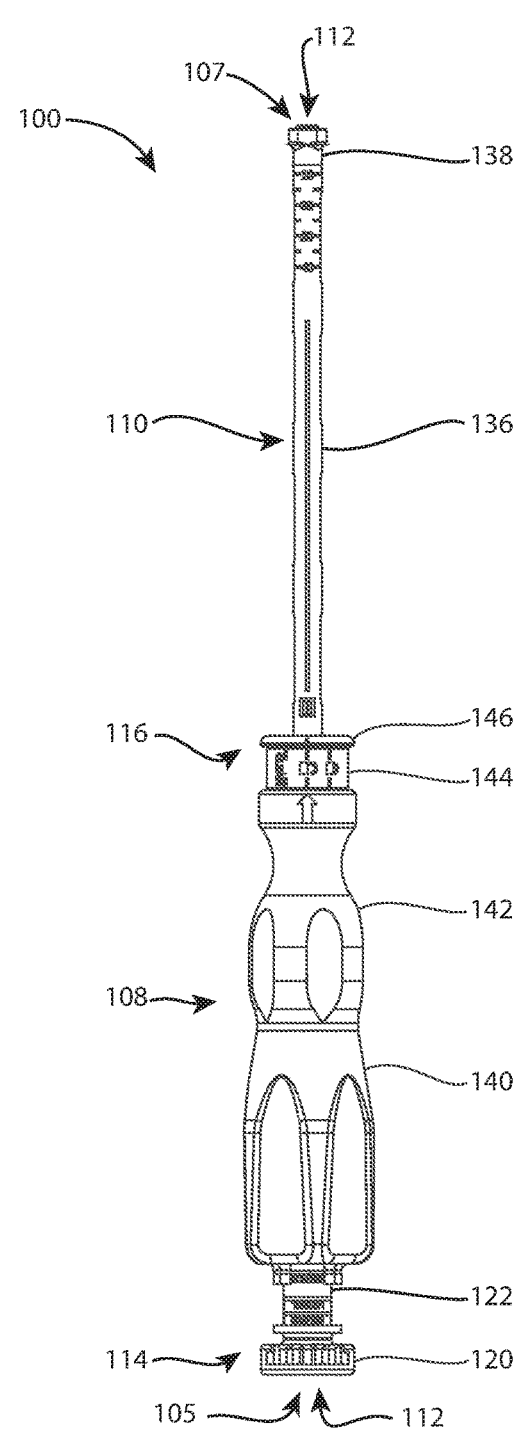
FIG. 1 is a top view of an insertion and expansion instrument.
Figure 2:
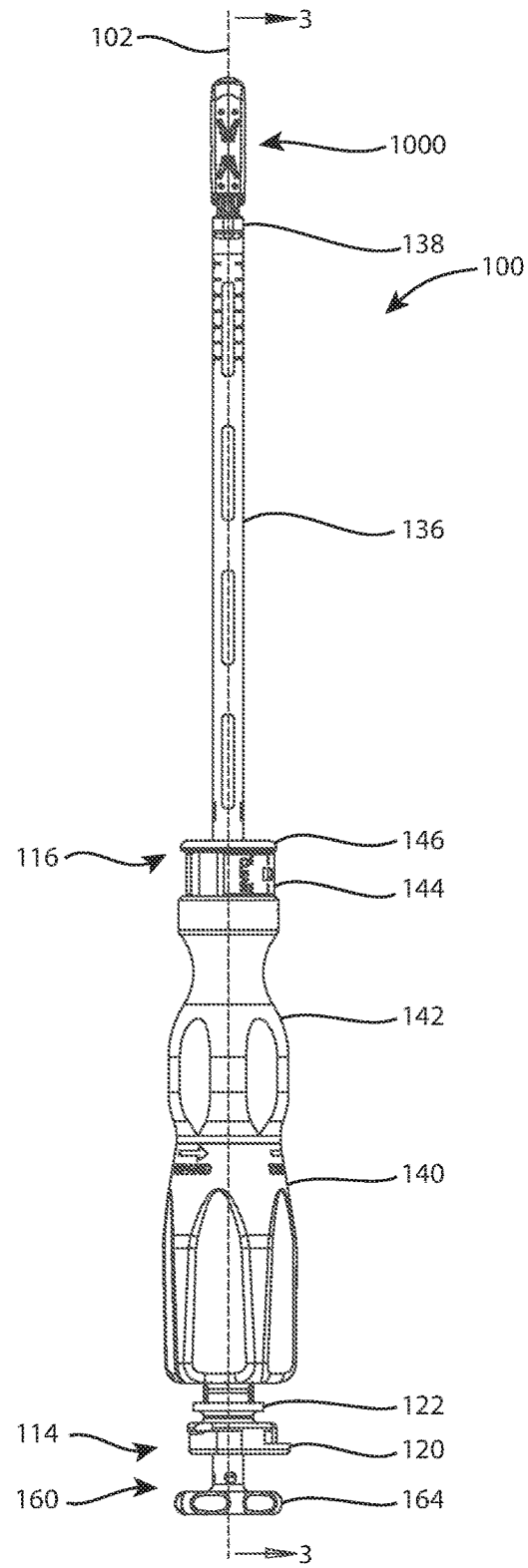
FIG. 2 is a side view of the instrument of FIG. 1 with a draw bar assembly inserted into the instrument and an expandable intervertebral implant connected to a distal end of the instrument.

Referring to FIGS. 1 and 2, an instrument 100 for insertion and expansion of an intervertebral implant is disclosed. The instrument 100 extends from a proximal end 105 to a distal end 107 along a longitudinal instrument axis 102. The instrument 100 includes a handle portion 108 and a shaft portion 110. In FIG. 2, an expandable intervertebral implant 1000 is connected to the instrument distal end 107 and a draw bar assembly 160 is received in the instrument 100 for expansion of the implant.

Figure 3:
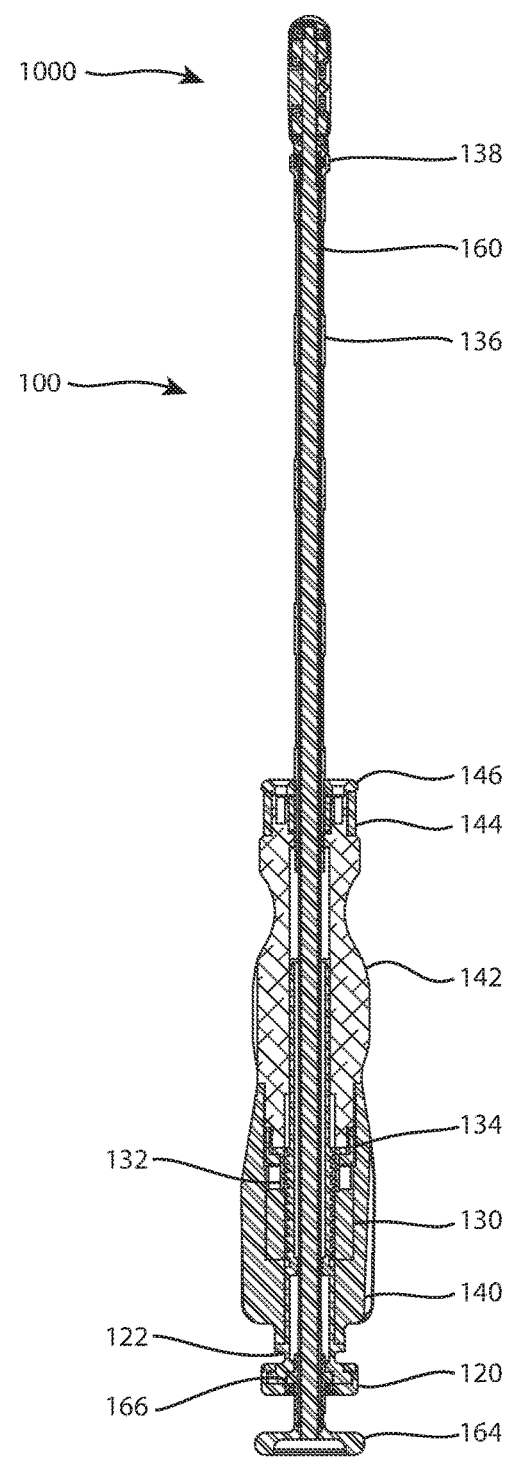
FIG. 3 is a cross-sectional view of the instrument and implant of FIG. 2 taken along line 3-3 of FIG. 2.
Figure 4:
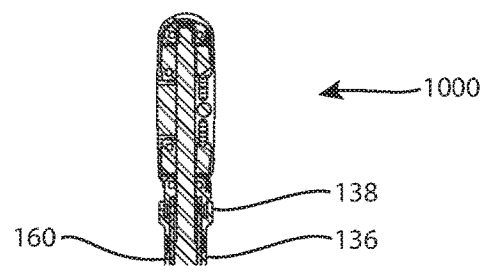
FIG. 4 is a distal detail cross-sectional view of the instrument and implant of FIG. 3.
Figure 5:
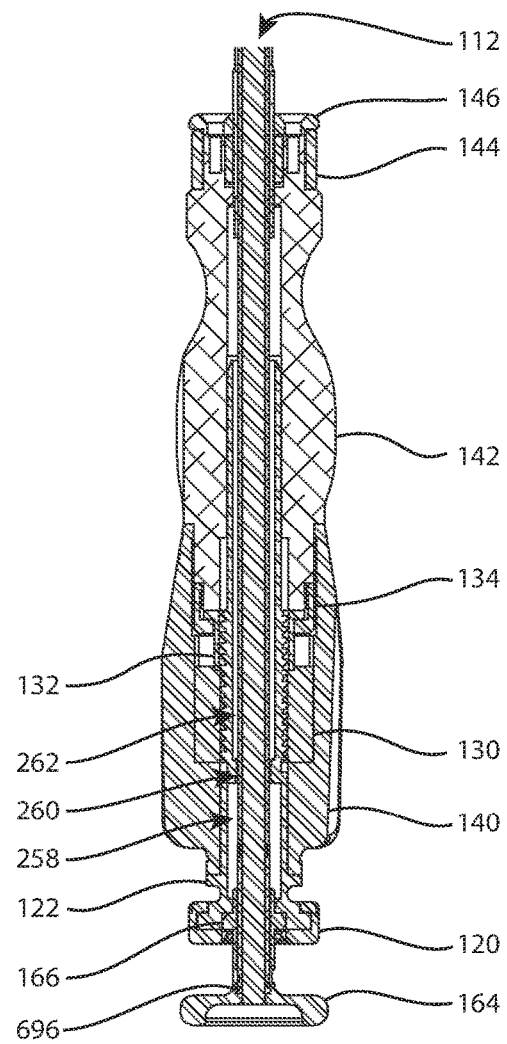
FIG. 5 is a proximal detail cross-sectional view of the instrument of FIG. 3.
Figure 6:
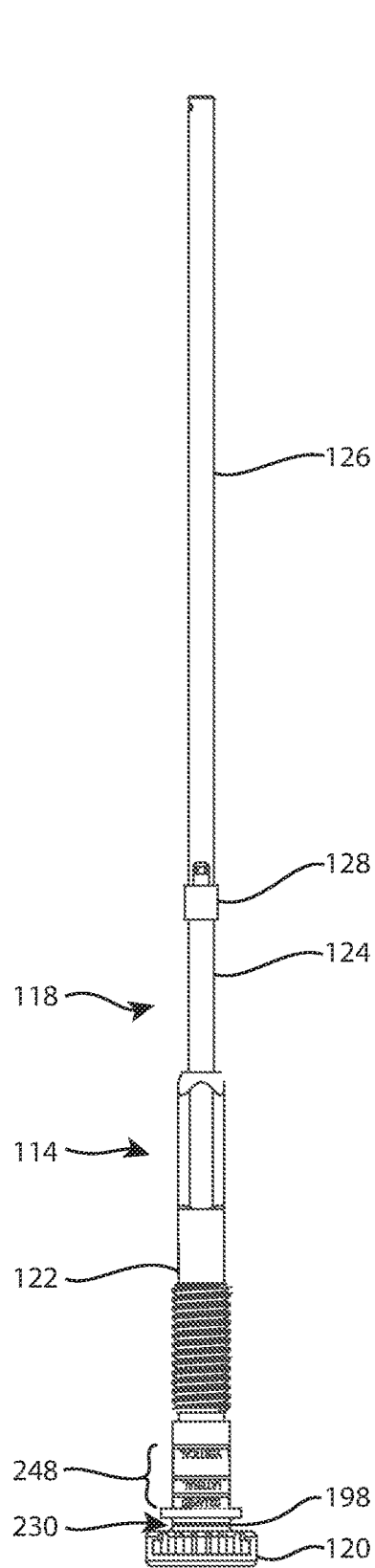
FIG. 6 is a top view of the instrument of FIG. 1 in a first partially assembled state.
Figure 7:
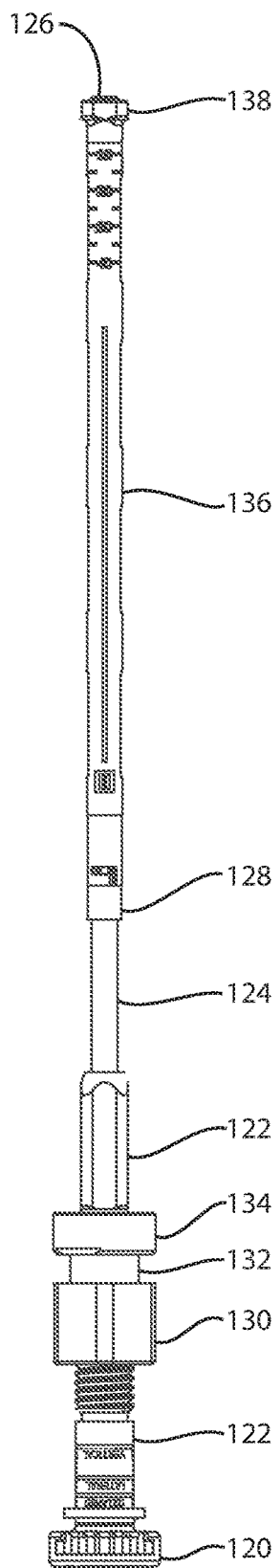
FIG. 7 is a top view of the instrument of FIG. 1 in a second partially assembled state.
Figure 8:
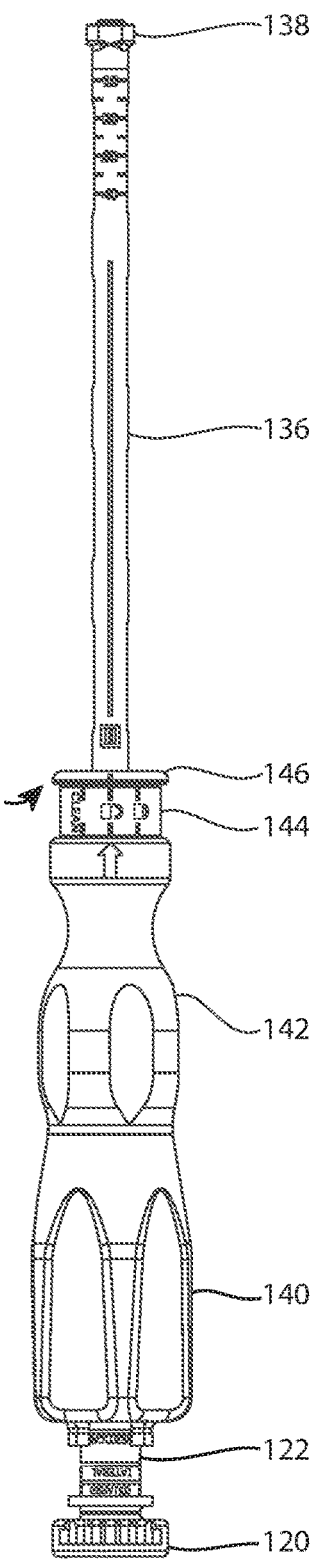
FIG. 8 is a top view of the instrument of FIG. 1 in a fully assembled state.

Referring to FIGS. 3-8, components and features of instrument 100 are disclosed. As seen in FIGS. 3 and 6, instrument 100 includes a lock collar 120 attachable to a shuttle 122. A proximal lock tube 124 extends distally from the shuttle 122, and a distal lock tube 126 extends distally from the proximal lock tube. A lock tube coupling 128 couples the proximal and distal lock tubes 124, 126 together. The lock collar 120, shuttle 122, and proximal and distal lock tubes 124, 126 are cannulated, surrounding a longitudinal instrument bore 112 extending along the longitudinal instrument axis 102. As seen in FIGS. 3 and 7, a threaded driver 130, standoff 132, and standoff nut 134 are coupled to the shuttle 122. An inserter shaft 136 extends distally from lock tube coupling 128, and an inserter connector 138 is at the distal end of the inserter shaft 136. The outer inserter shaft 136 may include one or more openings that aid in cleaning the instrument. As seen in FIGS. 3 and 8, the fully assembled instrument further includes an expansion knob 140, inserter handle 142, selector ring 144, and impaction cap 146. Markings or indicia 248 on the shuttle 122 or another component may provide indication when a particular step of implant expansion is attained. In one example the words "collapsed", "lateral" and "vertical" may be indicated when the implant is in collapsed, laterally expanded, and vertically expanded configurations, respectively. In other embodiments, letters, numbers, symbols, or other markings may be used to indicate stages of insertion and/or expansion.

Figure 9:
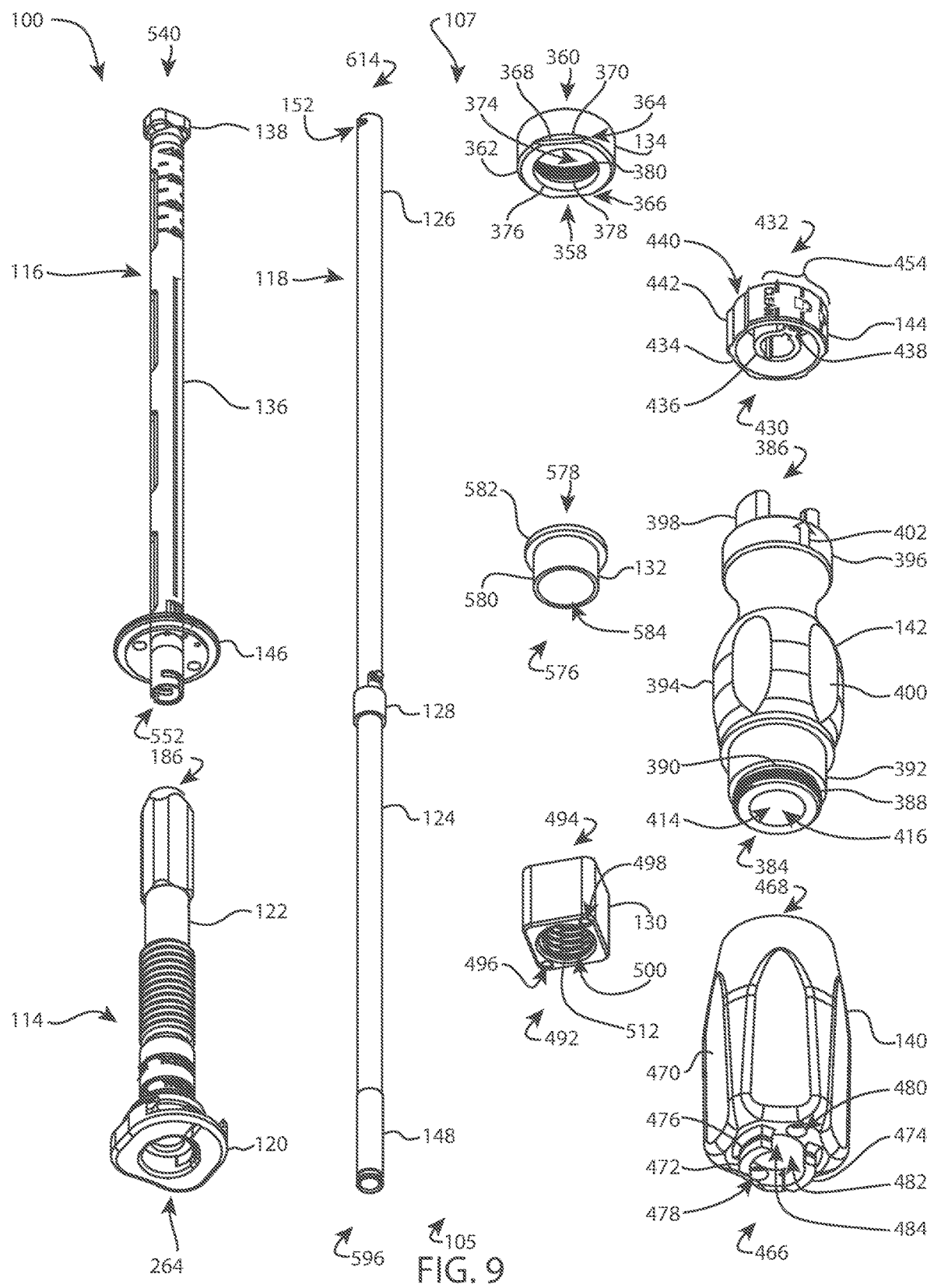
FIG. 9 is an exploded perspective view of the instrument of FIG. 1.
Figure 10:
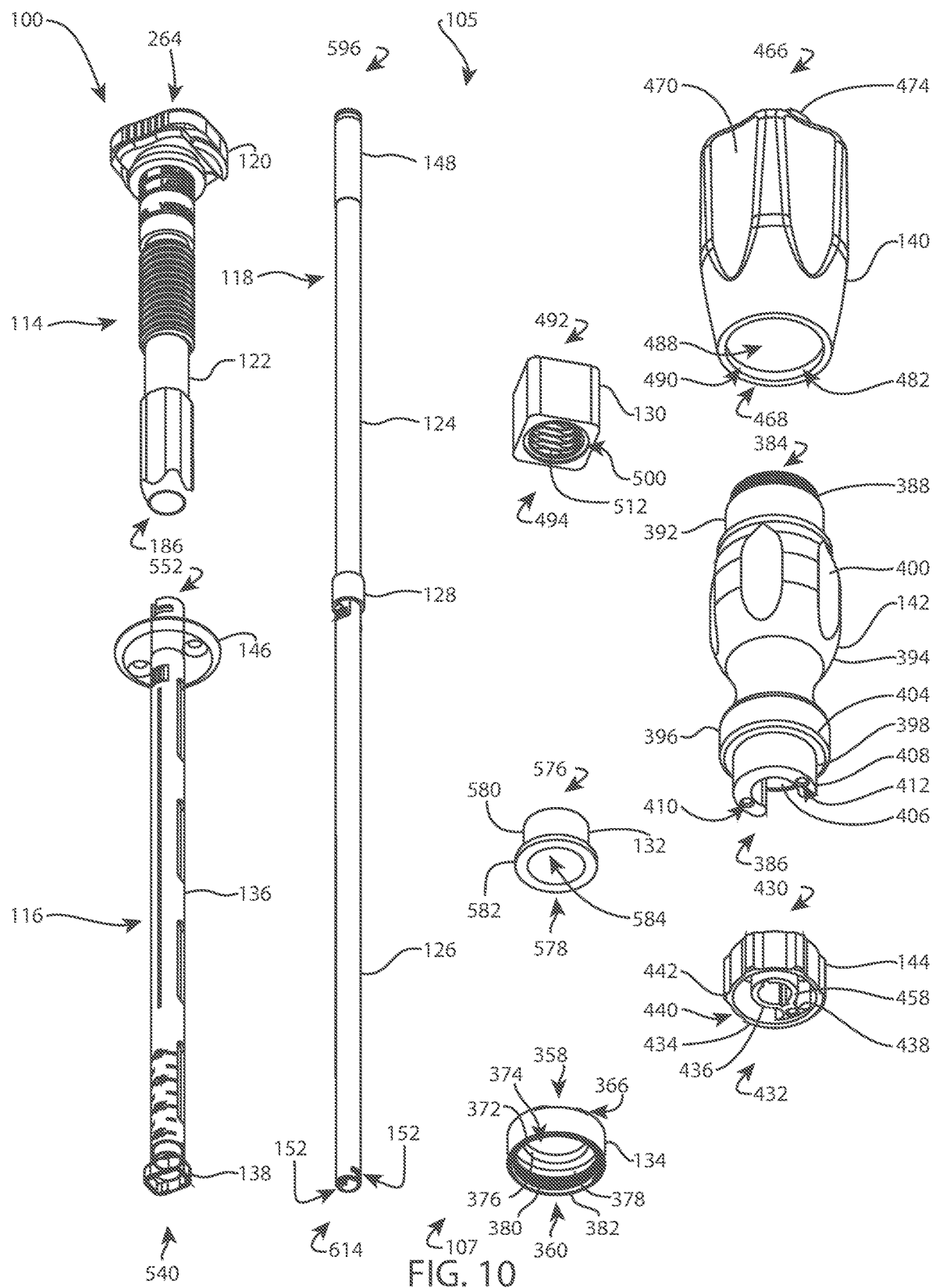
FIG. 10 is another exploded perspective view of the instrument of FIG. 1, from a different direction.

Referring to FIGS. 9 and 10, the instrument 100 may include a shuttle assembly 114, a standoff nut 134, an inserter handle 142, a selector ring 144, an expansion knob 140, a threaded driver 130, a shaft assembly 116, a standoff 132, and a lock tube assembly 118.

Figure 11:
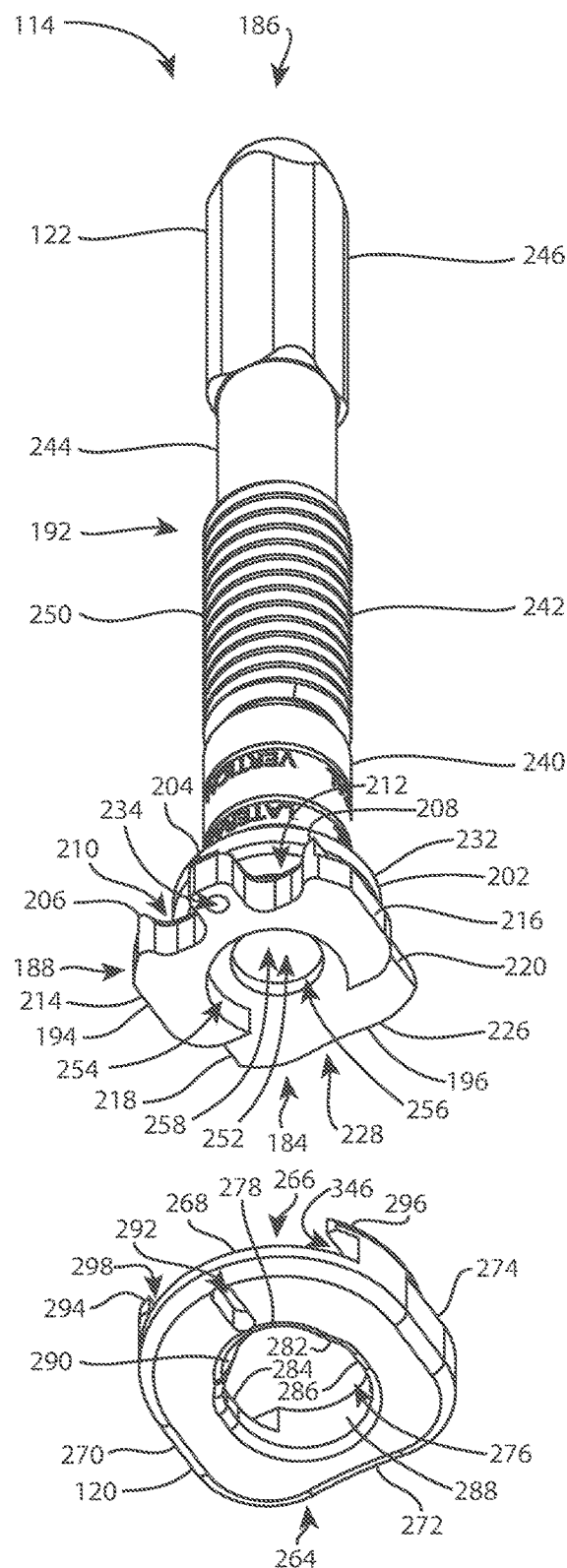
FIG. 11 is an exploded perspective view of a shuttle assembly of the instrument of FIG. 1.
Figure 12:
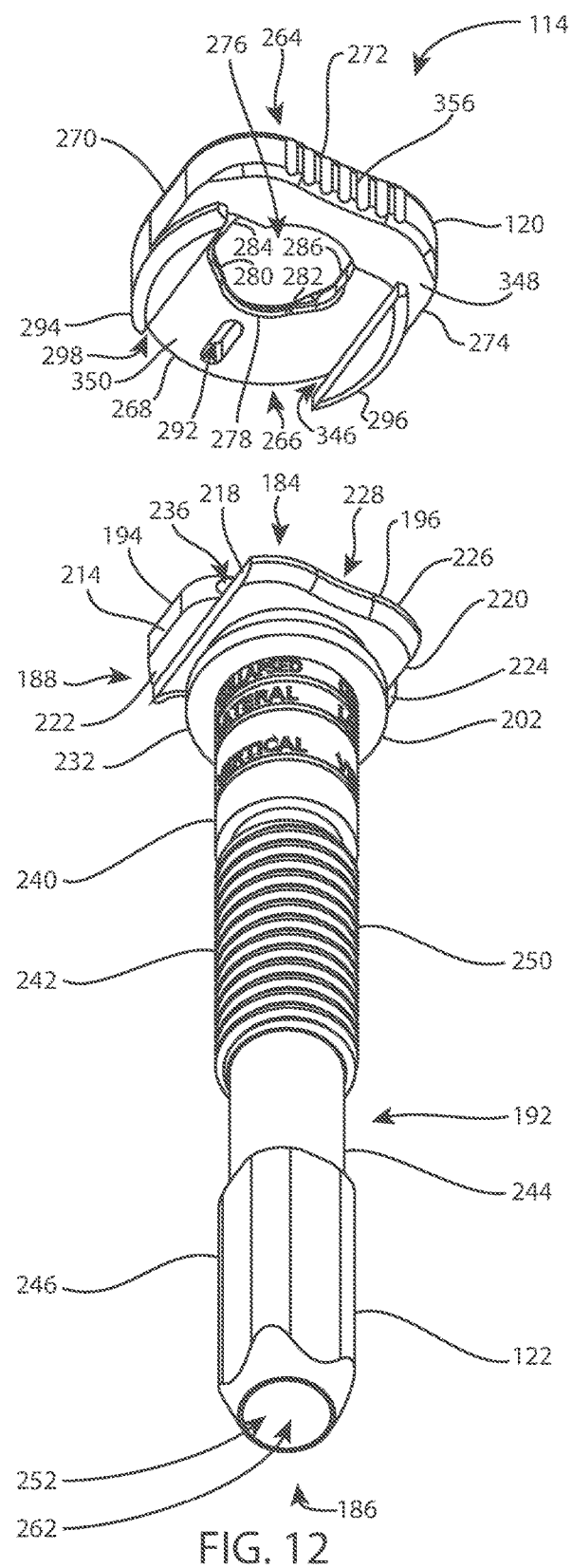
FIG. 12 is another exploded perspective view of the shuttle assembly of FIG. 11, from a different direction.
Figure 13:
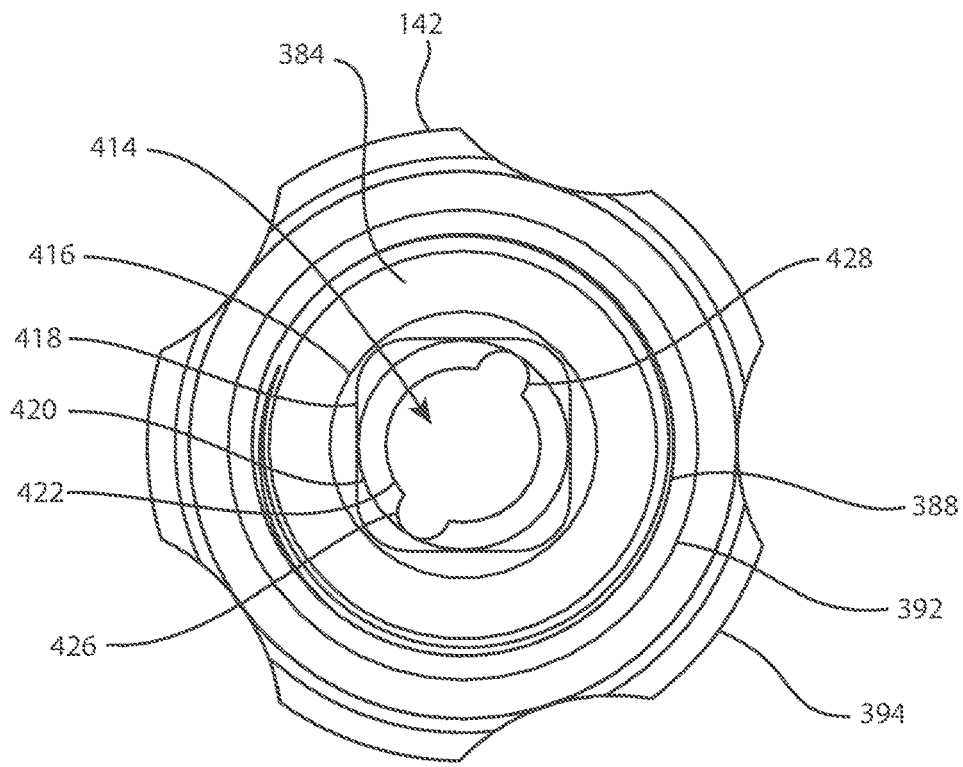
FIG. 13 is a proximal end view of an inserter handle of the instrument of FIG. 9.

Referring to FIGS. 11 and 12, the shuttle assembly 114 may include a shuttle 122 and a lock collar 120.

The shuttle 122 extends between a proximal end 184 and a distal end 186. The proximal end may include a head 188. A shaft 192 may extend from the head 188 toward the distal end 186. The head 188 may be wider than the shaft 192, as shown.

The head 188 may include, from proximal to distal, first, second, third (FIG. 6), and fourth levels 194, 196, 198, 202. The first level 194 may have a generally rectangular cross section and may overhang the shaft 192 on three sides, as shown. The first level 194 may include a tab 204 that protrudes from a first side of the first level. The tab 204 may be flanked by bilateral teeth 206, 208 that may also protrude from the first side of the first level. The teeth 206, 208 may be smaller and/or shorter than the tab 204. Bilateral indentations 210, 212 may be present between the tab 204 and the teeth 206, 208. The second and third overhanging sides 214, 216 of the first level 194 may be flat. A hole 234 may extend through the tab 204 and may be parallel to the shaft 192. Bilateral holes 236, 238 may extend into the first level 194 opposite the tab 204. Hole 236 is visible in FIG. 12; hole 238 is hidden by the second level 196. The second level 196 may have a generally rectangular cross section and may overhang the shaft 192 all around. The second level 196 may include the tab 204, the teeth 206, 208, and the indentations 210, 212 arranged on a first overhanging side of the second level. Second and third overhanging sides 218, 220 may be flat, and may be parallel to the sides 214, 216. The side 218 may be recessed relative to the side 214 to form a ledge 222. The side 220 may be recessed relative to the side 216 to form a ledge 224. A fourth overhanging side 226 may include a shallow central indentation 228 opposite the tab 204. The third level 198 (FIG. 6) may have a circular cross section and may include a circumferential groove 230. The fourth level 202 may have a circular cross section and may include a circumferential flange 232.

The shaft 192 may include, from proximal to distal, first, second, third, and fourth outer portions 240, 242, 244, 246. The first outer portion 240 may have a circular cross section and may include indicia 248 (FIG. 6) such as lines and/or text to indicate various implant configurations, such as collapsed, laterally expanded, and/or vertically expanded. The outer diameter of the first outer portion 240 may be equal to the minor diameter in the groove 230. The second outer portion 242 may include external threads 250. The major diameter of the threads 250 may be equal to the outer diameter of the first outer portion 240. The third outer portion 244 may have a circular cross section. The outer diameter of the third outer portion 244 may be smaller than the minor diameter of the threads 250. The fourth outer portion 246 may have a generally rectangular cross section. The cross section may be square with rounded corners as shown. Two opposite flat sides of the fourth outer portion 246 may be parallel to the sides 214, 216 and/or the sides 218, 220. The width across the flat sides may be equal to the outer diameter of the third outer portion 244. The width across the rounded corners may be greater than the outer diameter of the third outer portion 244 and may be less than the outer diameter of the first outer portion 240.

The shuttle 122 may include a central longitudinal hole 252 that extends through the shuttle between the proximal end 184 and the distal end 186. The hole 252 may include, from proximal to distal, first, second, third, fourth (FIG. 5), and fifth inner portions 254, 256, 258, 260, 262. Each of these inner portions may have a circular cross section. The first inner portion 254 may extend into the proximal end 184 through the first level 194 and may end at the second level 196. The first inner portion 254 may be referred to as a counterbore associated with the second inner portion 256. The first inner portion 254 may break through the side of the first level 194 opposite the tab 204. The second inner portion 256 may extend through the second level 196. The diameter of the second inner portion 256 may be less than the diameter of the first inner portion 254. The third inner portion 258 may extend through the third and fourth levels 198, 202 and most of the first outer portion 240, and may end just proximal to the second outer portion 242. There may be a short conical tapered transition between the second inner portion 256 and the third inner portion 258. The diameter of the third inner portion 258 may be less than the diameter of the first inner portion 254 and may be greater than the diameter of the second inner portion 256. The fourth inner portion 260 (FIG. 5) may extend between the third and fifth inner portions 258, 262. The fourth inner portion 260 may begin just proximal to the second outer portion 242 and may end just distal to the first outer portion 240. There may be a short conical tapered transition between the third inner portion 258 and the fourth inner portion 260. The diameter of the fourth inner portion 260 may be less than the diameter of the second inner portion 256. The fifth inner portion 262 may extend into the distal end 186 through the fourth and third outer portions 246, 244 and most of the second outer portion 242, and may end just distal to the first outer portion 240. The diameter of the fifth inner portion 262 may be less than the diameter of the first inner portion 254 and may be greater than the diameter of the second inner portion 256. The diameter of the fifth inner portion 262 may be equal to the diameter of the third inner portion 258.

The lock collar 120 extends between a proximal side 264 and a distal side 266. The lock collar 120 may have a generally D-shaped profile in a proximal view, with a curved side 268 and three substantially flat sides 270, 272, 274. The proximal side 264 may be flat. A central hole 276 may extend through the lock collar 120 between the proximal side 264 and the distal side 266. The hole 276 may be non-circular in a proximal view. The hole 276 may include a first curved side 278, flat tapered sides 280, 282, flat parallel sides 284, 286, and a second curved side 288. Transitional fillet surfaces may be present between some or all of the sides 278, 280, 282, 284, 286, 288. A conical surface 290 may be associated with the first curved side 278, and may taper into the hole 276 from the proximal side 264. A slot 292 may extend through the lock collar 120 from the proximal side 264 to the distal side 266. The slot 292 may be located between the curved side 268 and the first curved side 278 and may be elongated in a direction from the curved side 268 to the flat side 272. The distal side 266 may include bilateral feet 294, 296 that protrude distally on either side of the hole 276. The foot 294 may be associated with the flat side 270. The foot 296 may be associated with the flat side 274. In a distal view, the outer profile of the curved side 268 may be concentric with the outer profiles of the feet 294, 296. The inner profiles of the feet 294, 296 may be flat and parallel to each other, and may also be parallel to the flat sides 270, 274. The feet 294, 296 may be undercut. An undercut groove 298 may extend along the inner profile of the foot 294 and an undercut groove 346 may extend along the inner profile of the foot 296. Taken together, the feet 294, 296 and undercut grooves 298, 346 may form a T-slot across the distal side 266. The distal side 266 may include a first surface 348 that is proximal to the distal aspect of the feet 294, 296. The first surface 348 may be at the same or a similar level as the distal-most surfaces of the undercut grooves 298, 346. The distal side 266 may include a second surface 350 that is proximal to the first surface 348. The second surface 350 may be at the same or a similar level as the proximal-most surfaces of the undercut grooves 298, 346. Bilateral holes 352, 354 (not shown) may extend into the lock collar, between the first surface 348 and the second surface 350, along a direction from the curved side 268 to the flat side 272. The bilateral holes 352, 354 may be complementary to the bilateral holes 236, 238 in the head 188 of the shuttle 122. The flat side 272 may include friction features 356, such as alternating ridges and grooves, knurling, grit blast, or the like.

The shuttle assembly 114 may be assembled by orienting the lock collar 120 relative to the head 188 of the shuttle 122 so that the proximal end 184 and the proximal side 264 face the same way, the side 226 and the side 272 face the same way, and the sides 218, 220 are aligned between the feet 294, 296; and sliding the lock collar 120 along a direction from the flat side 272 to the curved side 268 so that the first level 194 is received in the undercut grooves 298, 346 and the second level 196 is received between the feet 294, 296. Bilateral pins or compression springs (not shown) may be inserted into the bilateral holes 236, 238 and 352, 354. A pin (not shown) may be inserted through the slot 292 and into the hole 234. When compression springs are inserted in the holes 236, 238 and 352, 354 and a pin is inserted through the slot 292 and into the hole 234, the springs bias the lock collar 120 toward a position in which the pin contacts the end of the slot 292 that is closest to the outer curved side 268.

Referring to FIGS. 9 and 10, the standoff nut 134 extends between a proximal side 358 and a distal side 360. The standoff nut 134 may be a generally cylindrical part. The proximal side 358 may include a circumferential outer chamfer 362 and/or bilateral notches 364, 366. Each notch may include a longitudinal surface 368 and a transverse surface 370. The distal side 360 may include a circumferential outer chamfer 372. A central hole 374 may extend through the standoff nut 134 between the proximal side 358 and the distal side 360. The hole 374 may include, from proximal to distal, first, second, and third inner portions 376, 378, 380. The first inner portion 376 may have a circular cross section. The second inner portion 378 may have a circular cross section, and may have a larger diameter than the first portion 376. The second inner portion 378 may have a flat proximal end. The third inner portion 380 may have internal threads, which may have a major diameter the same or similar to the diameter of the second portion 378. The hole 374 may include an inner chamfer 382 at the distal side 360.

Referring to FIGS. 5,9,10,13, and 14, the inserter handle 142 extends between a proximal end 384 and a distal end 386. The inserter handle 142 may be generally circular in cross section. The inserter handle 142 may include, from proximal to distal, first, second, third, fourth, fifth, and sixth outer portions 388, 390, 392, 394, 396, 398. The first outer portion 388 may be cylindrical with external threads. The second outer portion 390 may be cylindrical with a diameter that may be the same or similar to the minor diameter of the external threads of the first outer portion 388. The third outer portion 392 may be cylindrical with a diameter that may be greater than the major diameter of the external threads of the first outer portion 388. The fourth outer portion 394 may be generally hourglass-shaped and may include friction features 400, such as longitudinal grooves, alternating ridges and grooves, knurling, grit blast, or the like. The fifth outer portion 396 may be cylindrical with a diameter that may be greater than the diameter of the third outer portion 392. The fifth outer portion 396 may include indicia 402, such as a distally-pointing arrow as shown, and/or an outer chamfer 404. The sixth outer portion 398 may be cylindrical with a diameter that may be the same or similar to the diameter of the second outer portion 390. The sixth outer portion 398 may include a short base portion 406 which may be directly adjacent to the fifth outer portion 396, and a collar portion 408 which is at the distal end 386. The collar portion 408 may be horseshoe-shaped or C-shaped in cross section, with an open side that faces the distally-pointing arrow indicium 402. Bilateral holes 410, 412 may extend proximally into the ends of the collar portion 408 (the ends of the C-shape).

The inserter handle 142 may include a central longitudinal hole 414 that extends through the inserter handle between the proximal end 384 and the distal end 386. The hole 414 may include, from proximal to distal, first, second, third, fourth, and fifth inner portions 416, 418, 420, 422, 424. The first inner portion 416 may have a circular cross section and may extend distally through the first and second outer portions 388, 390 and most of the third outer portion 392, and may end proximal to the fourth outer portion 394. The second inner portion 418 may have a generally rectangular cross section. The cross section may be square with rounded corners as shown, and the open side of the collar portion 408 may face one of the flat sides. The width across the flat sides and the width across the rounded corners may each be less than the diameter of the first inner portion 416. The second inner portion 418 may extend to a location that is near the middle of the overall proximal-distal length of the inserter handle 142. The third inner portion 420 may have a circular cross section. The diameter of the third inner portion 420 may be the same or similar to the width across the flat sides of the second inner portion 418. The third inner portion 420 may end just proximal to the sixth outer portion 398. The fourth inner portion 422 may have a circular cross section. The diameter of the fourth inner portion 422 may be less than the width across the flat sides of the second inner portion 418 or the diameter of the third inner portion 420. Bilateral longitudinal grooves 426, 428 may extend along the fourth inner portion 422. The width across the grooves 426, 428 may be the same or similar to the width across the flat sides of the second inner portion 418 or the diameter of the third inner portion 420. The groove 428 may point into the open side of the collar portion 408, near the end with the hole 412. The grooves 426, 428 may point into the rounded corners of the second inner portion 418. The fourth inner portion 422 may end just distal to the fifth outer portion 396, or near the middle of the overall proximal-distal length of the base portion 406. The fifth inner portion 424 may have a circular cross section and may be continuous with the inner wall of the collar portion 408. The diameter of the fifth inner portion 424 may be less than the width across the rounded corners of the second inner portion 418, greater than the width across the flat sides of the second inner portion or the diameter of the third inner portion 420, and greater than the width across the grooves 426, 428. The fifth inner portion 424 may be referred to as a shallow counterbore associated with the fourth inner portion 422.

Figure 15:
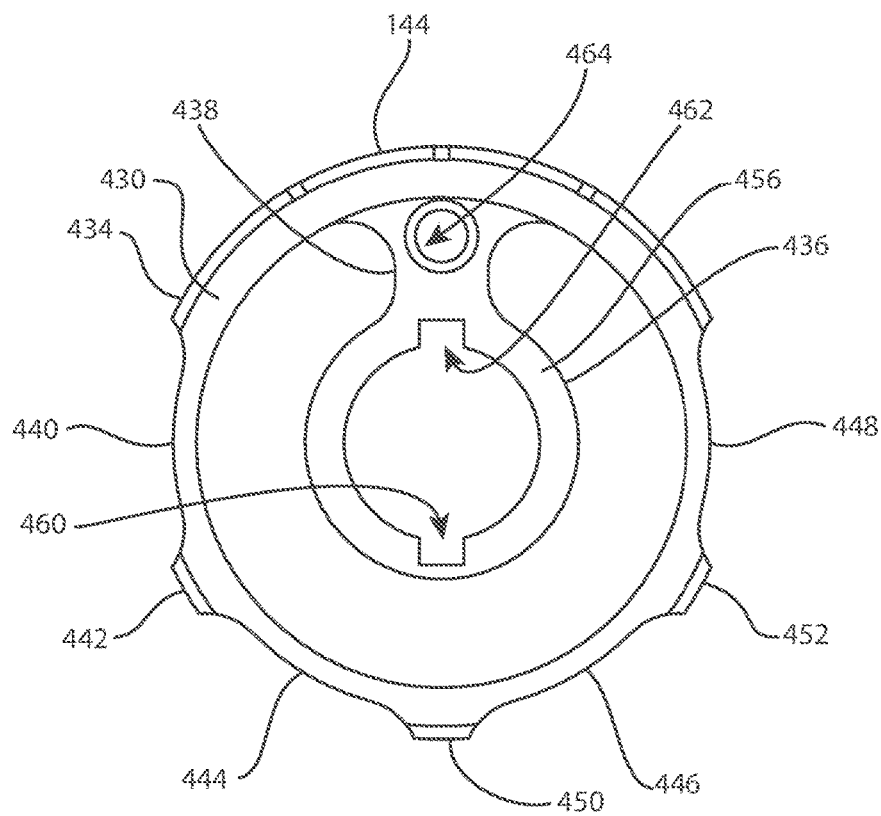
FIG. 15 is a proximal end view of a selector ring of the instrument of FIG. 9.
Figure 16:
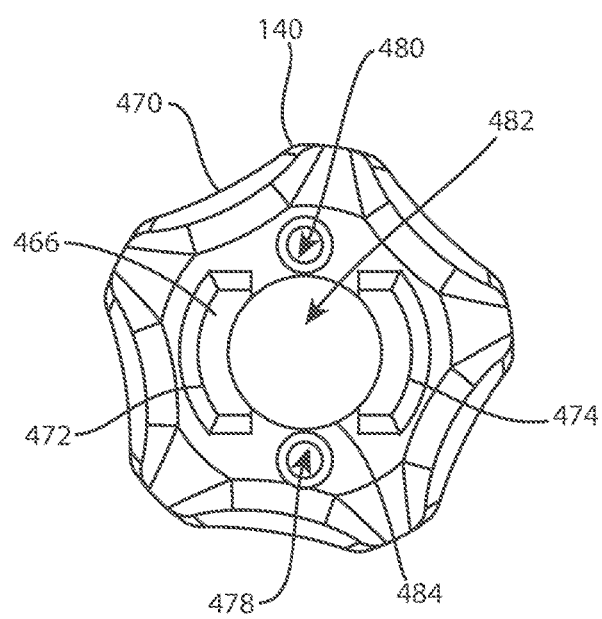
FIG. 16 is a proximal end view of an expansion knob of the instrument of FIG. 9.
Figure 17:
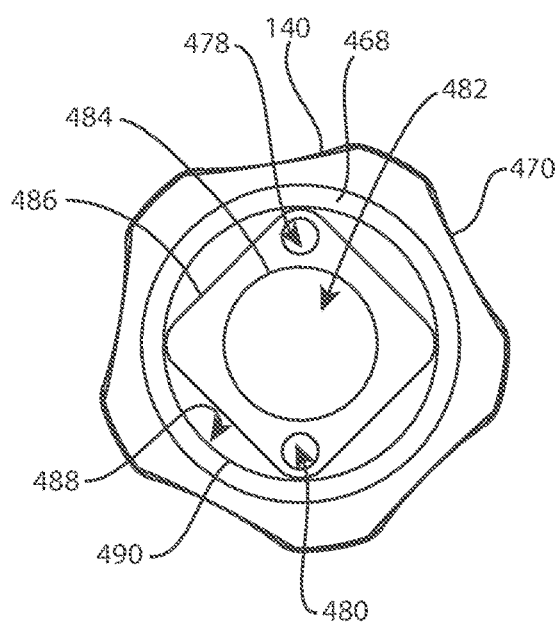
FIG. 17 is a distal end view of the expansion knob of the instrument of FIG. 9.

Referring to FIGS. 9, 10, and 15, the selector ring 144 extends between a proximal side 430 and a distal side 432. The selector ring 144 may include an outer ring 434, an inner ring 436 within the outer ring, and an arm 438 that connects the inner ring to the outer ring. The outer ring 434 may be a generally cylindrical part with flat proximal and distal sides 430, 432. The outer surface of the outer ring 434 may include a longitudinal groove 440 and a longitudinal rib 442. The illustrated example includes four longitudinal grooves 440, 444, 446, 448 and three longitudinal ribs 442, 450, 452. The outer surface of the outer ring 434 may also include indicia 454 such as lines, text, and/or icons as shown to indicate various settings, such as a locked setting, an unlocked setting, and a setting for cleaning. The inner surface of the outer ring 434 may be cylindrical. The inner ring 436 may be a generally cylindrical part with flat proximal and distal sides 456, 458. The proximal side 456 may be recessed relative to the proximal side 430 and the distal side 458 may be recessed relative to the distal side 432. The outer surface of the inner ring 436 may be cylindrical as shown. The inner surface of the inner ring 436 may be cylindrical with bilateral longitudinal rectangular grooves 460, 462. The arm 438 may extend between the inner surface of the outer ring 434 and the outer surface of the inner ring 436. The arm 438 may be aligned with the groove 462. The arm 438 may have a longitudinal hole 464 that extends between the proximal and distal sides 456, 458.

Referring to FIGS. 9,10,16, and 17, the expansion knob 140 extends between a proximal end 466 and a distal end 468. The expansion knob 140 may be generally circular in cross section. The expansion knob 140 may be wider toward the proximal end 466 and narrower toward the distal end 468. The expansion knob 140 may include friction features 470, such as longitudinal grooves, alternating ridges and grooves, knurling, grit blast, or the like. Bilateral tabs 472, 474 may extend proximally. The tabs 472, 474 may have circular outer and inner profiles. The outer sides of the tabs 472, 474 may include indicia 476, such as transverse lines as shown. Bilateral holes 478, 480 may extend distally into the expansion knob 140 and may be located between the tabs 472, 474 (i.e., rotated 90 degrees away from the tabs). The holes 478, 480 may include proximal counterbores.

The expansion knob 140 may include a central longitudinal hole 482 that extends through the expansion knob between the proximal end 466 and the distal end 468. The hole 482 may include, from proximal to distal, first, second, third, and fourth inner portions 484, 486, 488, 490. The first inner portion 484 may have a circular cross section. The first inner portion 484 may extend distally about one third of the overall proximal-distal length of the expansion knob 140. The second inner portion 486 may have a generally rectangular cross section. The cross section may be square with rounded corners as shown. The width across the flat sides and the width across the rounded corners may each be greater than the diameter of the first inner portion 484. The second inner portion 486 may extend distally about one third of the overall proximal-distal length of the expansion knob 140, in other words, the second inner portion may occupy the middle third of the overall proximal-distal length of the expansion knob. The third inner portion 488 may have a circular cross section. The diameter of the third inner portion 488 may be greater than the width across the rounded corners of the second inner portion 486. The third inner portion 488 may end just proximal to the distal end 468. The fourth inner portion 490 may have a circular cross section. The diameter of the fourth inner portion 490 may be the same, similar to, or greater than the width across the rounded corners of the second inner portion 486 and less than the diameter of the third inner portion 488. The fourth inner portion 490 may form a shallow undercut with the third inner portion 488.

Figure 18:
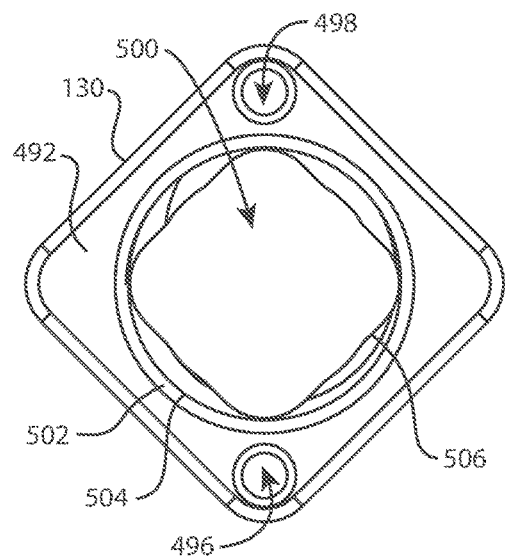
FIG. 18 is a proximal end view of a threaded driver of the instrument of FIG. 9.
Figure 19:
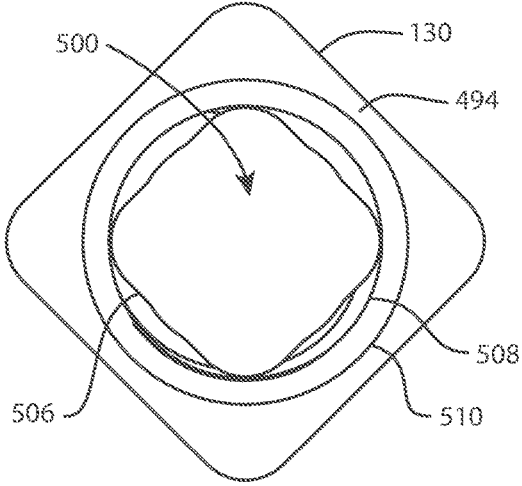
FIG. 19 is a distal end view of the threaded driver of the instrument of FIG. 9.

Referring to FIGS. 9,10,18, and 19, the threaded driver 130 extends between a proximal end 492 and a distal end 494. The threaded driver 130 may be referred to as an actuator. The threaded driver 130 may be a rectangular solid, and may be a cube. Referring to FIGS. 18 and 19, the threaded driver 130 may have rounded corners in a proximal or distal view. Bilateral holes 496, 498 may extend into the proximal end 492 about a third of the overall proximal-distal length of the threaded driver 130. The holes 496, 498 may be located in opposite corners of the proximal end 492. The proximal ends of the holes 496, 498 may include shallow countersinks. The threaded driver 130 may include a central longitudinal hole 500 that extends through the threaded driver between the proximal end 492 and the distal end 494. The hole 500 may include, from proximal to distal, first, second, third, fourth, and fifth inner portions 502, 504, 506, 508, 510. The first inner portion 502 may be a shallow conical countersink around the hole 500 in the proximal end 492. The second inner portion 504 may be a shallow cylindrical counterbore. The third inner portion 506 may include internal threads 512 that receive the external threads 250 of the shuttle 122. Referring to FIGS. 18 and 19, the cross-sectional shape of the third inner portion 506 may be the superposition of a circle defining the minor diameter of the internal threads 512 and a rectangle. The minor diameter of the internal threads 512 may be smaller than the diameter of the second inner portion 504. The major diameter of the internal threads 512 may be greater than the diameter of the second inner portion 504. The rectangle may be a square, and may have rounded corners. The width across the flat sides may be slightly less than the minor diameter of the internal threads 512. The width across the corners may be slightly less than the major diameter of the internal threads 512. The fourth inner portion 508 may be a shallow cylindrical counterbore, with a diameter greater than the minor diameter of the internal threads 512 and less than the major diameter of the internal threads 512. The diameter of the fourth inner portion 508 may be equal to, or similar to, the diameter of the second inner portion 504. The fifth inner portion 510 may be a shallow counterbore around the hole 500 in the distal end 494, with a diameter greater than the major diameter of the internal threads 512.

Referring to FIGS. 9,10, 22, and 23, the shaft assembly 116 may include an impaction cap 146, an inserter connector 138, and an inserter shaft 136.

Figure 22:
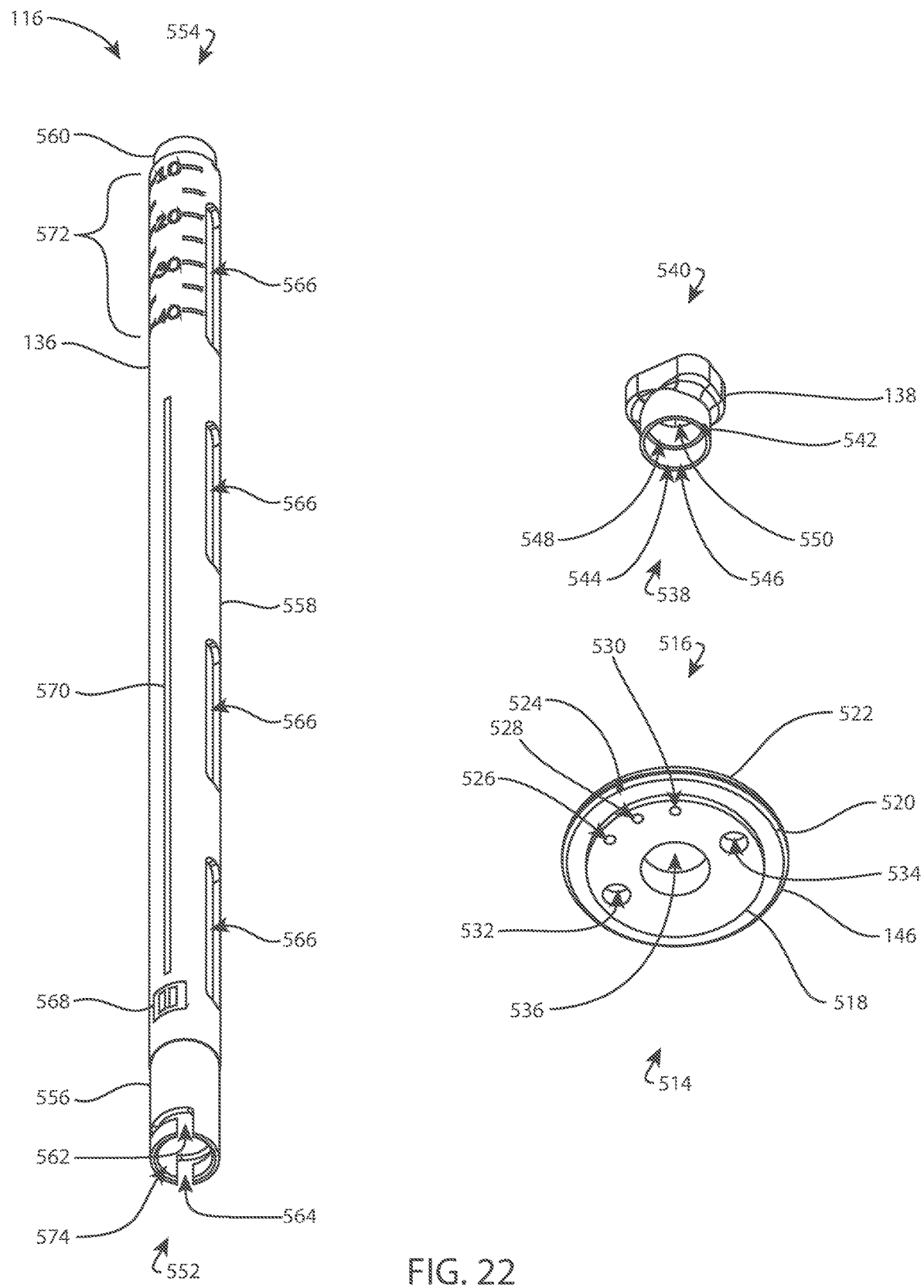
FIG. 22 is an exploded perspective view of a shaft assembly of the instrument of FIG. 1.
Figure 23:
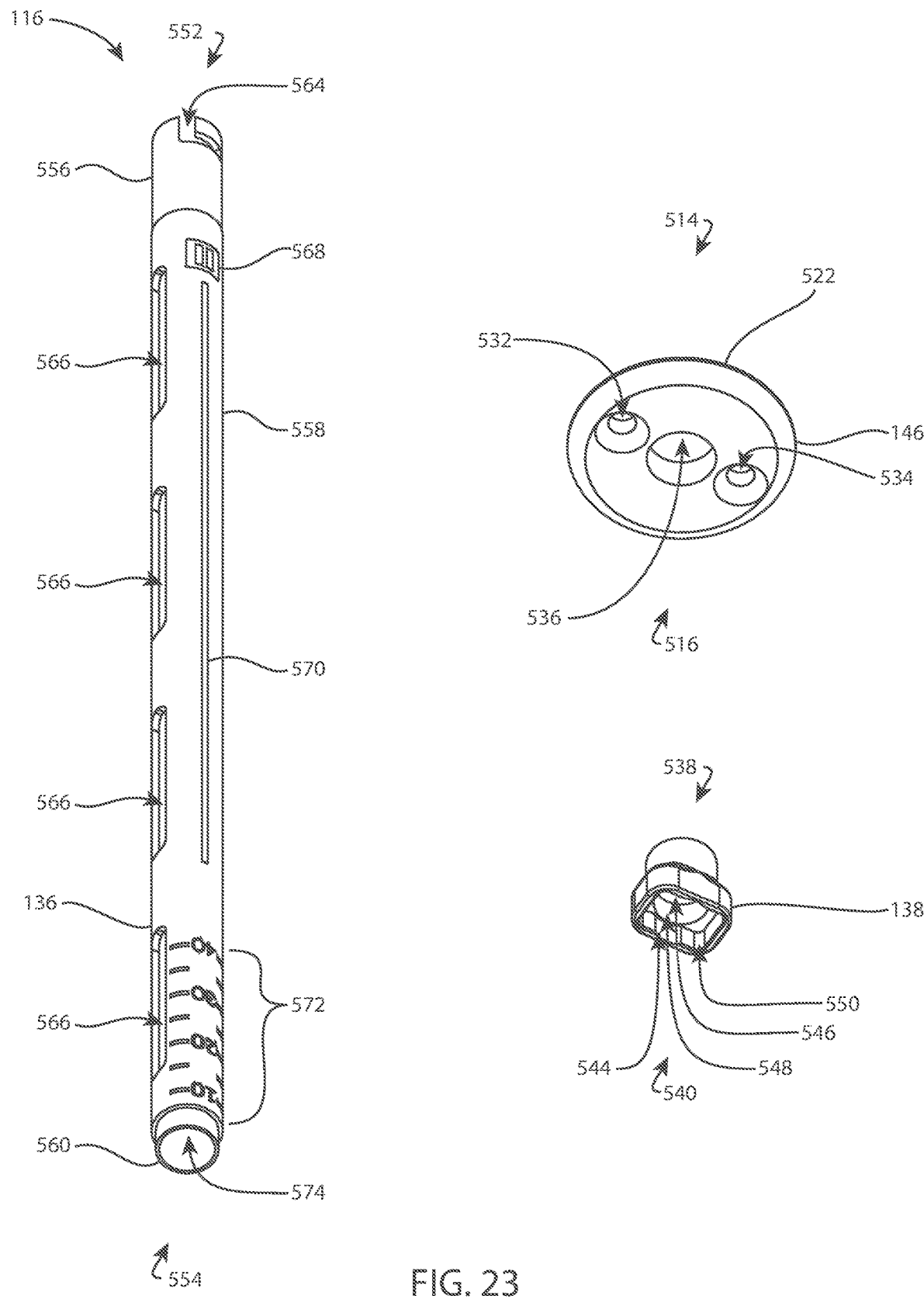
FIG. 23 is another exploded perspective view of the shaft assembly of FIG. 22, from a different direction.
Figure 24:
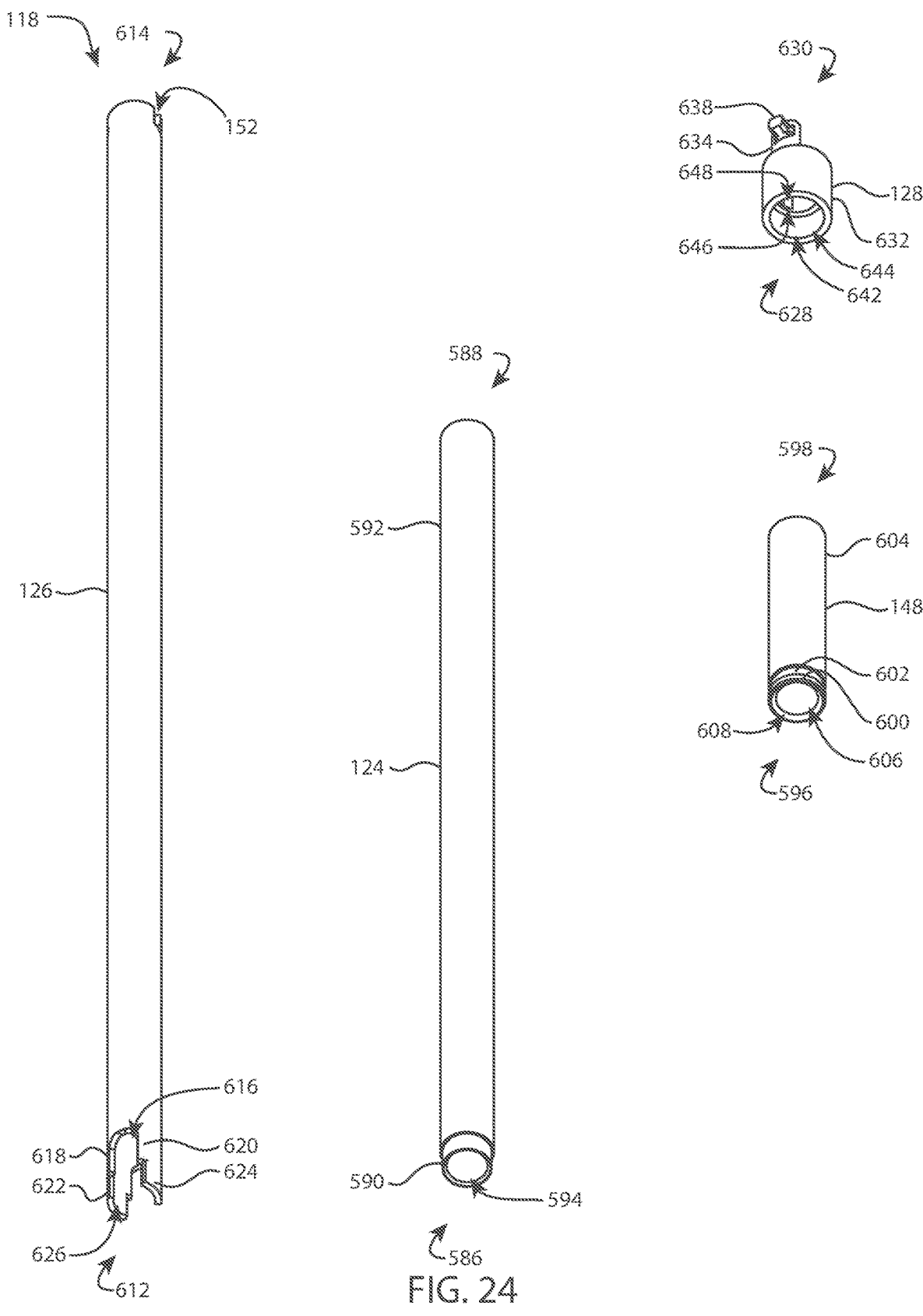
FIG. 24 is an exploded perspective view of a lock tube assembly of the instrument of FIG. 1.
Figure 25:
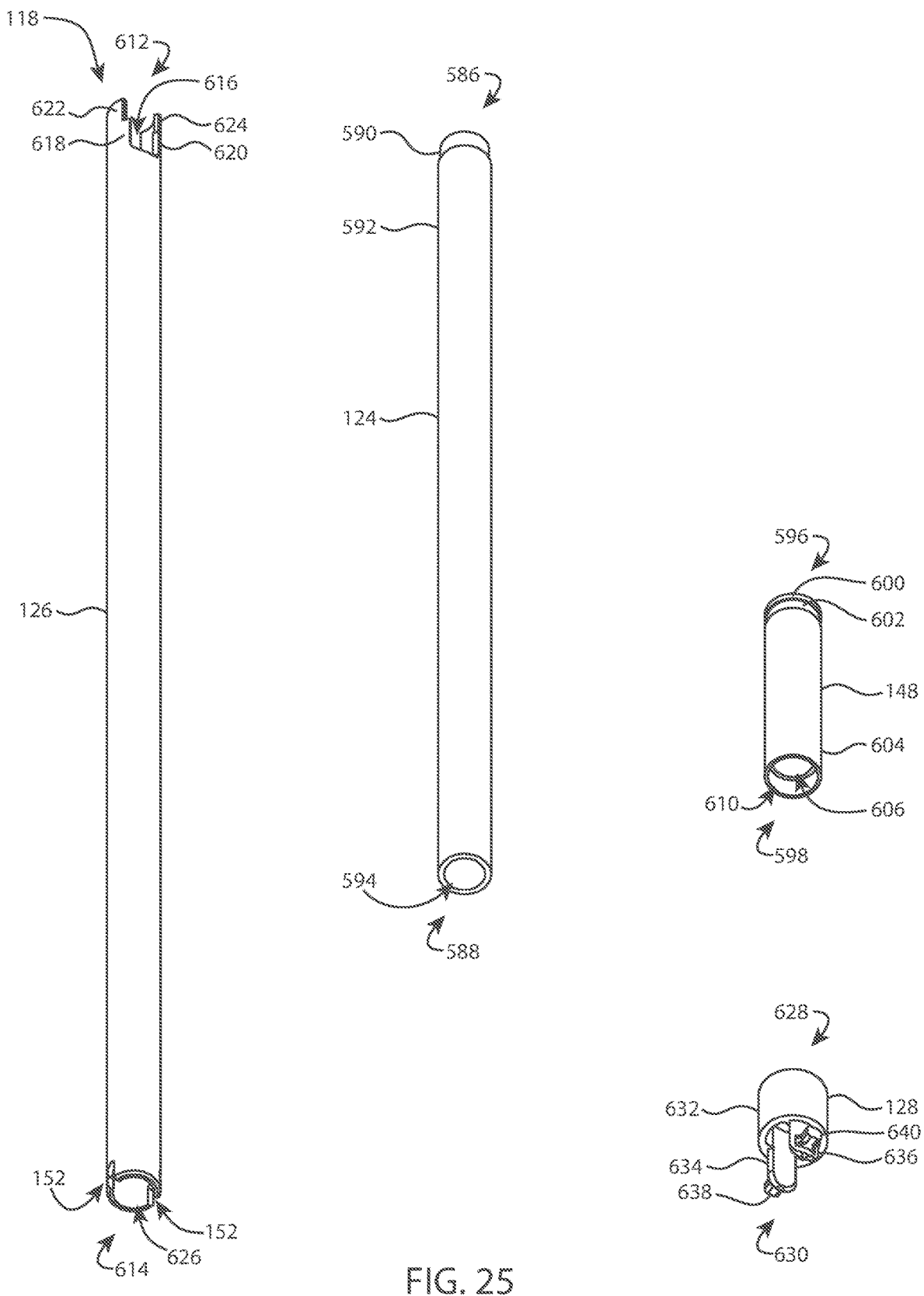
FIG. 25 is another exploded perspective view of the lock tube assembly of FIG. 24, from a different direction.

The impaction cap 146 extends between a proximal side 514 and a distal side 516. The impaction cap 146 may be circular in a proximal or distal view. The impaction cap 146 may include, from proximal to distal, first, second, and third outer portions 518, 520, 522. The first outer portion 518 may be cylindrical. The second outer portion 520 may be conical, and may be referred to as a chamfer. The third outer portion 522 may be cylindrical, and may have a diameter greater than the diameter of the first outer portion 518. An outer distal edge of the third outer portion 522 may be rounded. Indicia 524, such as the mark 524 shown in FIG. 22, may be included on the third outer portion 522. One or more dimples 526 may be included in the proximal side; three evenly spaced dimples 526, 528, 530 are shown. The middle dimple 528 may be aligned with the mark 524. Bilateral holes 532, 534 may extend through the impaction cap 146 between the proximal and distal sides 514, 516. The holes 532, 534 may be symmetrically located relative to the mark 524. Referring to FIG. 23, each hole 532, 534 may include a conical distal countersink. A central hole 536 may extend through the impaction cap 146 between the proximal and distal sides 514, 516.

The inserter connector 138 extends between a proximal end 538 and a distal end 540. The proximal end 538 may be circular in a proximal view. A notch 542 may be present in an outer proximal edge of the proximal end 538. The notch 542 may be rounded or semicircular in a side view. The distal end 540 may be rectangular in a distal view. The distal end 540 may have rounded corners in the distal view. The major dimension (length) of the rectangle may be aligned with the notch 542. The inserter connector 138 may include a central longitudinal hole 544 that extends through the inserter connector between the proximal end 538 and the distal end 540. The hole 544 may include, from proximal to distal, first, second, and third inner portions 546, 548, 550. The first inner portion 546 may have a circular cross section and may extend distally about one third of the overall proximal-distal length of the inserter connector 138. The first inner portion 546 may have a flat distal end. The second inner portion 548 may have a circular cross section with a diameter less than the first inner portion 546. The second inner portion 548 may extend distally about one third of the overall proximal-distal length of the inserter connector 138. Referring to FIG. 23, the cross-sectional shape of the third inner portion 550 may be the superposition of a circle and a rectangle. The diameter of the circle may be less than the diameter of the first inner portion 546 and greater than the diameter of the second inner portion 548. The major dimension (length) of the rectangle may be greater than the diameter of the first inner portion 546, and may be aligned with the major dimension (length) of the rectangle of the distal end 540. The minor dimension (width) of the rectangle may be less than the diameter of the circle, and may be less than the diameter of the second inner portion 548. The rectangle may have rounded corners. The third inner portion 550 may have a flat proximal end. An inner distal edge of the rectangle may be chamfered.

The inserter shaft 136 extends between a proximal end 552 and a distal end 554. The inserter shaft 136 may be a tubular part with circular outer and inner cross-sectional shapes. The inserter shaft 136 may include, from proximal to distal, first, second, and third outer portions 556, 558, 560. The first outer portion 556 may include a pair of shaped slots 562, 564 which each include an approximately 90° bend. The slots 562, 564 may extend longitudinally into the proximal end 552 before making the approximately 90° bend. Each slot 562, 564 may extend through one wall of the first outer portion 556. The outer diameter of the second outer portion 558 may be greater than the outer diameter of the first outer portion 556. The second outer portion 558 may occupy most of the overall proximal-distal length of the inserter shaft 136. The second outer portion 558 may include one or more openings 566. Four openings 566 are shown evenly spaced along the length of the second outer portion 558. Each opening 566 may extend through one wall of the second outer portion 558, or through both walls as shown. The second outer portion 558 may include one or more indicia or markings. Three indicia are shown, from proximal to distal: a sideways "8" 568, a longitudinal line 570, and a set of numerals and transverse lines 572. The indicia may be repeated on the opposite side of the second outer portion 558 as shown in FIGS. 22 and 23. The outer diameter of the third outer portion 560 may be less than the outer diameter of the first outer portion 556. The inserter shaft 136 may include a central longitudinal hole 574 that extends through the inserter shaft between the proximal end 552 and the distal end 554. The hole 574 may be chamfered around its proximal inner edge. The diameter of the hole 574 may be the same as, or similar to, the diameter of the second inner portion 548 of the inserter connector.

The shaft assembly 116 may be assembled by inserting the first outer portion 556 of the inserter shaft 136 into the central hole 536 of the impaction cap 146 so that the proximal side 514 and the proximal end 552 face the same direction, the distal side 516 abuts the proximal end of the second outer portion 558, and the mark 524 is aligned with the sideways "8" 568 and/or the longitudinal line 570; and by inserting the third outer portion 560 of the inserter shaft 136 into the first inner portion 546 of the inserter connector 138 so that the major dimension of the rectangle of the distal end 540 is transverse to, or perpendicular to, the sideways "8" 568 and/or the longitudinal line 570. The shaft assembly 116 may be a weldment. Alternatively, the impaction cap 146, inserter connector 138, and/or inserter shaft 136 may be combined into a single part.

Referring to FIGS. 9 and 10, the standoff 132 extends between a proximal end 576 and a distal end 578. The standoff 132 may be a tubular part with circular outer and inner cross-sectional shapes. The standoff 132 may include, from proximal to distal, first and second outer portions 580, 582. The first outer portion 580 may extend over most of the overall proximal-distal length of the standoff 132. The outer diameter of the second outer portion 580 may be greater than the outer diameter of the first outer portion 580 so that the second outer portion 580 forms a flange around the distal end 578. The standoff 132 may include a central longitudinal hole 584 that extends through the standoff between the proximal end 576 and the distal end 578.

Referring to FIGS. 9, 10, 24, and 25, the lock tube assembly 118 may include a proximal lock tube 124, a proximal lock tube end part 148, a distal lock tube 126, and a lock tube coupling 128.

The proximal lock tube 124 extends between a proximal end 586 and a distal end 588. The proximal lock tube 124 may be a tubular part with circular outer and inner cross-sectional shapes. The proximal lock tube 124 may include, from proximal to distal, first and second outer portions 590, 592. The first outer portion 590 may extend distally a short distance. The diameter of the second outer portion 592 may be greater than the diameter of the first outer portion 590. The second outer portion 592 may extend over most of the overall proximal-distal length of the proximal lock tube 124. The proximal lock tube 124 may include a central longitudinal hole 594 that extends through the proximal lock tube between the proximal end 586 and the distal end 588. The hole 594 may be chamfered around its proximal inner edge.

The proximal lock tube end part 148 extends between a proximal end 596 and a distal end 598. The proximal lock tube end part 148 may be a tubular part with circular outer and inner cross-sectional shapes. The proximal lock tube end part 148 may include, from proximal to distal, first, second, and third outer portions 600, 602, 604. The first outer portion 600 may extend distally a short distance, and may include a chamfer around its proximal outer edge. The diameter of the second outer portion 602 may be less than the diameter of the first outer portion 600. The second outer portion 602 may also extend distally a short distance. The diameter of the third outer portion 604 may be greater than the diameter of the second outer portion 602, and may be equal to the diameter of the first outer portion 600. Thus, the second outer portion 602 may be referred to as an exterior groove around the proximal end 596. There may be a short tapered transition between the distal end of the second outer portion 602 and the proximal end of the third outer portion 604. The proximal lock tube end part 148 may include a central longitudinal hole 606 that extends through the proximal lock tube end part between the proximal end 596 and the distal end 598. The hole 606 may include a chamfer 608 around its proximal inner edge, and may include a distal counterbore 610. The inner diameter of the hole 606 may be the same as, or similar to, the inner diameter of the hole 594.

The distal lock tube 126 extends between a proximal end 612 and a distal end 614. The distal lock tube 126 may be a tubular part with circular outer and inner cross-sectional shapes. The proximal end 612 may include a transverse notch 616 that extends through both walls of the distal lock tube 126. The notch 616 may include a rounded distal end. The notch 616 may divide the proximal end 612 into a pair of tabs 618, 620. The notch 616 may step up in width proximally and correspondingly, each tab 618, 620 may step down in width proximally to form fingers 622, 624. The distal end 614 may be chamfered around its outer distal edge. With brief reference to FIG. 49, the distal end 614 may include a pair of shaped slots 152 which each include an approximately 90° bend. The slots 152 may extend longitudinally into the distal end 614 before making the approximately 90° bend. Each slot 152 may extend through one wall of the distal lock tube 126. The distal lock tube 126 may include a central longitudinal hole 626 that extends through the distal lock tube between the proximal end 612 and the distal end 614. The inner diameter of the hole 626 may be the same as, or similar to, the inner diameter of the hole 594.

Figure 20:
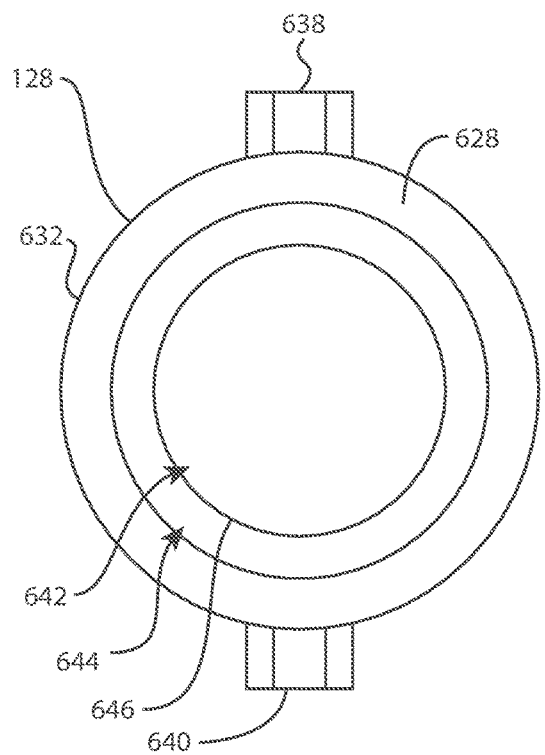
FIG. 20 is a proximal end view of a lock tube coupling of the lock tube assembly of FIG. 24.
Figure 21:
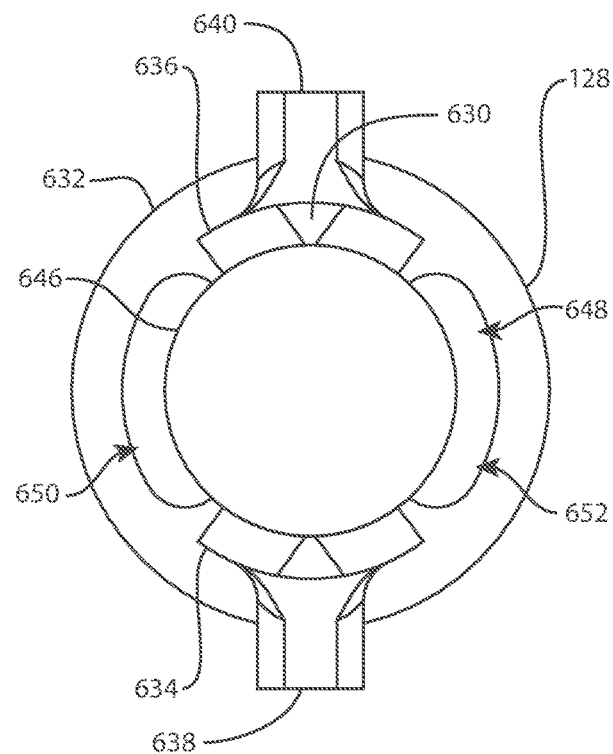
FIG. 21 is a distal end view of the lock tube coupling of the lock tube assembly of FIG. 24.

Referring to FIGS. 24, 25, 20, and 21, the lock tube coupling 128 extends between a proximal end 628 and a distal end 630. The lock tube coupling 128 may be a tubular part. The lock tube coupling 128 may include a proximal body 632 which may have a circular cross-sectional outer shape, and may extend distally about half or three-fifths of the overall proximal-distal length of the lock tube coupling 128. Bilateral tabs 634, 636 may protrude distally from opposite sides of the body 632. The tabs 634, 636 may be inset relative to the outer diameter of the body 632. The distal portions of the tabs 634, 636 may include posts 638, 640, respectively. The posts 638, 640 may protrude outwardly from the outer sides of the tabs 634, 636, and may protrude beyond the outer diameter of the body 632 as shown in FIGS. 20 and 21. The lock tube coupling 128 may include a central longitudinal hole 642 that extends through the lock tube coupling between the proximal end 628 and the distal end 630. The hole 642 may include, from proximal to distal, first, second, and third inner portions 644, 646, 648. The first inner portion 644 may have a circular cross section and may extend distally about a third of the overall proximal-distal length of the lock tube coupling 128, or about half of the length of the body 632. The second inner portion 646 may have a circular cross section with a diameter less than the diameter of the first inner portion 644. The diameter of the second inner portion 646 may be the same as, or similar to, the inner diameter of the hole 594. The second inner portion 646 may extend distally only a short distance as a complete diameter, but sections of it may extend through the distal end to form the inner sides of the tabs 634, 636. The third inner portion 648 may have a non-circular cross section that includes bilateral alcoves 650, 652 in the distal walls of the body 632 between the tabs 634, 636 (in other words, the alcoves 650, 652 are located 90° away from the tabs 634, 636).

The lock tube assembly 118 may be assembled by inserting the first outer portion 590 of the proximal lock tube 124 into the distal counterbore 610 of the proximal lock tube end part 148; inserting the distal end 588 of the proximal lock tube 124 into the first inner portion 644 of the lock tube coupling 128; and inserting the proximal end 612 of the distal lock tube 126 into the third inner portion 648 of the lock tube coupling 128 so that the fingers 622, 624 are received in the alcoves 650, 652 and the tabs 634, 636 are received in the notch 616. The hole 594 of the proximal lock tube 124, the hole 606 of the proximal lock tube end part 148, the hole 626 of the distal lock tube 126, and the second inner portion 646 of the hole 642 of the lock tube coupling 128 may together form the longitudinal instrument bore 112. The proximal lock tube 124, proximal lock tube end part 148, distal lock tube 126, and lock tube coupling 128 may be permanently connected, for example by welding. Alternatively, the proximal lock tube 124, proximal lock tube end part 148, distal lock tube 126, and/or lock tube coupling 128 may be combined into a single part.

The instrument 100 may be assembled by coupling the shaft assembly 116 to the lock tube assembly 118; coupling the selector ring 144 to the shaft assembly 116 and lock tube assembly 118; coupling the inserter handle 142 to the shaft assembly 116, lock tube assembly 118, and selector ring 144; coupling the standoff 132 and the standoff nut 134 to the shaft assembly 116, lock tube assembly 118, selector ring 144, and inserter handle 142; coupling the threaded driver 130 and the shuttle assembly 114 to the expansion knob 140; coupling the shuttle assembly, threaded driver, and expansion knob 140 to the shaft assembly 116, lock tube assembly 118, selector ring 144, and inserter handle 142.

Coupling the shaft assembly 116 to the lock tube assembly 118 may include inserting the distal end 614 of the distal lock tube 126 into the hole 574 in the proximal end 552 of the inserter shaft 136, advancing the lock tube assembly 118 distally until the posts 638, 640 enter the shaped slots 562, 564, and twisting the lock tube assembly 118 counterclockwise so that the posts 638, 640 are captured in the shaped slots 562, 564.

Coupling the selector ring 144 to the shaft assembly 116 and lock tube assembly 118 may include inserting the proximal end 596 of the proximal lock tube end part 148 into the inner ring 436 of the selector ring 144 and advancing the lock tube assembly 118 proximally until the posts 638, 640 enter the grooves 460, 462 and the hole 464 is aligned with the middle dimple 528. A compression spring or a ball detent may be received in the hole 464 to engage the dimples 526, 528, 530.

Coupling the inserter handle 142 to the shaft assembly 116, lock tube assembly 118, and selector ring 144 may include inserting the proximal end 596 of the proximal lock tube end part 148 into the hole 414 in the distal end 386 of the inserter handle 142, advancing the lock tube assembly 118 proximally until the collar portion 408 enters the space between the outer ring 434 and the inner ring 436, and inserting fasteners such as screws through the holes 532, 410 and the holes 534, 412.

Coupling the standoff 132 and the standoff nut 134 to the shaft assembly 116, lock tube assembly 118, selector ring 144, and inserter handle 142 may include inserting the proximal end 596 of the proximal lock tube end part 148 into the hole 584 in the distal end 578 of the standoff 132, advancing the lock tube assembly 118 proximally until the distal end 578 abuts the proximal end 384 of the inserter handle 142, inserting the proximal end 596 into the hole 374 in the distal side 360 of the standoff nut 134, advancing the lock tube assembly 118 proximally until the distal side 360 abuts the proximal end 384, and engaging the internal threads of the third inner portion 380 with the external threads of the first outer portion 388 to make a tight connection. The notches 364, 366 may facilitate tightening.

Coupling the threaded driver 130 and the shuttle assembly 114 to the expansion knob 140 may include inserting the proximal end 492 of the threaded driver 130 into the hole 482 in the distal end 468 of the expansion knob 140, aligning the hole 478 with the hole 496, advancing the threaded driver 130 proximally into the second inner portion until the proximal end 492 abuts the proximal end of the second inner portion 486, inserting the distal end 186 of the shuttle 122 into the hole 482 in the proximal end 466 of the expansion knob 140, advancing the shuttle assembly 114 distally until the distal end 186 abuts the proximal end 492 of the threaded driver 130, aligning the fourth outer portion 246 with the third inner portion 506, advancing the shuttle assembly 114 farther distally until the distal end of the second outer portion 242 abuts the proximal end 492, and engaging the external threads 250 of the second outer portion 242 with the internal threads 512 of the third inner portion 506 until the shuttle assembly 114, expansion knob 140, and threaded driver 130 achieve a snug connection.

Coupling the shuttle assembly 114, threaded driver 130, and expansion knob 140 to the shaft assembly 116, lock tube assembly 118, selector ring 144, and inserter handle 142 may include inserting the proximal end 596 of the proximal lock tube end part 148 into the hole 252 in the distal end 186 of the shuttle; advancing the lock tube assembly 118 proximally until the fifth inner portion 510 of the threaded driver 130 receives the proximal end 576 of the standoff 132, the third inner portion 488 of the expansion knob 140 receives the standoff nut 134, the fourth inner portion 490 of the expansion knob 140 receives the third outer portion 392 of the inserter handle 142, the distal end 468 of the expansion knob 140 abuts the distal end of the third outer portion 392, and the second inner portion 418 of the hole 414 of the inserter handle 142 receives the fourth outer portion 246 of the 122; and inserting fasteners such as screws through the holes 478, 496 and the holes 480, 498.

The instrument 100 may be operated by sliding the lock collar 120, rotating the selector ring 144, or rotating the expansion knob 140.

Referring to FIGS. 11 and 12, the lock collar 120 is coupled to the shuttle 122 so that the lock collar 120 can slide relative to the shuttle 122 along a direction established by the undercut grooves 298, 346, feet 294, 296, and slot 292. The travel of the lock collar 120 may be limited by the presence of a pin in the slot 292 and the hole 234 of the shuttle 122. In this arrangement, the lock collar 120 may slide between a first position and a second position. In the first position, the pin may contact the end of the slot 292 that is closest to the first curved side 278 of the hole 276. The first position may be referred to as an open or unlocked position. In the second position, the pin may contact the end of the slot 292 that is closest to the outer curved side 268. The second position may be referred to as a closed or locked position. The lock collar 120 may be biased toward the second position.

Figure 14:
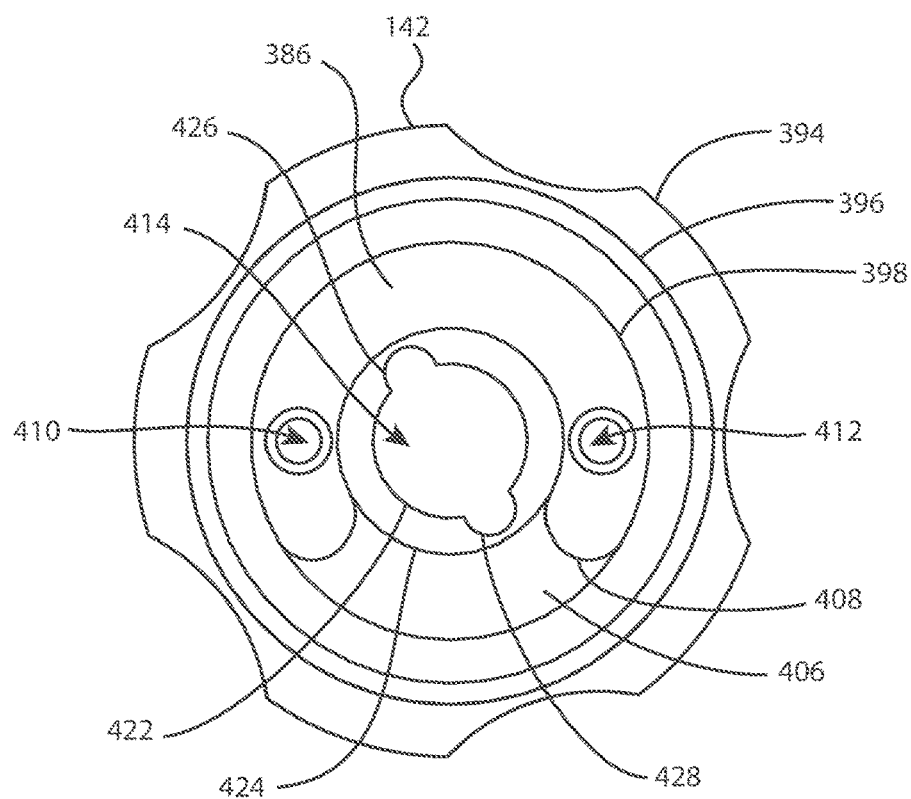
FIG. 14 is a distal end view of the inserter handle of the instrument of FIG. 9.

Referring to FIGS. 9, 10, and 15, the selector ring 144 is coupled to the posts 638, 640 of the lock tube coupling 128 so that rotation of the selector ring 144 causes rotation of the lock tube assembly 118 relative to the rest of the instrument 100. Referring to FIGS. 14 and 15, rotation of the selector ring 144 is limited by the presence of the collar portion 408 in the space between the outer ring 434 and the inner ring 436. In the example shown, the selector ring 144 is rotatable between a first position and a third position. In the first position, the arm 438 may contact the end of the collar portion 408 that includes the hole 412, the hole 464 may align with the dimple 530, the indicia 454 for the cleaning setting may align with the distally-pointing arrow indicium 402, the posts 638, 640 may be positioned in the shaped slots 562, 564 so that the posts are free to slide axially out of the slots, and the posts 638, 640 may be aligned with the grooves 426, 428. The first position may be referred to as a cleaning position because the lock tube assembly 118 and/or other parts of the instrument 100 are positioned for disassembly for cleaning or reassembly after cleaning. In the third position, the arm 438 may contact the end of the collar portion 408 that includes the hole 410, the hole 464 may align with the dimple 526, the indicia 454 for the locked setting may align with the distally-pointing arrow indicium 402, the posts 638, 640 may be positioned in the shaped slots 562, 564 so that the posts are captured in the slots, the posts 638, 640 may be rotated out of alignment with the grooves 426, 428, and the shaped slots 152 may be positioned with their distal openings aimed into the corners of the third inner portion 550 of the hole 544 of the inserter connector 138. The third position may be referred to as a locked position because the parts of the instrument 100 are positioned to lock the implant 1000 to the instrument. The selector ring 144 may be rotatable to a second position which is between the first and third positions. In the second position, the arm 438 may be centered in the open side of the collar portion 408, the hole 464 may align with the dimple 528, the indicia 454 for the unlocked setting may align with the distally-pointing arrow indicium 402, the posts 638, 640 may be positioned in the shaped slots 562, 564 so that the posts are captured in the slots, the posts 638, 640 may be rotated out of alignment with the grooves 426, 428, and the shaped slots 152 may be positioned with their distal openings aimed along the major dimension (length) of the third inner portion 550 of the hole 544 of the inserter connector 138. The second position may be referred to as an unlocked position because the parts of the instrument 100 are positioned so that the implant 1000 may be coupled to or decoupled from the instrument 100.

Referring to FIGS. 9-12, 13, 14, and 16-19, the expansion knob 140 is coupled to the shuttle assembly 114, the threaded driver 130, and the inserter handle 142 so that rotation of the expansion knob 140 causes linear translation of the shuttle assembly 114 along the longitudinal instrument axis 102 without rotation of the shuttle assembly 114 about the axis 102. The threaded driver 130 is received in the second inner portion 486 of the hole 482 of the expansion knob 140 so that rotation of the expansion knob 140 causes rotation of the threaded driver 130. The external threads 250 of the second outer portion 242 of the shuttle 122 are received by the internal threads 512 of the third inner portion 506 of the threaded driver 130 and the fourth outer portion 246 of the shuttle 122 is received in the second inner portion 418 of the hole 414 of the inserter handle 142 so that rotation of the threaded driver 130 causes linear translation of the shuttle assembly 114 along the longitudinal instrument axis 102. In the example shown, the shuttle assembly 114 is movable between a first position and a third position. In the first position, the distal side of the flange 232 of the shuttle 122 may abut the proximal end 466 (tabs 472, 474) of the expansion knob 140, the proximal end of the external threads 250 of the second outer portion of the shuttle 122 may be even with, or close to, the proximal end 492 of the threaded driver 130, and the indicia 248 of the shuttle 122 for the collapsed configuration may be aligned with the indicia 476 of the expansion knob 140. The first position may be referred to as a collapsed position for this reason. In the third position, the distal end of the external threads 250 may be even with, or close to, the distal end 494 of the threaded driver 130, and the indicia 248 of the shuttle 122 for the vertically expanded configuration may be aligned with the indicia 476 of the expansion knob 140. The third position may be referred to as a vertically expanded position for this reason. The shuttle assembly 114 may be movable to a second position which is between the first and third positions. In the second position, the distal end of the external threads 250 may be even with, or close to, the proximal end 358 of the standoff nut 134 and the indicia 248 of the shuttle 122 for the laterally expanded configuration may be aligned with the indicia 476 of the expansion knob 140. The second position may be referred to as a laterally expanded position for this reason. The shuttle assembly 114 may be movable to any number of positions between the first and third positions due to the threaded interconnection between the shuttle 122 and the threaded driver 130.

Various additional tools may be used with instrument 100 to implant and expand an intervertebral implant. The instrument 100 and selected additional tools may be provided in a kit and may be collectively referred to as an instrument system 115. FIGS. 26-30 disclose additional tools of the instrument system 115, including a draw bar assembly 160, a graft funnel 170, a tamp assembly 180, and a screwdriver assembly 190. The draw bar assembly 160 may include a threaded tip 162 and a handle 164. The screwdriver assembly 190 may be assembled with a screw holder 200 to hold and drive a lockout screw 654 into an implant such as implant 1000 to lock the implant in an expanded configuration. The instrument system 115 may be used to implant and/or expand other expandable implants.

Figure 31:
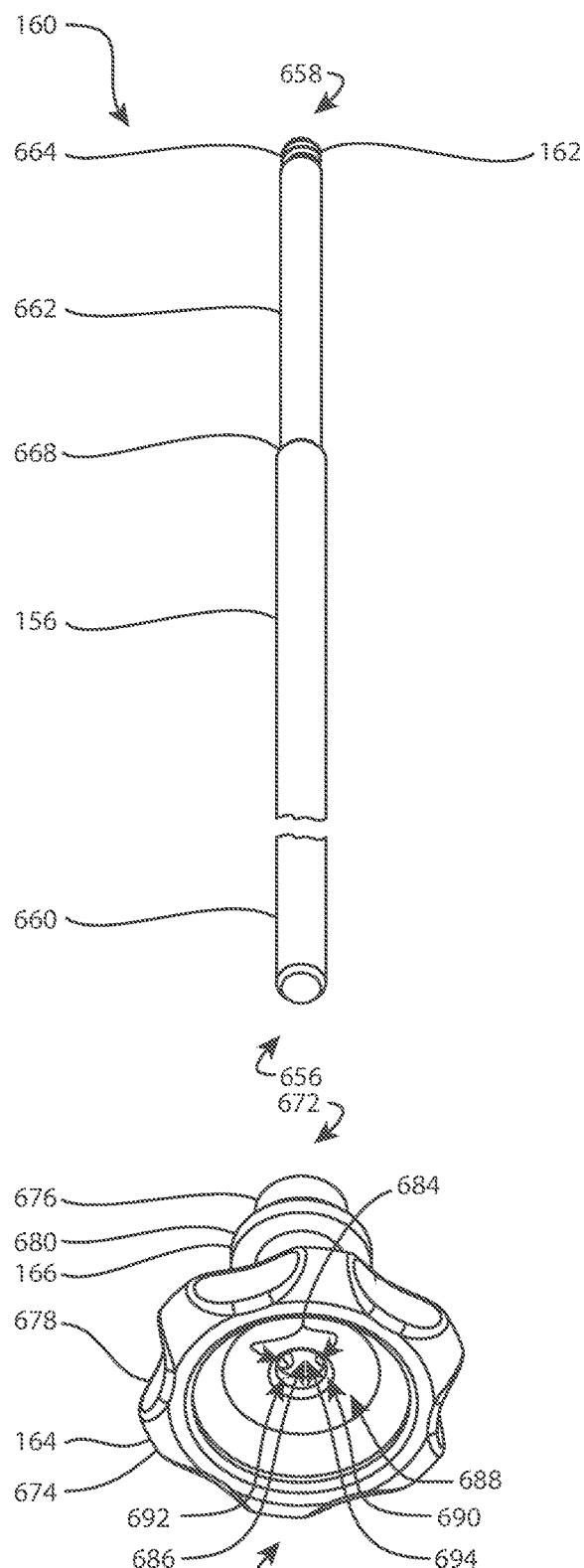
FIG. 31 is an exploded perspective view of the draw bar assembly of FIG. 26.
Figure 32:
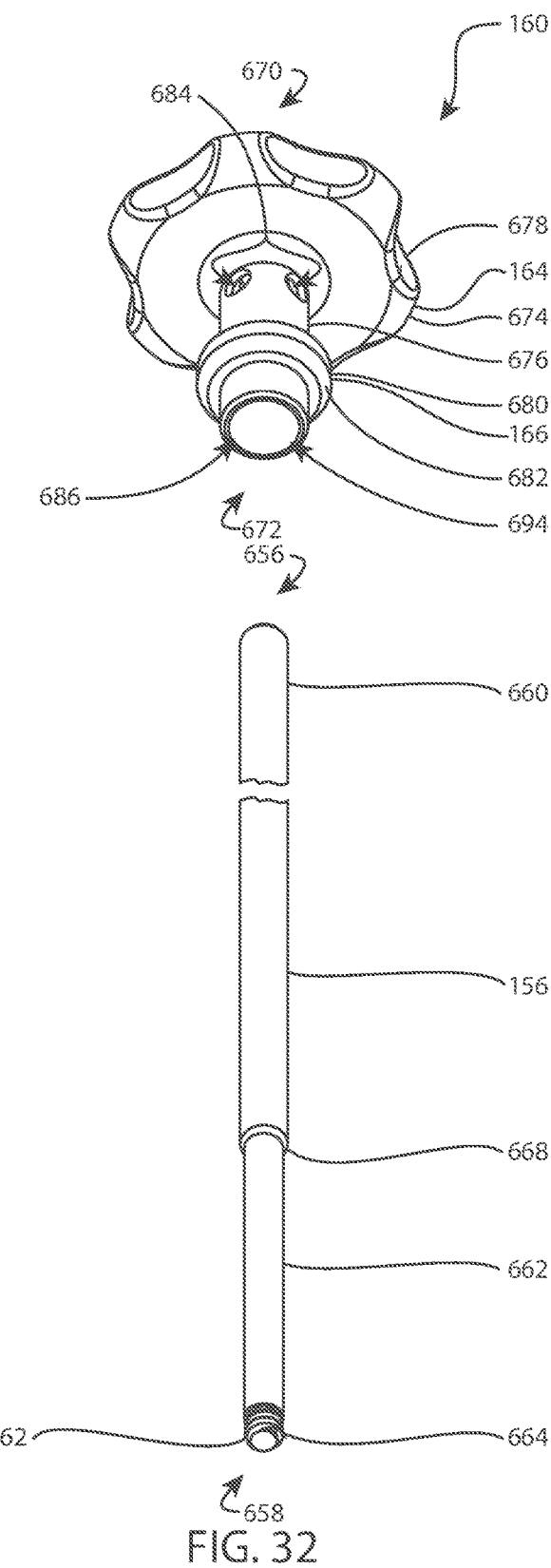
FIG. 32 is another exploded perspective view of the draw bar assembly of FIG. 26, from a different direction.

Referring to FIGS. 26, 31, and 32, the draw bar assembly 160 may include a draw bar 156 and a draw bar knob or handle 164.

The draw bar 156 extends between a proximal end 656 and a distal end 658. The draw bar 156 may be a cylindrical shaft as shown. The draw bar 156 may include, from proximal to distal, first, second, and third outer portions 660, 662, 664. The first outer portion 660 may extend distally most of the overall proximal-distal length of the draw bar 156, and may be chamfered around its proximal outer edge. The diameter of the second outer portion 662 may be less than the diameter of the first outer portion 660. A tapered shoulder 668 may be included between the first and second outer portions 660, 662. The third outer portion 664 may include the threaded tip 162 with external threads. The major diameter of the threads may be less than the diameter of the second outer portion 662.

The draw bar handle 164 extends between a proximal end 670 and a distal end 672. The draw bar handle 164 may include, from proximal to distal, a knob body 674 and a shaft 676. The knob body 674 may be generally disc-shaped with an outer diameter that is greater than its proximal-distal length. The knob body 674 may include one or more grip features 678 such as the six rim scallops shown. The outer diameter of the shaft 676 may be less than the outer diameter of the knob body 674 and the proximal-distal length of the shaft may be greater than the proximal-distal length of the knob body 674. The shaft 676 may include a flange 680 (annulus 166) that extends circumferentially around a middle portion of the shaft. The flange 680 may include a distal chamfer 682. The shaft 676 may include one or more holes 684 that extend transversely into, or through, the shaft; two through holes 684 are shown just distal to the distal side of the knob body 674. The two through holes 684 are perpendicular to each other. The draw bar handle 164 may include a central longitudinal hole 686 that extends through the draw bar handle between the proximal end 670 and the distal end 672. The hole 686 may include, from proximal to distal, first, second, third, and fourth inner portions 688, 690, 692, 694. The first inner portion 688 may have a circular cross section and may extend distally about half, or most, of the proximal-distal length of the knob body 674. The first inner portion 688 may have a flat distal end. A circumferential fillet radius may be present around the proximal inner edge of the first inner portion 688. A circumferential fillet radius may be present in the distal inner corner of the first inner portion 688. The second inner portion 690 may be conical. The second inner portion 690 may be referred to as a countersink or circumferential chamfer associated with the third inner portion 692. The major diameter of the second inner portion 690 may be less than the diameter of the first inner portion 688. The third inner portion 692 may have a circular cross section and may extend distally to the same or similar level as the distal side of the knob body 674. The diameter of the third inner portion 692 may be less than the diameter of the first inner portion 688. The fourth inner portion 694 may have a circular cross section and may extend distally through the distal end of the 672 of the draw bar handle 164. The diameter of the fourth inner portion 694 may be less than the diameter of the first inner portion 688 and greater than the major diameter of the second inner portion 690 and the diameter of the third inner portion 692. The fourth inner portion 694 may have a flat proximal end. The hole(s) 684 may extend into a proximal end of the fourth inner portion 694.

The draw bar assembly 160 may be assembled by inserting the proximal end 656 of the draw bar 156 into the hole 686 of the draw bar handle 164 so that the first portion 660 is received in the third inner portion 692 and the proximal end 656 is at the same or similar level with the distal end of the first inner portion 688. A circumferential gap 696 may exist between the outer surface of the first portion 660 and the inner surface of the fourth inner portion 694. See FIG. 5. The draw bar 156 and draw bar handle 164 may be permanently connected, for example by welding. Alternatively, the draw bar 156 and draw bar handle 164 may be combined into a single part.

The draw bar 156 may be received in the lock tube assembly 118, more specifically in the hole 606 of the proximal lock tube end part 148, the hole 594 of the proximal lock tube 124, the second inner portion 646 of the hole 642 of the lock tube coupling 128, and the hole 626 of the distal lock tube 126.

Figure 33:
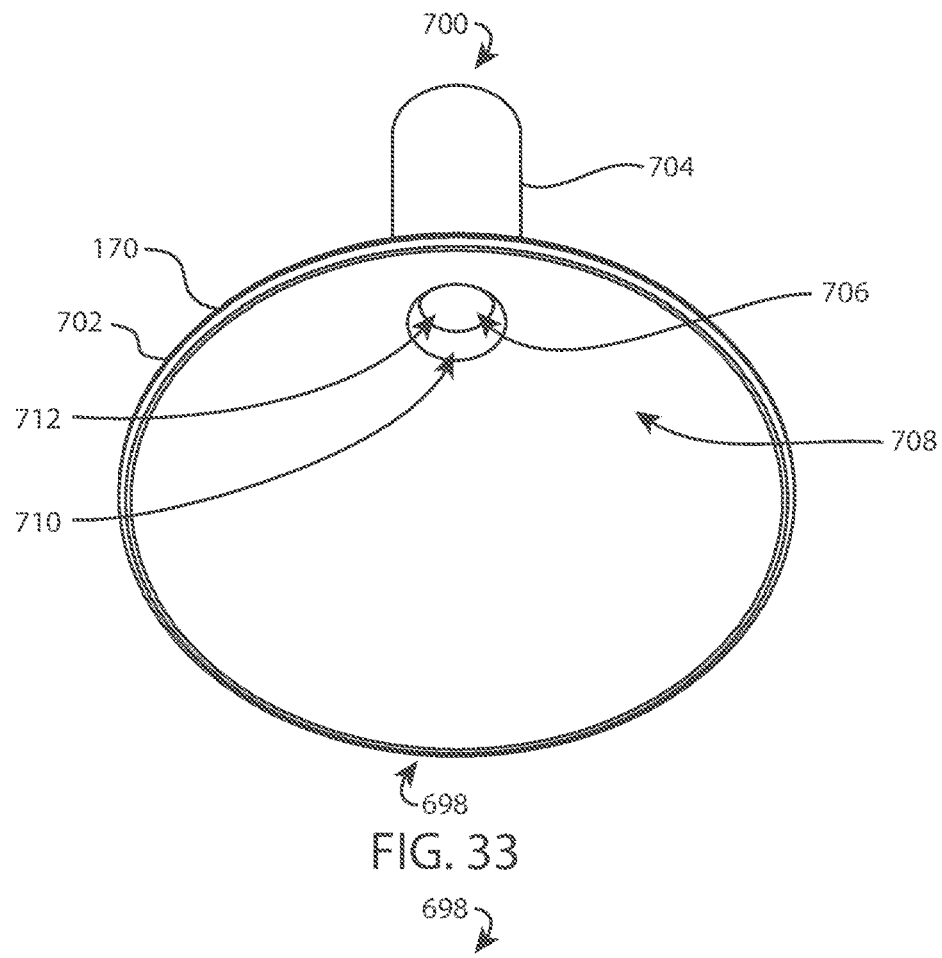
FIG. 33 is a perspective view of the funnel of FIG. 28.
Figure 34:
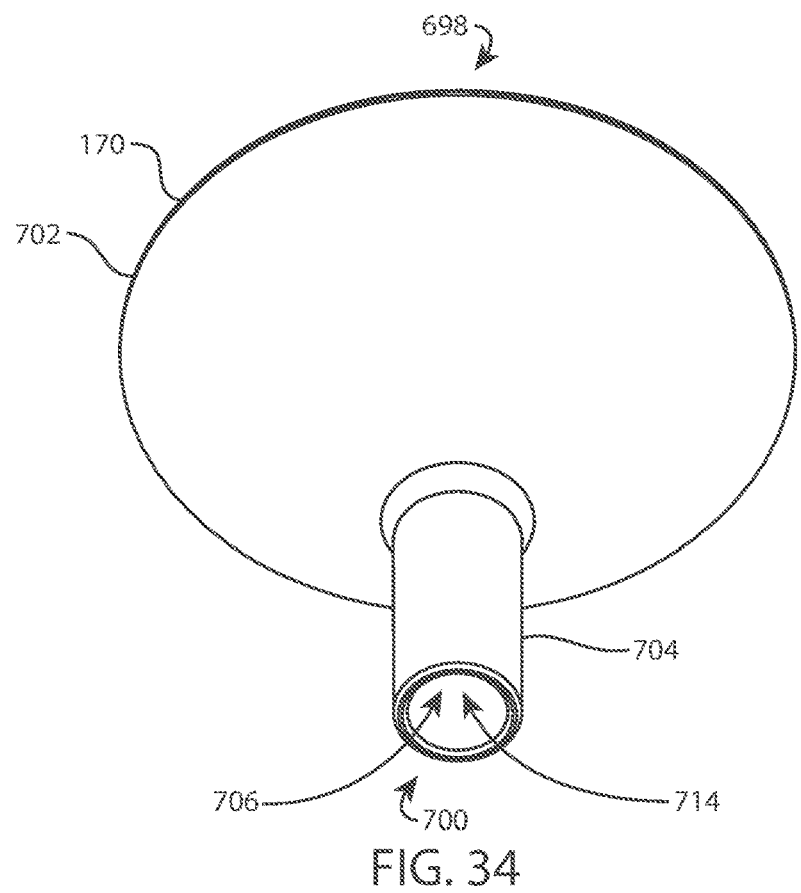
FIG. 34 is another perspective view of the funnel of FIG. 28, from a different direction.

Referring to FIGS. 28, 33, and 34, the graft funnel 170 extends between a proximal end 698 and distal end 700. The graft funnel 170 may include a proximal mouth 702 and a distal stem 704. The mouth 702 and the stem 704 may have circular cross sections. The mouth 702 may be conical or otherwise tapered. The diameter of the stem 704 may be much less than the diameter of the mouth 702. The graft funnel 170 may include a central longitudinal hole 706 that extends through the graft funnel between the proximal end 698 and the distal end 700. The hole 706 may include, from proximal to distal, first, second, third, and fourth inner portions 708, 710, 712, 714. Each of these inner portions may have a circular cross section. The first inner portion 708 may be conical or otherwise tapered, and may be shaped like the mouth 702. The second inner portion 710 may be described as a fillet radius transition or throat between the first inner portion 708 and the third inner portion 712. The second inner portion 710 may be at the same or similar level as the transition between the mouth 702 and the stem 704. The diameter of the third inner portion 712 may be less than the minor diameter of the first inner portion 708. The fourth inner portion 714 may extend proximally about half or more of the proximal-distal length of the stem 704. The diameter of the fourth inner portion 714 may be greater than the diameter of the third inner portion 712. The proximal end of the fourth inner portion 714 may be flat, and a circumferential chamfer may be present at the inner edge between the third and fourth inner portions 712, 714.

The stem 704 may be received by the second inner portion 256 of the hole 252 of the shuttle 122 of the shuttle assembly 114. The fourth inner portion 714 may receive the proximal end 596 of the proximal lock tube end part 148 of the lock tube assembly 118. The diameter of the third inner portion 712 may be the same as or similar to the diameter of the hole 606.

Figures 35, 36:
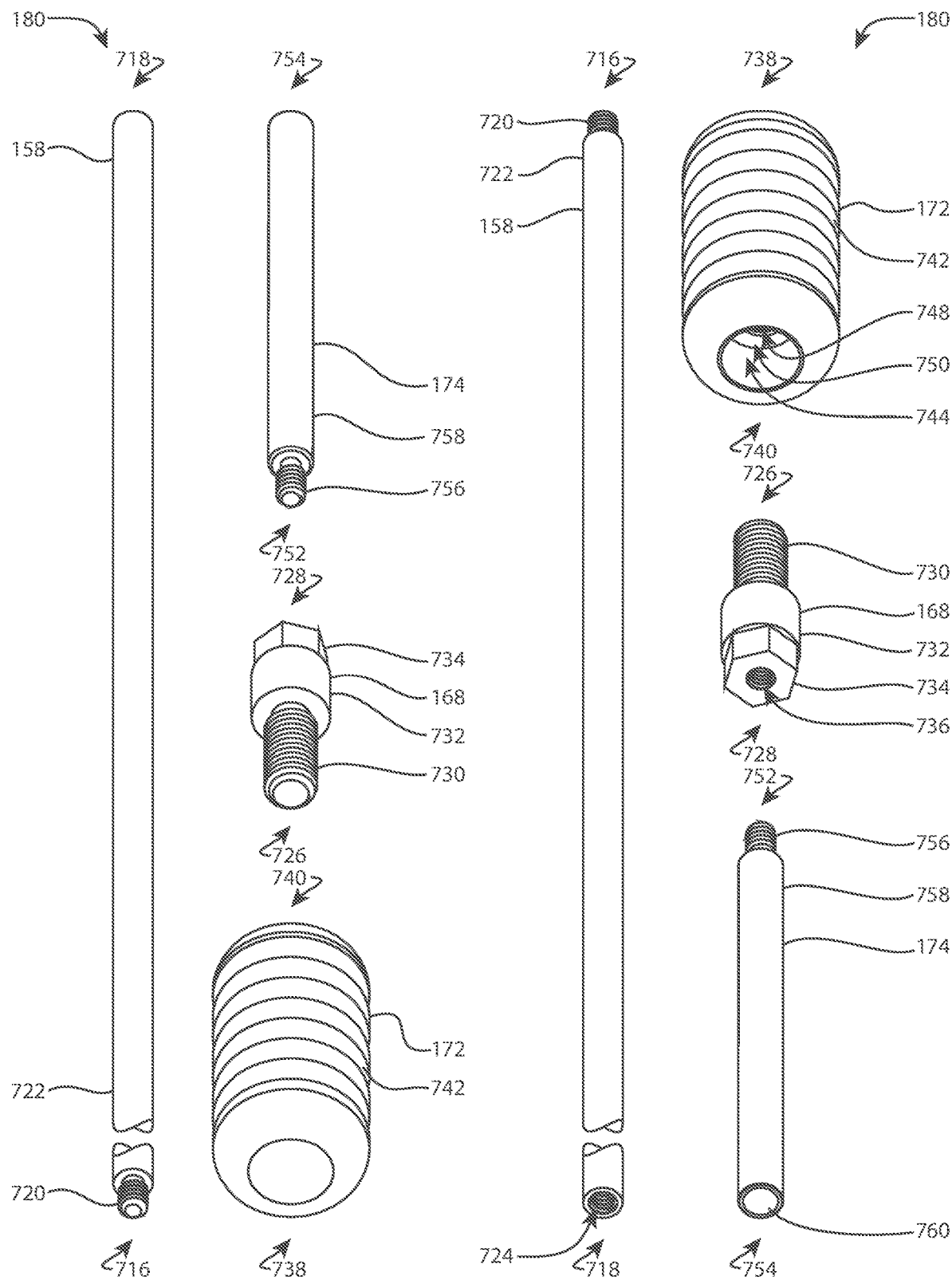
FIG. 35 is an exploded perspective view of the tamp assembly of FIG. 27.
FIG. 36 is another exploded perspective view of the tamp assembly of FIG. 27, from a different direction.

Referring to FIGS. 27, 35, and 36, the tamp assembly 180 may include a tamp shaft 158, a tamp shaft top part 168, a tamp handle 172, and a tamp shaft tip part 174.

The tamp shaft 158 extends between a proximal end 716 and a distal end 718. The tamp shaft 158 may be a cylindrical shaft as shown. The tamp shaft 158 may include a proximal externally threaded portion 720 and a distal smooth portion 722. The diameter of the distal smooth portion 722 may be greater than the major diameter of the proximal externally threaded portion 720. The tamp shaft 158 may include a central longitudinal internally threaded hole 724 that extends proximally into the distal end 718.

The tamp shaft top part 168 extends between a proximal end 726 and a distal end 728. The tamp shaft top part 168 may include a proximal externally threaded portion 730, a middle smooth cylindrical portion 732, and a distal torque fitting 734, such as the hexagonal key shown. The diameter of the middle smooth cylindrical portion 732 may be greater than the major diameter of the proximal externally threaded portion 730. The outer diameter of the distal torque fitting 734 may be less than the diameter of the middle smooth cylindrical portion 732. The tamp shaft top part 168 may include a central longitudinal internally threaded hole 736 that extends proximally into the distal end 728.

The tamp handle 172 extends between a proximal end 738 and a distal end 740. The tamp handle 172 may be a cylindrical part with rounded proximal and distal ends 738, 740 as shown. The tamp handle 172 may include one or more friction features 742, such as the series of shallow circumferential grooves shown. The tamp handle 172 may include a central longitudinal hole 744 that extends proximally into the distal end 740. The hole 744 may extend proximally about half, or most, of the proximal-distal overall length of the tamp handle 172. The hole 744 may include, from proximal to distal, first, second, and third inner portions 746, 748, 750 of approximately equal proximal-distal lengths. Each of the inner portions may have a circular cross section. The first inner portion 746 is not visible in FIG. 36. The first inner portion 746 may be a blind hole included for ease of manufacturing the second inner portion 748, which has internal threads. The minor diameter of the threads may be equal to or similar to the diameter of the first inner portion 750. The diameter of the third inner portion 750 may be greater than the major diameter of the threads. The third inner portion 750 may be referred to as a counterbore around the second inner portion 748. The proximal end of the third inner portion 750 may be flat.

The tamp shaft tip part 174 extends between a proximal end 752 and a distal end 754. The tamp shaft tip part 174 may be a cylindrical shaft as shown. The tamp shaft tip part 174 may include a proximal externally threaded portion 756 and a distal smooth portion 758. The diameter of the distal smooth portion 758 may be greater than the major diameter of the proximal externally threaded portion 756. The distal end 754 may have a concave surface 760.

The tamp assembly 180 may be assembled by threading the proximal externally threaded portion 730 of the tamp shaft top part 168 into the second inner portion 748 of the hole 744 of the tamp handle 172 so that the middle smooth cylindrical portion 732 is received in the third inner portion 750, threading the proximal externally threaded portion 720 of the tamp shaft 158 into the hole 736 of the tamp shaft top part 168, and threading the proximal externally threaded portion 756 of the tamp shaft tip part 174 into the hole 724 of the tamp shaft 158. The tamp assembly 180 may be a weldment. Alternatively, the tamp shaft 158, tamp shaft top part 168, tamp handle 172, and/or tamp shaft tip part 174 may be combined into a single part.

The outer diameters of the distal smooth portion 722 of the tamp shaft 158 and the distal smooth portion 758 of the tamp shaft tip part 174 may be received in the inner diameter of the third inner portion 712 of the hole 706 of the graft funnel 170 and in the lock tube assembly 118, more specifically in the hole 606 of the proximal lock tube end part 148, the hole 594 of the proximal lock tube 124, the second inner portion 646 of the hole 642 of the lock tube coupling 128, and the hole 626 of the distal lock tube 126.

Referring to FIGS. 29, 30, 37, and 38, the screwdriver assembly 190 may include a handle 176, a shaft 178, a screw holder 200, and a screw holder catch 182.

The handle 176 extends between a proximal end 762 and a distal end 764. The handle 176 may include a proximal grip portion 766 with one or more friction features 768 such as the four generally pear-shaped indentations shown, and a distal shaft 770. The shaft 770 may include a proximal first portion 772 and a distal second portion 774. The first portion 772 may include one or more friction features 776, such as the series of shallow circumferential grooves shown. The first portion 772 may be a sleeve that is longitudinally movable relative to the second portion 774. A central longitudinal D-shaped hole 778 may extend proximally into the distal end 764. One or more balls (not shown) may be captured between the first and second portions 111, 774 and may protrude at least partially into the D-shaped hole 778 when the first portion 772 is in a first position relative to the second portion 774. The balls may be free to move radially away from the hole 778 when the first portion 772 is in a second position relative to the second portion 774. The first portion 772 may be biased towards the first position.

The shaft 178 extends between a proximal end 780 and a distal end 782. The shaft 178 may be generally cylindrical as shown. The shaft 178 may include, from proximal to distal, first, second, third, fourth, and fifth outer portions 784, 786, 788, 790, 792. The first outer portion 784 may have a generally circular cross section, and may include a unilateral longitudinal flat 794 so that the first outer portion 784 is complementary to the D-shaped hole 778 in the shaft 770 of the handle 176. A circumferential groove 796 may extend around the circular side of the first outer portion 784 to engage the balls in the shaft 770 of the handle 176. The diameter of the second outer portion 786 may be greater than the diameter of the first outer portion 784. The second outer portion 786 may extend over most of the proximal-distal length of the shaft 178. The third outer portion 788 may include external threads. The major diameter of the threads may be less than the diameter of the second outer portion 786. The fourth outer portion 790 may have a circular cross section and may be smooth. The diameter of the fourth outer portion 790 may be the same as, or similar to, the minor diameter of the threads of the third outer portion 788. The fifth outer portion 792 may include a torque fitting 798 such as the hexagonal key shown.

Referring to FIGS. 39-42, the screw holder 200 extends between a proximal end 800 and a distal end 802. The screw holder 200 may be a tubular part with generally circular outer and inner cross-sectional shapes. The screw holder 200 may include, from proximal to distal, first and second outer portions 804, 806. The first outer portion 804 may have a generally circular cross section, and may extend distally over most of the proximal-distal length of the screw holder 200. Bilateral flats 808, 810 may be included at or near the middle of the proximal-distal length of the first outer portion. A longitudinal slot 812 may extend through one wall of the first outer portion 804, and may be located between the flats 808, 810. The proximal end of the slot 812 may be at the same or similar level as the proximal ends of the flats 808, 810. The proximal end of the slot 812 may include a circular counterbore 814. The distal end of the slot 812 may extend distally about twice as far as the distal ends of the flats 808, 810. The slot 812 may be rectangular or oval. The second outer portion 806 may taper inwardly toward the distal end 802. The second outer portion 806 may be conical. The second outer portion 806 may include a notch 816 that extends proximally from the distal end 802 through one wall of the second outer portion 806. The notch 816 may be rectangular or square, and may have rounded corners. The notch 816 may be in line with the slot 812. The screw holder 200 may include a central longitudinal hole 818 that extends through the screw holder between the proximal end 800 and the distal end 802. The hole 818 may include, from proximal to distal, first, second, and third inner portions 820, 822, 824. The first inner portion 820 may include internal threads. The diameter of the second inner portion 822 may be less than, equal to, or similar to the minor diameter of the threads. The proximal end of the second inner portion 822 may be proximal to the proximal ends of the flats 808, 810. The distal end of the second inner portion 822 may be distal to the proximal end of the notch 816, and may be at or near the middle of the proximal-distal length of the notch 816. A short tapered surface may be included at the transition between the second and third inner portions 822, 824. The second inner portion 822 may include a unilateral longitudinal alcove 826 extending into one wall of the second inner portion 822. The alcove 826 may be in line with the slot 812 and the notch 816. The diameter of the third inner portion 824 may be less than the major diameter of the threads of the first inner portion 820, and may be greater than the minor diameter of the threads.

The screw holder catch 182 extends between a proximal end 828 and a distal end 830. The screw holder catch 182 may be a generally plate-like part, and may include, from proximal to distal, first, second, and third portions 832, 834, 836. The first portion 832 may have a size and shape that is complementary to the slot 812 of the screw holder 200. The proximal end of the first portion 832 may include a circular shelf 838 that is complementary to the counterbore 814. The second portion 834 may be offset from the first portion 832 in a direction opposite the shelf 838, and may be substantially parallel to the first portion 832. The second portion 834 may include a longitudinal arcuate groove 840 that faces the same direction as the shelf 838. The third portion 836 may have a size and shape that is complementary to the notch 816 of the screw holder 200. The third portion 836 may be in line with the first portion 832 (thus offset from the second portion in a direction toward the shelf 838). The third portion 836 may include a distal tooth 842 that faces the same direction as the shelf 838.

The screwdriver assembly 190 may be assembled by coupling the screw holder catch 182 to the screw holder 200 so that the shelf 838 is in the counterbore 814, the second portion 834 is in the alcove 826, the third portion 836 is in the notch 816, and the groove 840 faces the interior of the screw holder 200; threading the first inner portion 820 of the hole 818 of the screw holder 200 onto the third outer portion 788 of the shaft 178; and inserting the first outer portion 784 of the shaft 178 into the D-shaped hole 778 of the handle 176 so that the balls engage the groove 796. Alternatively, the handle 176, shaft 178, screw holder 200, and/or screw holder catch 182 may be combined into a single part.

The outer diameters of the first outer portion 804 of the screw holder 200 and the second outer portion 786 of the shaft 178 may be received in the inner diameter of the third inner portion 712 of the hole 706 of the graft funnel 170 and in the lock tube assembly 118, more specifically in the hole 606 of the proximal lock tube end part 148, the hole 594 of the proximal lock tube 124, the second inner portion 646 of the hole 642 of the lock tube coupling 128, and the hole 626 of the distal lock tube 126.

Figure 44:
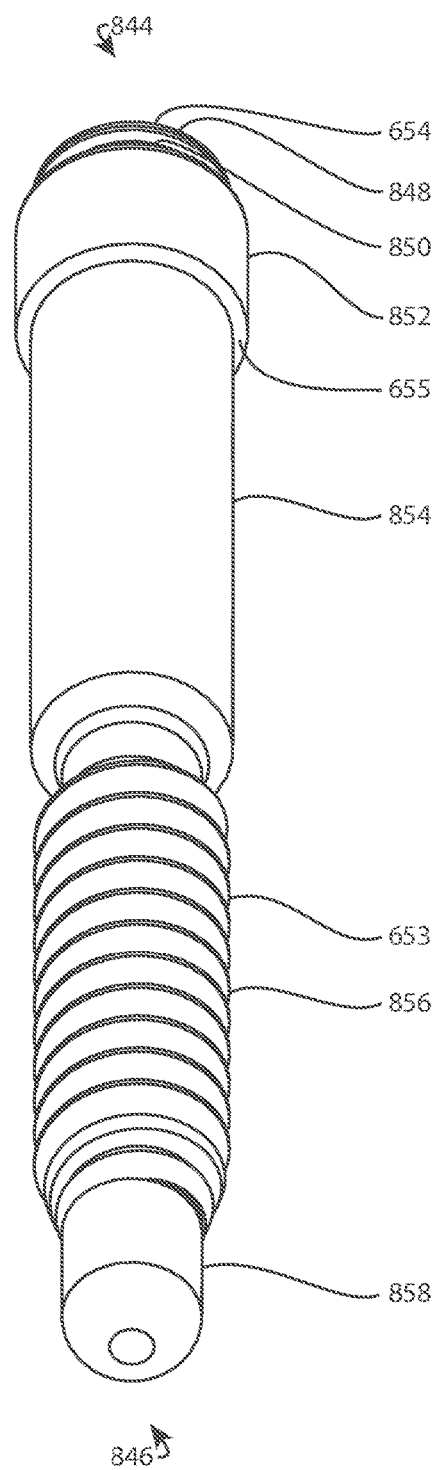
FIG. 44 is another perspective view of the lockout screw of FIG. 29, from a different direction.

Referring to FIGS. 43 and 44, the lockout screw 654 extends between a proximal end 844 and a distal end 846. The lockout screw 654 may include, from proximal to distal, first, second, third, fourth, fifth, and sixth portions 848, 850, 852, 854, 856, 858, each with a circular cross section. The first portion 848 may include a rounded outer proximal circumferential edge, and may extend a short distance in the proximal-distal direction. The first portion 848 may form a circumferential lip orflange around the proximal end of the lockout screw 654. The diameter of the second portion 850 may be less than the diameter of the first portion 848. There may be a 90 degree corner between the first portion 848 and the second portion 850. The diameter of the third portion 852 may be greater than the diameter of the first portion 848. There may be a 90 degree corner between the second portion 850 and the third portion 852, so that the second portion 850 forms a circumferential groove between the first and third portions 848, 852. The third portion 852 may have a rounded outer proximal circumferential edge. The diameter of the fourth portion 854 may be the same as or similar to the diameter of the first portion 848, greater than the diameter of the second portion 850, and less than the diameter of the third portion 852. There may be a shoulder 655 between the third and fourth portions 852, 854. The shoulder 655 may taper, and may be conical. The fourth portion 854 may extend distally to about the middle of the proximal-distal length of the lockout screw 654. The fifth portion 856 may include an externally threaded portion 653. The major diameter of the threads may be the same as or similar to the diameter of the fourth portion 854. There may be a tapered transition between the fourth and fifth portions 854, 856. The diameter of the sixth portion 858 may be the same as or similar to the minor diameter of the threaded portion 653. The sixth portion 858 may have a smooth shaft and may include a rounded outer distal circumferential edge. The lockout screw 654 may include a torque fitting 860 in or on the proximal end 844, such as the hexagonal socket shown. The lockout screw 654 is described in pending U.S. patent application Ser. No. 15/244,446.

The outer diameter of the third portion 852 of the lockout screw 654 may be received in the inner diameter of the third inner portion 712 of the hole 706 of the graft funnel 170 and in the lock tube assembly 118, more specifically in the hole 606 of the proximal lock tube end part 148, the hole 594 of the proximal lock tube 124, the second inner portion 646 of the hole 642 of the lock tube coupling 128, and the hole 626 of the distal lock tube 126.

The lockout screw 654 may be coupled to the screwdriver assembly 190 by coupling the torque fitting 798 of the shaft 178 to the torque fitting 860 of the lockout screw 654, inserting the first portion 848 of the lockout screw 654 into the third inner portion 824 of the screw holder 200, and engaging the tooth 842 of the screw holder catch 182 in the second portion 850 of the lockout screw 654. Alternatively, the lockout screw 654 may be coupled to the screwdriver assembly 190 by inserting the first portion 848 of the lockout screw 654 into the third inner portion 824 of the screw holder 200, engaging the tooth 842 of the screw holder catch 182 in the second portion 850 of the lockout screw 654, coupling the torque fitting 798 of the shaft 178 to the torque fitting 860 of the lockout screw 654, and threading the first inner portion 820 of the hole 818 of the screw holder 200 onto the third outer portion 788 of the shaft 178. The lockout screw 654 may be decoupled from the screwdriver assembly 190 by reversing these steps.

Figure 45:
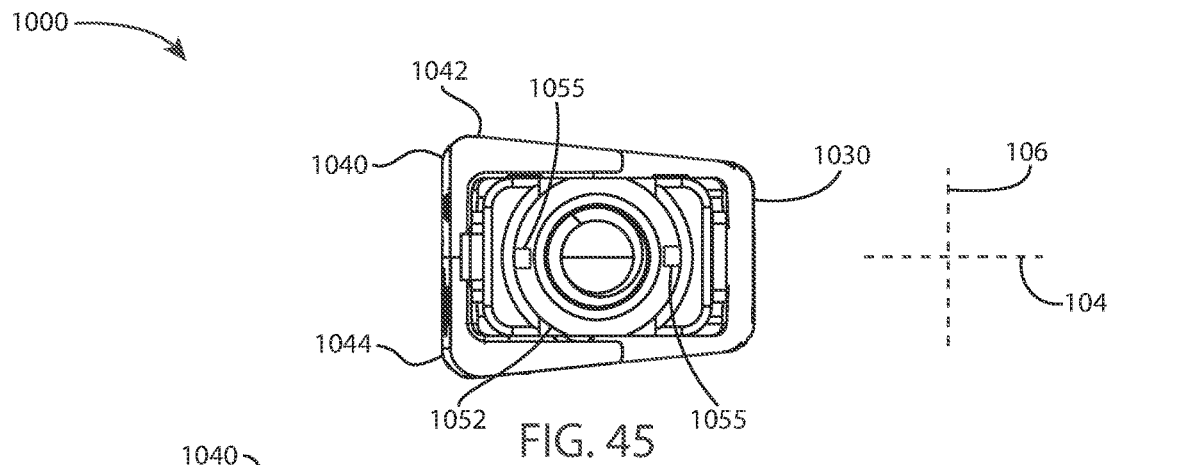
FIG. 45 is a rear or second end view of the implant of FIG. 2 in a collapsed configuration.
Figure 46:
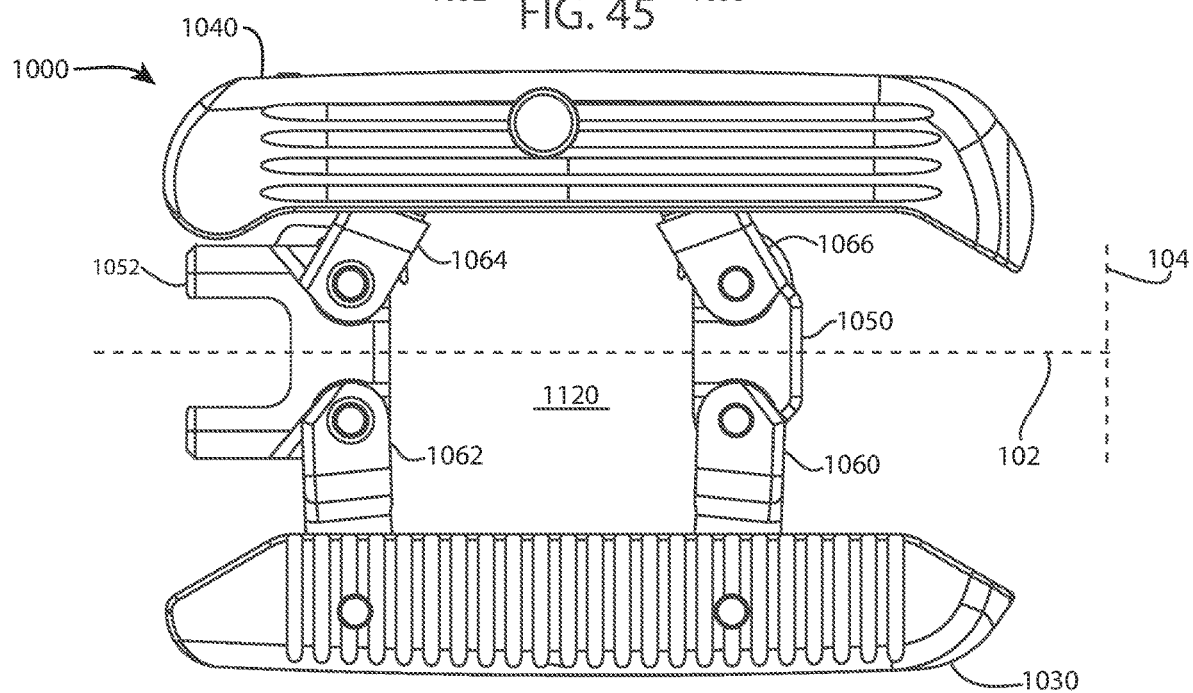
FIG. 46 is a top view of the implant of FIG. 2.
Figure 47:
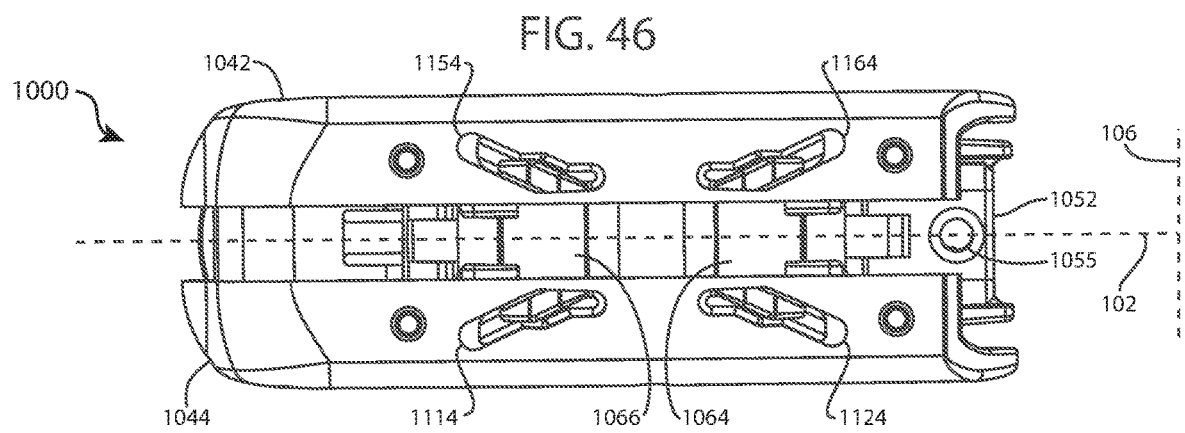
FIG. 47 is a side view of the implant of FIG. 2.

Referring to FIGS. 45-47, implant 1000 is expandable along a horizontal or lateral or transverse or medial-lateral axis 104 and a vertical or cephalocaudal axis 106. Implant 1000 includes a first support member 1040 and a second support member 1030, the support members connected by a first end body 1050 and a second end body 1052. First support member 1040 may include an upper support body 1042 and a lower support body 1044. A pair of connection pins 1055 project from the second end body 1052. A plurality of link members 1060, 1062, 1064, 1066 pivotably connect each of the first and second end bodies 1050, 1052 to each of the support members 1030, 1040. Lower support body 1044 includes ramped expansion slots 1114, 1124, and upper support body includes ramped expansion slots 1154, 1164. The implant 1000 is representative of the intervertebral cages described in pending U.S. patent application Ser. No. 15/244,446.

Figure 48:
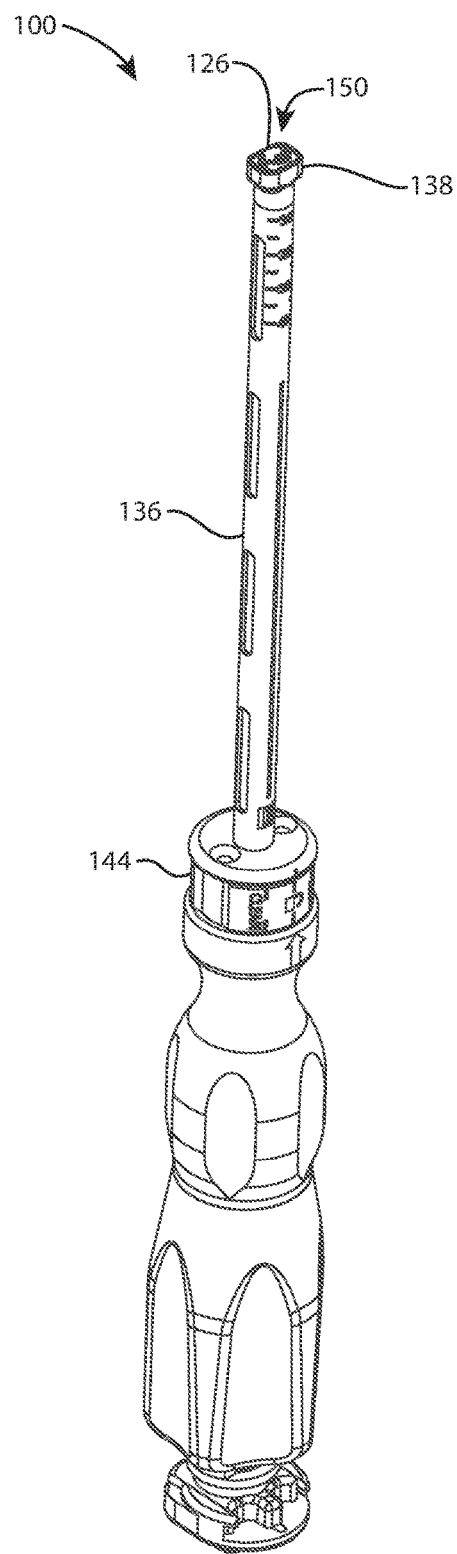
FIG. 48 is an isometric view of the instrument of FIG. 1 in an unlocked configuration.
Figure 49:
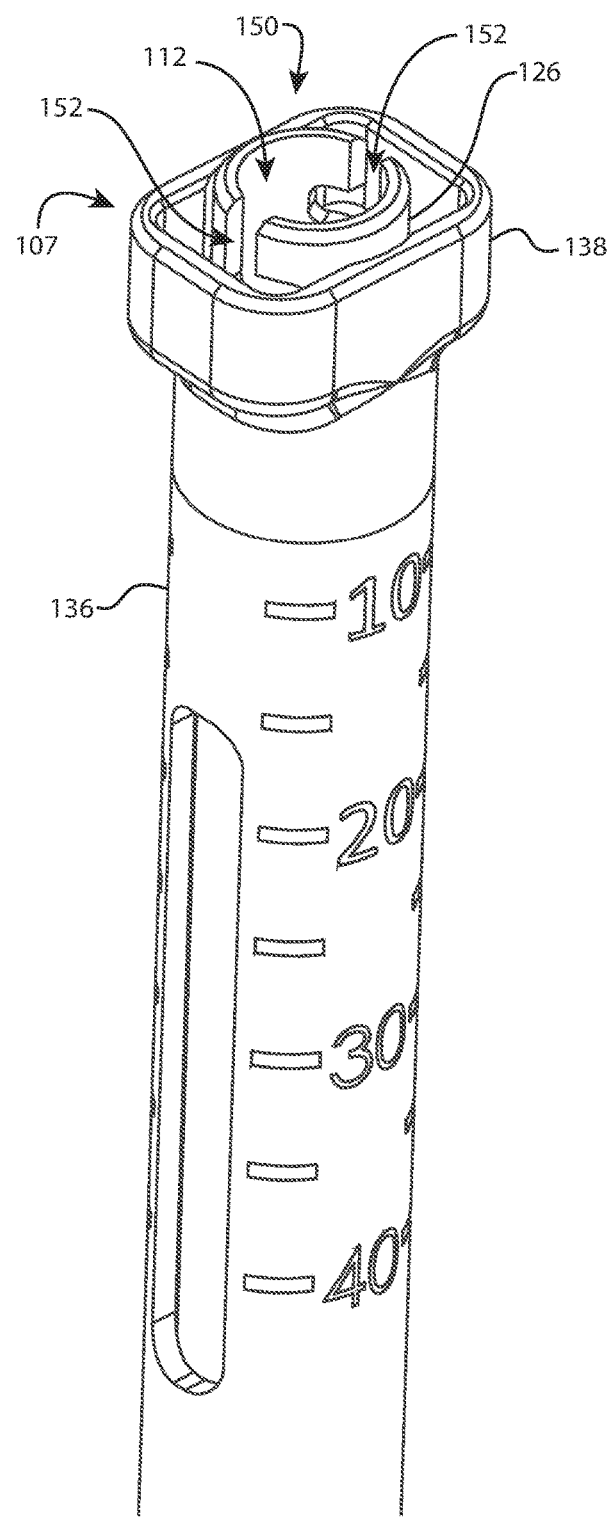
FIG. 49 is a closeup view of a distal end of the instrument of FIG. 48.

Referring to FIGS. 48-59, methods for inserting and expanding an expandable intervertebral implant with instrument system 115 are shown. The instrument 100, as seen in FIGS. 48 and 49, includes a bayonet receiver 150 at the distal end 107 of the distal lock tube 126. The bayonet receiver 150 includes a pair of shaped slots 152 which each include an approximately 90° bend. The slots are in the distal end 614 of the distal lock tube 126 of the lock tube assembly 118. The bayonet receiver 150 may also include the inserter connector 138 of the shaft assembly 116. In one step of the method, the implant 1000 is attached to the distal end 107 of the instrument 100. The connection pins 1055 are received in the shaped slots 152 of the bayonet receiver 150 so that the implant 1000 extends distally from the instrument 100. The distal lock tube 126 is rotated so that the pins 1055 traverse the 90° bend of the shaped slots 152, forming a bayonet connection 154 and locking the implant 1000 to the instrument 100. The implant second end body 1052 may be stabilized against rotation by its fit within the third inner portion 550 of the inserter connector 138. Other embodiments within the scope of the disclosure may include a threaded connection between the implant 1000 and instrument 100 instead of the bayonet connection. In an embodiment, the distal lock tube 126 may be rotated via rotation of the selector ring 144. In an embodiment, the lock tube is rotated 30° to complete the bayonet connection. The lock tube assembly (distal lock tube 126, lock tube coupling 128, proximal lock tube 124) may additionally be unlocked from the inserter shaft 136 and removed from the instrument 100 for cleaning.

Figure 50:
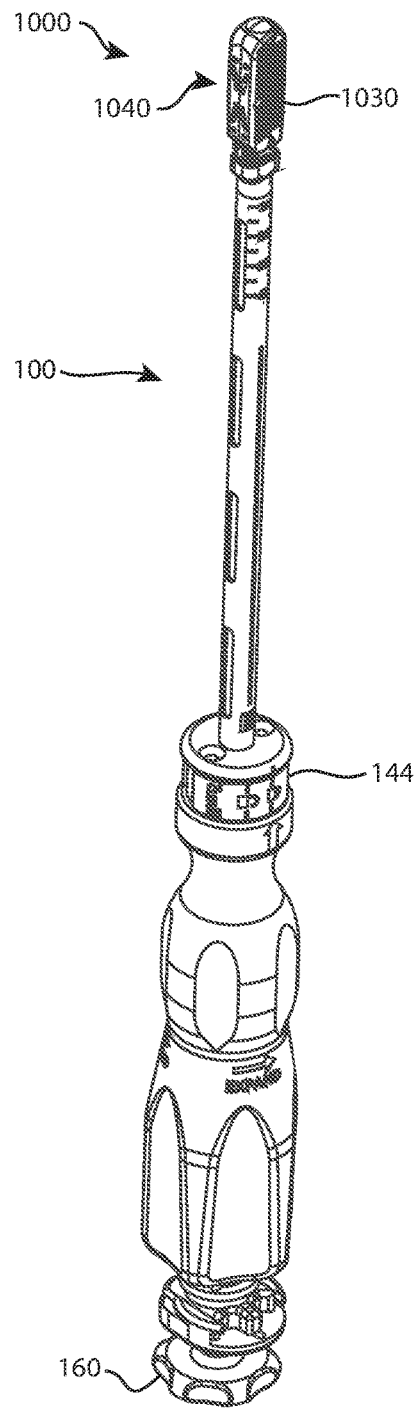
FIG. 50 is an isometric view of the instrument of FIG. 1 with the implant of FIG. 2 connected to the distal end of the instrument.
Figure 51:
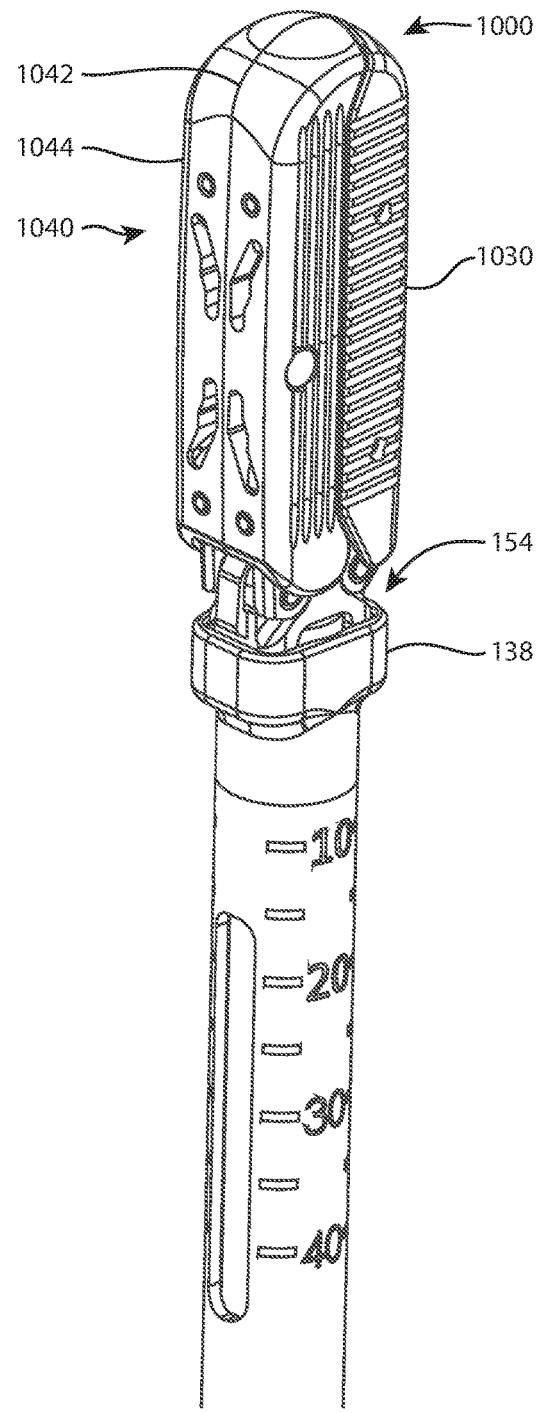
FIG. 51 is a closeup view of the distal end of the instrument and implant of FIG. 50.

Referring to FIGS. 26, 50, and 51, another step of the method includes inserting the draw bar assembly 160 distally through the instrument bore 112. The distal threaded tip 162 of the draw bar assembly 160 passes through the implant second end body 1052 and is threadably engaged with the implant first end body 1050. The instrument lock collar 120 may be actuated to engage the instrument shuttle 122 with an annulus 166 near the proximal end of the draw bar assembly 160. The lock collar 120 may be moved to its first position, the draw bar assembly 160 may be advanced within the instrument bore 112 until the annulus is distal to the lock collar 120, and the lock collar 120 may be moved to its second position. When the draw bar assembly 160 is inserted into connection with implant 1000 but before expansion of the implant, indicia 248 or markings may indicate the implant is in the collapsed configuration.

Figure 52:
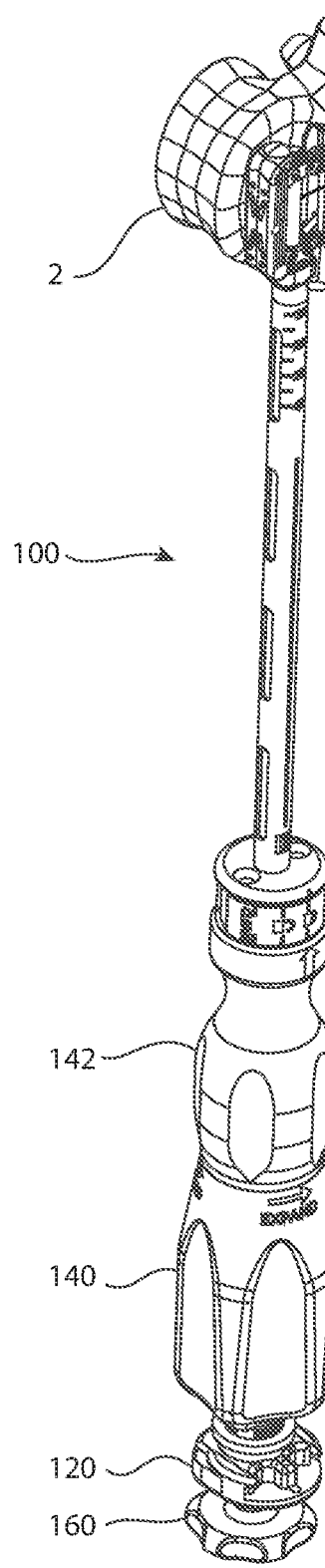
FIG. 52 is an isometric view of the instrument and implant of FIG. 50, the implant adjacent a vertebral body and in a laterally expanded configuration.
Figure 53:
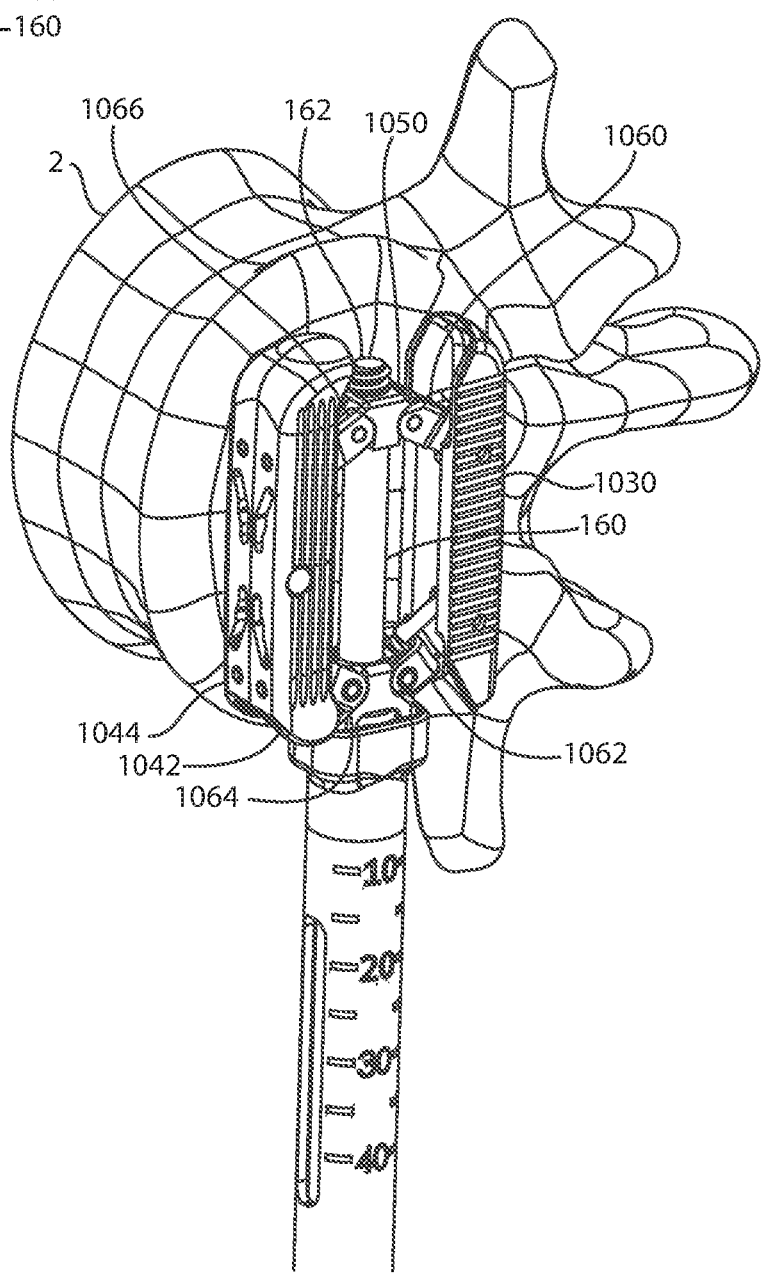
FIG. 53 is a closeup view of the distal end of the instrument, implant, and vertebra of FIG. 52.

Referring to FIGS. 52 and 53, the instrument 100 may be used to insert the implant 1000 into a prepared intervertebral space between a first vertebra 2 and a second vertebra (not shown for clarity), in another step of the method. The implant 1000 may be positioned in the intervertebral space before or after insertion of the draw bar assembly 160 into the instrument 100.

When the implant is properly positioned in the intervertebral space and the draw bar assembly 160 is inserted into the instrument 100, in another step of the method the expansion knob 140 is rotated, turning threaded driver 130. The knob 140, threaded driver 130 and shuttle 122 form a motion conversion mechanism to convert rotational motion to linear or axial motion along the longitudinal instrument axis 102. Interaction of threaded driver 130 with shuttle 122 translates shuttle 122 and draw bar assembly 160 proximally, providing axial force in a first direction along axis 102 to draw the implant first end 1050 proximally toward the implant second end 1052 to laterally expand the implant in a second direction perpendicular to the first direction, along axis 104. As the axial force is applied to the implant, the link members 1060, 1062, 1064, 1066 pivot outward away from the central longitudinal axis 102, carrying the first and second support members 1040, 1030 away from one another along axis 104, laterally expanding the implant. Stop surfaces on the implant end bodies and the support members may interact to limit the lateral expansion. When the lateral expansion is attained, indicia 248 or markings on the instrument may indicate the implant is in the laterally expanded configuration.

Figure 54:
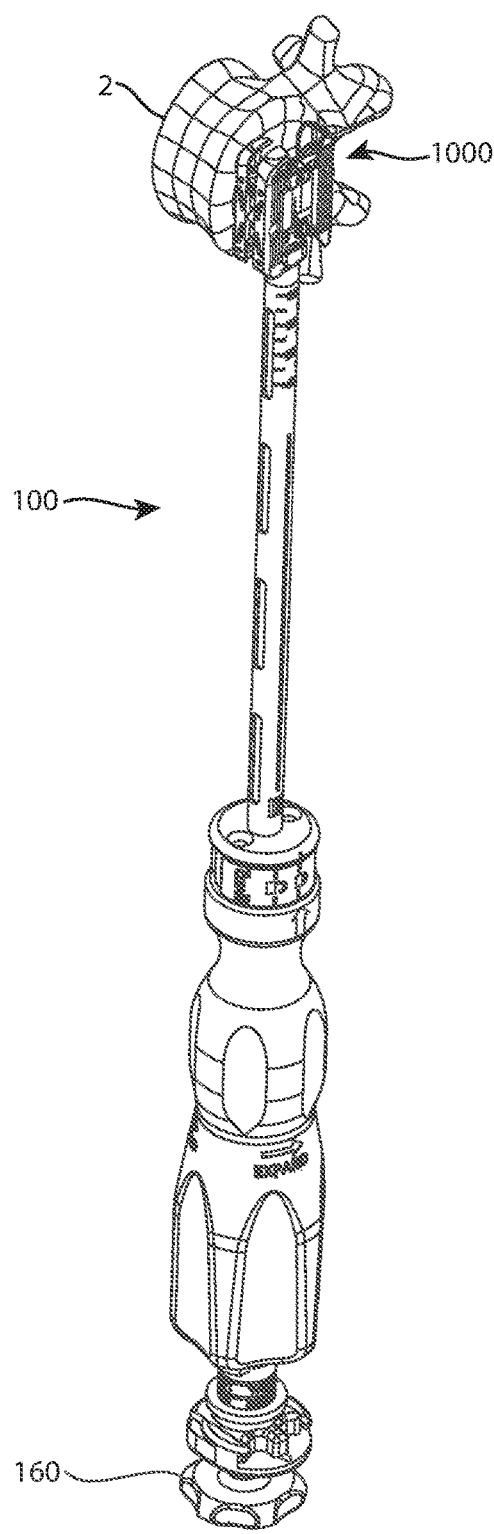
FIG. 54 is an isometric view of the instrument and implant of FIG. 52, the implant adjacent a vertebral end body and in a laterally and vertically expanded configuration.
Figure 55:
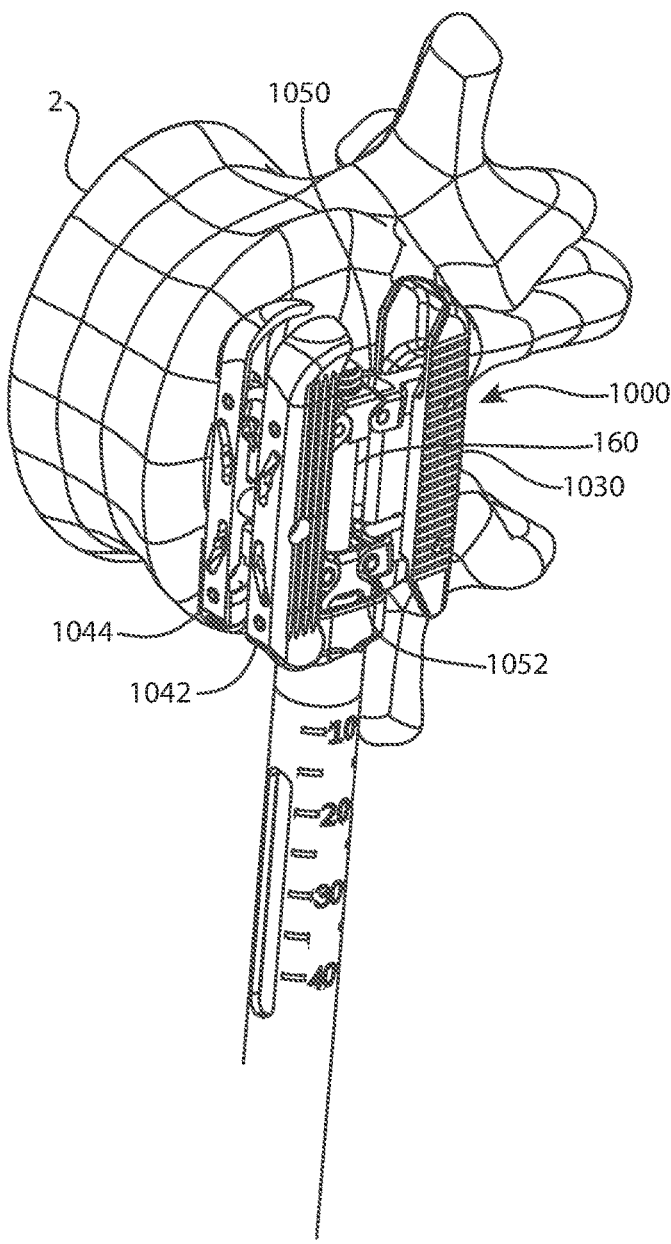
FIG. 55 is a closeup view of the distal end of the instrument, implant, and vertebra of FIG. 54.
Figure 56:
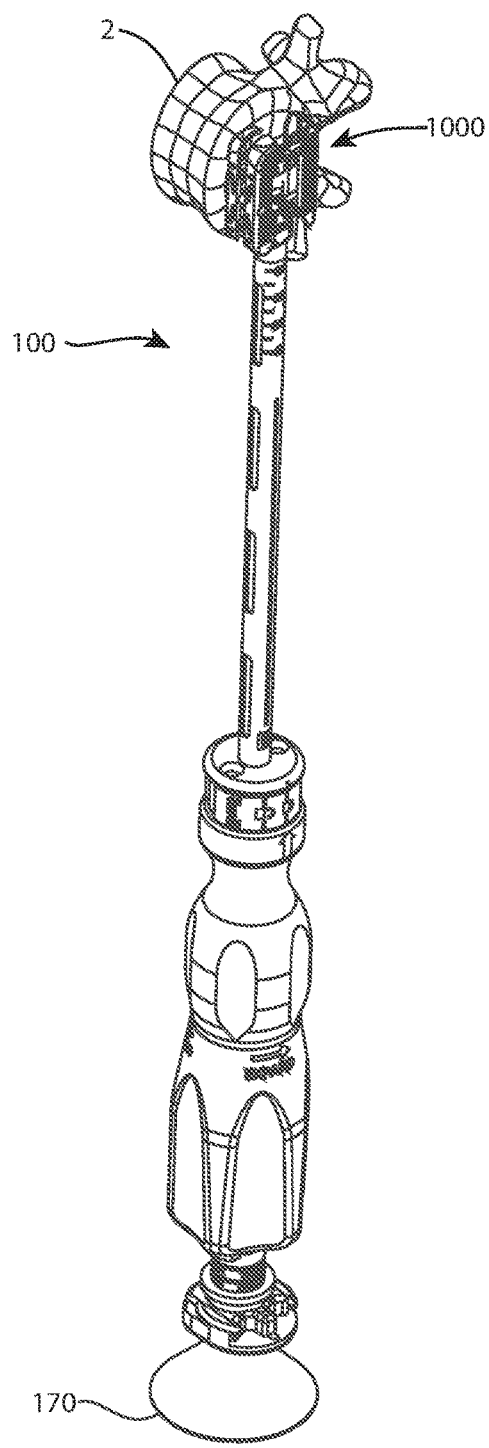
FIG. 56 is an isometric view of the instrument and implant of FIG. 54, the implant adjacent a vertebral end body and in a laterally and vertically expanded configuration, and the funnel of FIG. 28 connected to a proximal end of the instrument.
Figure 57:
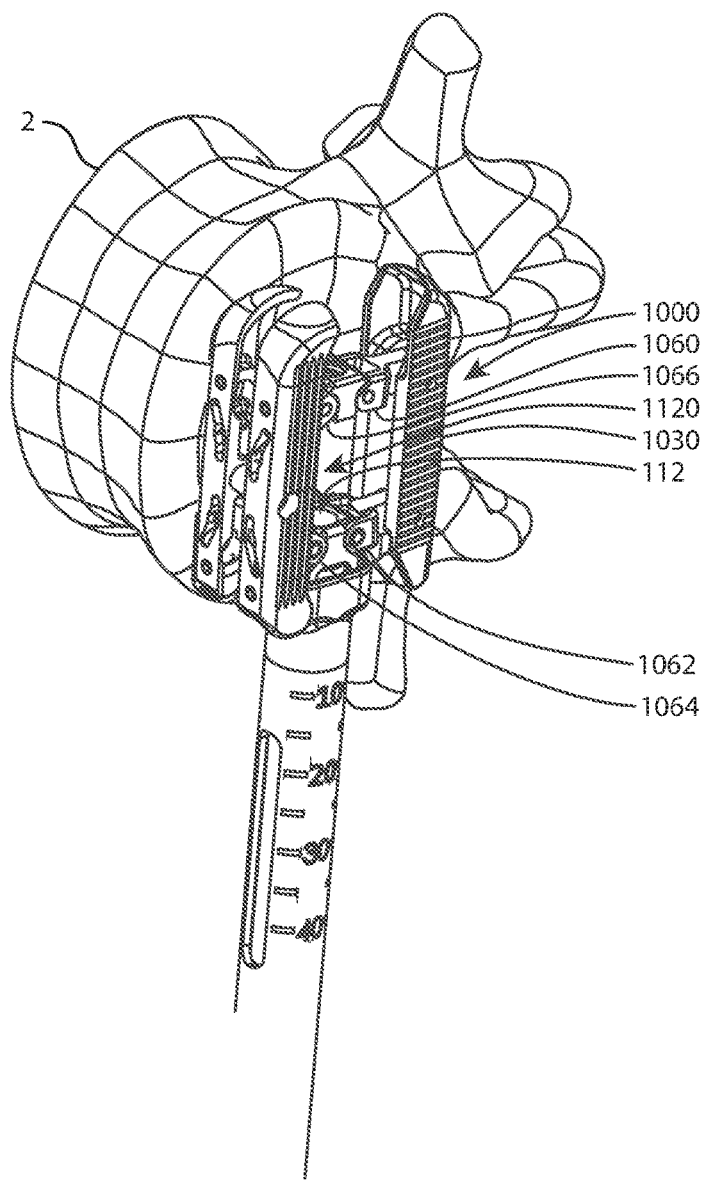
FIG. 57 is a closeup view of the distal end of the instrument, implant, and vertebra of FIG. 56.
Figure 58:
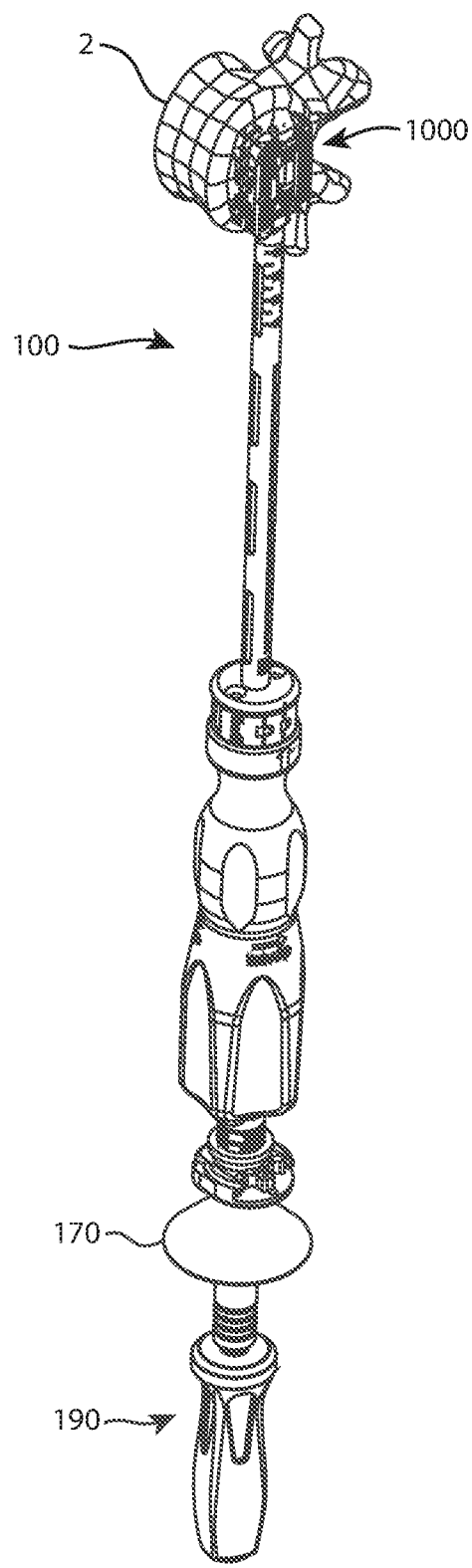
FIG. 58 is an isometric view of the instrument and implant of FIG. 56, the implant adjacent a vertebral end body and in a laterally and vertically expanded configuration, the lockout screw of FIG. 29 extending through the implant and the screwdriver assembly of FIG. 29 inserted through the instrument.
Figure 59:
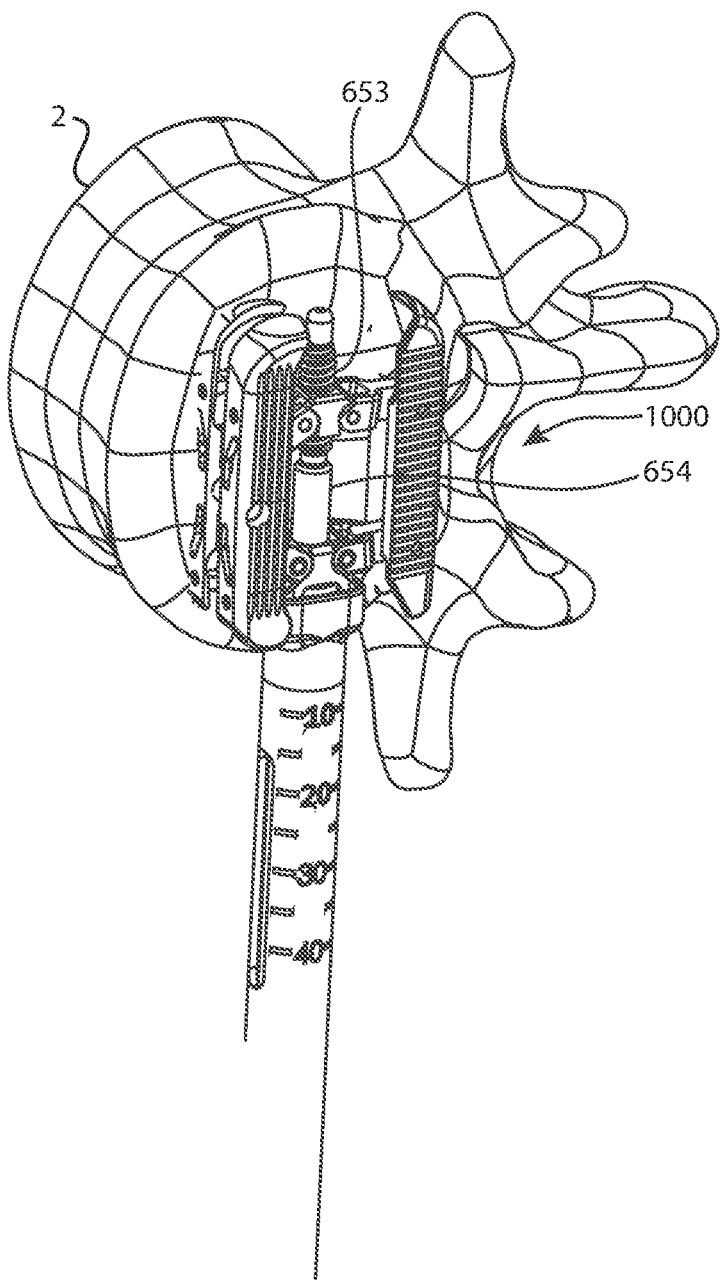
FIG. 59 is a closeup view of the distal end of the instrument, implant, and vertebra of FIG. 58.
Figure 64:
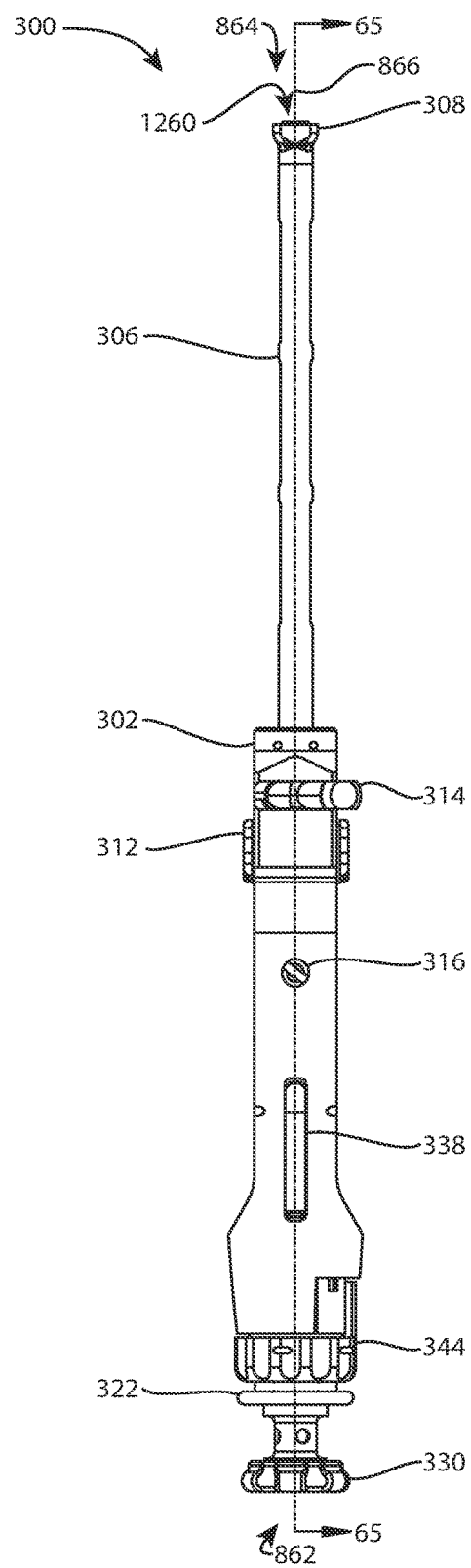
FIG. 64 is a top view of another insertion and expansion instrument.
Figure 65:
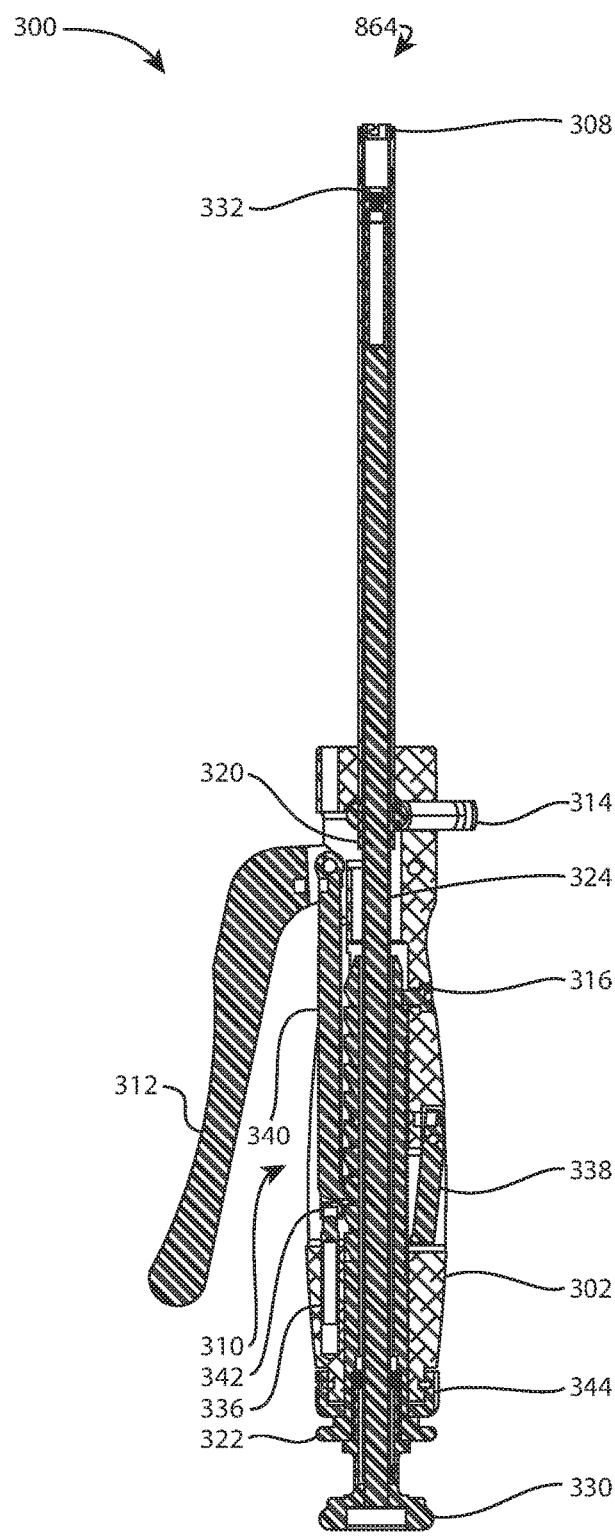
FIG. 65 is a cross-sectional view of the instrument of FIG. 64, taken along line 65-65 of FIG. 64.
Figure 67:
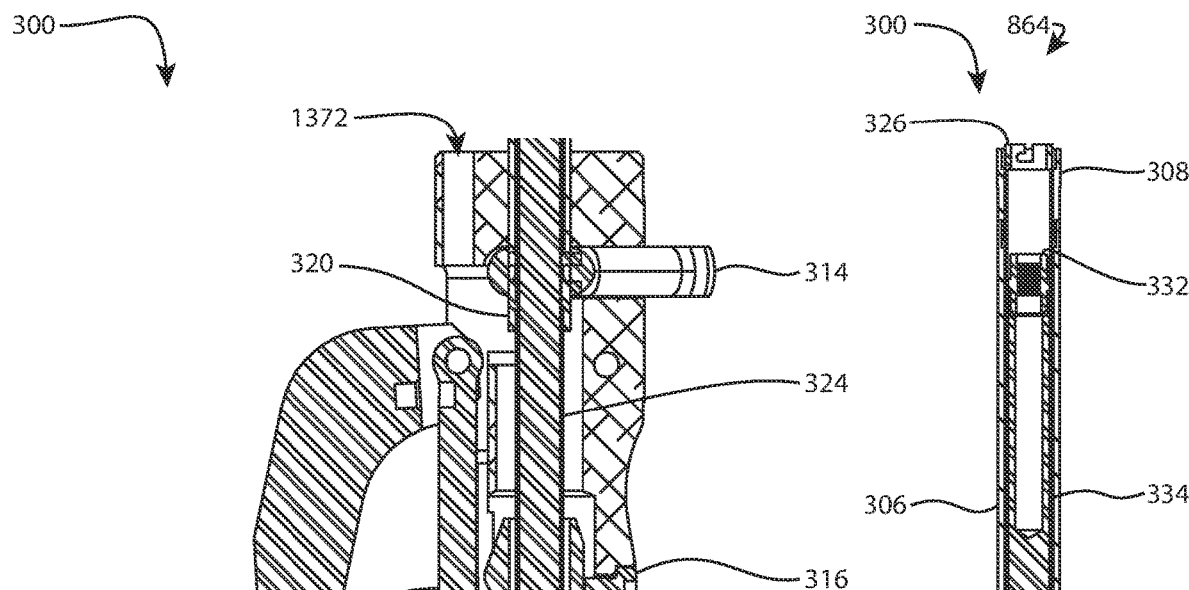
FIG. 67 is a distal detail cross-sectional view of the instrument of FIG. 65.
Figure 66:
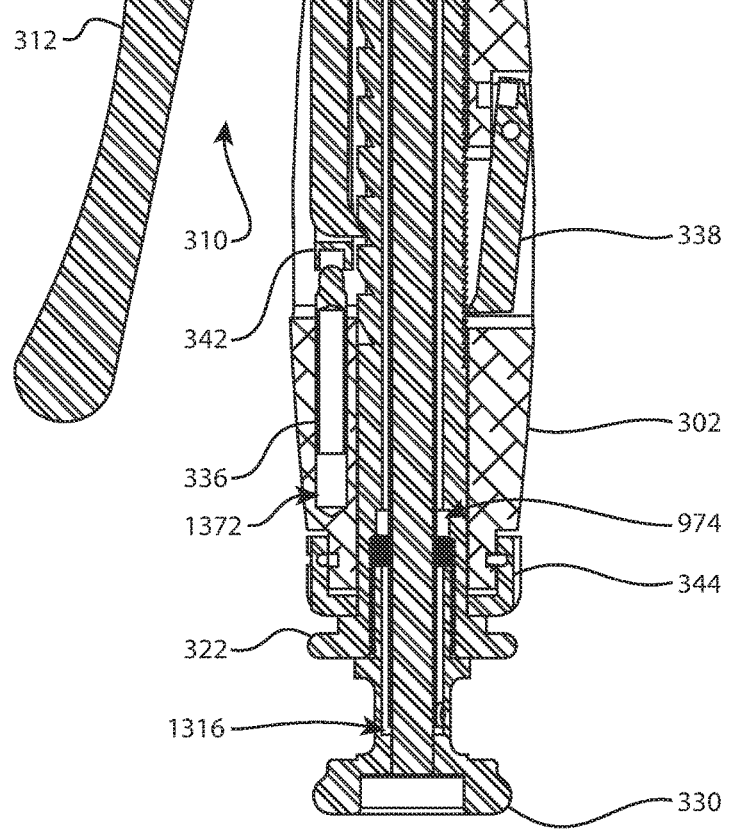
FIG. 66 is a proximal detail cross-sectional view of the instrument of FIG. 65.
Figure 70:
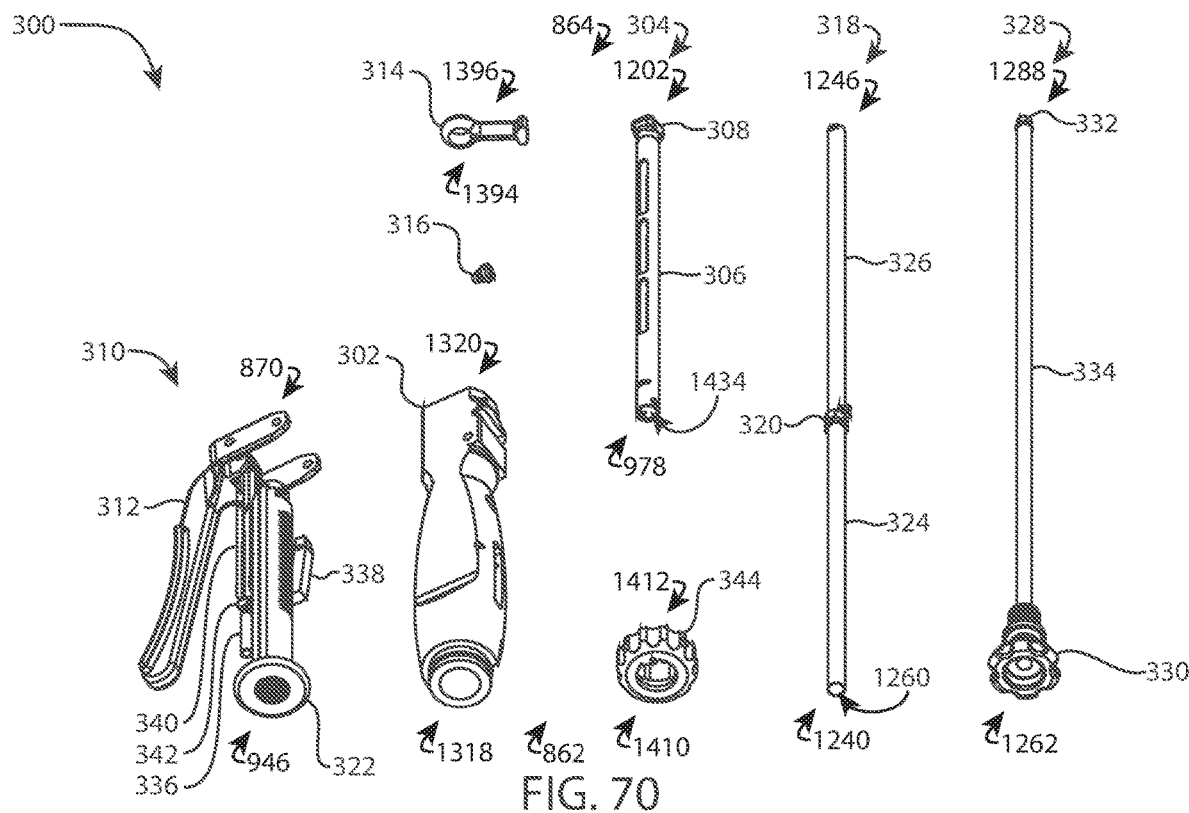
FIG. 70 is an exploded perspective view of the instrument of FIG. 64.
Figure 71:
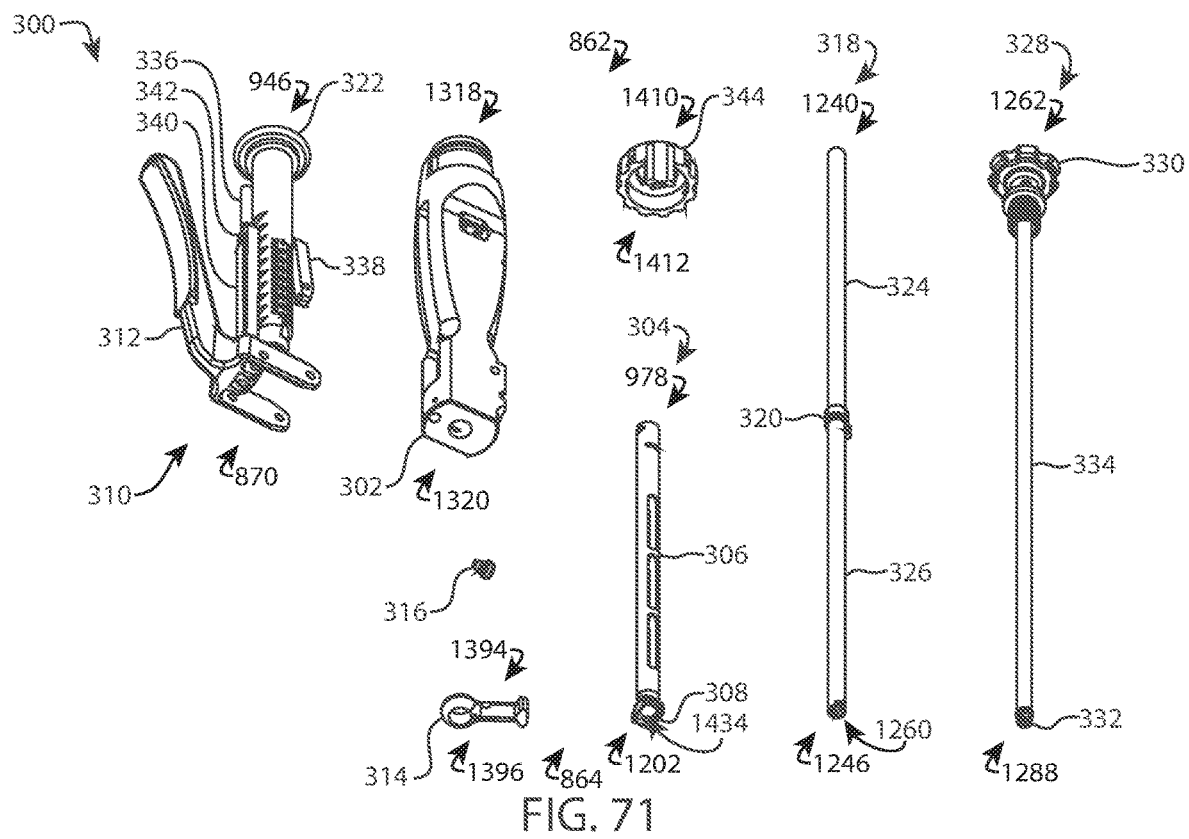
FIG. 71 is another exploded perspective view of the instrument of FIG. 64, from a different direction.
Figure 72:
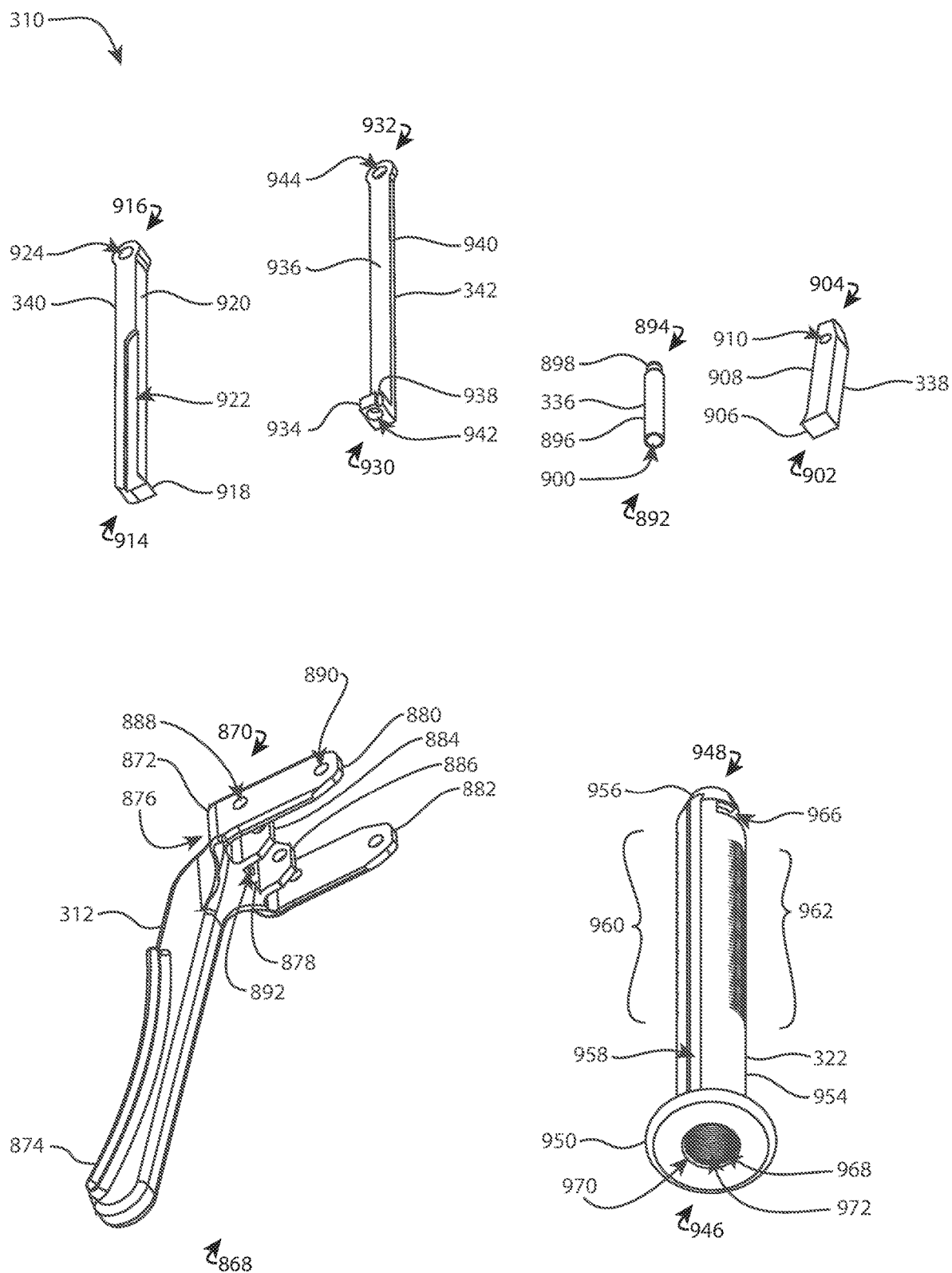
FIG. 72 is an exploded perspective view of a ratchet mechanism of the instrument of FIG. 64.
Figure 73:
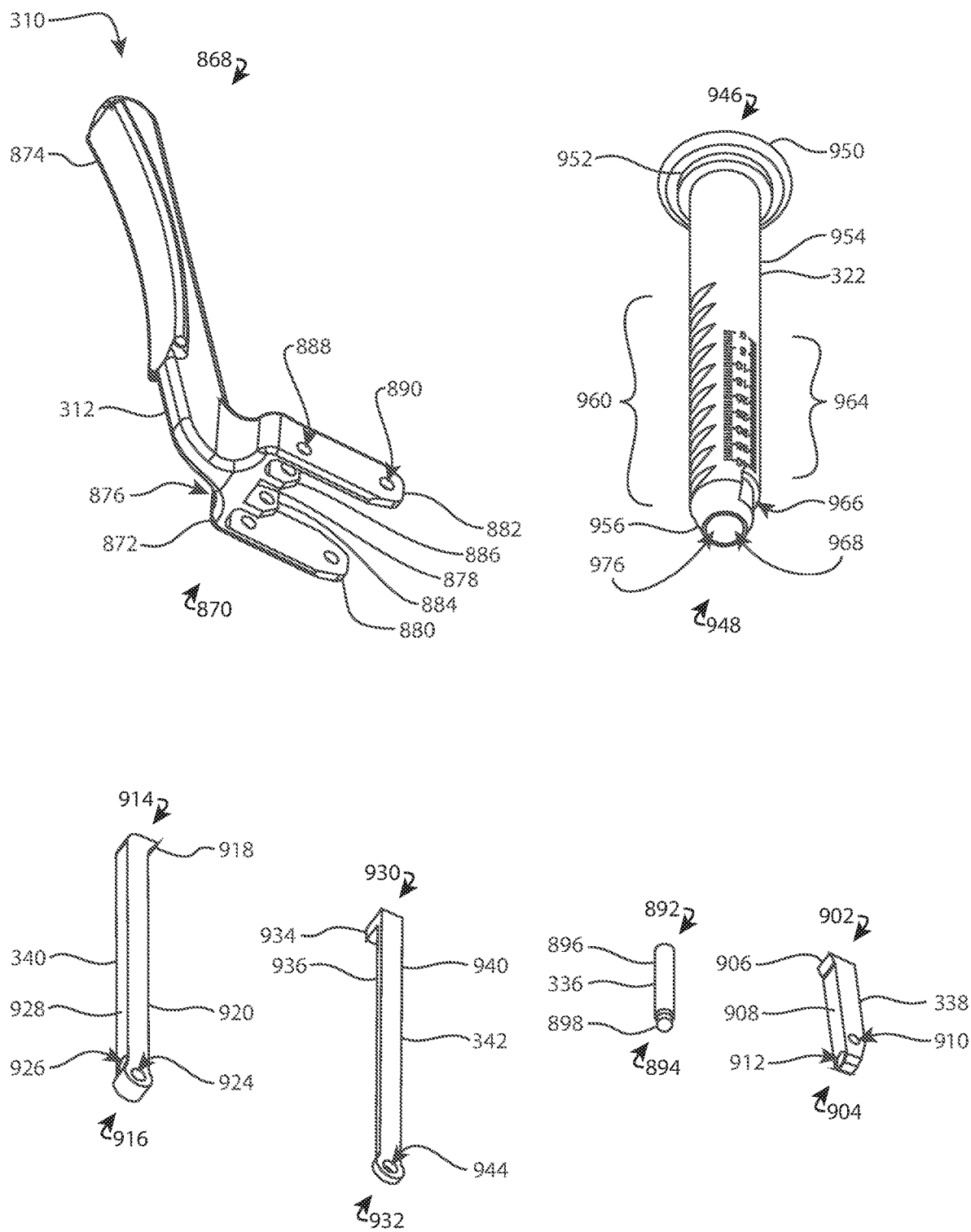
FIG. 73 is another exploded perspective view of the ratchet mechanism of FIG. 72, from a different direction.
Figure 74:
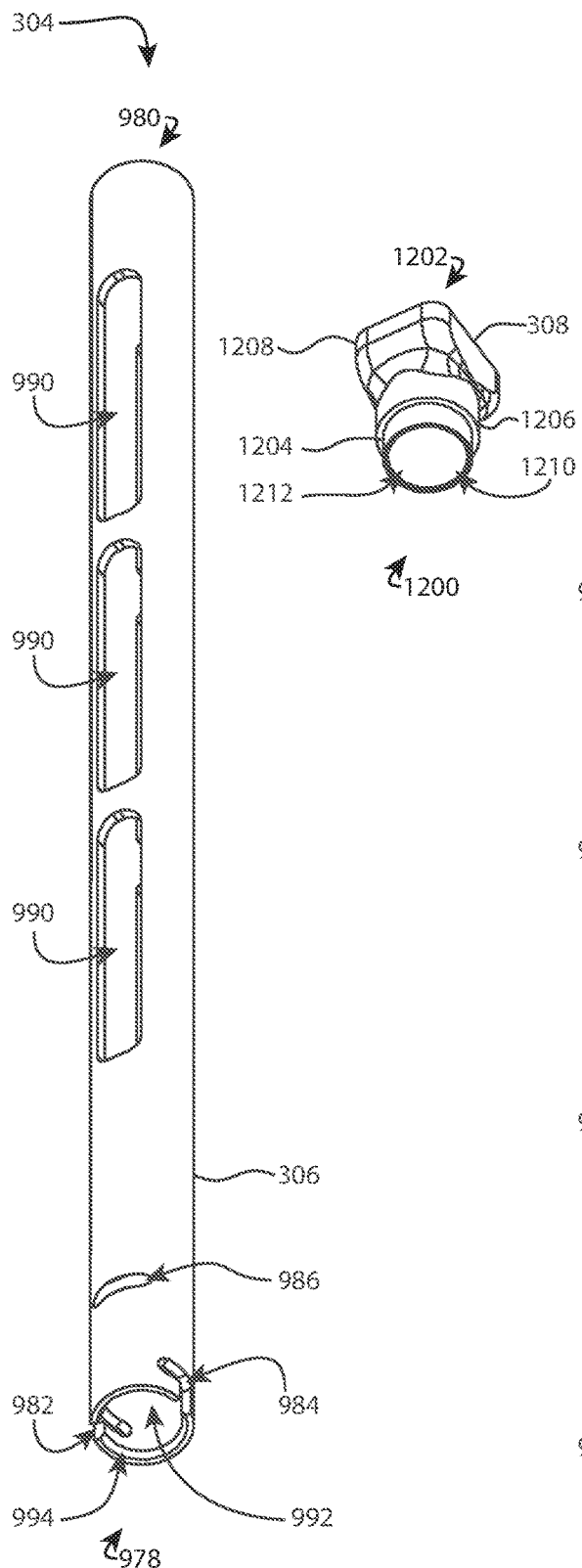
FIG. 74 is an exploded perspective view of a shaft assembly of the instrument of FIG. 64.
Figure 75:
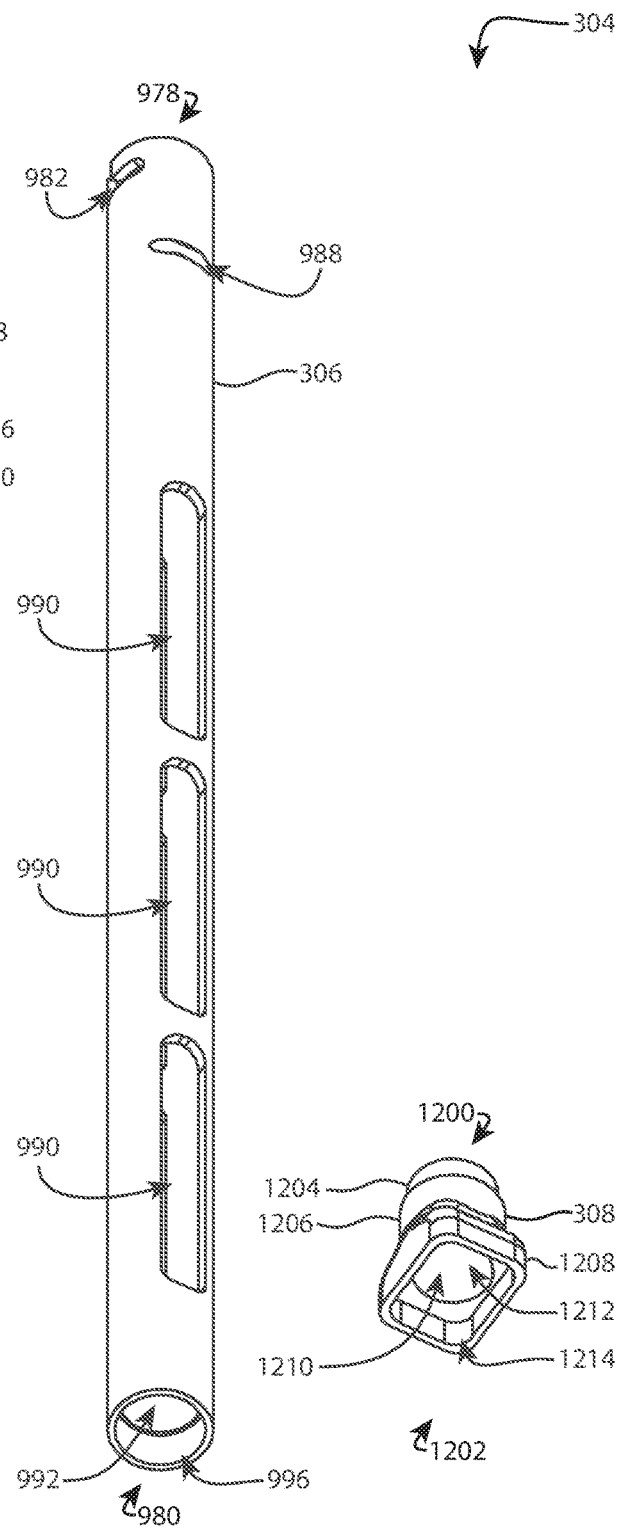
FIG. 75 is another exploded perspective view of the shaft assembly of FIG. 74, from a different direction.
Figures 76, 77:
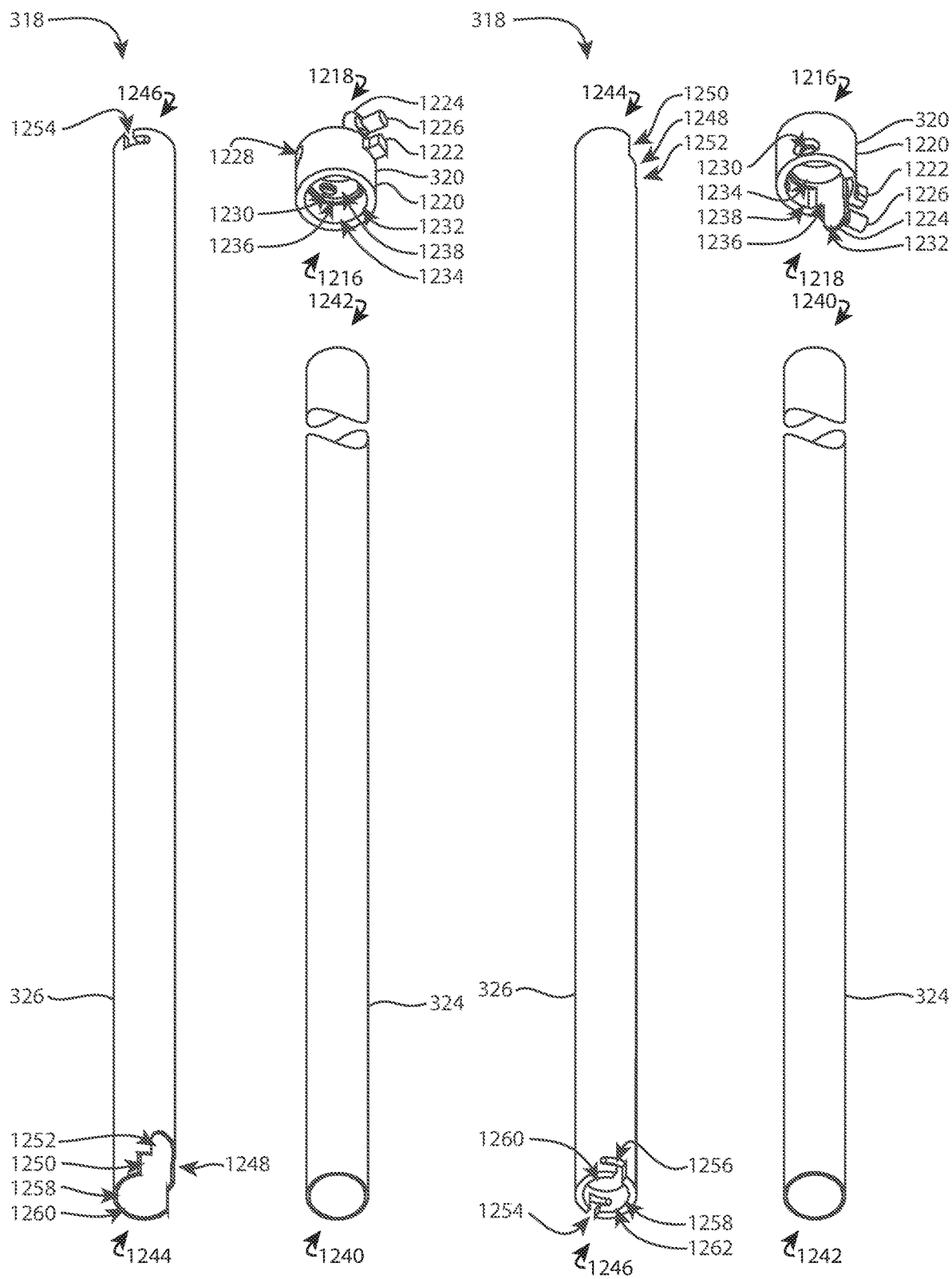
FIG. 76 is an exploded perspective view of a lock tube assembly of the instrument of FIG. 64.
FIG. 77 is another exploded perspective view of the lock tube assembly of FIG. 76, from a different direction.
Figure 78:
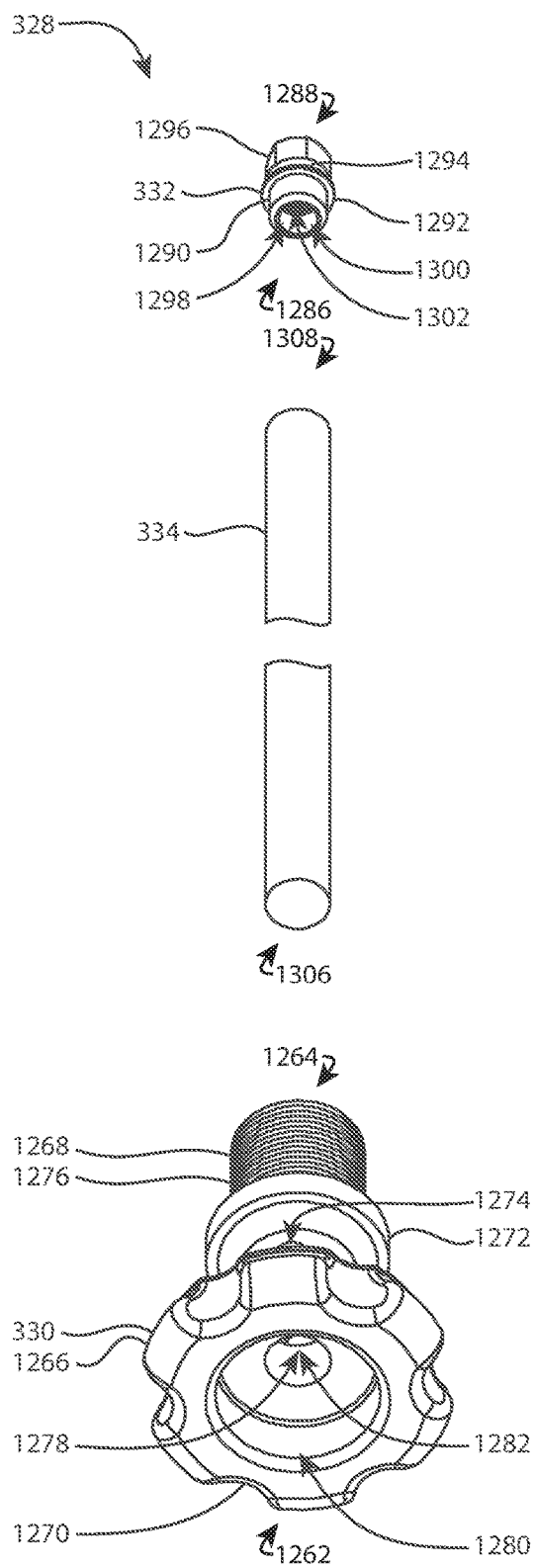
FIG. 78 is an exploded perspective view of a draw bar assembly of the instrument of FIG. 64.
Figure 79:
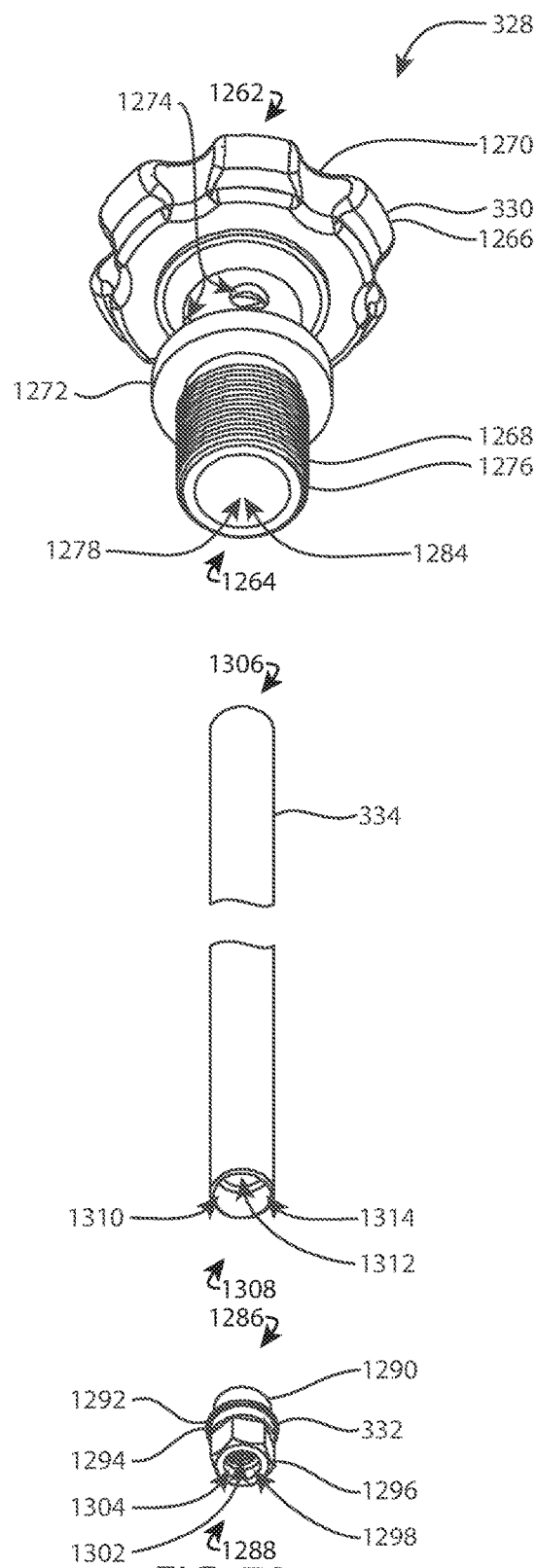
FIG. 79 is another exploded perspective view of the draw bar assembly of FIG. 78, from a different direction.
Figure 80:
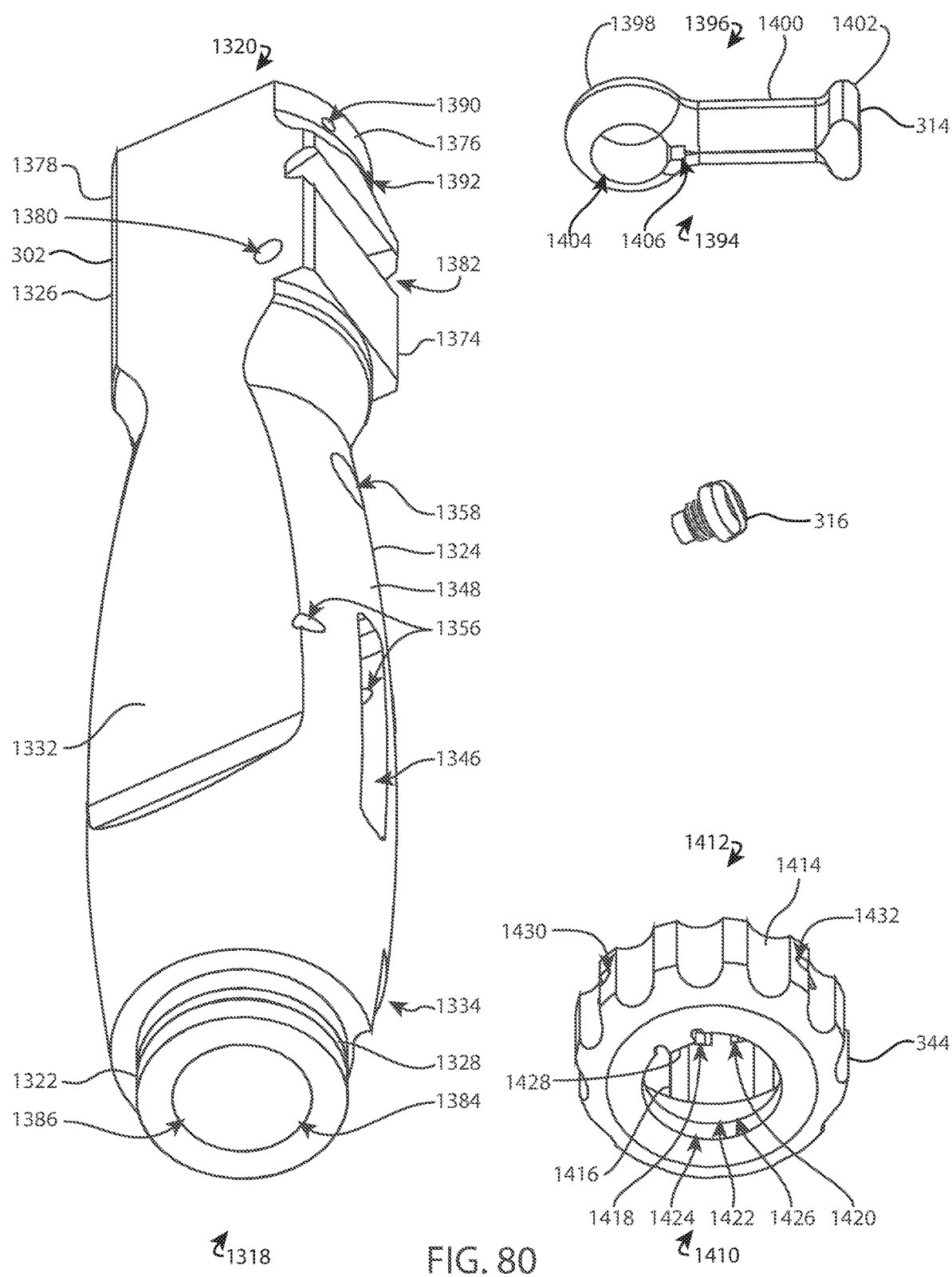
FIG. 80 is an exploded perspective view of a handle, a lock lever, a stop screw, and a release ring of the instrument of FIG. 64.
Figure 81:
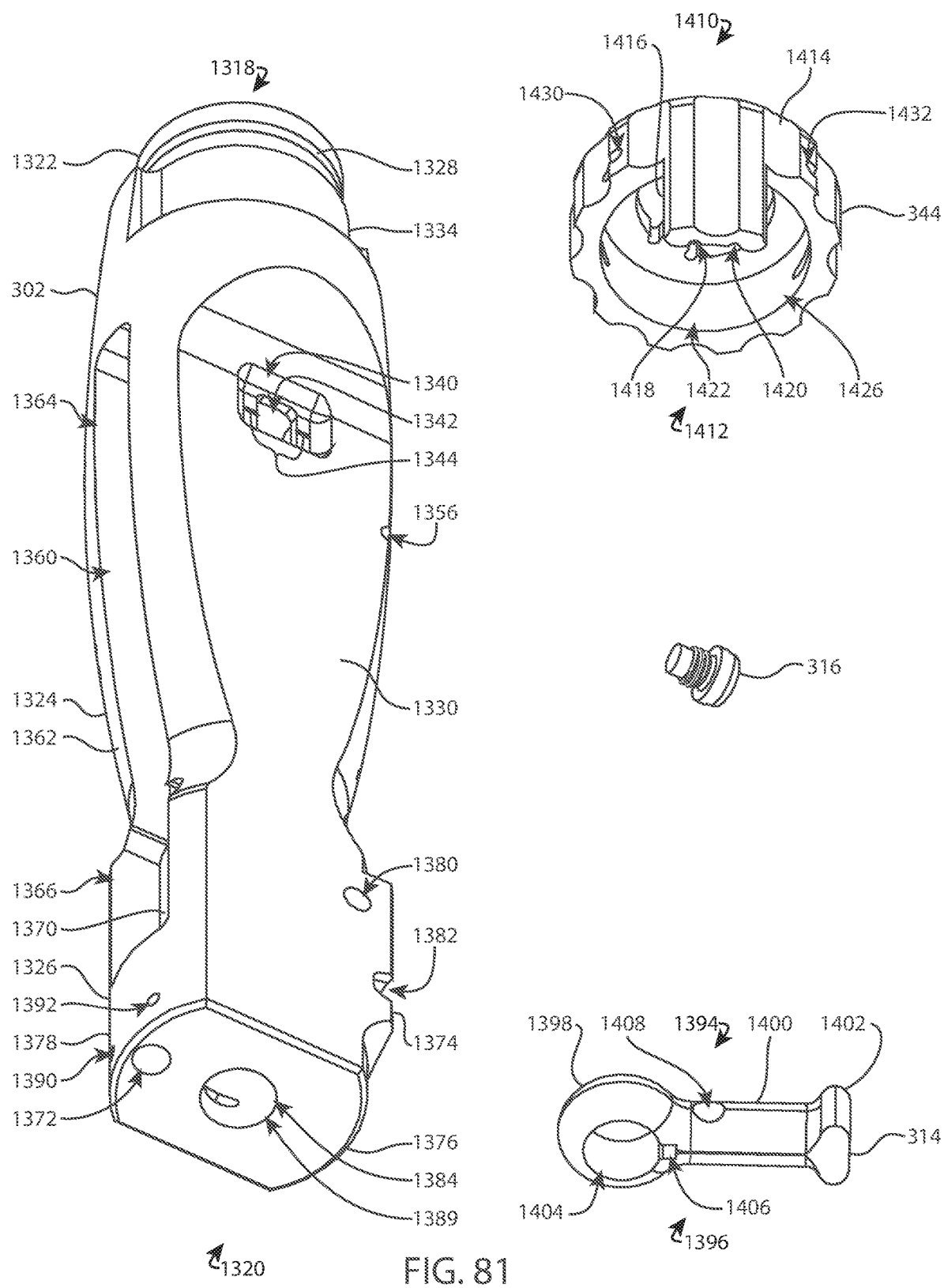
FIG. 81 is another exploded perspective view of the handle, lock lever, stop screw, and release ring of FIG. 80, from a different direction.
Figure 82:
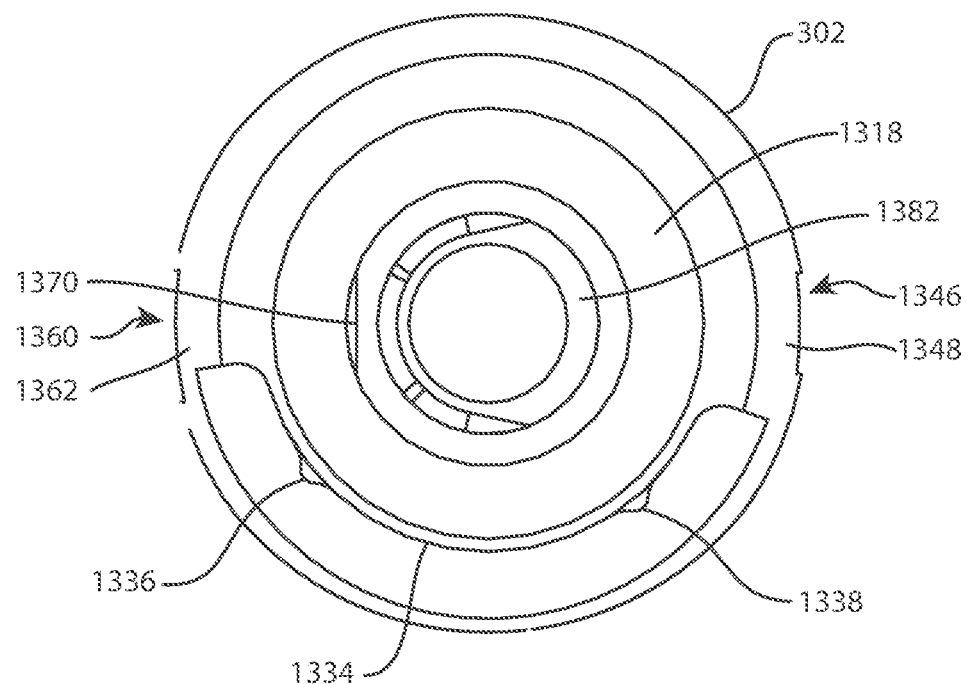
FIG. 82 is a proximal end view of an inserter handle of the instrument of FIG. 70.
Figure 83:
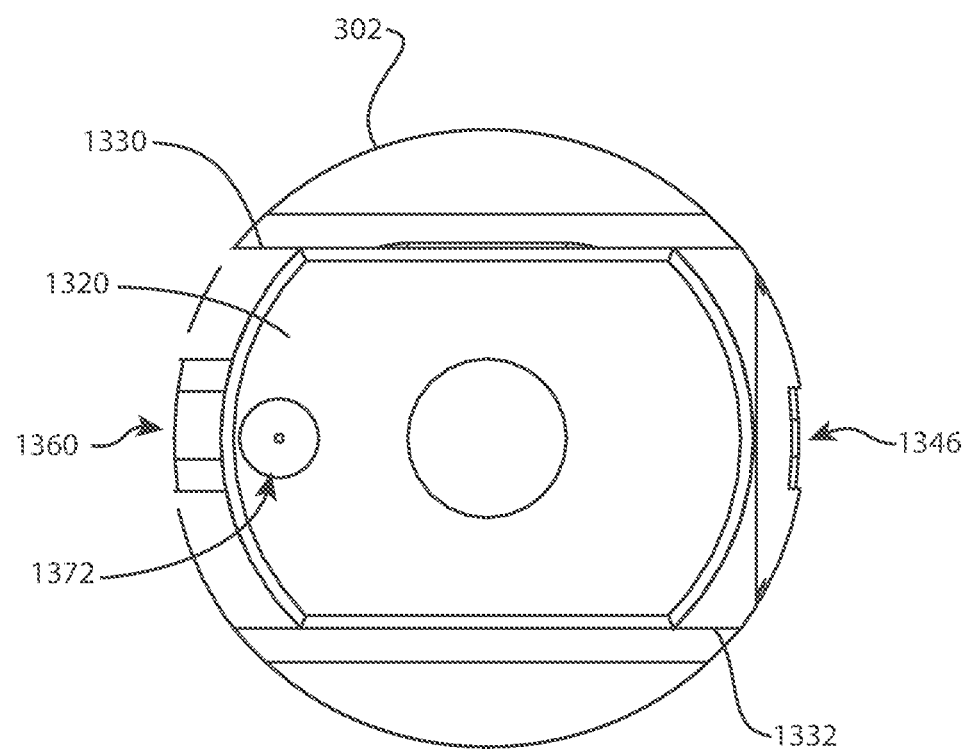
FIG. 83 is a distal end view of the inserter handle of the instrument of FIG. 70.
Figure 84:
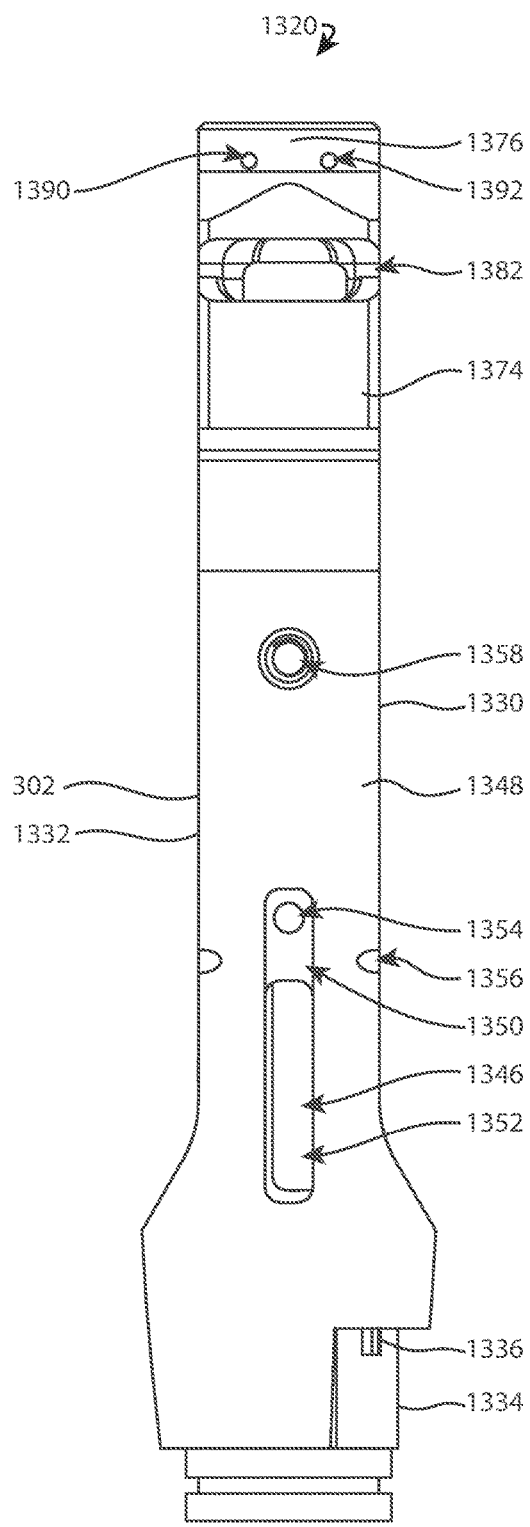
FIG. 84 is a right side view of the inserter handle of the instrument of FIG. 70.
Figure 85:
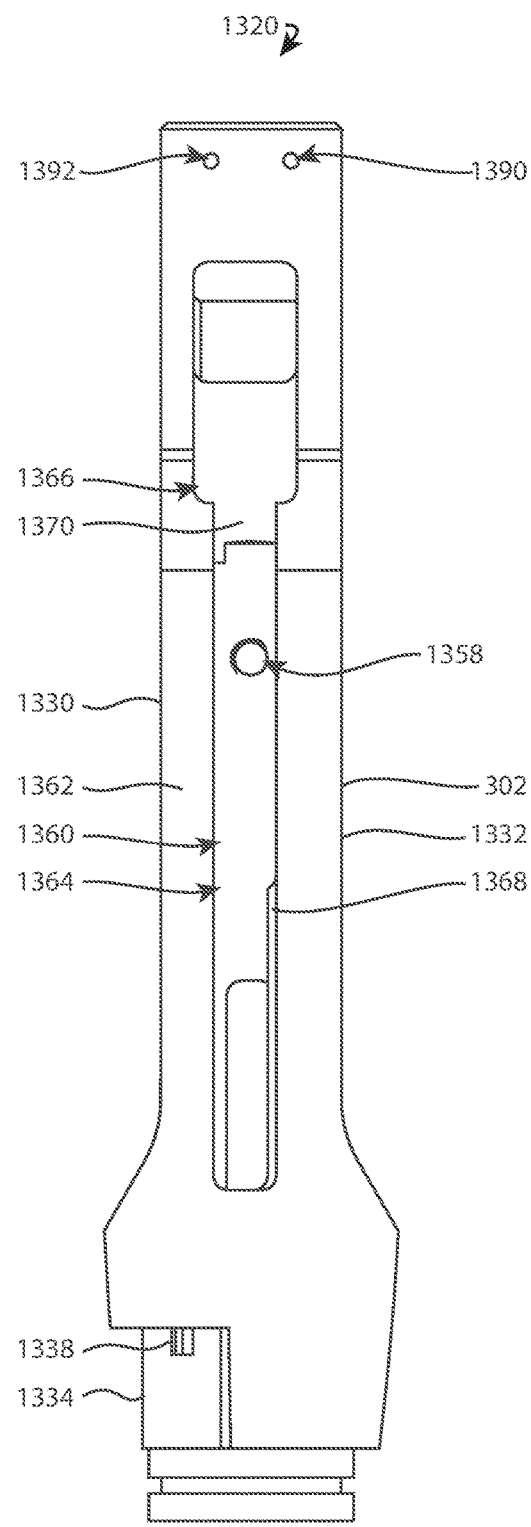
FIG. 85 is a left side view of the inserter handle of the instrument of FIG. 70.

In another step of the method, the implant 1000 is expanded vertically. Referring to FIGS. 54 and 55, the expansion knob 140 is rotated farther to continue to translate draw bar assembly 160 proximally along the longitudinal instrument axis 102. The continued axial force along the first direction causes the link members 1064, 1066 within the implant 1000 to travel along the expansion slots 1114, 1124, 1154, 1164 in the upper and lower support bodies 1042, 1044, urging the upper and lower support bodies away from one another and vertically expanding the first support member 1040 along a third direction indicated by axis 106, perpendicular to the first and second directions. When the vertical expansion is attained, indicia 248 or markings on the instrument may indicate the implant is in the vertically expanded configuration.

It is appreciated that the expansion knob may be actuated in discrete steps to first laterally and then vertically expand the implant, or the expansion knob may be actuated in a continuous motion to first laterally and then vertically expand the implant. It is also appreciated that in another embodiment, the vertical expansion of the implant may precede the horizontal expansion. In the embodiment shown, only the first support member 1040 expands vertically; the height of the second support member 1030 is fixed. This may provide a lordotic correction between the first and second vertebrae. In other embodiments, the first support member 1040 may be fixed and the second support member 1030 may be vertically expandable, or the first and second support members 1040, 1030 may both be vertically expandable. When expansion is complete, the draw bar assembly 160 may be disengaged from the shuttle 122 by actuating the lock collar 120, unthreaded from the implant 1000 and removed from the instrument 100.

In another step of the method, graft material may be inserted through the instrument into the expanded implant 1000. Referring to FIGS. 27, 28, 56, and 57, funnel 170 may be connected to the proximal end of instrument bore 112. Graft material may be inserted axially through the funnel 170 and bore 112 and deposited into the implant inner chamber 1120. The tamp assembly 180 may be deployed through instrument 100 to push and pack the graft through the bore 112 and in the chamber 1120.

In another step of the method, a locking fastener such as lockout screw 654 may be inserted through the instrument and into fixed engagement with the expanded implant 1000, to lock the implant in the horizontally and vertically expanded configuration. Referring to FIGS. 29, 30, 58, and 59, screw 654 may be loaded into screw holder 200 and connected to a distal end of screwdriver assembly 190. A distal tip of screwdriver assembly 190 may include a tip 792 shaped to complementarily engage the proximal end of screw 654. Screwdriver assembly 190, with attached screw holder 200 and screw 654, may be inserted longitudinally through bore 112 of instrument 100. The screwdriver assembly 190 may be actuated to engage a threaded portion 653 of screw 654 with the threaded first end body 1050 of implant 1000. As the screw is driven distally, a proximal shoulder 655 of screw 654 may abut a surface of the second end body 1052, rigidly locking the cage in the expanded configuration. Screw holder 200 may include a release feature or mechanism to release screw 654 from the holder 200 after the screw is in engagement with implant 1000. For example, the screw holder catch 182 may be biased to disengage the tooth 842 from the second portion 850 of the screw 654 when the screw is engaged with the implant 1000. When deployment and release of screw 654 is complete, the screwdriver assembly 190 and attached screw holder 200 may be withdrawn from the instrument 100.

Referring to FIGS. 60-63, implant 1000 is shown in situ after insertion between the first vertebral body 2 and the second vertebral body. In the embodiment depicted, support members 1040 and 1030 have been expanded horizontally along an anterior-posterior direction to provide support between the first and second vertebral bodies. Support member 1040 has been expanded vertically along a cephalocaudal direction to provide a lordotic correction between the first and second vertebrae. It is appreciated that in other embodiments of the invention, both support members could be expanded vertically, or support member 1030 could be solely expanded vertically to provide a kyphotic correction. One or more implants 1000 may be implanted between first and second vertebrae. Other approaches may be used within the scope of the disclosure, including lateral, transforaminal and anterior. One or more implants may be inserted in any orientation relative to the first and second vertebrae.

Referring to FIGS. 64-71, another insertion and expansion instrument is shown. Instrument 300 may be deployed to insert and expand implant 1000 or another expandable intervertebral implant. Instrument 300 may include a bayonet or other connection to removably connect implant 1000 to the instrument. Instrument 300 includes a ratchet mechanism 310 operable by a lever 312 to axially translate a shuttle 322 and draw bar assembly 328 proximally. The ratchet mechanism 310 may be referred to as an actuator. Similar to instrument 100, translation of draw bar assembly 328 provides axial force to laterally and/or vertically expand the connected implant. Other tools such as the funnel 170, tamp assembly 180, and screwdriver assembly 190 disclosed herein may be used, or adapted for use, with instrument 300 to deposit graft material within the implant and secure a locking fastener such as screw 654.

Instrument 300 extends between a proximal end 862 and a distal end 864 along a longitudinal instrument axis 866. Instrument 300 may include the ratchet mechanism 310, the lever 312, the shuttle 322 which may be similar to shuttle 122, an inserter handle 302 which may be similar to inserter handle 142, a shaft assembly 304 which may be similar to shaft assembly 116, an inserter shaft 306 which may be similar to inserter shaft 136, a distal tip part 308 which may be similar to inserter connector 138, a lock lever 314, a stop screw 316, a lock tube assembly 318 which may be similar to lock tube assembly 118, a lock tube coupling 320 which may be similar to lock tube coupling 128, a proximal lock tube 324 which may be similar to proximal lock tube 124, a distal lock tube 326 which may be similar to distal lock tube 126, a draw bar assembly 328 which may be similar to draw bar assembly 160, a draw bar knob 330 which may be similar to handle 164, a draw bar tip part 332, a draw bar 334 which may be similar to draw bar 156, a spring plunger 336, a ratchet 338, a lever link 340, a return link 342, and/or a release ring 344.

Referring to FIGS. 70-73, the ratchet mechanism 310 may include the lever 312, spring plunger 336, ratchet 338, lever link 340, and return link 342. The ratchet mechanism 310 may include the shuttle 322.

The lever 312 extends between a proximal end 868 and a distal end 870. The lever 312 may include a body 872 and an arm 874. The arm 874 may extend proximally obliquely away from an outer side 876 of the body 872. An opposite inner side 878 of the body may include a pair of outer arms 880, 882 forming an outer clevis, and a pair of inner arms 884, 886 forming an inner clevis. The inner arms 884, 886 may be located between the outer arms 880, 882. The inner arms 884, 886 may be shorter than the outer arms 880, 882, and may extend from the inner side 878 about one third as far as the outer arms. The arms 880, 882, 884, 886 may all be parallel as shown, and may be perpendicular to the inner side 878. A first hole 888 may extend through the arms 880, 882, 884, 886 near the inner side 878. A second hole 890 may extend through the outer arms 880, 882 near the free ends of the outer arms. The first and second holes 888, 890 may be parallel to the inner side 878. A third hole 892 may extend into the inner side 878 between the inner arms 884, 886. The third hole 892 may be parallel to the arms 880, 882, 884, 886.

The spring plunger 336 extends between a proximal end 892 and a distal end 894. The spring plunger 336 may be a generally cylindrical shaft with circular cross sections as shown. The spring plunger 336 may include, from proximal to distal, first and second outer portions 896, 898. The first outer portion 896 may extend distally most of the proximal-distal length of the spring plunger 336. The diameter of the second outer portion 898 may be less than the diameter of the first outer portion 896. There may be a tapered transition between the first and second outer portions 896, 898. The second outer portion 898 may include a rounded distal outer edge. A central longitudinal hole 900 may extend distally into the proximal end of the spring plunger 336. The hole 900 may extend distally almost as far as the first outer portion 896.

The ratchet 338 extends between a proximal end 902 and a distal end 904. The ratchet 338 may have a rectangular or square cross section as shown. A tooth 906 may protrude from an inner side 908 of the ratchet 338. The tooth 906 may be located along an inner proximal edge of the ratchet 338. A first hole 910 may extend through the ratchet 338 near the distal end 904 and may be parallel to the tooth 906. A second hole 912 may extend into the inner side 908 near the distal end 904 and may be perpendicular to the first hole 910. The second hole 912 may be between the first hole 910 and the distal end 904.

The lever link 340 extends between a proximal end 914 and a distal end 916. The lever link 340 may have a rectangular or square cross section as shown. A tooth 918 may protrude from an inner side 920 of the lever link 340. The tooth 918 may be located along an inner proximal edge of the lever link 340. A unilateral notch 922 may extend along the lever link 340 so as to intersect a proximal portion of the inner side 920 and an inner portion of the proximal end 916, so that the tooth 918 is thinner than the distal end 916. A first hole 924 may extend through the lever link 340 near the distal end 916 and may be parallel to the tooth 918. A second hole 926 may extend into an outer side 928 of the lever link 340 opposite the inner side 920 near the distal end 916 and may be perpendicular to the first hole 924. The first hole 924 may be between the second hole 926 and the distal end 916.

The return link 342 extends between a proximal end 930 and a distal end 932. The return link 342 may have a rectangular or square cross section as shown. A foot 934 may protrude from a first side 936 of the return link 342. The foot 934 may be located at the proximal end 930 of the return link 342. The foot 934 may extend perpendicular to the proximal-distal length of the return link 342. A unilateral notch 938 may extend along the return link 342 so as to intersect a proximal portion of an inner side 940 of the return link and an inner portion of the proximal end 930. A first hole 942 may extend distally into the proximal end 930 and the foot 934. A second hole 944 may extend through the return link 342 near the distal end 932 and may be parallel to the foot 934.

The shuttle 322 extends between a proximal end 946 and a distal end 948. The shuttle 322 may include, from proximal to distal, first, second, third, and fourth outer portions 950, 952, 954, 956. The first outer portion 950 may have a circular cross section and rounded proximal and distal outer circumferential edges. The proximal-distal length of the first outer portion 950 may be less than its diameter. The second outer portion 952 may have a circular cross section with a diameter that is less than the diameter of the first outer portion 950. The second outer portion 952 may form a square (90 degree) inner corner with the first outer portion 950. The proximal-distal length of the second outer portion 952 may be the same as or similar to the length of the first outer portion 950. The third outer portion 954 may have a circular cross section with a diameter that is less than the diameter of the second outer portion 952. The third outer portion 952 may form a square inner corner with the second outer portion 952. The third outer portion 954 may extend over most of the proximal-distal length of the shuttle 322. The fourth outer portion 956 may have a circular cross section that tapers down in diameter toward the distal end 948. The fourth outer portion 956 may be conical. A unilateral longitudinal groove 958 may extend along the second and third outer portions 952, 954 and may run out in the fourth outer portion 956. The groove 958 may have a rectangular or square cross section with a rounded proximal end at the proximal end of the second outer portion 952. A first series of transverse grooves 960 may extend across the third outer portion 954 and may be located 90 degrees from the longitudinal groove 958. There may be ten grooves 960 as shown, or another number. The size and shape of the grooves 960 may be complementary to the tooth 918 of the lever link 340. A second series of transverse grooves 962 may extend across the third outer portion 954 and may be located 90 degrees from the longitudinal groove 958 and 180 degrees from the first series of transverse grooves 960. There may be 54 grooves 962 as shown, or another number. The size and shape of the grooves 960 may be complementary to the tooth 906 of the ratchet 338. Indicia 964 may be included along the third outer portion 954 opposite the longitudinal groove 958. The indicia 964 may include transverse lines and numerals as shown, or other markings or engravings. A unilateral shaped slot 966 may extend proximally into the distal end of the third outer portion 954 and may run out in the fourth outer portion 956. The proximal end of the slot 966 may make a 90 degree bend toward the longitudinal groove 958. The slot 966 may have a rectangular or square cross section. The slot 966 and other similarly shaped slots disclosed herein may be referred to as a bayonet slot.

The shuttle 322 may include a central longitudinal hole 968 that extends through the shuttle between the proximal end 946 and the distal end 948. The hole 968 may include, from proximal to distal, first, second, third, and fourth inner portions 970, 972, 974, 976, each with a circular cross section. The first inner portion 970 may be a shallow countersink around the proximal end of the hole 968. The second inner portion 972 may have internal threads. The minor diameter of the threads may be the same as or similar to the minor diameter of the first inner portion 970. The third inner portion 974 may be smooth, with a diameter that is less than the minor diameter of the threads of the second inner portion 972. See FIG. 66. The distal end of the third inner portion 974 may have a square (90 degree) inner corner. The fourth inner portion 976 may be smooth, with a diameter that is less than the diameter of the third inner portion 974.

Referring to FIGS. 70, 71, 74, and 75, the shaft assembly 304 may include the inserter shaft 306 and distal tip part 308.

The inserter shaft 306 extends between a proximal end 978 and a distal end 980. The inserter shaft 306 may be a tubular part with circular outer and inner cross-sectional shapes. The inserter shaft 306 may include a pair of shaped slots 982, 984 which each include an approximately 90 degree bend. The slots 982, 984 may extend longitudinally into the proximal end 978 before making the bend. Each slot 982, 984 may extend through one wall of the inserter shaft 306. The inserter shaft 306 may include bilateral transverse grooves 986, 988 which may be located 90 degrees from, and distal to, the slots 982, 984. The inserter shaft 306 may include one or more openings 990. Three openings 990 are shown spaced along the inserter shaft 306 distal to the transverse grooves 986, 988. Each opening 990 may extend through one wall of the inserter shaft 306, or through both walls as shown. The inserter shaft 306 may include a central longitudinal hole 992 that extends through the inserter shaft between the proximal end 978 and the distal end 980. The hole 992 may include a proximal countersink 994 and/or a distal counterbore 996.

The distal tip part 308 extends between a proximal end 1200 and a distal end 1202. The proximal end 1200 may be circular in a proximal view. The distal end 1202 may be rectangular in a distal view. The distal end 1202 may have rounded corners in the distal view. The distal tip part 308 may include, from proximal to distal, first, second, and third outer portions 1204, 1206, 1208. The first outer portion 1204 may have a circular cross section and may extend distally about one fourth of the proximal-distal length of the distal tip part 308. The second outer portion 1206 may have a circular cross section and may have a diameter that is greater than the diameter of the first outer portion 1204. The second outer portion 1206 may form a square (90 degree) inner corner with the first outer portion 1204. The third outer portion 1208 may include the rectangular distal end 1202, and may also include a curvaceous transition surface that blends with the second outer portion 1206. The distal tip part 308 may include a central longitudinal hole 1210 that extends through the distal tip part between the proximal end 1200 and the distal end 1202. The hole 1210 may include, from proximal to distal, first and second inner portions 1212, 1214. The first inner portion 1212 may have a circular cross section and may extend distally about two thirds to three fourths of the overall proximal-distal length of the distal tip part 308. The cross-sectional shape of the second inner portion 1214 may be rectangular or square. The rectangle or square may have rounded corners. The major dimension (length) of the rectangle may be greater than the diameter of the first inner portion 1212, and may be aligned with the major dimension (length) of the rectangle of the distal end 1202. The minor dimension (width) of the rectangle may be greater than the diameter of the first inner portion 1212. The second inner portion 1214 may have a flat proximal end.

The shaft assembly 304 may be assembled by inserting the first outer portion 1204 of the distal tip part 308 into the counterbore 996 of the inserter shaft 306 and aligning the length of the rectangle of the third outer portion 1208 to extend over the transverse grooves 986, 988. The inserter shaft 306 and distal tip part 308 may be permanently connected, for example by welding. Alternatively, the inserter shaft 306 and distal tip part 308 may be combined into a single part. The inner diameters of the hole 992 of the inserter shaft 306 and the first inner portion 1212 of the hole 1210 of the distal tip part 308 may be the same or similar, and together they may form a shaft assembly bore 1434. See FIGS. 70 and 71.

Referring to FIGS. 70, 71, 76, and 77, the lock tube assembly 318 may include the lock tube coupling 320, proximal lock tube 324, and distal lock tube 326.

The lock tube coupling 320 extends between a proximal end 1216 and a distal end 1218. The lock tube coupling 320 may be a tubular part. The lock tube coupling 320 may include a proximal body 1220 which may have a circular cross-sectional outer shape, and may extend distally about half or three-fifth of the overall proximal-distal length of the lock tube coupling 320. A first lateral post 1222 may extend radially outwardly from the distal end of the body 1220. A unilateral tab 1224 may protrude distally from the body 1220, and may be located in line with the first lateral post 1222. The outer surface of the tab 1224 may be radially inset relative to the outer diameter of the body 1220. A second lateral post 1226 may protrude radially outwardly from the tab 1224. The second lateral post 1226 may protrude radially beyond the outer diameter of the body 1220 as shown. The second lateral post 1226 may be distal to and in line with the first lateral post 1222. First and second holes 1228, 1230 may extend through one wall of the body 1220 on either side of a location opposite the first lateral post 1222, or in other words, each hole may be located about 135 degrees away from the first lateral post 1222. The lock tube coupling 320 may include a central longitudinal hole 1232 that extends through the lock tube coupling between the proximal end 1216 and the distal end 1218. The hole 1232 may include, from proximal to distal, first, second, and third inner portions 1234, 1236, 1238. The first inner portion 1234 may have a circular cross section and may extend distally about a third of the overall proximal-distal length of the lock tube coupling 320, or about half of the length of the body 1220. The second inner portion 1236 may have a circular cross section with a diameter less than the diameter of the first inner portion 1234. The second inner portion 1236 may extend distally only a short distance as a complete diameter, but a section of it may extend through the distal end 1218 to form the inner side of the tab 1224. The third inner portion 1238 may have a non-circular cross section that is a C-shaped alcove in the distal wall of the body 1220 opposite the tab 1224. The alcove may extend around more than 180 degrees of arc.

The proximal lock tube 324 extends between a proximal end 1240 and a distal end 1242. The proximal lock tube 324 may be a tubular part with circular outer and inner cross-sectional shapes and constant outer and inner diameters.

The distal lock tube 326 extends between a proximal end 1244 and a distal end 1246. The distal lock tube 326 may be a tubular part with circular outer and inner cross-sectional shapes. The proximal end 1244 may include a unilateral notch 1248 that extends distally into one side of the distal lock tube 326. The notch 1248 may extend around less than 180 degrees of arc. The notch 1248 may include, from proximal to distal, first and second portions 1250, 1252. The first portion 1250 may have a flat distal end with square corners. The second portion 1252 may be narrower than the first portion 1250. The second portion 1252 may have a flat distal end with round corners. The distal end 1246 may include a pair of shaped slots 1254, 1256 which each include an approximately 90° bend. The slots 1254, 1256 may extend longitudinally into the distal end 1246 before making the approximately 90° bend. Each slot 1254, 1256 may extend through one wall of the distal lock tube 326. The distal lock tube 326 may include a central longitudinal hole 1258 that extends through the distal lock tube between the proximal end 612 and the distal end 614. The hole 1258 may include, from proximal to distal, first and second inner portions 1260, 1262. The first inner portion 1260 may extend distally for most of the proximal-distal length of the distal lock tube 326, and may have a flat distal end. The diameter of the second inner portion 1262 may be less than the diameter of the first inner portion 1260.

The lock tube assembly 318 may be assembled by inserting the distal end 1242 of the proximal lock tube 324 in the first inner portion 1234 of the lock tube coupling 320, and inserting the proximal end 1244 of the distal lock tube 326 in the third inner portion 1238 of the lock tube coupling 320 so that the tab 1224 is received in the second portion 1252 of the notch 1248. The lock tube coupling 320, proximal lock tube 324, and distal lock tube 326 may be permanently connected, for example by welding. Alternatively, the lock tube coupling 320, proximal lock tube 324, and/or distal lock tube 326 may be combined into a single part. The inner diameters of the second inner portion 1236 of the hole 1232 of the lock tube coupling 320, proximal lock tube 324, and first inner portion 1260 of the hole 1258 of the distal lock tube 326 may all be the same or similar, and together they may form a longitudinal instrument bore 1260. See FIGS. 64, 70, and 71. The distal lock tube 326 and the body 1220 of the lock tube coupling 320 may fit within the bore 1434 of the shaft assembly 304. The post 1226 of the lock tube coupling 320 may fit within either slot 982, 984 of the inserter shaft 306 of the shaft assembly 304.

Referring to FIGS. 70, 71, 78, and 79, the draw bar assembly 328 may include the draw bar knob 330, draw bar tip part 332, and draw bar 334.

The draw bar knob 330 extends between a proximal end 1262 and a distal end 1264.

The draw bar handle 330 extends between a proximal end 1262 and a distal end 1264. The draw bar handle 330 may include, from proximal to distal, a knob body 1266 and a shaft 1268. The knob body 1266 may be generally disc-shaped with an outer diameter that is greater than its proximal-distal length. The knob body 1266 may include one or more grip features 1270 such as the six rim scallops shown. The outer diameter of the shaft 1268 may be less than the outer diameter of the knob body 1266 and the proximal-distal length of the shaft may be greater than the proximal-distal length of the knob body 1266. The shaft 1268 may include a flange 1272 or annulus that extends circumferentially around a middle portion of the shaft. The flange 1272 may have square proximal and distal outer circumferential edges. The shaft 1268 may include one or more holes 1274 that extend transversely into, or through, the shaft; two through holes 1274 are shown between the distal side of the knob body 1266 and the proximal side of the flange 1272. The two through holes 1274 are perpendicular to each other. A distal portion of the shaft 1268 may include external threads 1276. The outer diameter of the flange 1272 may be greater than the major diameter of the threads 1276. The minor diameter of the threads 1276 may be greater than the outer diameter of the remaining smooth portions of the shaft 1268. The draw bar handle 330 may include a central longitudinal hole 1278 that extends through the draw bar handle between the proximal end 1262 and the distal end 1264. The hole 1278 may include, from proximal to distal, first, second, and third inner portions 1280, 1282, 1284. The first inner portion 1280 may have a circular cross section and may extend distally about half, or most, of the proximal-distal length of the knob body 1266. The first inner portion 1280 may have a flat distal end. A circumferential fillet radius may be present around the proximal inner edge of the first inner portion 1280. A circumferential fillet radius may be present in the distal inner corner of the first inner portion 1280. The second inner portion 1282 may have a circular cross section and may extend distally between the distal side of the knob body 1266 and the holes 1274. The diameter of the second inner portion 1282 may be less than the diameter of the first inner portion 1280. The third inner portion 1284 may have a circular cross section and may extend distally through the distal end of the 1264 of the draw bar handle 330. The diameter of the third inner portion 1284 may be less than the diameter of the first inner portion 1280 and greater than the diameter of the second inner portion 1282. The third inner portion 1284 may have a flat proximal end. The hole(s) 1274 may extend into a proximal end of the third inner portion 1284.

The draw bar tip part 332 extends between a proximal end 1286 and a distal end 1288. The draw bar tip part 332 may include, from proximal to distal, first, second, third, and fourth outer portions 1290, 1292, 1294, 1296. The first outer portion 1290 may have a circular cross section and may extend distally about one third to half of the overall proximal-distal length of the draw bar tip part 332. An outer proximal edge of the first outer portion 1290 may include a circumferential chamfer. The second outer portion 1292 may have a circular cross section and may extend distally only a short distance. The diameter of the second outer portion 1292 may be greater than the diameter of the first outer portion 1290. The second outer portion 1292 may be referred to as a flange or annulus around a middle portion of the draw bar tip part 332. The third outer portion 1294 may have a circular cross section. The diameter of the third outer portion 1294 may be greater than the diameter of the first outer portion 1290 and less than the diameter of the second outer portion 1292. The fourth outer portion 1296 may be a torque fitting, such as the hexagonal key shown. An outer distal edge of the fourth outer portion 1296 may include a circumferential chamfer. The draw bar tip part 332 may include a central longitudinal hole 1298 that extends through the draw bar tip part between the proximal end 1286 and the distal end 1288. The hole 1298 may include, from proximal to distal, first, second, and third inner portions 1300, 1302, 1304. The first inner portion 1300 may have a circular cross section. The distal end of the first inner portion 1300 may be proximal to the second outer portion 1292. The second inner portion 1302 may include internal threads. The major diameter of the threads may be less than the diameter of the first inner portion 1300. The third inner portion 1304 may have a circular cross section. The diameter of the third inner portion 1304 may be less than the diameter of the first inner portion 1300 and greater than the major diameter of the threads of the second inner portion 1302.

The draw bar 334 extends between a proximal end 1306 and a distal end 1308. The draw bar 334 may be a cylindrical shaft as shown. The draw bar 334 may include a central longitudinal hole 1310 that extends proximally into the distal end 1308 of the draw bar 334. The hole 1310 may include, from proximal to distal, first and second inner portions 1312, 1314. The first inner portion 1312 may have a circular cross section. The second inner portion 1314 may have a circular cross section with a diameter greater than the diameter of the first inner portion 1312.

The draw bar assembly 328 may be assembled by inserting the proximal end 1306 of the draw bar 334 in the second inner portion 1282 of the hole 1278 of the draw bar handle 330 so that the proximal end 1306 is at the same or similar level with the distal end of the first inner portion 1280, and inserting the first outer portion 1290 of the draw bar tip part 332 in the second inner portion 1314 of the hole 1310 of the draw bar 334. A circumferential gap 1316 may exist between the outer surface of the draw bar 334 and the inner surface of the third inner portion 1284. See FIG. 66. The draw bar knob 330, draw bar tip part 332, and draw bar 334 may be permanently connected, for example by welding. Alternatively, the draw bar knob 330, draw bar tip part 332, and/or draw bar 334 may be combined into a single part. The draw bar tip part 332 and draw bar 334 may fit within the bore 1260 of the lock tube assembly 318. The proximal end 1240 of the proximal lock tube 324 may fit in the gap 1316.

Referring to FIGS. 66, 70, 71, and 80-85, the inserter handle 302 extends between a proximal end 1318 and a distal end 1320. The inserter handle 302 may include, from proximal to distal, first, second, and third outer portions 1322, 1324, 1326. The first outer portion 1322 may be cylindrical with a circumferential groove 1328 centrally located along the proximal-distal length of the first outer portion 1322. The groove 1328 may have square inner corners. The second outer portion 1324 may extend distally over most of the overall proximal-distal length of the inserter handle 302. The second outer portion 1324 may be generally hourglass shaped or otherwise contoured to be comfortably and ergonomically gripped by a user's hand. The third outer portion 1326 may extend over about one fourth of the overall proximal-distal length of the inserter handle 302. The third outer portion 1326 may include flat front and back surfaces 1330, 1332 which may extend proximally from the distal end 1320 over the third outer portion 1326 and most of the proximal-distal length of the second outer portion 1324. The third outer portion 1326 may include a rectangular or square boss 1374 which protrudes from a right side 1376 of the third outer portion. The boss 1374 may extend from a middle portion of the proximal-distal length of the third outer portion 1326. A left side 1378 of the third outer portion 1326 may be a portion of a cylinder.

The inserter handle 302 may include a unilateral recess 1334 that extends distally into the second outer portion. The recess 1334 may be on the same side as the front surface 1330. The recess 1334 may be arcuate, and may extend around less than 180 degrees of arc. The recess 1334 may include bilateral ridges 1336, 1338 as seen best in FIG. 82. The ridges 1336, 1338 may extend proximally a short distance from the distal end of the recess 1334. A pocket 1340 may be located in the proximal region of the front surface 1330. A window 1342 may be located within the pocket 1340. The window 1342 may extend through the front side of the inserter handle 302. The pocket 1340 may include indicia 1344 such as the transverse lines shown bracketing the window 1342. A hole 1380 may extend through the inserter handle 302 between the front and back sides and may be located in the proximal right portion of the third outer portion 1326.

A longitudinal slot 1346 may extend into a right side 1348 of the second outer portion 1324 of the inserter handle 302. The slot 1346 may be rectangular with rounded corners. The proximal end of the slot 1346 may be proximal to the pocket 1340 and the distal end of the slot may be distal to the pocket. A distal portion 1350 of the slot 1346 may be shallow, with a flat bottom, and a proximal portion 1352 of the slot may be deep. The distal portion 1350 may extend over the distal one third of the overall proximal-distal length of the slot 1346. The distal portion 1350 may include a hole 1354 in the bottom near the distal end. A transverse hole 1356 may extend through the inserter handle 302 between the front and back sides so as to intersect the side walls of the distal portion 1350 proximal to the hole 1354. A hole 1358 may extend into the right side 1348 of the second outer portion 1324 of the inserter handle 302 distal to the slot 1346. The hole 1358 may include internal threads and a counterbore to complement the stop screw 316. A transverse slot 1382 may extend into the right side 1376 of the third outer portion 1326. The slot 1382 may extend into a distal portion of the boss 1374. The slot 1382 may taper in the transverse direction, becoming narrower as the slot extends into the third outer portion 1326. See FIG. 82.

A longitudinal slot 1360 may extend into a left side 1362 of the second and third outer portions 1324, 1326 of the inserter handle 302. The proximal end of the slot 1360 may be at the same or similar level as the proximal end of the slot 1346 and the distal end of the slot may extend about half of the overall proximal-distal length of the third outer portion 1326. A proximal portion 1364 of the slot 1360 may be narrower than a distal portion 1366 of the slot. The proximal and distal portions 1364, 1366 may each be rectangular with rounded corners. The distal end of the proximal portion 1364 may be distal to the hole 1358 and proximal to the third outer portion 1326. A unilateral narrow ledge 1368 may extend along a proximal back side wall within the proximal portion 1364. A platform 1370 may extend between the side walls of the proximal and distal portions 1364, 1366. The proximal end of the platform 1370 may be distal to the hole 1358 and proximal to the distal end of the proximal portion 1364, and the distal end of the platform may be located about one third of the overall proximal-distal length of the third outer portion 1326, or about one half of the overall proximal-distal length of the distal portion 1366. The platform 1370 may be deeper within the inserter handle 302 than the ledge 1368. A longitudinal hole 1372 may extend proximally into the distal end 1320 of the inserter handle 302 and into the proximal end wall of the proximal portion 1364 of the slot 1360. See FIG. 66.

The inserter handle 302 may include a central longitudinal hole 1384 that extends through the inserter handle between the proximal end 1318 and the distal end 1320. The hole 1384 may include, from proximal to distal, first, second, and third inner portions 1386, 1388, 1389. Each of these inner portions may have a circular cross section. The first inner portion 1386 may extend distally to the proximal end of the platform 1370. The diameter of the second inner portion 1388 may be less than the diameter of the first inner portion 1386. The second inner portion 1388 may extend distally to intersect the slot 1382. The diameter of the third inner portion 1389 may be less than the diameter of the second inner portion 1388. The window 1342, proximal portion 1352 of the slot 1346, hole 1358, and proximal portion 1364 of the slot 1360 may open into the first inner portion 1386.

The distal portion 1366 of the slot 1360, distal to the platform 1370, and the slot 1382 may open into the second inner portion 1388. Bilateral holes 1390, 1392 may extend through the inserter handle 302 between the right and left sides near the distal end 1320. The holes 1390, 1392 may intersect the third inner portion 1389.

The lock lever 314 extends between a proximal side 1394 and a distal side 1395. The lock lever 314 may include a ring 1398, a stem 1400, and a cap 1402. The stem 1400 may extend from one side of the ring 1398. The cap 1402 may be an enlargement at the free end of the stem 1400. A central longitudinal hole 1404 may extend through the lock lever 314 between the proximal and distal sides 1394, 1396. A keyway 1406 may also extend through the lock lever 314 between the proximal and distal sides 1394, 1396 along an inner wall of the hole 1404 at the base of the stem 1400. A hole 1408 may extend into the stem 1400 near the ring 1398.

The stop screw 316 may be a dog point screw that is complementary to the hole 1358. The stop screw 316 may have a pan head or cheese head.

The release ring 344 extends between a proximal end 1410 and a distal end 1412. The release ring 344 may include one or more friction features 1414, such as the twelve rim scallops shown. The release ring 344 may include a unilateral tab 1416 that may extend distally. An inner side of the tab 1416 may include two longitudinal grooves 1418, 1420 that extend through the distal end 1412. A central longitudinal hole 1422 may extend through the release ring 344 between the proximal and distal sides 1410, 1412. The hole 1422 may include, from proximal to distal, first and second inner portions 1424, 1426. The first inner portion 1424 may have a generally circular cross section with a unilateral key 1428 extending radially into the hole 1422 at the proximal end 1410. The key 1428 may be generally opposite the tab 1416, but may be offset several degrees from being exactly opposite the tab. For example, the key 1428 may be 155 degrees away from the tab 1416. The second inner portion 1426 may have a circular cross section with a diameter that is greater than the diameter of the first inner portion 1424. The proximal end of the second inner portion 1426 may be flat. The inner side of the tab 1416 may be radially offset outwardly from the second inner portion 1426. Bilateral transverse holes 1430, 1432 may extend through the release ring 344. The holes 1430, 1432 may intersect the second inner portion 1426.

The instrument 300 may be assembled by coupling the release ring 344, ratchet 338, stop screw 316, and spring plunger 336 to the inserter handle 302, coupling the lever link 340 and return link 342 to the lever 312, coupling the sub-assembly of the lever link 340, the return link 342, and the lever 312 to the inserter handle 302 (with spring plunger 336), coupling the shaft assembly 304 and the lock lever 314 to the inserter handle 302, inserting the lock tube assembly 318 into the shaft assembly 304, coupling the shuttle 322 to the inserter handle 302 (with stop screw 316 and release ring 344), inserting the draw bar assembly 328 into the lock tube assembly 318, and coupling the draw bar assembly 328 to the shuttle 322. These steps may be performed in any order.

Coupling the release ring 344 to the inserter handle 302 may include inserting the first outer portion 1322 of the inserter handle 302 into the second inner portion 1426 of the hole 1422 of the release ring 344 so that the tab 1416 is in the recess 1334 between the ridges 1336, 1338, aligning the holes 1430, 1432 with the groove 1328, and inserting pins into the holes 1430, 1432 and the groove 1328.

Coupling the ratchet 338 to the inserter handle 302 may include inserting a compression spring (not shown) into the holes 912, 1354, inserting the ratchet 338 into the slot 1346 with the tooth 906 facing into the first inner portion 1386 of the hole 1384, aligning the holes 1356, 910, and inserting a pin (not shown) through the holes 1356, 910. The spring may bias the ratchet 338 to protrude into the first inner portion 1386.

Coupling the stop screw 316 to the inserter handle 302 may include inserting the dog point (tip) of the screw into the hole 1358, engaging the complementary threads, and tightening the screw in the hole 1358.

Coupling the spring plunger 336 to the inserter handle 302 may include inserting a compression spring (not shown) into the hole 900 of the spring plunger 336 and inserting the proximal end 892 of the spring plunger 336 into the proximal portion of the hole 1372 of the inserter handle 302 so that the second outer portion 898 protrudes distally into the proximal portion 1364 of the slot 1360.

Coupling the lever link 340 and the return link 342 to the lever 312 may include positioning the distal end 916 of the lever link 340 between the inner arms 884, 886 of the lever 312, next to the arm 884, with the hole 924 aligned with the hole 888 and the tooth 918 facing away from the arm 874; positioning the distal end 932 of the return link 342 between the inner arms 884, 886, next to the arm 886, with the hole 944 aligned with the hole 888 and the foot 934 facing towards the proximal end 914 of the lever link; and inserting a pin (not shown) through the holes 888, 924, 944 to hingedly connect the lever link 340 and the return link 342 to the lever 312. The pin may only extend through the inner arms 884, 886, the lever link 340, and the return link 342. A compression spring (not shown) may be inserted in the holes 892, 926 to bias the lever link 340 away from the lever 312.

Coupling the sub-assembly of the lever link 340, the return link 342, and the lever 312 to the inserter handle 302 (with spring plunger 336) may include inserting the inner arms 884, 886 of the lever 312 into the distal portion 1366 of the slot 1360 of the inserter handle 302 so that the inserter handle 302 is between the outer arms 880, 882 and the lever link 340 and the return link 342 extend into the proximal portion 1364 of the slot 1360, inserting the second outer portion 898 of the spring plunger 336 into the hole 942 of the return link 342, and inserting a pin (not shown) into the holes 890, 1380. The spring plunger 336 and associated compression spring may bias the lever 312 away from the inserter handle 302. The ledge 1368 fits in the notch 922 to control the depth to which the tooth 918 extends into the first inner portion 1386 of the hole 1384.

Coupling the shaft assembly 304 and the lock lever 314 to the inserter handle 302 may include inserting the ring 1398 of the lock lever 314 into the slot 1382 of the inserter handle 302 so that the stem 1400 and cap 1402 extend laterally outside the slot 1382 and the hole 1408 faces the front surface 1330, inserting the proximal end 978 of the inserter shaft 306 into the third inner portion 1389 of the hole 1384 in the distal end 1320 of the inserter handle 302 and into the hole 1404 of the lock lever 314, aligning the grooves 986, 988 with the holes 1390, 1392, and inserting pins (not shown) into the holes 1390, 1392 and grooves 986, 988. A compression spring (not shown) may be inserted in the hole 1408 to bear against a front wall of the slot 1382. The spring may bias the lock lever 314 toward the back surface 1332.

Inserting the lock tube assembly 318 into the shaft assembly 304 may include inserting the distal end 1246 of the distal lock tube 326 into the hole 992 in the proximal end 978 of the inserter shaft 306, advancing the lock tube assembly 318 into the shaft assembly 304 until the body 1220 of the lock tube coupling 320 enters the hole 992 and the post 1226 enters the slot 982 or the slot 984, and twisting the lock tube assembly 318 relative to the shaft assembly 304 to move the post 1226 past the slot bend. When the shaft assembly 304, lock lever 314, inserter handle 302, and lock tube assembly 318 are operatively assembled, the body 1220 of the lock tube coupling 320 may fit in the hole 1404 of the lock lever 314 and the posts 1222, 1226 of the lock tube coupling 320 may fit in the keyway 1406 of the lock lever 314.

Coupling the shuttle 322 to the inserter handle 302 (with stop screw 316 and release ring 344) may include inserting the proximal end 1240 of the proximal lock tube 324 in the fourth inner portion 976 of the hole 968 at the distal end 948 of the shuttle 322, inserting the key 1428 of the release ring 344 in the groove 958 at the distal end 948 of the shuttle 322, sliding the shuttle 322 into the first inner portion 1386 of the hole 1384 until the dog point of the stop screw 316 slides into the slot 966, and twisting the release ring 344 and shuttle 322 relative to the inserter handle 302 to move the dog point past the slot bend.

When the instrument 300 is operatively assembled as described in the preceding steps, the proximal lock tube 324 is in the hole 968 of the shuttle 322, the tooth 918 of the lever link may engage the grooves 960 of the shuttle 322, the tooth 906 of the ratchet 338 may engage the grooves 962 of the shuttle 322, and a portion of the indicia 964 of the shuttle 322 may be exposed through the window 1342 of the inserter handle 302.

Inserting the draw bar assembly 328 into the lock tube assembly 318 may include inserting the distal end 1288 of the draw bar tip 332 into the inner diameter of the proximal end 1240 of the proximal lock tube 324 and advancing the draw bar assembly 328 into the lock tube assembly 318 until the proximal end 1240 enters the gap 1316.

Coupling the draw bar assembly 328 to the shuttle 322 may include engaging the internal threads of the second inner portion 972 of the hole 968 of the shuttle 322 with the external threads 1276 of the draw bar handle 330 and tightening the threads until the flange 1272 abuts the proximal end 946 of the shuttle 322.

The instrument 300 may be operated by rotating the release ring 344, pivoting the lock lever 314, and pivoting the lever 312.

The release ring 344 may be coupled to the shuttle 322 by the key 1428 in the groove 958 so that the shuttle is free to slide axially relative to the release ring, and the shuttle is rotationally coupled to the release ring so that rotation of the release ring causes rotation of the shuttle. When the release ring 344 is rotated so that the groove 1420 engages the ridge 1338, the slot 966 of the shuttle 322 may be free to slide axially relative to the stop screw 316 and the grooves 960, 962 may rotate out of engagement with the teeth 918, 906, respectively. When the release ring 344 is rotated so that the groove 1418 engages the ridge 1336, the slot 966 may capture the stop screw 316 past the slot bend. Thus the release ring 344 and the stop screw 316 cooperate to connect or disconnect the shuttle 322 and the inserter handle 302.

The lock lever 314 may be coupled to the lock tube coupling 320 by the posts 1222, 1226 in the keyway 1406 so that the lock tube coupling is free to slide axially relative to the lock lever, and the lock tube coupling is rotationally coupled to the lock lever so that rotation of the lock lever 314 causes rotation of the lock tube coupling. When the lock lever 314 is rotated toward the front surface 1330 of the inserter handle 302, the posts 1222, 1226 may be free to slide axially relative to the keyway 1406 and the slot 982 or 984 of the inserter shaft 306. When the lock lever 314 is rotated toward the back surface 1332, the slot 982 or 984 may capture the post 1226 past the slot bend. The lock lever 314 may be biased toward the back surface 1332. The lock lever 314 thus connects or disconnects the lock tube assembly 318 and the shaft assembly 304.

The lever 312 and associated ratchet mechanism 310 may be coupled to the other parts of the instrument 300 so that actuation of the lever causes proximal axial translation of the shuttle 322 relative to the inserter handle 302. Pivoting the lever 312 away from the inserter handle 302 may move the lever link 340 distally relative to the shuttle 322. Pivoting the lever 312 toward the inserter handle 302 may move the lever link 340 proximally. When the tooth 918 is engaged in a groove 960, pivoting the lever 312 toward the inserter handle 302 also may cause linear translation of the shuttle 322 proximally along the longitudinal instrument axis 866 without rotation of the shuttle 322 about the axis 866. Thus the lever link 340 may be referred to as a drive link of the ratchet mechanism 310. The tooth 906 of the ratchet 338 may engage the grooves 962 to prevent the shuttle 322 from moving distally.

Referring to FIGS. 86-91, another insertion and expansion instrument is shown. Instrument 1500 may be deployed to insert and expand implant 1000, implant 1100 as shown, or another expandable intervertebral implant. Other tools such as the draw bar assembly 160, funnel 170, tamp assembly 180, and screwdriver assembly 190 disclosed herein may be used, or adapted for use, with instrument 1500 to deploy an implant, deposit graft material within the implant, and secure a locking fastener such as screw 654.

The instrument 1500 may differ from instruments 100 and 300 in at least the following attributes. The draw bar may be engaged by a slider button/lever that may prevent the draw bar from rotating, and may engage the rotating portion of the inserter handle to enable expansion. The slider button/lever may reduce the potential for incorrect user inputs, i.e., poka-yoke. The draw bar length may be adjustable so that one draw bar may be compatible with multiple implant lengths. The handle may be removable from the tube portion of the instrument 1500 to minimize the mass attached to the implant during bone graft insertion or other steps in the methods of use. Minimizing the instrument mass attached to the implant, and the associated moment arm through the center of gravity of the instrument mass, may minimize unintended motion or misalignment of the implant during steps in the methods of use. The funnel may be used to unthread the inserter shaft (implant retainer shaft) from the implant, for example, after installation of the lockout screw 654.

The instrument 1500 may include an inserter connector 1502 which may be similar to inserter connector 138 or distal tip part 308, a connector plate 1504 which may be similar to impaction cap 146, an inserter shaft 1506 which may be similar to inserter shaft 136 or 306, an implant retainer shaft 1508 which may function similar to lock tube assembly 118 or 318, a connector button 1510, a thumb wheel 1514, a wheel axle 1516, an inserter handle 1518, a knob strike plate 1520, a spline insert 1522, a rotation lock ring 1524, a cam lever 1526, a slider button 1528, a threaded slider 1530, a top knob part 1532, a bottom knob part 1534, and a draw bar assembly 1536 which may be similar to draw bar assembly 160 or 328. The instrument 1500 may also include various pins, screws and/or bolts, springs, ball detents, and the like. These parts may be basic off-the-shelf components, and they are generally not shown in this disclosure. The instrument 1500 extends from a proximal end 1538 to a distal end 1540 along a longitudinal instrument axis 1542.

Figure 92:
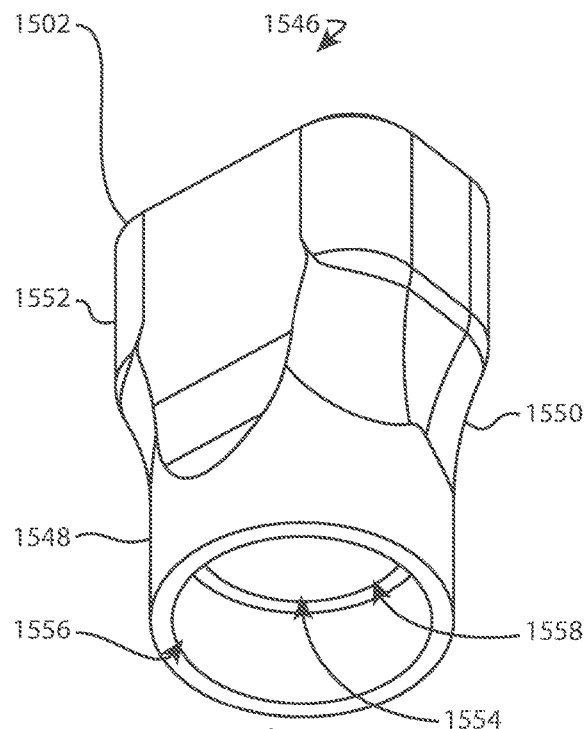
FIG. 92 is a perspective view of an inserter connector of the instrument of FIG. 86.
Figure 93:
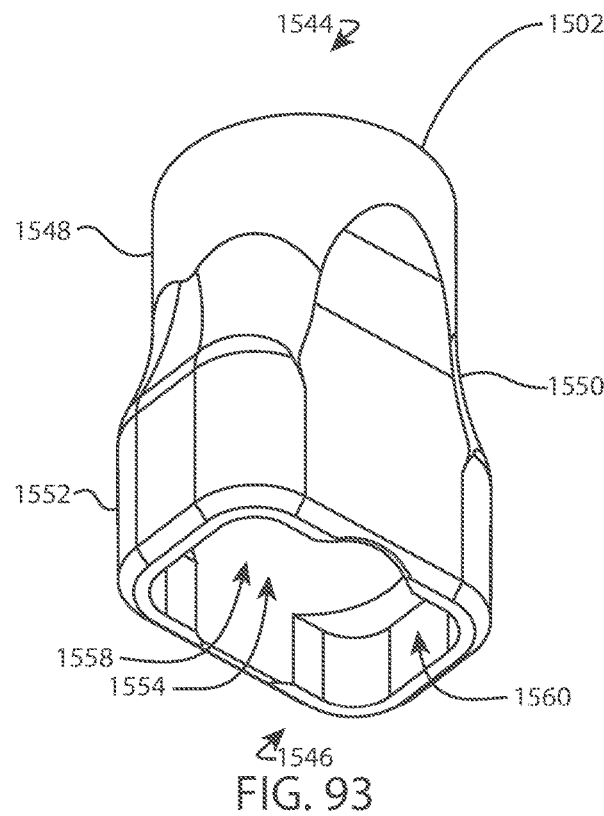
FIG. 93 is another perspective view of the inserter connector of FIG. 92, from a different direction.

Referring to FIGS. 92 and 93, the inserter connector 1502 extends between a proximal end 1544 and a distal end 1546. The proximal end 1544 may be circular in a proximal view. The distal end 1546 may be rectangular in a distal view. The distal end 1546 may have rounded corners in the distal view. The inserter connector 1502 may include, from proximal to distal, first, second, and third outer portions 1548, 1550, 1552. The first outer portion 1548 may have a circular cross section and may extend distally about one fourth to one third of the proximal-distal length of the inserter connector 1502. The second outer portion 1550 may be a curvaceous transition surface that blends between the first and third outer portions 1548, 1552. The third outer portion 1552 may include the rectangular distal end 1546. An outer distal edge of the rectangle may be chamfered. The inserter connector 1502 may include a central longitudinal hole 1554 that extends through the distal tip part between the proximal end 1544 and the distal end 1546. The hole 1554 may include, from proximal to distal, first, second, and third inner portions 1556, 1558, 1560. The first inner portion 1556 may have a circular cross section and may extend distally about one fourth to one third of the overall proximal-distal length of the inserter connector 1502. The second inner portion 1558 may have a circular cross section with a diameter that is less than the diameter of the first inner portion 1556. The cross sectional shape of the third inner portion 1560 may be the superposition of a circle and a rectangle. The diameter of the circle may be less than the diameter of the first inner portion 1556 and the same as or similar to the diameter of the second inner portion 1558. The major dimension (length) of the rectangle may be greater than the diameter of the first inner portion 1556, and may be aligned with the major dimension (length) of the rectangle of the third outer portion 1552. The minor dimension (width) of the rectangle may be less than the diameter of the circle, and may be less than the diameter of the second inner portion 1558. The rectangle may have rounded corners. The third inner portion 1560 may have a flat proximal end.

Figure 94:
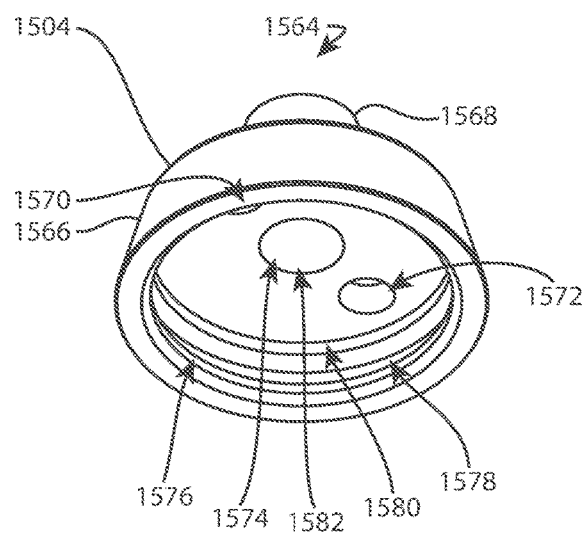
FIG. 94 is a perspective view of a connector plate of the instrument of FIG. 86.
Figure 95:
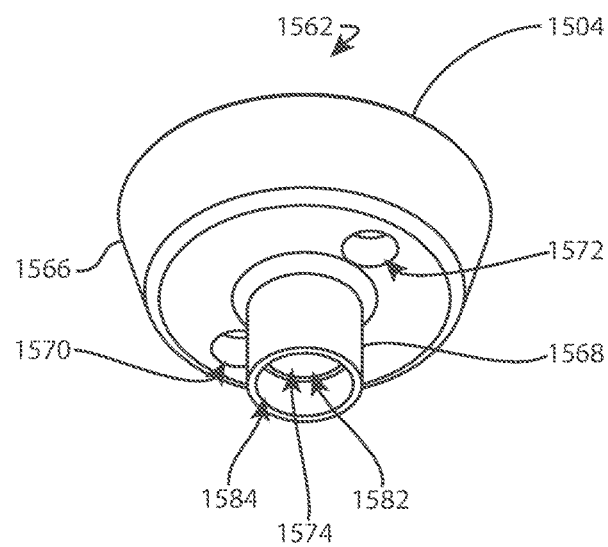
FIG. 95 is another perspective view of the connector plate of FIG. 94, from a different direction.

Referring to FIGS. 94 and 95, the connector plate 1504 extends between a proximal side 1562 and a distal side 1564. The connector plate 1504 may be circular in a proximal or distal view. The connector plate 1504 may include, from proximal to distal, first and second outer portions 1566, 1568. The first outer portion 1566 may taper inwardly from proximal to distal, and may be conical. The first outer portion 1566 may have a flat distal end. The second outer portion 1568 may be cylindrical, with a diameter that is less than the minor diameter of the first outer portion 1566. Bilateral holes 1570, 1572 may extend through the connector plate 1504 between the proximal and distal sides 1562, 1564. A central longitudinal hole 1574 may extend through the connector plate 1504 between the proximal and distal sides 1562, 1564. The hole may include, from proximal to distal, first, second, third, fourth, and fifth inner portions 1576, 1578, 1580, 1582, 1584. Each inner portion may have a circular cross section. The first inner portion 1576 may have a short proximal-distal length and a circumferential chamfer around an inner proximal edge. The second inner portion 1578 may have a diameter that is greater than the diameter of the first inner portion 1576. The third inner portion 1580 may have a diameter that is the same as or similar to the diameter of the first inner portion 1576, and less than the diameter of the second inner portion 1578. There may be a tapered transition between the second and third inner portions 1578, 1580. The distal end of the third inner portion 1580 may be flat and may be proximal to the distal end of the first outer portion 1566. The fourth inner portion 1582 may have a diameter that is less than the diameter of the first inner portion 1576. The fifth inner portion 1584 may have a diameter that is less than the diameter of the first inner portion 1576 and greater than the diameter of the fourth inner portion 1582.

Referring to FIGS. 96 and 97, the inserter shaft 1506 extends between a proximal end 1586 and a distal end 1588. The inserter shaft 1506 may be a tubular part with circular outer and inner cross-sectional shapes. The inserter shaft 1506 may include, from proximal to distal, first, second, and third outer portions 1590, 1592, 1594. The first outer portion 1590 may have a short proximal-distal length. The outer diameter of the second outer portion 1592 may be greater than the outer diameter of the first outer portion 1590. The second outer portion 1592 may occupy most of the overall proximal-distal length of the inserter shaft 1506. The second outer portion 1592 may include one or more openings 1596. Four openings 1596 are shown evenly spaced along the length of the second outer portion 1592. Each opening 1596 may extend through one wall of the second outer portion 1592, or through both walls as shown. The outer diameter of the third outer portion 1594 may be the same as or similar to the outer diameter of the first outer portion 1590 and less than the outer diameter of the second outer portion 1592. The inserter shaft 1506 may include a central longitudinal hole 1598 that extends through the inserter shaft between the proximal end 1586 and the distal end 1588.

The inserter connector 1502, connector plate 1504, and inserter shaft 1506 may be coupled together in a shaft assembly 1600 like shaft assembly 116 or 304. See FIGS. 86 and 87. The shaft assembly 1600 may also include two pins (not shown) that protrude proximally from the holes 1570, 1572 in the connector plate 1504. The shaft assembly 1600 may be assembled by inserting the first outer portion 1590 of the inserter shaft 1506 in the fourth inner portion 1582 of the connector plate 1504 and inserting the third outer portion 1594 in the first inner portion 1556 of the inserter connector 1502. The holes 1570, 1572 may be aligned adjacent to the long sides of the rectangle of the third outer portion 1552. The shaft assembly 1600 may be a weldment. The diameters of the second inner portion 1558 of the inserter connector 1502, the fourth inner portion 1582 of the connector plate 1504, and the hole 1598 of the inserter shaft 1506 may be the same or similar, and together, they may form a shaft assembly bore.

Referring to FIGS. 98 and 99, the implant retainer shaft 1508 extends between a proximal end 1602 and a distal end 1604. The implant retainer shaft 1508 may include, from proximal to distal, first, second, and third outer portions 1606, 1608, 1610. The first outer portion 1606 may be an elongated torque fitting, such as the hexagonal key shown. The second outer portion 1608 may extend over most of the proximal-distal length of the implant retainer shaft 1508, and may have a circular cross section with a diameter that is less than the minor diameter of the first outer portion 1606. The third outer portion 1610 may include external threads. The major diameter of the threads may be the same as or similar to the diameter of the second outer portion 1608. A central longitudinal hole 1612 may extend through the implant retainer shaft 1508 between the proximal and distal ends 1602, 1604.

Figure 100:
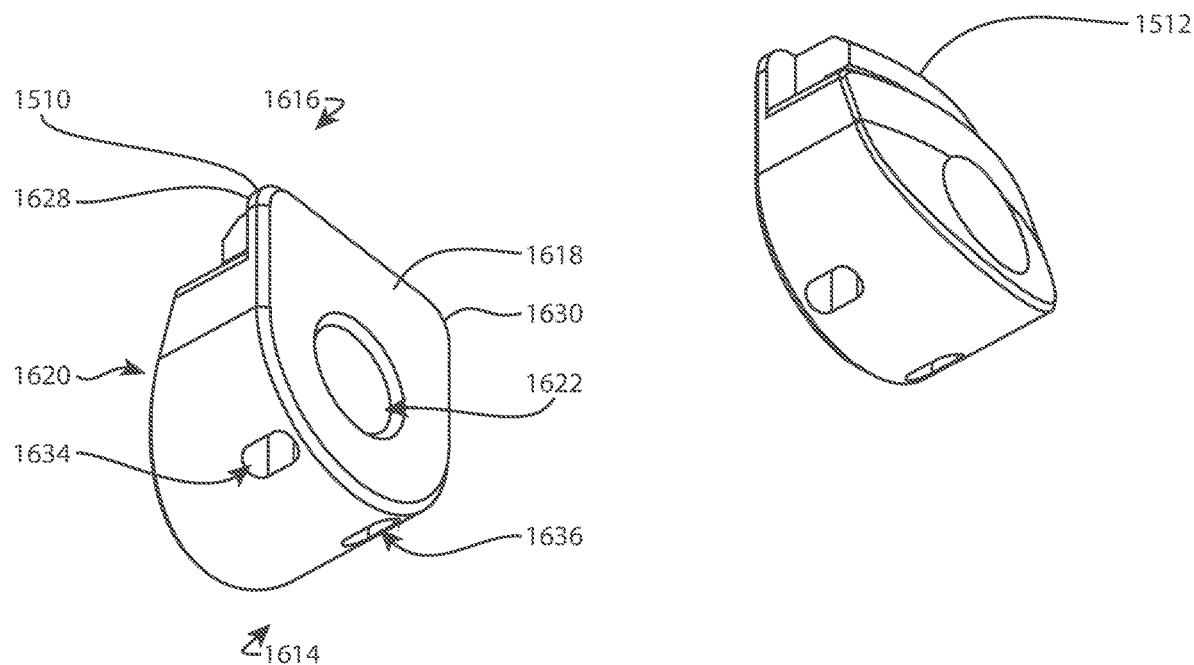
FIG. 100 is a perspective view of connector buttons of the instrument of FIG. 86.
Figure 101:
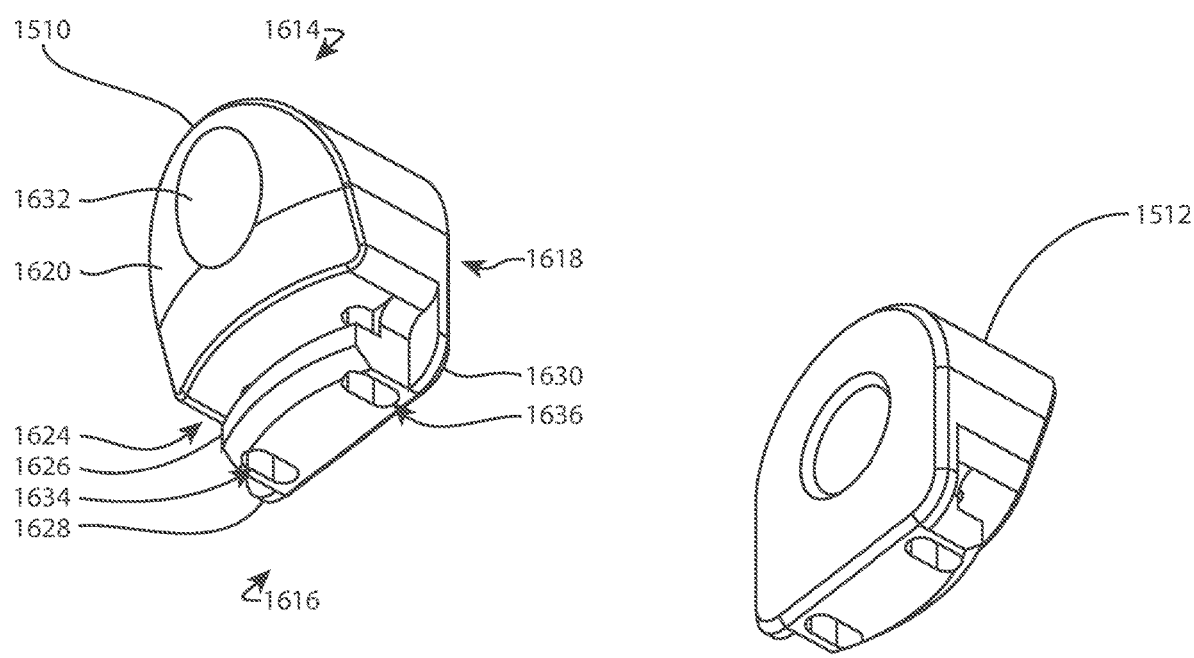
FIG. 101 is another perspective view of the connector buttons of FIG. 100, from a different direction.

Referring to FIGS. 100 and 101, the connector button 1510 extends between a proximal end 1614 and a distal end 1616. The connector button 1510 may have a flat inner side 1618 and an opposite outer side 1620. A hole 1622 may extend into the inner side 1618. A transverse groove 1624 may extend across the outer side 1620 near the proximal end 1614 so as to form a corresponding ledge 1626 along the outer proximal edge of the connector button 1510. Bilateral thin ears 1628, 1630 may be located at either end of the ledge 1626, forming the inner proximal corners of the connector button 1510. A dimple 1632 may be present on the outer side 1620. Bilateral slots 1634, 1636 may extend through the connector button 1510 parallel to the inner side 1618 and through the ledge 1626. The slots 1634, 1636 may intersect the groove 1624. A second connector button 1512 is shown. The connector button 1512 may be a mirror image of the connector button 1510.

Figure 102:
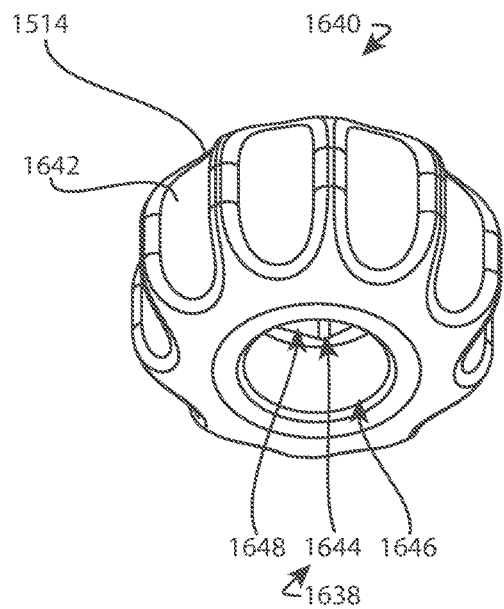
FIG. 102 is a perspective view of a thumb wheel of the instrument of FIG. 86.
Figure 103:
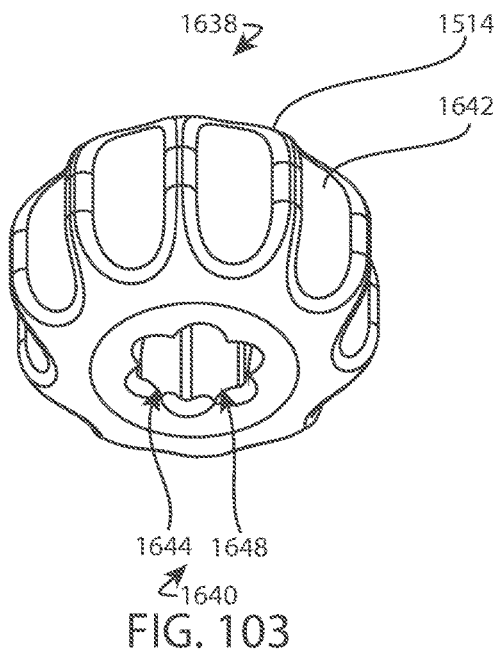
FIG. 103 is another perspective view of the thumb wheel of FIG. 102, from a different direction.

Referring to FIGS. 102 and 103, the thumb wheel 1514 extends between a proximal side 1638 and a distal side 1640. The thumb wheel 1514 may be a generally disc- or ring-shaped part with one or more friction features 1642 arranged around its outer perimeter, such as the ten scallops shown. A central longitudinal hole 1644 may extend through the thumb wheel 1514 between the proximal and distal sides 1638, 1640. The hole 1644 may include, from proximal to distal, first and second inner portions 1646, 1648. The first inner portion 1646 may have a circular cross section and may extend distally about two fifths to half of the overall proximal-distal length of the thumb wheel 1514. The second inner portion 1648 may be a torque fitting such as the hexagonal hole shown. The major dimension of the second inner portion 1648 may be less than the diameter of the first inner portion 1646.

Figure 104:
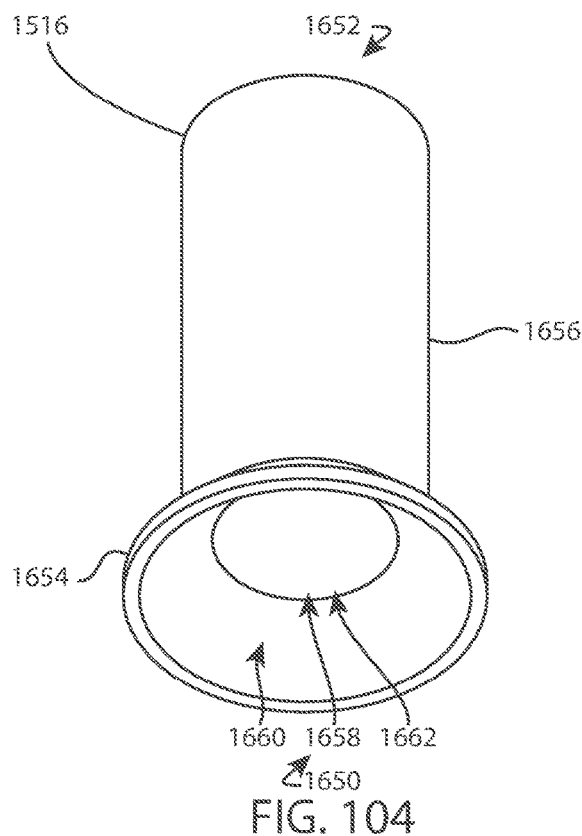
FIG. 104 is a perspective view of a wheel axle of the instrument of FIG. 86.
Figure 105:
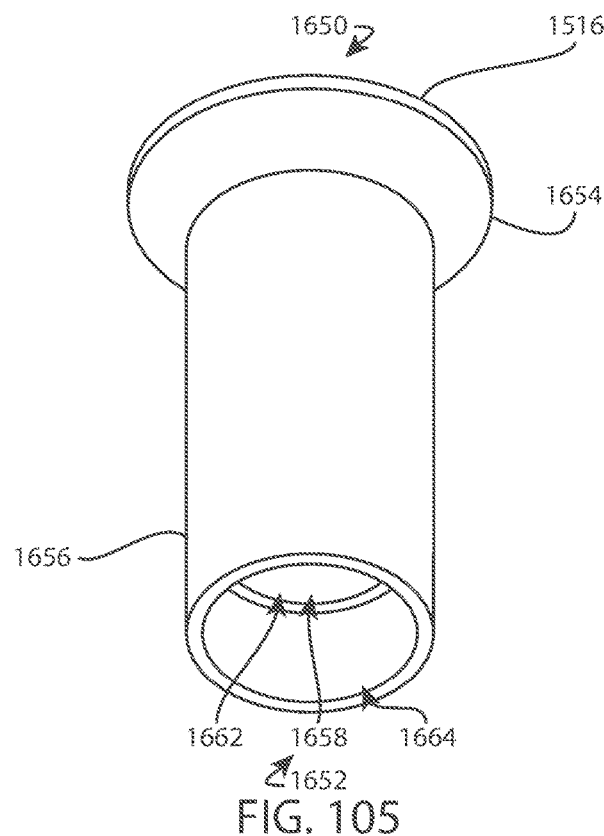
FIG. 105 is another perspective view of the wheel axle of FIG. 104, from a different direction.

Referring to FIGS. 104 and 105, the wheel axle 1516 extends between a proximal end 1650 and a distal end 1652. The wheel axle 1516 may be a funnel shaped part with a wide proximal mouth 1654 and a narrow distal stem 1656 or shaft. The mouth 1654 may taper towards the stem 1656. A central longitudinal hole 1658 may extend through the wheel axle 1516 between the proximal and distal ends 1650, 1652. The hole 1658 may include, from proximal to distal, first, second, and third inner portions 1660, 1662, 1664. The first inner portion 1660 may have a round cross sectional shape and may correspond to the outer shape of the mouth 1654. The second inner portion 1662 may have a circular cross sectional shape and may extend distally into the stem 1656. The third inner portion 1664 may have a circular cross section with a diameter that is greater than the diameter of the second inner portion 1662.

Referring to FIGS. 106-108, the inserter handle 1518 extends between a proximal end 1668 and a distal end 1670. The inserter handle 1518 may include, from proximal to distal, first, second, third, and fourth outer portions 1672, 1674, 1676, 1678. The first outer portion 1672 may have a circular cross section and a short proximal-distal length. The second outer portion 1674 may have a circular cross section with a diameter that is less than the diameter of the first outer portion 1672. The third outer portion 1676 may be generally hourglass shaped or otherwise contoured to be comfortably and ergonomically gripped by a user's hand. The proximal diameter of the third outer portion 1676 may be greater than the diameter of the first outer portion 1672, so that the second outer portion 1674 forms a circumferential groove between the first and third outer portions 1672, 1676. The fourth outer portion 1678 may have a circular cross section with a diameter that is less than the distal diameter of the second outer portion 1674 and the distal diameter of the third outer portion 1676. A transverse hole 1680 may extend through the inserter handle 1518 in the third outer portion 1676 along a first direction, which will be referred to as a front-back direction. The hole 1680 may be rectangular or square and may have rounded corners. A pocket 1682 may extend transversely into the inserter handle 1518 along a second direction, which will be referred to as a right-left direction, which is 90 degrees from the first direction. The pocket 1682 may extend proximally into the third outer portion 1674 and distally into the fourth outer portion 1678. The pocket may be D-shaped, with a flat distal side and a curved proximal side. A second pocket 1684 may extend into the inserter handle 1518 opposite the pocket 1682, and may be a mirror image of the pocket 1682. A central longitudinal hole 1686 may extend through the inserter handle 1518 between the proximal and distal ends 1668, 1670. The hole 1686 may include, from proximal to distal, first, second, third, and fourth inner portions 1688, 1690, 1692, 1694. The first inner portion 1688 may have a cross section that includes a circular portion that is concentric with the second, third, and fourth inner portions 1690, 1692, 1694, and an alcove portion 1696 that extends radially away from the circular portion toward a first side of the inserter handle 1518, which will be referred to as a front side. The distal end of the first inner portion 1688 may be flat. A hole 1698 may extend distally within the alcove portion 1696, and may be centered within the alcove portion. The hole 1698 may include a counterbore 1700. The second inner portion 1690 may taper inwardly as it extends distally. The second inner portion 1690 may be conical. The major diameter of the second inner portion may be less than the diameter of the circular portion of the first inner portion 1688. The third inner portion 1692 may have a circular cross section and may extend distally to the hole 1680. The fourth inner portion 1694 may have a circular cross section with a diameter that is the same as or similar to the diameter of the third inner portion 1692. Bilateral holes 1702, 1704 may extend proximally into the distal end 1670 of the inserter handle 1518. The holes 1702, 1704 may be located toward the front and back. Bilateral holes 1706, 1708 may extend proximally into the distal end 1670, and into the proximal wall of the pocket 1682. Bilateral holes 1710, 1712 may extend proximally into the distal end 1670, and into the proximal wall of the pocket 1684.

Referring to FIGS. 109 and 110, the knob strike plate 1520 extends between a proximal end 1714 and a distal end 1716. The knob strike plate 1520 may have flat left and right sides 1718, 1720 and an hourglass shape in a left or right view. The knob strike plate 1520 may include one or more openings 1722. Two openings 1722 are shown extending along a front to back direction. Each opening 1722 may extend through one wall of the knob strike plate 1520, or through both walls as shown. A central longitudinal hole 1724 may extend through the knob strike plate 1520 between the proximal and distal ends 1716. The hole 1724 may include, from proximal to distal, first, second, and third inner portions 1726, 1728, 1730. The first inner portion 1726 may include a generally circular central portion with bilateral longitudinal grooves 1732, 1734 extending along the front and back, so that the first inner portion 1726, taken as a whole, has a noncircular cross section. The first inner portion 1726 may extend distally over most of the proximal-distal length of the knob strike plate 1520, and may have a flat distal end. The second inner portion 1728 may have a circular cross section with a diameter that is less than the diameter of the circular central portion of the first inner portion 1726. The second inner portion 1728 may have a short proximal-distal length. Bilateral holes 1736, 1738 may extend distally through the second inner portion 1728, and may be aligned with the grooves 1732, 1734. The holes 176,
1738 may be countersunk. The third inner portion 1730 may have a generally rectangular cross section, and may have rounded corners. The major dimension (length) of the rectangle may be greater than the diameter of the circular central portion of the first inner portion 1726, and may extend along a front to back direction. The third inner portion 1730 may extend through the front side of the knob strike plate 1520, so that the front side has a distal notch. The minor dimension (width) of the rectangle may be less than the diameter of the circular central portion of the first inner portion 1726 and greater than the diameter of the second inner portion 1728. Bilateral teeth 1740, 1742 may protrude toward each other from the left and right walls of the third inner portion 1730 near the front side.

Figure 111:
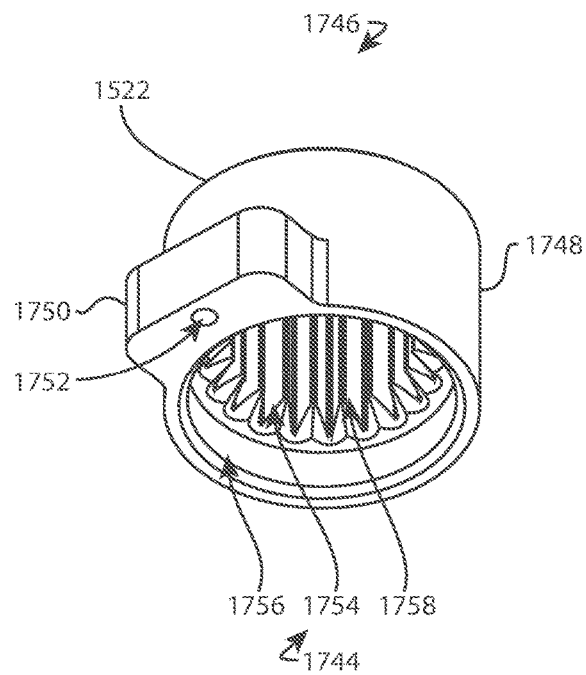
FIG. 111 is a perspective view of a spline insert of the instrument of FIG. 86.
Figure 112:
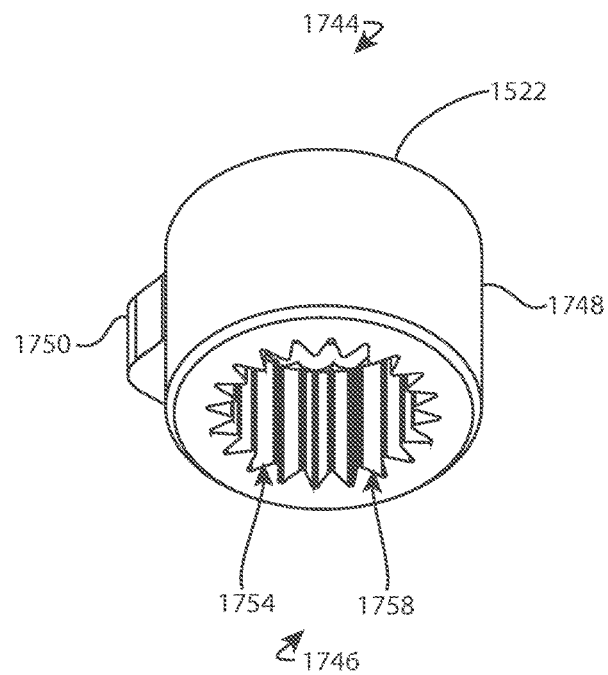
FIG. 112 is another perspective view of the spline insert of FIG. 111, from a different direction.

Referring to FIGS. 111 and 112, the spline insert 1522 extends between a proximal end 1744 and a distal end 1746. The spline insert 1522 may have a cylindrical body 1748 with a unilateral tab 1750 extending radially outward from the proximal end 1744. A longitudinal hole 1752 may extend through the tab 1750. The hole 1752 may be countersunk on the distal side of the tab 1750. A central longitudinal hole 1754 may include, from proximal to distal, first and second inner portions 1756, 1758. The first inner portion 1756 may have a circular cross section and may include a shallow countersink or chamfer around an inner proximal edge. The second inner portion 1758 may include a torque fitting such as the internal spline as shown.

Figure 113:
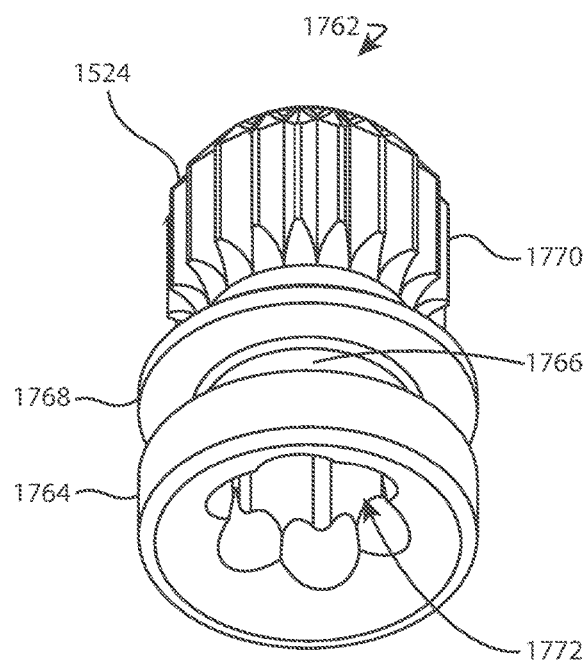
FIG. 113 is a perspective view of a rotation lock ring of the instrument of FIG. 86.
Figure 114:
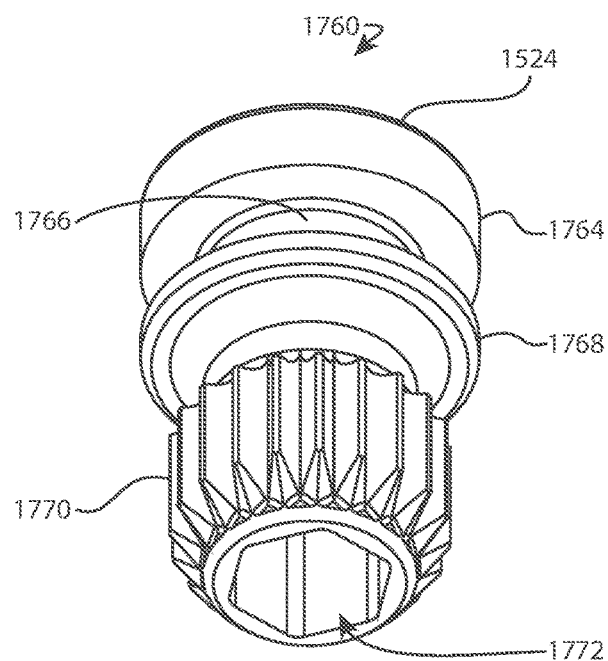
FIG. 114 is another perspective view of the rotation lock ring of FIG. 113, from a different direction.

Referring to FIGS. 113 and 114, the rotation lock ring 1524 extends between a proximal end 1760 and a distal end 1762. The rotation lock ring 1524 may include, from proximal to distal, first, second, third, and fourth outer portions 1764, 1766, 1768, 1770. The first outer portion 1764 may have a circular cross section and may include a rounded outer proximal edge. The second outer portion 1766 may have a circular cross section with a diameter that is less than the diameter of the first outer portion 1764. The third outer portion 1768 may have a circular cross section with a diameter that is the same as or similar to the diameter of the first outer portion 1764. A distal outer edge of the third outer portion may include a circumferential chamfer. The fourth outer portion 1770 may include a torque fitting such as the external spline shown. The fourth outer portion 1770 may be complementary to the second inner portion 1758 of the spline insert 1522. A central longitudinal torque fitting 1772 may extend through the rotation lock ring 1524 between the proximal and distal ends 1760, 1762. The torque fitting 1772 may be a hexagonal hole as shown. The proximal end 1760 of the rotation lock ring may be concave. The spline insert 1522 and the rotation lock ring 1524 together may be referred to as a rotation locking mechanism.

Figures 115, 116:
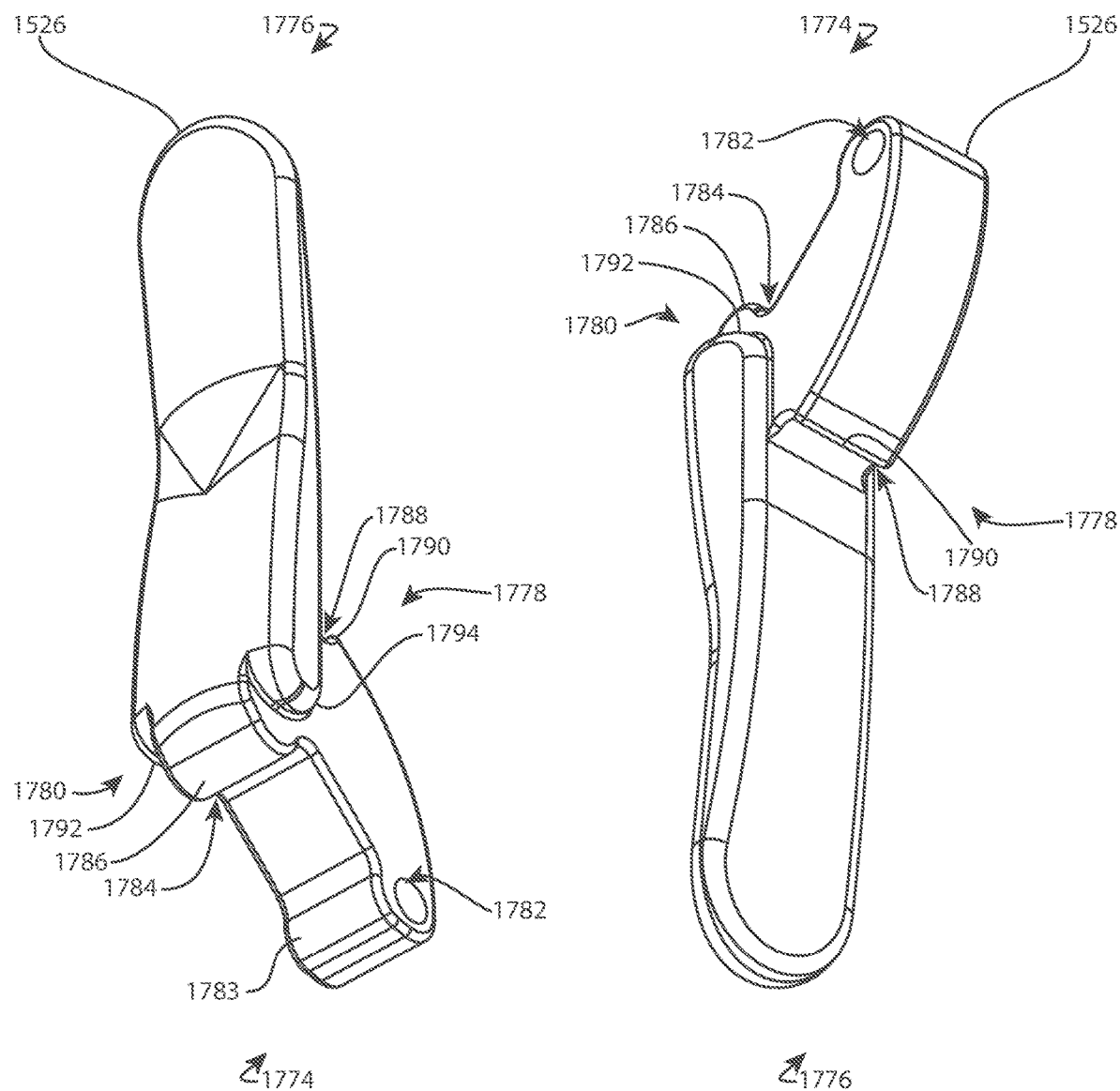
FIG. 115 is a perspective view of a cam lever of the instrument of FIG. 86.
FIG. 116 is another perspective view of the cam lever of FIG. 115, from a different direction.

Referring to FIGS. 115 and 116, the cam lever 1526 extends between a proximal end 1774 and a distal end 1776. The cam lever 1526 may include, from proximal to distal, first and second portions 1778, 1780. The first portion 1778 may include a hole 1782, a first notch 1784, a protrusion 1786, a second notch 1788, and a tooth 1790. The hole 1782 may extend transversely through the cam lever 1526. The hole 1782 may be near the proximal end 1774. A proximal/outer bearing surface 1783 may be located next to the hole 1782; the surface 1783 may be referred to as a first fulcrum of the cam lever 1526. The first notch 1784 and the protrusion 1786 may extend transversely across an outer side of the cam lever 1526 distal to the hole 1782. The protrusion 1786 may be directly adjacent to a distal or outer side of the first notch 1784. The protrusion 1786 may be referred to as a second fulcrum of the cam lever 1526. The second notch 1788 and the tooth 1790 may extend transversely across an inner side of the cam lever 1526 distal to the hole 1782. The tooth 1790 may be directly adjacent to a proximal or inner side of the second notch 1788. The second notch 1788 and the tooth 1790 may be distal to the first notch 1784 and the protrusion 1786. The second portion 1780 may be a distally extending arm for actuation by a user. The second portion 1780 may be wider than the first portion 1778 so that rounded shoulders 1792, 1794 are formed at the border between the first and second portions 1778, 1780. The shoulders 1792, 1794 may face proximally and inwardly.

Figures 117, 118:
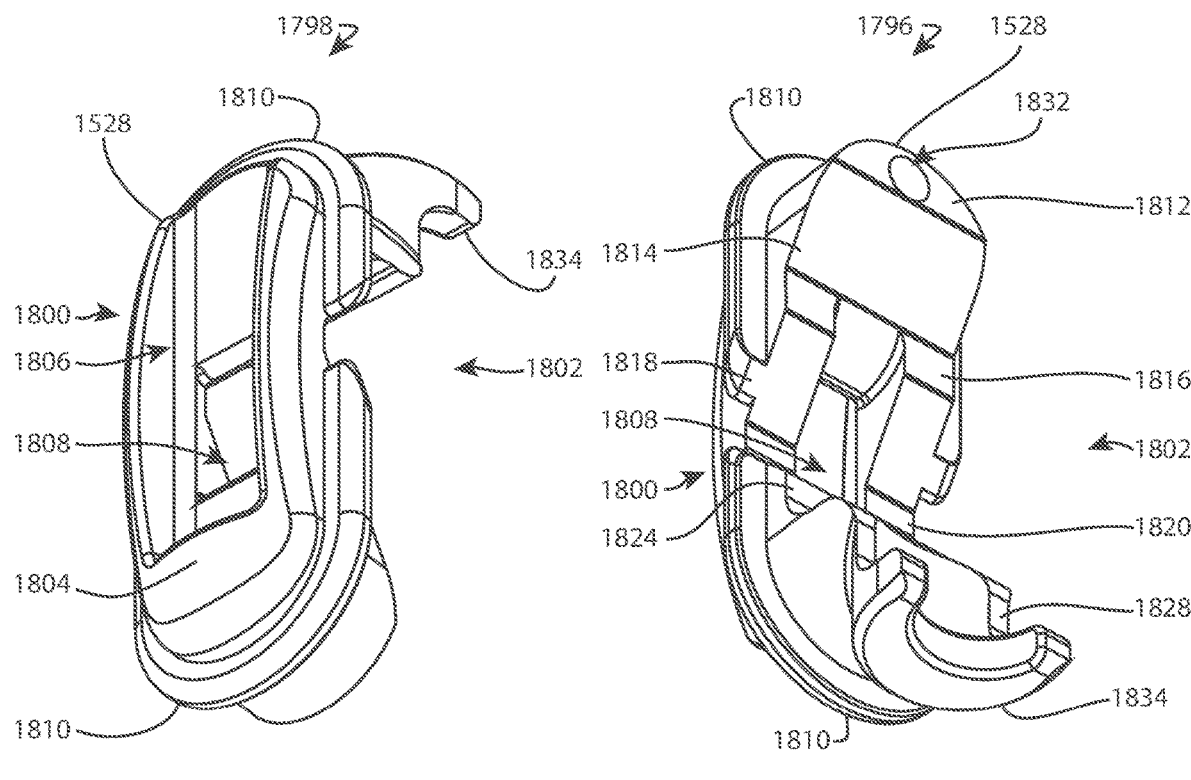
FIG. 117 is a perspective view of a slider button of the instrument of FIG. 86.
FIG. 118 is another perspective view of the slider button of FIG. 117, from a different direction.
Figure 119:
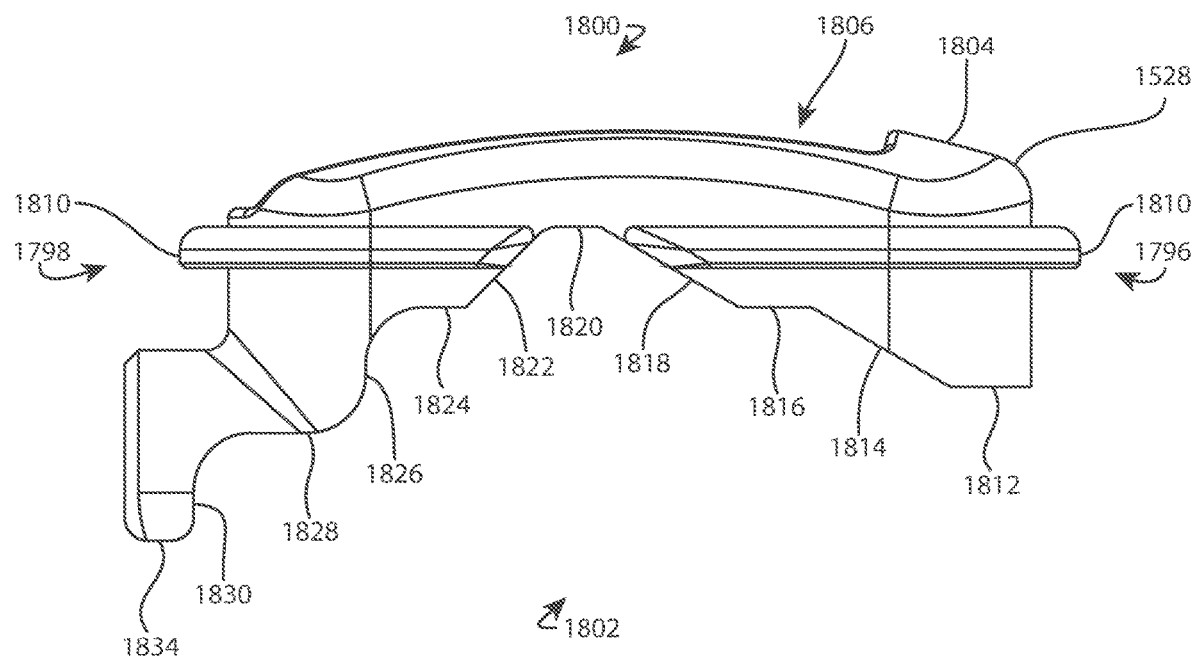

Referring to FIGS. 117-119, the slider button 1528 extends between a proximal end 1796 and a distal end 1798, and an outer side 1800 and an inner side 1802. The outer side 1800 may include an oval domed surface 1804 with a longitudinal central trough 1806. The trough 1806 may be generally rectangular and may extend through the distal end 1798. A window 1808 may extend through the slider button 1528 between the outer and inner sides 1800, 1802. The window 1808 may be rectangular, with its major dimension (length) extending along a proximal-distal direction. A flange 1810 may encircle the surface 1804 and may serve as a boundary between the outer and inner sides 1800, 1802. The flange 1810 may be discontinuous in the vicinity of the window 1808. The inner side 1802 may include, from proximal to distal, first, second, third, fourth, fifth, sixth, seventh, eighth, ninth, and tenth portions 1812, 1814, 1816, 1818, 1820, 1822, 1824, 1826, 1828, 1830. The first portion 1812 may be parallel to the flange 1810 at a first distance from the inner side of the flange 1810. A hole 1832 may extend outwardly into the first portion 1812 near the proximal end 1796. The second portion 1814 may slope between the first and third portions 1812, 1816. The third portion 1816 may be parallel to the flange 1810 at a second distance from the inner side of the flange, wherein the second distance is less than the first distance. The fourth portion 1818 may slope between the third and fifth portions 1816, 1820. The fourth portion 1818 may be parallel to the second portion 1814. The fifth portion 1820 may be parallel to the flange 1810 at the same or similar level with the outer side of the flange. The sixth portion 1822 may slope between the fifth and seventh portions 1820, 1824. The seventh portion 1824 may be parallel to the flange 1810 and at the same or similar level with the third portion 1816. The eighth portion 1826 may curve between the seventh and ninth portions 1824, 1828. The ninth portion 1828 may be parallel to the flange 1810 at a third distance from the inner side of the flange 1810, wherein the third distance is greater than the first distance. The tenth portion 1830 may protrude a fourth distance from the inner side of the flange 1810, and may extend distally past the flange. The tenth portion 1830 may include a semicircular yoke 1834 that opens away from the flange 1810.

Figure 120:
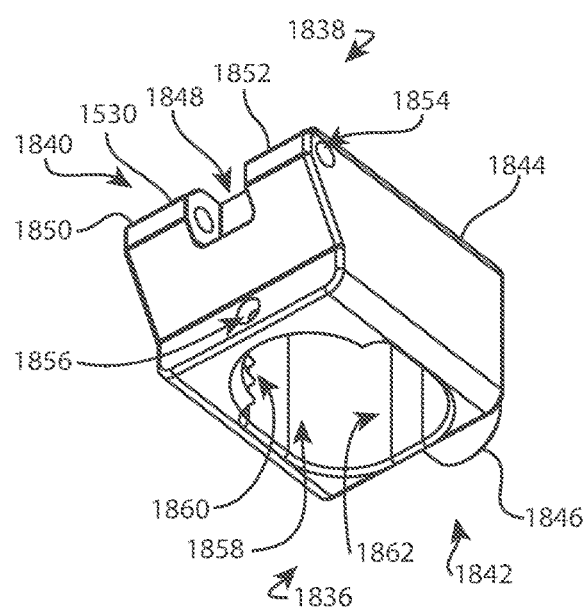
Figure 121:
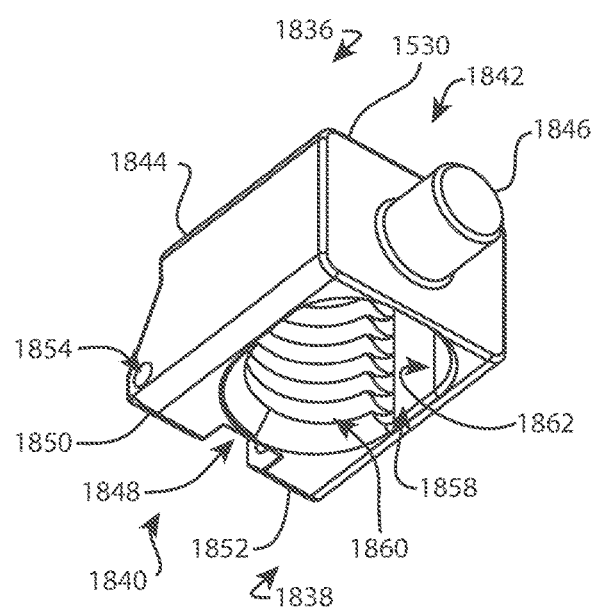

Referring to FIGS. 119 and 120, the threaded slider 1530 extends between a proximal end 1836 and a distal end 1838, and an outer side 1840 and an inner side 1842. The threaded slider 1530 may be referred to as an actuator. The threaded slider 1530 may include a rectangular body 1844 with a post 1846 extending from the inner side 1842. The outer side 1840 may ramp outwardly from proximal to distal. A notch 1848 may extend into the distal outer edge of the body 1844 between bilateral protrusions 1850, 1852. A transverse hole 1854 may extend through the threaded slider 1530, through the protrusions 1850, 1852 and intersecting the notch 1848. A shallow hole 1856 or dimple may extend inwardly into the outer side 1840 near the proximal end 1836 in line with the notch 1854. A longitudinal hole 1858 extends through the threaded slider 1530 between the proximal and distal ends 1836, 1838. The hole 1858 may include a first side portion 1860 toward the outer side 1840 and a second side portion 1862 toward the inner side 1842. The first side portion 1860 may include internal threads around about 180 degrees of arc, i.e., along a half cylinder. The second side portion 1862 may be smooth, D-shaped, and larger than the major diameter of the internal threads of the first portion 1860.

Figure 122:
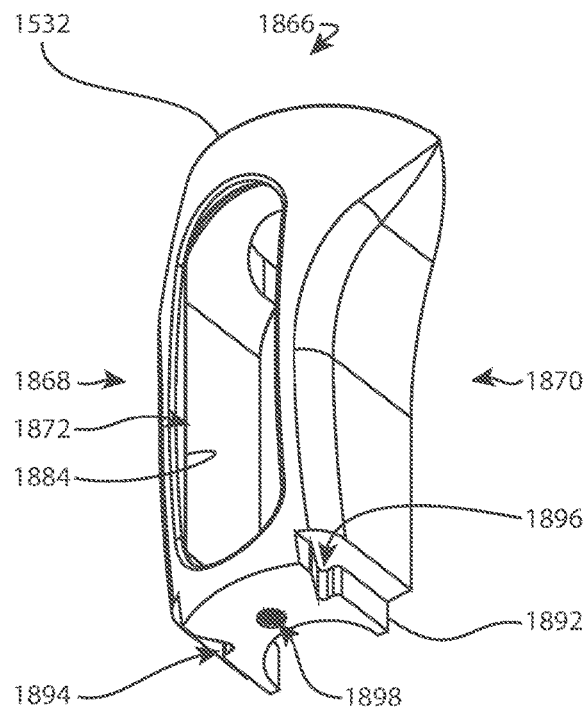
Figure 123:
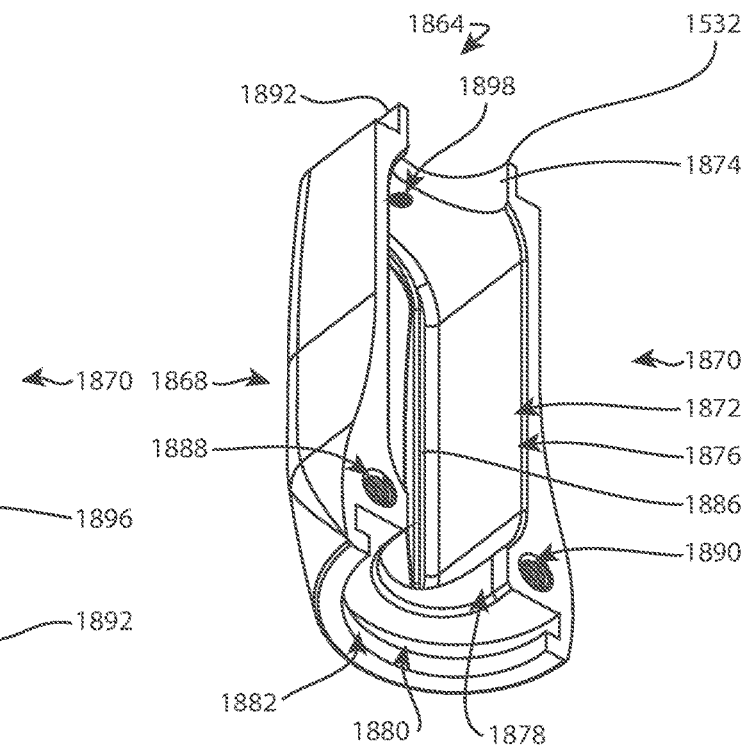

Referring to FIGS. 122-123, the top knob part 1532 extends between a proximal end 1864 and a distal end 1866, and an outer side 1868 and an inner side 1870. The outer side 1868 may be domed. A window 1872 may extend through the top knob part 1532 between the outer and inner sides 1868, 1870. The window 1872 may be oval or rectangular, with its major dimension (length) extending along a proximal-distal direction. The inner side 1868 may be generally concave, and may include, from proximal to distal, first, second, third, fourth, and fifth portions 1874, 1876, 1878, 1880, 1882. The first portion 1874 may have a semicircular cross section and a short proximal-distal length. The second portion 1876 may be oval or rectangular, with its major dimension extending along a proximal-distal direction. The second portion 1876 may be aligned with the window 1872, and may extend over most of the proximal-distal length of the top knob part 1532. Bilateral longitudinal ledges 1884, 1886 may extend along the inner edges of the window 1872. The third portion 1878 may have a semicircular or half-oval cross section and a short proximal-distal length. The first and third portions 1878 may have the same or similar diameters (or radii), with the third portion 1878 offset toward the outer side 1868. The fourth portion 1880 may have a semicircular cross section and a short proximal-distal length. The diameter of the fourth portion 1880 may be greater than the diameter of the first portion 1874. The fourth portion 1880 may be concentric with the first portion 1874. The fifth portion 1882 may have a semicircular cross section and a short proximal-distal length. The diameter of the fifth portion 1882 may be greater than the diameter of the first portion 1874 and less than the diameter of the fourth portion 1880. The fifth portion 1882 may be concentric with the first portion 1874. When taken together, the fourth portion 1880 may be referred to as a groove or undercut and the fifth portion 1882 may be referred to as a lip or overhang. Bilateral holes 1888, 1890 may extend into the inner side 1870 on either side of the third portion 1878. The holes 1888, 1890 may include internal threads. The proximal end 1864 may include a protrusion 1892 that is complementary to the third inner portion 1730 of the knob strike plate 1520. The protrusion 1892 may be generally rectangular and may include bilateral notches 1894, 1896 to receive the teeth 1740, 1742. An internally threaded hole 1898 may extend distally into the protrusion 1892 between the notches 1894, 1899 and beside the first portion 1874.

Figure 124:
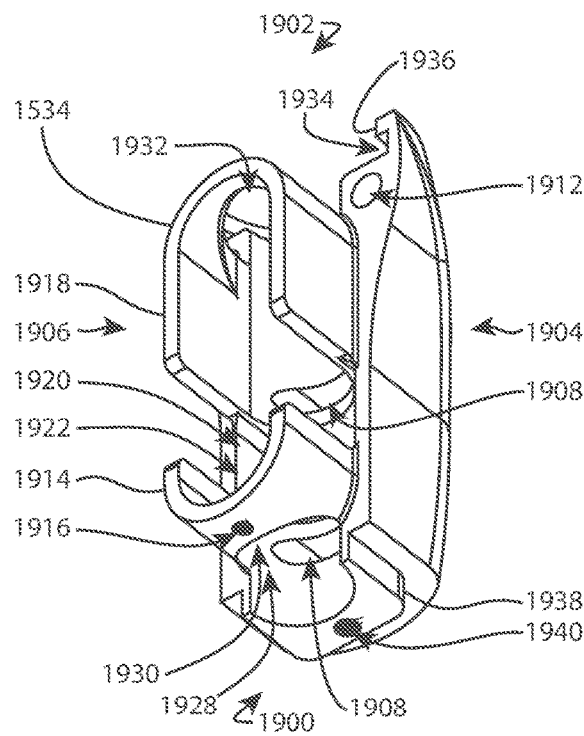
Figure 125:
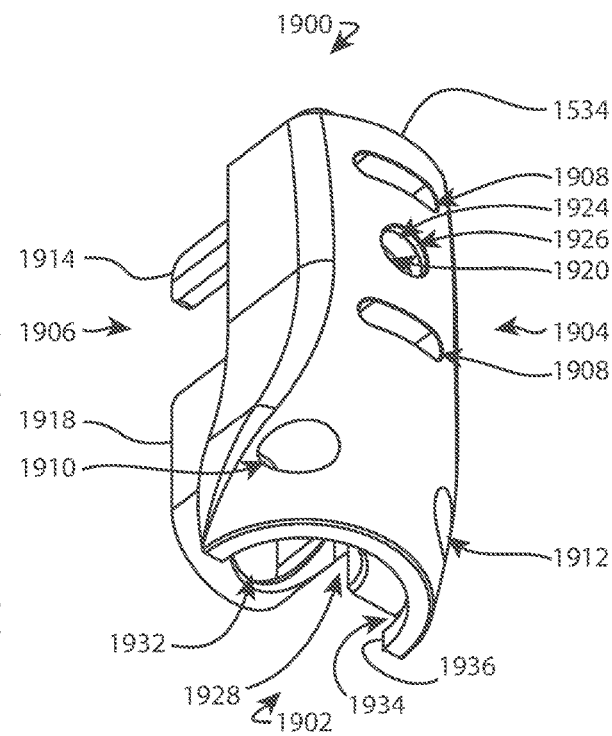

Referring to FIGS. 124 and 125, the bottom knob part 1534 extends between a proximal end 1900 and a distal end 1902, and an outer side 1904 and an inner side 1906. The outer side 1904 may be domed. One or more openings 1908 may extend through the bottom knob part 1534 between the outer and inner sides 1902, 1904. Two openings 1908 are shown. Bilateral holes 1910, 1912 may extend into the outerside 1904 near the distal end 1902. The holes 1910, 1912 may include counterbores. A semicircular wall 1914 or shell may protrude from the inner side 1906 near the proximal end 1900 so that a convex side of the wall 1914 faces proximally. The wall 1914 may include a distally extending internally threaded through hole 1916. A U-shaped or part-oval wall 1918 may protrude from the inner side 1906 near the distal end 1902 so that a convex side of the wall 1918 faces distally. A hole 1920 may extend through the bottom knob part 1534 between the outer and inner sides 1904, 1906. The hole 1920 may be located between the distal end of the wall 1914 and the proximal end of the wall 1918. The hole 1920 may include, from inner to outer, first, second, and third inner portions 1922, 1924, 1926. The first inner portion 1922 may have a rectangular or square cross section and may extend outwardly over most of the inner-outer thickness of the bottom knob part 1534. The first inner portion 1922 may have a flat outer end. The second inner portion 1924 may have a circular cross section with a diameter that is less than the minor dimension of the first inner portion 1922. The second inner portion 1924 may have a flat outer end. The third inner portion 1926 may have a circular cross section with a diameter that is less than the diameter of the second inner portion 1924. A longitudinal hole 1928 may extend through the bottom knob part 1534 between the proximal and distal ends 1900, 1902. The hole 1928 may include, from proximal to distal, first, second, third, and fourth inner portions 1930, 1932, 1934, 1936. The first inner portion 1930 may have a circular cross section and may extend distally into the proximal region of the wall 1918. The second inner portion 1932 may have the same or similar diameter (radius) as the first inner portion 1930, but may be elongated toward the outer side 1904 to form an oval cross section. The second inner portion 1932 may extend through the distal end of the wall 1918. The third inner portion 1934 may have a semicircular cross section with a diameter that is greater than the diameter of the first inner portion 1930, and a short proximal-distal length. The fourth inner portion 1936 may have a semicircular cross section with a diameter that is greater than the diameter of the first inner portion 1930 and less than the diameter of the third inner portion 1934, and a short proximal-distal length. When taken together, the third inner portion 1934 may be referred to as a groove or undercut and the fourth inner portion 1936 may be referred to as a lip or overhang.

The proximal end 1900 may include a protrusion 1938 that is complementary to the third inner portion 1730 of the knob strike plate 1520 when taken together with the protrusion 1892 of the top knob part 1532. The outer profile of the protrusion 1938 may be rectangular or square. An internally threaded hole 1940 may extend distally into the protrusion 1938 beside the first inner portion 1930.

The connector buttons 1510, 1512, thumb wheel 1514, wheel axle 1516, inserter handle 1518, knob strike plate 1520, spline insert 1522, rotation lock ring 1524, cam lever 1526, slider button 1528, threaded slider 1530, top knob part 1532, and bottom knob part 1534 may be coupled together in a handle assembly 1942. See FIG. 87.

The handle assembly 1942 may be assembled by coupling the connector button 1510 to the inserter handle 1518; coupling the thumb wheel 1514, wheel axle 1516, and spline insert 1522 to the inserter handle 1518; coupling the cam lever 1526, slider button 1528, threaded slider 1530, rotation lock ring 1524, and the top knob part 1532 together; coupling the top and bottom knob parts 1532, 1534 to the inserter handle 1518; and coupling the knob strike plate 1520 to the top and bottom knob parts 1532, 1534.

Coupling the connector button 1510 to the inserter handle 1518 may include inserting a compression spring (not shown) in the hole 1622, orienting the connector button 1510 and inserter handle 1518 with the proximal ends 1614, 1668 facing the same direction and the inner side 1618 facing into the pocket 1682, inserting the connector button 1510 into the pocket 1682, and inserting pins (not shown) into holes 1706, 1708 and slots 1634, 1636. Coupling the connector button 1512 to the inserter handle 1518 may include similar steps with pocket 1684 and holes 1710, 1712.

Coupling the thumb wheel 1514, wheel axle 1516, and spline insert 1522 to the inserter handle 1518 may include orienting the thumb wheel 1514 and inserter handle 1518 with the proximal ends 1638, 1668 facing the same direction, inserting the thumb wheel 1514 into the hole 1680, inserting a compression spring (not shown) into the third inner portion 1664 of the wheel axle 1516, inserting the distal end 1652 of the wheel axle 1516 through the third inner portion 1692 of the inserter handle 1518 and into the first inner portion 1646 of the thumb wheel 1516, inserting the distal end 1746 of the spline insert 1522 into the first inner portion 1688 of the inserter handle 1518, inserting the tab 1750 into the alcove portion 1696, and inserting a pin (not shown) into holes 1752, 1698.

Coupling the cam lever 1526, slider button 1528, threaded slider 1530, rotation lock ring 1524, and the top knob part 1532 together may include inserting a ball detent (not shown) in the hole 1832 of the slider button 1528; inserting the first portion 1778 of the cam lever 1526 through the window 1808 of the slider button from the outer side 1800 so that the second portion 1780 extends outwardly, the protrusion 1786 faces proximally, and the tooth 1790 faces distally; inserting the first portion 1778 into the notch 1848 of the threaded slider 1530 between the protrusions 1850, 1852 so that the outwardly ramped outer side 1840 abuts the fourth portion 1818; inserting a pin (not shown) into holes 1854, 1782; engaging the yoke 1834 with the first and second outer portions 1764, 1766 of the rotation lock ring 1524 so that the proximal ends 1760, 1796 face the same direction; and inserting the second portion 1780 and slider button 1528 into the window 1872 of the top knob part 1532 from the inner side 1870 so that the flange 1810 rests against the ledges 1884, 1886 and the proximal ends 1864, 1796 face the same direction.

Coupling the top and bottom knob parts 1532, 1534 to the inserter handle 1518 may include engaging the first outer portion 1672, the fourth portion 1880, and the third inner portion 1934; engaging the second outer portion 1674, the fifth portion 1882, and the fourth inner portion 1936 so that the inner sides 1870, 1904 are facing; and inserting screws (not shown) in the holes 1910, 1888 and the holes 1912, 1890. When this step is performed after the preceding steps, the post 1846 of the threaded slider 1530 is in the hole 1920 of the bottom knob part 1534.

Coupling the knob strike plate 1520 to the top and bottom knob parts 1532, 1534 may include abutting the inner sides 1870, 1904 so that the proximal ends 1864, 1900 face the same direction, inserting the protrusions 1892, 1938 into the third inner portion 1730 so that the notches 1894, 1896 receive the teeth 1740, 1742, and inserting screws (not shown) in the holes 1736, 1898, 1916 and the holes 1738, 1940.

The handle assembly 1942 may be operated by pressing the connector buttons 1510, 1512, rotating the thumb wheel 1514, pivoting the cam lever 1526, and rotating the knob strike plate 1520, top knob part 1532, and bottom knob part 1534.

Pressing the connector buttons 1510, 1512 of the handle assembly 1942 may enable the connector plate 1504 of the shaft assembly 1600 to be disconnected from the handle assembly, and may also enable or facilitate connecting the shaft assembly to the handle assembly. The connector buttons 1510, 1512 are biased outwardly so that the handle assembly will retain the shaft assembly.

Turning the thumb wheel 1514 may rotate the implant retainer shaft 1508 to connect and disconnect the instrument 1500 and implant 1100. More specifically, turning the thumb wheel 1514 may engage and disengage the external threads of the third outer portion 1610 of the implant retainer shaft 1508 and the internal threads 1155 of the second end body 1152 of the implant 1100.

Pivoting the cam lever 1526 may engage and disengage the internal threads of the first side portion 1860 of the hole 1858 of the threaded slider 1530 and the externally threaded portion 2036 of the shaft 2032 of the threaded shaft 1954, discussed below. Pivoting the cam lever 1526 inwardly (distally) may also lock the slider button 1528 in its distal position, due to the interaction of the tooth 1790 with the distal edge of the window 1808. Pivoting the cam lever 1526 outwardly may provide sufficient mechanical advantage to overcome residual friction and/or potential energy within the instrument 1500 after expanding the implant 1100, to disengage the threads of the threaded slider 1530 from the threaded shaft 1954. The mechanical advantage may be due first to the interaction of the first fulcrum, surface 1783, with the proximal edge of the window 1808, and second to the interaction of the second fulcrum, protrusion 1786, with the proximal portion of the trough 1806 next to the proximal edge of the window 1808.

Rotating the knob strike plate 1520, top knob part 1532, and bottom knob part 1534 relative to the inserter handle 1518 may cause linear translation of the draw bar assembly 1536 along the longitudinal instrument axis 1542 without rotation of the draw bar assembly 1536 about the axis 1542, due to the engaged threads of the threaded slider 1530 and the threaded shaft 1954, and the sixth outer portion 1974 of the handle 1944 in the torque fitting 1772 of the rotation lock ring 1524.

Referring to FIGS. 126-129, the draw bar assembly 1536 may include a handle 1944, a pull rod 1946, a set screw 1948, a button 1950, a button spring 1952, a threaded shaft 1954, a retainer 1956, and a retainer spring 1958.

The handle 1944 extends between a proximal end 1960 and a distal end 1962. The handle 1944 may include, from proximal to distal, first, second, third, fourth, fifth, and sixth outer portions 1964, 1966, 1968, 1970, 1972, 1974. The first outer portion 1964 may have the largest outer diameter of the handle 1944. Friction features 1976 may be included around the first outer portion 1964, such as the ten scallops shown. The second outer portion 1966 may have a circular cross section with a diameter that is less than the diameter of the first outer portion 1964. A transverse hole 1978 may extend through the second outer portion 1966. The hole 1978 may include, in sequence, first, second, and third inner portions 1980, 1982, 1984. The first inner portion 1980 may be rectangular or square, and may have a flat bottom. The second inner portion 1982 may have a circular cross section with a diameter that is less than the dimension of the first inner portion 1980. The third inner portion 1984 may also have a circular cross section, with a diameter that is less than the diameter of the second inner portion 1982. The third outer portion 1968 may have a circular cross section with a diameter less than the diameter of the second outer portion 1966, and a short proximal-distal length. The fourth outer portion 1970 may include external threads. The fifth outer portion 1972 may be a torque fitting, such as the hex key shown. The dimensions of the torque fitting may be less than the diameters of the first, second, and third outer portions 1964, 1966, 1968. The sixth outer portion 1974 may also be a torque fitting, such as the hex key shown. The dimensions of the sixth outer portion 1974 may be less than the dimensions of the fifth outer portion 1972. A central longitudinal hole 1986 may extend through the handle 1944 between the proximal and distal ends 1960, 1962. The hole 1986 may include, from proximal to distal, first, second, and third inner portions 1988, 1990, 1992. The first inner portion 1988 may have a short proximal-distal length and may include internal threads. The second inner portion 1990 may be smooth with a circular cross section with a diameter that is less than the minor diameter of the threads of the first inner portion 1988. The third inner portion 1992 may have a circular cross section with a diameter that is less than the diameter of the second inner portion 1990.

The pull rod 1946 extends between a proximal end 1994 and a distal end 1996. The pull rod 1946 may include, from proximal to distal, first, second, third, fourth, and fifth portions 1998, 2000, 2002, 2004, 2006. The first portion 1998 may have a generally circular cross section and a short proximal-distal length. The second portion 2000 may have the largest cross sectional dimension of the pull rod 1946. Bilateral longitudinal flats 2008, 2010 may extend along the first and second portions 1998, 2000. The dimension between the flats 2008, 2010 may be less than the diameter of the first portion 1998. A unilateral flat 2012 may extend along the second portion 2000 without affecting the first portion 1998. A transverse notch 2014 may extend into the second portion 2000 through the side with the flat 2012. Multiple notches may be present, for example a linear array of notches along the side with the flat 2012. The third portion 2002 may have a circular cross section with a diameter that is less than the diameter of the first portion 1998, and may be the same as or similar to the dimension between the flats 2008, 2010. The third portion 2002 may extend over most of the proximal-distal length of the pull rod 1946. The fourth portion 2004 may have a circular cross section with a diameter that is less than the diameter of the third portion 2002. The fifth portion 2006 may include external threads, with the major diameter of the threads the same as or similar to the diameter of the fourth portion 2004. The pull rod 1946 may include indicia 2016, such as text, icons, lines, or other markings.

The button 1950 may include a generally rectangular or square body 2018. A post 2020 may extend from the body 2018. A hole 2022 may extend through the body, transverse to the post 2020. The hole 2022 may be rectangular or oval in cross section, with the major dimension of the rectangle or oval extending in line with the post 2020. A rib 2024 may protrude from an inner wall of the hole adjacent to the post 2020. The rib 2024 may be oriented transverse to the hole 2022.

The threaded shaft 1954 extends between a proximal end 2026 and a distal end 2028. The threaded shaft 1954 may include a proximal head 2030 and a distal shaft 2032 extending from the head. The shaft 2032 may include a proximal smooth portion 2034 and a distal externally threaded portion 2036. Bilateral longitudinal troughs 2038, 2040 may extend across the junction between the head 2030 and the smooth portion 2034. The thread form of the threaded portion 2036 may be a buttress thread for high axial thrust in one direction. The load-bearing thread face may be substantially perpendicular to the thread axis. The load-bearing thread face of the threaded shaft 1954 may face toward the distal end 2028. A central longitudinal hole 2042 may extend through the threaded shaft 1954 between the proximal and distal ends 2026, 2028. The hole 2042 may be a torque fitting such as the hexagonal hole shown.

The retainer 1956 extends between a proximal end 2044 and a distal end 2046. The retainer 1956 may be a tubular part. Indicia 2048 may be present on the outer surface of the retainer, such as text, icons, graphics, lines, and the like. A central longitudinal hole 2050 may extend through the retainer 1956 between the proximal and distal ends 2044, 2046. The hole 2050 may include, from proximal to distal, first, second, third, and fourth inner portions 2052, 2054, 2056, 2058. The first inner portion 2052 may have a circular cross section. The second inner portion 2054 may include internal threads. The major diameter of the threads may be the same as or similar to the diameter of the first inner portion 2052. The third inner portion 2056 may have a circular cross section with a diameter that is the same as or similar to the minor diameter of the threads of the second inner portion 2054. The third inner portion 2056 may have a flat distal end. The fourth inner portion 2058 may have a circular cross section with a diameter that is less than the diameter of the third inner portion 2056.

The draw bar assembly 1536 may be assembled by inserting the spring 1952 into the second inner portion 1982 of the hole 1978 of the handle 1944; inserting the button 1950 into the hole 1978 of the handle 1944 so that the post 2020 is received in the third inner portion 1984 and the body 2018 is received in the first inner portion 1980; depressing the button 1950 while inserting the distal end 1996 of the pull rod 1946 into the hole 1986 in the proximal end 1960 of the handle 1944 and advancing the pull rod 1946 until the notch 2014 receives the rib 2024; tightening the set screw 1948 in the first inner portion 1988; inserting the distal end 1962 of the handle 1944 into the hole 2042 in the proximal end 2026 of the threaded shaft 1954 and advancing the handle 1944 until the hole 2042 receives the fifth outer portion 1972; inserting a retainer spring 1958 in each trough 2038, 2040; and inserting the distal end 2028 of the threaded shaft 1954 into the hole 2050 in the proximal end 2044 of the retainer 1956 and advancing the threaded shaft 1954 until the first inner portion 2052 of the retainer 1956 receives the third outer portion 1968 of the handle 1944, the second inner portion 2054 threads onto the fourth outer portion 1970, and the third inner portion 2056 receives the head 2030 of the threaded shaft 1954.

The draw bar assembly 1536 may be operated by depressing the button 1950 while sliding the pull rod 1946 proximally or distally to engage different notches like notch 2014. Different pull rods may be substituted in the draw bar assembly 1536 as well. Different draw bar lengths and/or configurations may be compatible with different implant lengths (in the collapsed configuration) or configurations (i.e., implants for anterior, posterior, lateral, or transforaminal interbody fusion and the like). The draw bar assembly 1536 may be an improvement in the art because it may be adjustable to provide the draw bar length that corresponds to any given implant length. Even if an incorrect draw bar length is initially selected, the draw bar assembly 1536 may be re-adjusted to the correct draw bar length quickly and easily, and with positive confirmation that the correct length has been chosen. The draw bar assembly 1536 also reduces instrument inventory versus a set of draw bars of different lengths.

The instrument 1500 may be assembled by coupling the implant retainer shaft 1508 to the handle assembly 1942, coupling the shaft assembly 1600 to the handle assembly 1942, and coupling the draw bar assembly 1536 to the handle assembly 1942.

Coupling the implant retainer shaft 1508 to the handle assembly 1942 may include inserting the proximal end 1602 of the implant retainer shaft 1508 into the fourth inner portion 1694 of the hole 1686 at the distal end 1670 of the inserter handle 1518 and advancing the implant retainer shaft 1508 until the first outer portion 1606 is received in the second inner portion 1648 of the hole 1644 of the thumb wheel 1514.

Coupling the shaft assembly 1600 to the handle assembly 1942 may include inserting the pins protruding proximally from the holes 1570, 1572 of the connector plate 1504 into the holes 1702, 1704 of the inserter handle 1518, inserting the proximal end 1668 of the inserter handle into the hole 1574 in the proximal side 1562 of the connector plate so that the first outer portion 1672 is received in the third inner portion 1580, the ledge 1626 of the connector button 1510 is received in the second inner portion 1578, and the first inner portion 1576 is received in the groove 1624 (likewise for connector button 1512). Optionally, the connector buttons 1510, 1512 may be depressed during this step.

Coupling the draw bar assembly 1536 to the handle assembly 1942 may include rotating the cam lever 1526 outwardly, inserting the distal end 1996 of the pull rod 1946 into the hole 1724 in the proximal end 1714 of the knob strike plate 1520 and advancing the draw bar assembly 1536 so that the fourth and fifth portions 2004, 2002 are received in the hole 1612 of the implant retainer shaft 1606, the sixth outer portion 1974 of the handle 1944 is received in the torque fitting 1772 of the rotation lock ring 1524 and the second inner portion 1662 of the wheel axle 1516, the threaded portion 2036 of the threaded shaft 1954 is received in the hole 1858 of the threaded slider 1530 and the hole 1928 of the bottom knob part 1534, and the retainer 1956 is received in the hole 1724 of the knob strike plate 1520. The draw bar assembly 1536 may slide into the handle assembly 1942 without rotation about the axis 1542. After the draw bar assembly 1536 is fully inserted into the handle assembly 1942, the cam lever 1526 may be rotated inwardly to engage the threads of the threaded slider 1530 and the threaded shaft 1954.

The instrument 1500 may be operated by pressing the connector buttons 1510, 1512, rotating the thumb wheel 1514, pivoting the cam lever 1526, and rotating the knob strike plate 1520, top knob part 1532, and bottom knob part 1534.

Various additional tools may be used with instrument 1500 to implant and expand an intervertebral implant. The instrument 1500 and selected additional tools may be provided in a kit and together they may be referred to as an instrument set or system. FIGS. 130-139 show additional tools for use with instrument 1500, including a trial assembly 2060, a funnel 2062, and a screwdriver assembly 2064.

Referring to FIGS. 130-133, the trial assembly 2060 may include a handle 2066, a block 2068, a head 2070, and a shaft 2072. A distal end 2074 of the shaft 2072 may be received in a proximal hole 2076 in the head 2070. The block 2068 may be received in a distal hole 2078 in the handle 2066. The block 2068 and hole 2078 may have complementary round proximal portions 2080 and complementary rectangular or square distal portions 2082, 2084. The block 2068 may be retained in the handle 2066 by a pin (not shown) through holes 2086, 2088. A proximal end 2090 of the shaft 2072 may be received in a distal hole 2092 in the block 2068. The head 2070, shaft 2072, and block 2068 may be a weldment. Alternatively, the handle 2066, block 2068, head 2070, and shaft 2072 may be combined in a single part. The trial assembly 2060 may include various markings or other indicia 2094 to convey the dimensions of the trial and the corresponding implant state (for example, expanded or collapsed).

Referring to FIGS. 134 and 135, the funnel 2062 may include a wide mouth 2096 that tapers inwardly to a narrow stem 2098 or spout. The stem 2098 may include a torque fitting 2100, which in this example is a hexagonal hole in the distal end of the stem. The torque fitting 2100 may be sized and shaped to receive the first outer portion 1606 at the proximal end 1602 of the implant retainer shaft 1508. This enables the funnel 2062 to be coupled to the implant retainer shaft 1508 for delivery of graft material, and it enables the funnel 2062 to be used to unthread the implant retainer shaft 1508, for example after the lockout screw 654 has been inserted. See FIGS. 157 and 158.

Referring to FIGS. 27, 35, 36, the tamp assembly 180 may be used with the instrument 1500 and implant 1100 as described above for the instrument 100 and implant 1000.

Referring to FIGS. 136-139, the screwdriver assembly 2064 may include a handle 2102 and a shaft 2104. The handle 2102 may be the same as or similar to the handle 176 of FIGS. 29, 37, and 38. The shaft 2104 may be the same as or similar to the shaft 178. A proximal end 2118 of the shaft 2104 may be received in a distal end 2120 of the handle 2102.

Referring to FIGS. 43 and 44, the lockout screw 654 may be used with the instrument 1500 and implant 1100 as described above for the instrument 100 and implant 1000.

Referring to FIGS. 140-142, implant 1100 is expandable along a horizontal or lateral or transverse or medial-lateral axis 104 and a vertical or cephalocaudal axis 106. Axis 102 is an anterior-posterior axis. Implant 1100 includes a first support member 1140 and a second support member 1130, the support members connected by a first end body 1150 and a second end body 1152. First support member 1140 may include an upper support body 1142 and a lower support body 1144. Second support member 1130 may include an upper support body 1132 and a lower support body 1134. Internal threads 1155 are included in the second end body 1152 for connection to the implant retainer shaft 1508. A plurality of link members 1160, 1162, 1166, 1168 pivotably connect each of the first and second end bodies 1150, 1152 to each of the support members 1130, 1140. Lower support body 1144 includes ramped expansion slots 1174, 1176, and upper support body 1142 includes ramped expansion slots 1170, 1172. A chamber 1122 may exist in the midst of the support bodies 1142, 1144, 1132, 1134, at least when the implant 1100 is expanded. The implant 1100 is representative of the intervertebral cages described in pending U.S. patent application Ser. No. 15/244,446.

Referring to FIGS. 143-160, methods are shown for inserting and expanding an expandable intervertebral implant with instrument 1500 and related instruments.

FIGS. 143 and 144 show a step of using the trial assembly 2060 in an intervertebral space to determine a suitable size for the implant 1100. The trial assembly 2060 may be inserted into the intervertebral space as shown and then rotated 90 degrees about its longitudinal axis to simulate implant vertical expansion.

FIGS. 145 and 146 show a step of coupling the instrument 1500 and implant 1100 together. Note that the cam lever 1526 has been rotated outwardly so that the draw bar assembly 1536 may be inserted into the instrument 1500 and rotated to engage the threads of the fifth portion 2006 of the pull rod 1946 of the draw bar assembly 1536 with internal threads of the first end body 1150 of the implant 1100.

FIGS. 147 and 148 show a step of locking the instrument 1500 and implant 1100 together. Note that the cam lever 1526 has been rotated inwardly (distally). With the cam lever in this position, the external spline of the fourth outer portion 1770 of the rotation lock ring 1524 is engaged with the internal spline of the second inner portion 1758 of the spline insert 1522 to prevent the draw bar assembly 1536 from rotating about the axis 1542, and the internal threads of the first side portion 1860 of the hole 1858 of the threaded slider 1530 engage the externally threaded portion 2036 of the threaded shaft 1954 of the draw bar assembly 1536 to prepare the instrument 1500 to be actuated to expand the implant 1100.

FIGS. 149 and 150 show a step of expanding the implant 1100 laterally. The knob strike plate 1520, top knob part 1532, and bottom knob part 1534 may be rotated together in a clockwise direction relative to the inserter handle 1518 to rotate the internal threads of the first side portion 1860 of the hole 1858 of the threaded slider 1530 relative to the externally threaded portion 2036 of the threaded shaft 1954 of the draw bar assembly 1536 to urge the draw bar assembly proximally to expand the implant 1100.

FIGS. 151 and 152 show a step of expanding the implant 1100 vertically. This step may be functionally continuous with the step of expanding the implant laterally. Note that implant 1100 features bilateral vertical expansion of the first and second support members 1140, 1130.

FIGS. 153 and 154 show a step of releasing the cam lever 1526 after implant expansion is complete. Releasing the cam lever 1526 disengages the external spline of the fourth outer portion 1770 of the rotation lock ring 1524 from the internal spline of the second inner portion 1758 of the spline insert 1522 so that the draw bar assembly 1536 can rotate about the axis 1542, and disengages the internal threads of the first side portion 1860 of the hole 1858 of the threaded slider 1530 from the externally threaded portion 2036 of the threaded shaft 1954 of the draw bar assembly 1536 by moving the threaded slider 1530 transverse to the axis 1542 so that the smooth second side portion 1862 of the hole 1858 approaches the externally threaded portion 2036.

FIGS. 155 and 156 show a step of unlocking the instrument 1500 and implant 1100. This step may be functionally continuous with the preceding step. At this point, the draw bar assembly 1536 may be removed from the instrument 1500.

FIG. 157 shows a step of removing the handle assembly 1942 from the shaft assembly 1600 and the implant retainer shaft 1508. The connector buttons 1510, 1512 are depressed to disconnect the shaft assembly 1600 from the handle assembly 1942, which also allows the implant retainer shaft 1508 to slide out. Note that the handle assembly 1942 may weigh much more than the shaft assembly 1600 and implant retainer shaft 1508 together, and the handle assembly 1942 is located at the opposite end of the shaft assembly 1600 from the implant 1100. Thus removing the handle assembly 1942 significantly reduces the force moment on the implant 1100 due to the weight of attached instrument apparatus. Force moment is the force times the moment arm. In the current step, the force is the weight of the handle assembly 1942 due at least to gravity. The moment arm is approximately the length of the shaft assembly 1600 modified with trigonometry to take into account the angle between the shaft assembly 1600 and true vertical, for example for TLIF, the length of the shaft assembly 1600 times the cosine of 30 degrees. The true moment arm is the horizontal distance between the centers of gravity of the implant 1100 and the handle assembly 1942. Additionally, the removable handle assembly 1942 shortens the length of the screwdriver 2064 and its associated force moment on the implant 1100.

FIG. 158 shows a step of coupling the funnel 2062 to the implant retainer shaft 1508 (not visible in this figure) and inserting the tamp assembly 180 through the funnel and into the shaft assembly 1600.

FIG. 159 shows a step of inserting the locking screw 654 using the screw driver assembly 2064 through the funnel 2062 and shaft assembly 1600. A step of using the funnel 2062 to unscrew the implant retainer shaft 1508 from the implant 1100 is not shown.

FIG. 160 shows a view of the implant 1100 in its final implanted state.

The terms "upper" and "lower", and "top" and "bottom", "front" and "rear" are used as relative terms herein for ease of description and understanding. It is understood that in embodiments of the disclosure, upper and lower entities may be reversed, as may top and bottom, front and rear.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An instrument comprising:
a pull rod that is removably connectable to a first end body of an implant via a threaded interconnection between the pull rod and the first end body of the implant, wherein the pull rod comprises a draw bar that is removably connectable to the first end body by rotation of the draw bar about a central longitudinal axis of the instrument;
an implant retainer shaft that is removably connectable to a second end body of the implant;
an actuator; and
a rotation lock;
wherein, when the pull rod is connected to the first end body, the implant retainer shaft is connected to the second end body, and the instrument is actuated, the pull rod and the first end body translate relative to the implant retainer shaft and the second end body along the central longitudinal axis without rotating about the central longitudinal axis during instrument actuation;
wherein instrument actuation comprises movement of the actuator in engagement with the draw bar to translate the draw bar relative to the implant retainer shaft and the second end body along the central longitudinal axis;
wherein when the rotation lock is engaged, the draw bar cannot rotate about the central longitudinal axis, wherein when the rotation lock is disengaged, the draw bar is free to rotate about the central longitudinal axis;
wherein the instrument comprises a first state in which the actuator is disengaged from the draw bar, the rotation lock is disengaged, and the draw bar is free to translate along and rotate about the central longitudinal axis;
wherein the instrument comprises a second state in which the actuator is engaged with the draw bar, the rotation lock is engaged, and the draw bar is prevented from rotating about the central longitudinal axis.

2. The instrument of claim 1, wherein the rotation lock comprises a rotation lock ring and a spline insert, wherein the rotation lock ring and the draw bar are fixed together for rotation about the central longitudinal axis, wherein the spline insert is fixed in translation along and rotation about the central longitudinal axis, wherein the spline insert is removably connectable to the rotation lock ring;
wherein when the rotation lock is engaged, the spline insert is connected to the rotation lock ring so that the rotation lock ring cannot rotate about the central longitudinal axis, wherein when the rotation lock is disengaged, the spline insert is disconnected from the rotation lock ring so that the rotation lock ring is free to rotate about the central longitudinal axis;
wherein the actuator and the rotation lock are coupled together so that the actuator engages the draw bar when the rotation lock is engaged and the actuator disengages from the draw bar when the rotation lock is disengaged.

3. The instrument of claim 2, wherein the draw bar comprises threads;
wherein the actuator comprises a threaded slider, wherein the threaded slider comprises threads that engage the threads of the draw bar, wherein instrument actuation comprises rotation of the threaded slider threads in engagement with the draw bar threads to translate the draw bar relative to the implant retainer shaft and the second end body along the central longitudinal axis.

4. An instrument comprising:
a pull rod that is removably connectable to a first end body of an implant by rotation of the pull rod relative to the first end body about a central longitudinal axis of the instrument to engage threads of the pull rod with threads of the first end body;
an implant retainer shaft that is removably connectable to a second end body of the implant;
an actuator; and a rotation lock;
wherein, when the pull rod is connected to the first end body, the implant retainer shaft is connected to the second end body, and the instrument is actuated, the pull rod and the first end body translate relative to the implant retainer shaft and the second end body along the central longitudinal axis of the instrument so that the first end body approaches the second end body, wherein the pull rod is prevented from rotating about the central longitudinal axis while the pull rod and the first end body are translating;
wherein instrument actuation comprises movement of the actuator in engagement with the pull rod to translate the pull rod relative to the implant retainer shaft and the second end body along the central longitudinal axis;
wherein when the rotation lock is engaged, the pull rod is prevented from rotating about the central longitudinal axis, wherein when the rotation lock is disengaged, the pull rod is free to rotate about the central longitudinal axis;
wherein the instrument comprises a first state in which the actuator is disengaged from the pull rod, the rotation lock is disengaged, and the pull rod is free to translate along and rotate about the central longitudinal axis;
wherein the instrument comprises a second state in which the actuator is engaged with the pull rod, the rotation lock is engaged, and the pull rod is prevented from rotating about the central longitudinal axis.

5. The instrument of claim 4, wherein the rotation lock comprises a rotation lock ring and a spline insert, wherein the rotation lock ring and the pull rod are fixed together for rotation about the central longitudinal axis, wherein the spline insert is fixed in translation along and rotation about the central longitudinal axis, wherein the spline insert is removably connectable to the rotation lock ring;
wherein when the rotation lock is engaged, the spline insert is connected to the rotation lock ring so that the rotation lock ring cannot rotate about the central longitudinal axis, wherein when the rotation lock is disengaged, the spline insert is disconnected from the rotation lock ring so that the rotation lock ring is free to rotate about the central longitudinal axis;
wherein the actuator and the rotation lock are coupled together so that the actuator engages the pull rod when the rotation lock is engaged and the actuator disengages from the pull rod when the rotation lock is disengaged.

6. The instrument of claim 5, wherein the pull rod comprises threads;
wherein the actuator comprises a threaded slider, wherein the threaded slider comprises threads that engage the threads of the pull rod, wherein instrument actuation comprises rotation of the threaded slider threads in engagement with the pull rod threads to translate the pull rod relative to the implant retainer shaft and the second end body along the central longitudinal axis.

7. An instrument comprising:
a draw bar that is removably threadedly connectable to a first end body of an implant by rotation of the draw bar relative to the first end body about a central longitudinal axis of the instrument, wherein the draw bar is carried at a first end of a first shaft;
an actuator; and
a rotation lock;
an implant retainer shaft that is removably connectable to a second end body of the implant, wherein the implant retainer shaft is carried at a first end of a second shaft;
wherein the instrument is actuatable to translate the draw bar toward the implant retainer shaft along the central longitudinal axis so that the draw bar does not rotate about the central longitudinal axis during instrument actuation;
wherein instrument actuation comprises movement of the actuator in engagement with the draw bar to translate the draw bar relative to the implant retainer shaft and the second end body along the central longitudinal axis;
wherein when the rotation lock is engaged, the draw bar cannot rotate about the central longitudinal axis, wherein when the rotation lock is disengaged, the draw bar is free to rotate about the central longitudinal axis;
wherein the instrument comprises a first state in which the actuator is disengaged from the draw bar, the rotation lock is disengaged, and the draw bar is free to translate along and rotate about the central longitudinal axis;
wherein the instrument comprises a second state in which the actuator is engaged with the draw bar, the rotation lock is engaged, and the draw bar is prevented from rotating about the central longitudinal axis.

8. The instrument of claim 7, wherein the rotation lock comprises a rotation lock ring and a spline insert, wherein the rotation lock ring and the draw bar are fixed together for rotation about the central longitudinal axis, wherein the spline insert is fixed in translation along and rotation about the central longitudinal axis, wherein the spline insert is removably connectable to the rotation lock ring;
wherein when the rotation lock is engaged, the spline insert is connected to the rotation lock ring so that the rotation lock ring cannot rotate about the central longitudinal axis, wherein when the rotation lock is disengaged, the spline insert is disconnected from the rotation lock ring so that the rotation lock ring is free to rotate about the central longitudinal axis;
wherein the actuator and the rotation lock are coupled together so that the actuator engages the draw bar when the rotation lock is engaged and the actuator disengages from the draw bar when the rotation lock is disengaged.

9. The instrument of claim 8, wherein the draw bar comprises threads;
wherein the actuator comprises a threaded slider, wherein the threaded slider comprises threads that engage the threads of the draw bar, wherein instrument actuation comprises rotation of the threaded slider threads in engagement with the draw bar threads to translate the draw bar relative to the implant retainer shaft and the second end body along the central longitudinal axis.

* * * * *

UNITED STATES PATENT AND TRADEMARK OFFICE
CERTIFICATE OF CORRECTION

Page 1 of 1

PATENT NO. : 10,993,815 B2
APPLICATION NO. : 15/793950
DATED : May 4, 2021
INVENTOR(S) : Darin Ewer et al.

It is certified that error appears in the above-identified patent and that said Letters Patent is hereby corrected as shown below:

On the Title Page

(73) Assignee: IMDS LLC, Providence, UT (US) should read --Amplify Surgical, Inc., Laguna Hills, CA (US)--.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*